(12) United States Patent
Yousef et al.

(10) Patent No.: US 12,358,963 B2
(45) Date of Patent: Jul. 15, 2025

(54) REGENERATIVE POLYPEPTIDES AND USES THEREOF

(71) Applicant: Juvena Therapeutics, Inc., Redwood City, CA (US)

(72) Inventors: Hanadie Yousef, Redwood City, CA (US); Jeremy O'Connell, Palo Alto, CA (US); Thach Mai, South San Francisco, CA (US); Rami Jaafar, San Francisco, CA (US); Zhihua Li, San Jose, CA (US)

(73) Assignee: Juvena Therapeutics, Inc., Redwood City, CA (US)

( * ) Notice: Subject to any disclaimer, the term of this patent is extended or adjusted under 35 U.S.C. 154(b) by 0 days.

(21) Appl. No.: 17/843,748

(22) PCT Filed: Dec. 22, 2020

(86) PCT No.: PCT/US2020/066658
§ 371 (c)(1),
(2) Date: Jun. 17, 2022

(87) PCT Pub. No.: WO2021/133822
PCT Pub. Date: Jul. 1, 2021

(65) Prior Publication Data
US 2023/0398187 A1  Dec. 14, 2023

Related U.S. Application Data

(60) Provisional application No. 62/953,431, filed on Dec. 24, 2019, provisional application No. 62/953,429, filed on Dec. 24, 2019, provisional application No. 62/953,427, filed on Dec. 24, 2019.

(51) Int. Cl.
| | | |
|---|---|---|
| C07K 14/50 | (2006.01) | |
| A61K 31/19 | (2006.01) | |
| A61K 38/30 | (2006.01) | |
| A61P 19/02 | (2006.01) | |
| A61P 21/06 | (2006.01) | |

(52) U.S. Cl.
CPC ............. *C07K 14/50* (2013.01); *A61K 31/19* (2013.01); *A61K 38/30* (2013.01); *A61P 19/02* (2018.01); *A61P 21/06* (2018.01)

(58) Field of Classification Search
None
See application file for complete search history.

(56) References Cited

U.S. PATENT DOCUMENTS

| | | |
|---|---|---|
| 5,061,620 A | 10/1991 | Tsukamoto et al. |
| 5,155,038 A | 10/1992 | Eyal et al. |
| 5,525,593 A | 6/1996 | Lake et al. |
| 5,622,932 A | 4/1997 | DiMarchi et al. |
| 5,843,780 A | 12/1998 | Thomson et al. |
| 6,200,806 B1 | 3/2001 | Thomson et al. |
| 6,686,179 B2 | 2/2004 | Fleer et al. |
| 6,994,857 B2 | 2/2006 | Rosen et al. |
| 7,029,913 B2 | 4/2006 | Thomson et al. |
| 7,355,018 B2 | 4/2008 | Glass |
| 7,396,918 B2 | 7/2008 | Glass et al. |
| 7,521,211 B2 | 4/2009 | Glass |
| 7,632,503 B2 | 12/2009 | Stitt et al. |
| 7,781,404 B2 | 8/2010 | Glass |
| 7,837,993 B2 | 11/2010 | Conboy et al. |
| 7,837,999 B2 | 11/2010 | Glass et al. |
| 7,981,864 B2 | 7/2011 | LeBowitz |
| 8,158,581 B2 | 4/2012 | Glass et al. |
| 8,334,365 B2 | 12/2012 | Rosen et al. |
| 8,445,434 B2 | 5/2013 | Glass et al. |
| 8,563,691 B2 | 10/2013 | LeBowitz et al. |
| 8,603,973 B2 | 12/2013 | Fu et al. |
| 9,114,094 B2 | 8/2015 | Fu et al. |
| 9,376,480 B2 | 6/2016 | Aoyagi-Scharber et al. |
| 9,469,683 B2 | 10/2016 | LeBowitz et al. |
| 9,758,763 B2 | 9/2017 | Conboy et al. |
| 9,771,408 B2 | 9/2017 | Aoyagi-Scharber et al. |

(Continued)

FOREIGN PATENT DOCUMENTS

| | | |
|---|---|---|
| CN | 110036024 A | 7/2019 |
| CN | 110229238 A | 9/2019 |

(Continued)

OTHER PUBLICATIONS

Bella et al.: Blockade of IGF2R improves muscle regeneration and ameliorates Duchenne muscular dystrophy. EMBO Mol Med. 12(1):e11019 pp. 1-18 (2020).
Chen: AB063. Development of a fusion protein combined alpha-galactosidase A and insulin-like growth factor 2 for treatment of Fabry disease. Annals of Translational Medicine 5. Suppl 2 p. 84 (2017).
Database: WPI Week 201082. Clarivate Analytics. Thomson Scientific, London, GB AN 2010-P24302XP002805690 (2017).
Duguay et al.: Post-translational processing of the insulin-like growth factor-2 precursor: analysis of O-glycosylation and endoproteolysis. Journal of Biological Chemistry. 273(29):18443-18451 (1998).

(Continued)

*Primary Examiner* — Sergio Coffa
(74) *Attorney, Agent, or Firm* — Wilson Sonsini Goodrich & Rosati

(57) ABSTRACT

Described herein are polypeptides comprising an FGF17, IGF2, or BMP7 amino acid sequence and an amino acid sequence from a heterologous polypeptide useful for the treatment of soft-tissue and muscle diseases, disorders, and injuries. Also described herein are synergistic combinations of a Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans. Also described are methods of treating muscle and soft-tissue diseases comprising administering the polypeptides and/or synergistic compositions.

20 Claims, 23 Drawing Sheets
Specification includes a Sequence Listing.

(56) References Cited

U.S. PATENT DOCUMENTS

| | | |
|---|---|---|
| 9,834,587 B2 | 12/2017 | Aoyagi-Scharber et al. |
| 9,834,588 B2 | 12/2017 | Aoyagi-Scharber et al. |
| 9,845,346 B2 | 12/2017 | Aoyagi-Scharber et al. |
| 10,040,840 B2 | 8/2018 | Antipov et al. |
| 10,265,372 B2 | 4/2019 | Conboy et al. |
| 10,301,369 B2 | 5/2019 | Aoyagi-Scharber et al. |
| 10,472,404 B2 | 11/2019 | Qin et al. |
| 10,571,467 B2 | 2/2020 | Singh et al. |
| 10,633,425 B2 | 4/2020 | Antipov et al. |
| 10,654,912 B2 | 5/2020 | Takahashi et al. |
| 10,821,155 B2 | 11/2020 | Yousef et al. |
| 10,874,750 B2 | 12/2020 | Do et al. |
| 11,046,751 B2 | 6/2021 | Takahashi et al. |
| 11,155,593 B2 | 10/2021 | Antipov et al. |
| 11,208,451 B2 | 12/2021 | Qin et al. |
| 11,254,725 B2 | 2/2022 | Aoyagi-Scharber et al. |
| 11,299,554 B2 | 4/2022 | Moore et al. |
| 11,351,231 B2 | 6/2022 | LeBowitz et al. |
| 11,401,348 B2 | 8/2022 | Lazar et al. |
| 11,466,066 B2 | 10/2022 | Pancook et al. |
| 11,491,243 B2 | 11/2022 | Do et al. |
| 11,634,474 B2 | 4/2023 | Takahashi et al. |
| 2003/0008821 A1 | 1/2003 | Detmar |
| 2003/0072761 A1 | 4/2003 | LeBowitz |
| 2006/0121018 A1 | 6/2006 | Lebowitz |
| 2006/0166328 A1 | 7/2006 | Glass et al. |
| 2006/0223753 A1 | 10/2006 | Glass |
| 2008/0241118 A1 | 10/2008 | Lebowitz |
| 2009/0018061 A1* | 1/2009 | Williams ......... A61K 38/1866 514/1.1 |
| 2009/0029914 A1 | 1/2009 | Rosen et al. |
| 2014/0038892 A1 | 2/2014 | Yayon et al. |
| 2015/0329614 A1 | 11/2015 | Fornaro et al. |
| 2016/0024580 A1 | 1/2016 | Masti |
| 2016/0271265 A1 | 9/2016 | Fischbeck et al. |
| 2017/0233447 A1 | 8/2017 | Qin |
| 2017/0239320 A1 | 8/2017 | Conboy et al. |
| 2017/0315117 A1 | 11/2017 | Singh et al. |
| 2017/0355744 A1 | 12/2017 | Aoyagi-Scharber et al. |
| 2017/0368173 A1 | 12/2017 | Kipps |
| 2018/0251770 A1 | 9/2018 | Friedland et al. |
| 2019/0240156 A1 | 8/2019 | Lim |
| 2020/0000882 A1 | 1/2020 | Yousef et al. |
| 2020/0002397 A1 | 1/2020 | Qin et al. |
| 2021/0038693 A1 | 2/2021 | Yousef et al. |
| 2021/0380654 A1 | 12/2021 | Dong et al. |
| 2022/0009991 A1 | 1/2022 | Antipov et al. |
| 2022/0031812 A1 | 2/2022 | Pfaff et al. |
| 2022/0127326 A1 | 4/2022 | Aoyagi-Scharber et al. |
| 2022/0162283 A1 | 5/2022 | Antipov et al. |
| 2022/0354934 A1 | 11/2022 | LeBowitz et al. |
| 2022/0409696 A1 | 12/2022 | Yousef et al. |
| 2023/0060624 A1 | 3/2023 | Fecteau et al. |
| 2023/0233711 A1 | 7/2023 | Do et al. |
| 2023/0241187 A1 | 8/2023 | LeBowitz et al. |
| 2023/0312663 A1 | 10/2023 | Yousef et al. |
| 2023/0405089 A1 | 12/2023 | Yousef et al. |
| 2024/0024423 A1 | 1/2024 | Yousef et al. |
| 2024/0043484 A1 | 2/2024 | Yousef et al. |
| 2024/0189397 A1 | 6/2024 | Yousef et al. |
| 2024/0294597 A1 | 9/2024 | Yousef et al. |

FOREIGN PATENT DOCUMENTS

| | | |
|---|---|---|
| CN | 115379850 A | 11/2022 |
| EP | 0394827 A1 | 10/1990 |
| EP | 1833847 B1 | 7/2011 |
| EP | 2241575 B1 | 6/2015 |
| EP | 3348635 B1 | 2/2021 |
| EP | 3813861 A1 | 5/2021 |
| EP | 4081235 A1 | 11/2022 |
| KR | 20100119437 A | 11/2010 |
| TW | 202019458 A | 6/2020 |
| WO | WO-8500831 A1 | 2/1985 |
| WO | WO-9114438 A1 | 10/1991 |
| WO | WO-9222311 A1 | 12/1992 |
| WO | WO-9303152 A1 | 2/1993 |
| WO | WO-9404030 A1 | 3/1994 |
| WO | WO-9740072 A2 | 10/1997 |
| WO | WO-0179258 A1 | 10/2001 |
| WO | WO-0179444 A2 | 10/2001 |
| WO | WO-2005033134 A2 | 4/2005 |
| WO | WO-2006074390 A2 | 7/2006 |
| WO | WO-2006081190 A2 | 8/2006 |
| WO | WO 2009/048540 | 4/2009 |
| WO | WO-2009137721 A2 | 11/2009 |
| WO | WO-2012037687 A1 | 3/2012 |
| WO | WO-2013166156 A2 | 11/2013 |
| WO | WO-2013170636 A1 | 11/2013 |
| WO | WO-2014082080 A2 | 5/2014 |
| WO | WO-2018100483 A1 | 6/2018 |
| WO | WO-2018189661 A2 | 10/2018 |
| WO | WO-2018200322 A1 | 11/2018 |
| WO | WO-2019213180 A1 | 11/2019 |
| WO | WO 2020/006273 | 1/2020 |
| WO | WO-2020132100 A1 | 6/2020 |
| WO | WO-2021072372 A1 | 4/2021 |
| WO | WO-2021133822 A1 | 7/2021 |
| WO | WO-2021133858 A1 | 7/2021 |
| WO | WO-2022271466 A1 | 12/2022 |
| WO | WO-2022271981 A2 | 12/2022 |

OTHER PUBLICATIONS

Ho et al.: PEDF-derived peptide promotes skeletal muscle regeneration through its mitogenic effect on muscle progenitor cells. Am J Physiol Cell Physiol. 309(3):C159-168 (2015).

Kan et al.: Insulin-like growth factor II peptide fusion enables uptake and lysosomal delivery of a-N-acetylglucosaminidase to mucopolysaccharidosis type IIIB fibroblasts. Biochem J. 458(2):281-289 (2014).

Kirk et al., Insulin-like growth factor-II delays early but enhances late regeneration of skeletal muscle. Journal of Histochemistry & Cytochemistry 51(12):1611-1620 (2003).

Mateos-Aierdi et al.: Muscle wasting in myotonic dystrophies: a model of premature aging. Front Aging Neurosci. 7:125 pp. 1-16 (2015).

McCarthy et al.: Effective fiber hypertrophy in satellite cell-depleted skeletal muscle. Development. 138(17):3657-66 (2011).

Motohashi et al.: Muscle satellite cell heterogeneity and self-renewal. Front Cell Dev Biol. 2:1. doi: 10.3389/fcell.2014.00001 (2014).

PCT/US2019/039567 International Search Report and Written Opinion dated Nov. 6, 2019.

PCT/US2020/066658 International Search Report and Written Opinion dated May 13, 2021.

PCT/US2020/066739 International Search Report and Written Opinion dated Jun. 3, 2021.

PCT/US2022/033059 International Search Report and Written Opinion dated Sep. 19, 2022.

Ranke et al.: Insulin-like growth factor binding-protein-3 (IGFBP-3). Best Practice & Research Clinical Endocrinology & Metabolism 29:701-711 (2015).

Rinderknecht et al.: Primary structure of human insulin-like growth factor II. FEBS Letters 89.2:283-286 (1978).

Shin et al.: Functional Properties of Antibody Insulin-like Growth Factor Fusion Proteins. Journal of Biological Chemistry. 269(7):4979-4985 (1994).

Smith et al.: IGF-II ameliorates the dystrophic phenotype and coordinately down-regulates programmed cell death. Cell death and Differentiation. 7:1109-1118 (2000).

Song et al.: MBNL1 reverses the proliferation defect of skeletal muscle satellite cells in myotonic dystrophy type 1 by inhibiting autophagy via the mTOR pathway. Cell Death Dis. 11(7):545 pp. 1-16 (2020) doi: 10.1038/s41419-020-02756-8.

Steinmetz et al.: Insulin-like growth factor 2 rescues aging-related memory loss in rats. Neurobiol Aging. 44:9-21 (2016).

(56) References Cited

OTHER PUBLICATIONS

Subramanian et al.: Thrombospondin-4 controls matrix assembly during development and repair of myotendinous junctions. Elife. 3:e02372 (2014).
Thornell et al.: Satellite cell dysfunction contributes to the progressive muscle atrophy in myotonic dystrophy type 1. Neuropathol Appl Neurobiol. 35(6):603-613 (2009).
U.S. Appl. No. 16/455,445 First Action Interview dated Mar. 23, 2020.
U.S. Appl. No. 16/455,445 Restriction Requirement dated Sep. 20, 2019.
U.S. Appl. No. 17/072,636 Office Action dated Apr. 27, 2023.
U.S. Appl. No. 17/072,636 Office Action dated Dec. 9, 2022.
U.S. Appl. No. 18/448,054 Office Action dated Nov. 3, 2023.
Vanhoutte et al.: Thrombospondin expression in myofibers stabilizes muscle membranes. Elife. 5:e17589 pp. 1-33 (2016).
Ward et al.: Disproportionate growth in mice with Igf-2 transgenes. Proc Natl Acad Sci U S A. 91(22):10365-10369 (1994).
Athens Research & Technology, product information for human thrombospondin Product # 16-20-201319, 2 pages.
Barghorn et al., Globular amyloid beta-peptide 1-42 oligomer—a homogenous and stable neuropathological protein in Alzheimer's . . . , 2005, J. Neurochem. vol. 95, pp. 834-847.
Bischoff et al., Cell cycle commitment of rat muscle satellite cells, 1990, J. Cell Biol. vol. 111, pp. 201-207.
Bischoff et al., Proliferation of muscle satellite cells on intact myofibers in culture, 1986, Developmental Biol vol. 115, pp. 129-139.
Buchli et al., Inhibition of Nogo: a key strategy to increase regeneration, plasticity and functional recovery of the lesioned central . . . , 2005, Ann Med vol. 37, pp. 556-567.
Capila et al., Heparin-protein interactions, 2002, Angew Chem Int Ed Engl vol. 41, pp. 391-412.
Carlson et al., Loss of stem cell regenerative capacity with aged niches, 2007, Aging Cell vol. 6, pp. 371-382.
Chung et al., Human embryonic stem cell lines generated without embryo destruction, 2008, Stem Cell vol. 2, pp. 113-117.
Conboy et al., Aging, stem cells and tissue regeneration: lessons from muscle, 2005, Cell Cycle vol. 4, pp. 407-410.
Conboy et al., Embryonic anti-aging niche, 2011, Aging vol. 3, pp. 555-553.
Conboy et al., Heterochronic parabiosis for the study of the effects of aging on stem cells and their niches, 2012, Cell Cycle vol. 11, pp. 22602267.
Conboy et al., Immuno-analysis and FACS sorting of adult muscle fiber-associated stem/precursor cells, 2010, Methods Mol Biol vol. 621, pp. 165-173.
Conboy et al., Notch-mediated restoration of regenerative potential to aged muscle, 2003, Science vol. 302, pp. 1575-1577.
Conboy et al., Preparation of adult muscle fiber-associated stem/precursor cells, 2010, Methods Mol Biol vol. 621, pp. 149-163.
Conboy et al., The regulation of notch signaling controls satellite cell activation and cell fate determoination in postnatal myogenesis, 2002, Dev Cell vol. 3, pp. 397-409.
Grounds et al., Age-associated changes in the response of skeletal muscle to exercise and regeneration, 1998, Ann NY Acad Sci vol. 854, pp. 78-91.
Jensen et al., Quantification of Alzhemier amyloid beta peptides ending at residues 40 and 42 by novel ELISA systems, 2000, Mol Med vol. 6, pp. 291-302.
Kuo et al., Water-soluble Abeta (N-40, N-42) oligomers in normal and Alzheimer disease brains, 1996, J Biol Chem vol. 271, pp. 4077-4081.
Ludwig et al., Feeder-independent culture of human ambryonic stem cells, 2006, Nature Methods vol. 3, pp. 637-646.
Malinowska et al., Genistein improves neuropathology and corrects behavior in a mouse model of neurodegenerative metabolic disease, 2010, PLoS ONE vol. 5, 9 pages.

Morrison et al., Propsective identification, isolation by flow cytometry, and in vivo self-renewal of mutlipotent mammalian neural crest cells, 1999, Cell vol. 96, pp. 737-749.
Morrison et al., Regulagtory mechanisms in stem cell biology, 1997, Cell vol. 88, pp. 287-298.
Nguyen et al., Surface plasmon resonance: a versatile technique for biosensor applications, 2015, Sensors vol. 15, pp. 10481-510.
Piantino et al., An injectable, biodegradabale hydrogel for trophic facotr delivery enhances axopnal rewiring and improves performance . . . , 2006, Exp Neurol vol. 201, pp. 359-367.
Yousef et al., hESC-secreted proteins can be enriched for multiple regenerative therapies by heparin-binding, 2013, Aging vol. 5, pp. 357-372.
Yousef et al., Mechanisms of action of hESC-secreted proteins that enhance human and mouse myogenesis, 2014, Aging vol. 6, pp. 602-620.
Frazier et al., Age-dependent regulation of skeletal muscle mitochondria by the thrombospondin-1 receptor CD47, 2011, Matrix Biology vol. 30, pp. 154-161.
Bergman, Daniel, et al., Insulin-Like Growth Factor 2 in Development and Disease: A Mini- Review. Gerontology 59:240-249 (2013).
Chichili, Reddy Vishnu Priyanka et al. Linkers in the Structural Biology of Protein-Protein Interactions. Protein Science vol. 22,2: pp. 153-167 (2013).
Chriett et al.: The histone deacetylase inhibitor sodium butyrate improves insulin signalling in palmitate-induced insulin resistance in L6 rat muscle cells through epigenetically-mediated up-regulation of Irs1. Molecular and Cellular Endocrinology. 439:224-232 (2017).
Co-pending U.S. Appl. No. 17/843,676, filed Jun. 17, 2022.
Co-pending U.S. Appl. No. 18/572,740, filed Dec. 20, 2023.
Co-pending U.S. Appl. No. 18/662,443, filed May 13, 2024.
EP20904271.2 European Search Report dated Jan. 8, 2024.
EP20906531.7 European Search Report dated Jan. 8, 2024.
Hayashi, Shinichiro, et al., Sequence of IGF-I, IGF-II, and HGF Expression in Regenerating Skeletal Muscle. Histochem Cell Biol122:427-434 (2004).
Kuo et al.: Microfracture and bone morphogenetic protein 7 (BMP-7) synergistically stimulate articular cartilage repair. Osteoarthritis and Cartilage. Elsevier. Amsterdam, NL. 14(11):1126-1135 (2006).
Malito, E et al. Amyloid Beta-Degrading Cryptidases: Insulin Degrading Enzyme, Presequence Peptidase, and Neprilysin. Cellular and Molecular Life Sciences vol. 65,16: pp. 2574-2585 (2008).
Ramilowski, Jordan A. A Draft Network of Ligand-Receptor-Mediated Multicellular Signalling in Human. Nature Communications vol. 6: pp. 7866 (2015).
Strohl, William R et al. Fusion Proteins for Half-Life Extension of Biologics as a Strategy to Make Biobetters. BioDrugs vol. 29,4: pp. 215-239 (2015).
Uchimura et al.: Insulin-Like Growth Factor Ii (IGF-II) Inhibits IL-1 [beta]-Induced Cartilage Matrix Loss and Promotes Cartilage Integrity in Experimental Osteoarthritis: OA. Journal of Cellular Biochemistry. 116(12):2858-1869(2015).
Ueda, Keisuke et al.: Albumin Fusion at the N-terminus or C-terminus of Human Lactoferrin Leads to Improved Pharmacokinetics and Anti-proliferative Effects on Cancer Cell Lines. European Journal of Pharmaceutical Sciences vol. 155: 105551 (2020).
U.S. Serial No. Office Action dated Jan. 23, 2024.
U.S. Appl. No. 17/072,636 Office Action dated Mar. 11, 2024.
U.S. Appl. No. 18/471,220 Office Action dated May 9, 2024.
Xie et al.: IGF-IR determines the fates of BCR/ABL leukemia. Journal of Hematology & Oncology. 8(3):1-9 (2015).
Zanou, Nadège, et al., Skeletal Muscle Hypertrophy and Regeneration: Interplay Between the Myogenic Regulatory Factors (MRFs) and Insulin-like Growth Factors (IGFs) Pathways. Cell Mol Life Sci 70(21):4117-4130 (2013).
Charge et al.: Cellular and Molecular Regulation of Muscle Regeneration. Physiological Reviews. American Physiological Society. US. 84:209-238 (2004).
EP20904271.2 Supplementary European Search Report dated Jun. 25, 2024.
Fountoulakis, Michael et al. Interferon Gamma Receptor Extracellular Domain Expressed as IgG Fusion Protein in Chinese Hamster

(56) References Cited

OTHER PUBLICATIONS

Ovary Cells. Purification, biochemical characterization, and stoichiometry of binding. Journal of Biological Chemistry 270(8):3958-3964 (1995).

Kamachi et al.: Induction of differentiation of muscle cells by introducing IGFII gene into ES cells—Transplantation therapy into muscle injury and muscle disease model mice—Translation of Inflammation and Regeneration. 25(4):301-302 (2005) Machine English Translation.

Kamochi et al.: Transplantation of Myocyte Precursors Derived from Embryonic Stem Cells Transfected with IGFII Gene in a Mouse Model of Muscle Injury. Experimental Transplantation. 82(4):516-526 (2006).

Osborn, Blaire L. et al. Pharmacokinetic and pharmacodynamic studies of a human serum albumin-interferon-alpha fusion protein in cynomolgus monkeys. Journal of Pharmacology and Experimental Therapeutics 303(2):540-548 (2002).

Sung, Cynthia et al. An IFN-Beta-albumin fusion protein that displays improved pharmacokinetic and pharmacodynamic properties in nonhuman primates. Journal of interferon & cytokine research 23(1):25-36 (2003).

Traunecker, Andre et al. Soluble CD4 molecules neutralize human immunodeficiency virus type 1. Nature 331(6151):84-86 (1988).

U.S. Appl. No. 18/662,443 Office Action dated Jul. 24, 2024.

U.S. Appl. No. 18/662,443 Office Action dated Oct. 25, 2024.

Yao, Zhengsheng et al. Effect of albumin fusion on the biodistribution of interleukin-2. Cancer Immunology, Immunotherapy 53(5):404-410 (2004). Published Online Nov. 18, 2003.

* cited by examiner

REGENERATIVE POLYPEPTIDES AND USES THEREOF

CROSS-REFERENCE TO RELATED APPLICATIONS

This application is a U.S. National Application of International Application No. PCT/US2020/066658, filed on Dec. 22, 2020, which claims priority to U.S. provisional application Ser. No. 62/953,431 filed Dec. 24, 2019, U.S. provisional application Ser. No. 62/953,429 filed Dec. 24, 2019, and U.S. provisional application Ser. No. 62/953,427 filed Dec. 24, 2019, which are incorporated herein by reference in their entireties.

STATEMENT AS TO FEDERALLY SPONSORED RESEARCH

This invention was made with government support under R43 AG071181 awarded by the National Institutes of Health. The government has certain rights in the invention.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "JTI015_ST25.txt", a creation date of Dec. 17, 2020, and a size of 208 kilobytes. The Sequence Listing filed via EFS-Web is part of the specification and is incorporated in its entirety by reference herein.

BACKGROUND

As the average life span increases, increasing emphasis is placed upon "healthy aging." Individuals would like to live more active lifestyles as they age, and as a result, many aging disorders can have a significant impact on the quality of life of aging individuals. Treatments directed to regenerative ends have utility for treating aging diseases. Additionally, many treatments for aging disorders can be applicable to younger individuals who have suffered illness, injury, or who possess genetic or developmental defects leading to premature tissue loss, wasting, or weakening.

SUMMARY

Described herein are polypeptides comprising an FGF17, IGF2, or BMP7 amino acid sequence and an amino acid sequence from a heterologous polypeptide useful for the treatment of soft-tissue and muscle diseases, disorders, and injuries. The IGF2 amino acid sequence can include an amino acid sequence at least about 90%, 95%, 97%, 98%, 99%, or 100% identical to the amino acid sequence set forth in SEQ ID NO: 89. The BMP7 amino acid sequence can include an amino acid sequence at least about 90%, 95%, 97%, 98%, 99%, or 100% identical to the amino acid sequence set forth in SEQ ID NO: 89. The BMP7 amino acid sequence can include a 15-30 amino acid fragment at least about 90%, 95%, 98%, 99% or 100% identical to the amino acid sequence set forth in SEQ ID NO: 93. The FGF17 amino acid sequence can include an amino acid sequence at least about 90%, 95%, 97%, 98%, 99%, or 100% identical to the amino acid sequence set forth in SEQ ID NO: 54. The FGF17 amino acid sequence can include a mutation selected from: deletion of amino acids G181-T203, deletion of amino acids 197-T203, deletion of amino acids 204-216, deletion of amino acids 181-216, R204Q/K207Q, deletion of amino acids 197-216, K191A/K193A/S200A, and combinations thereof. The FGF17, IGF2, and/or BMP7 can include at least one amino acid that is N-, C-, or O-linked glycosylated.

The heterologous polypeptide can be an immunoglobulin molecule or fragment thereof, an albumin molecule, a transferrin molecule, an XTEN sequence, a proline-alanine-serine polymer, a homo-amino acid polymer, a glycine-rich sequence, a gelatin-like polymer, an elastin-like peptide, a carboxy-terminal peptide, or combinations thereof. A fragment of an immunoglobulin molecule can include the hinge domain of an IgG, the CH2 domain of an IgG, the CH3 domain of an IgG, or any combination thereof. The immunoglobulin molecule or fragment thereof can include one or more mutations that reduce the effector function of the fragment of the immunoglobulin molecule. Also described herein are combinations of a Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans.

Described herein are methods of treating muscle and soft-tissue diseases comprising administering the polypeptides and/or compositions combining a polypeptide with a small chain fatty acid, mTOR activator, and/or glycosaminoglycan. Muscle diseases that can be treated include, for example, acute and chronic muscle wasting diseases or conditions, such as sarcopenia, cachexia, muscular dystrophies, and muscle injury. Soft tissue regeneration can be useful to treat acute and chronic muscle wasting diseases or conditions.

DETAILED DESCRIPTION

Figure 1A:
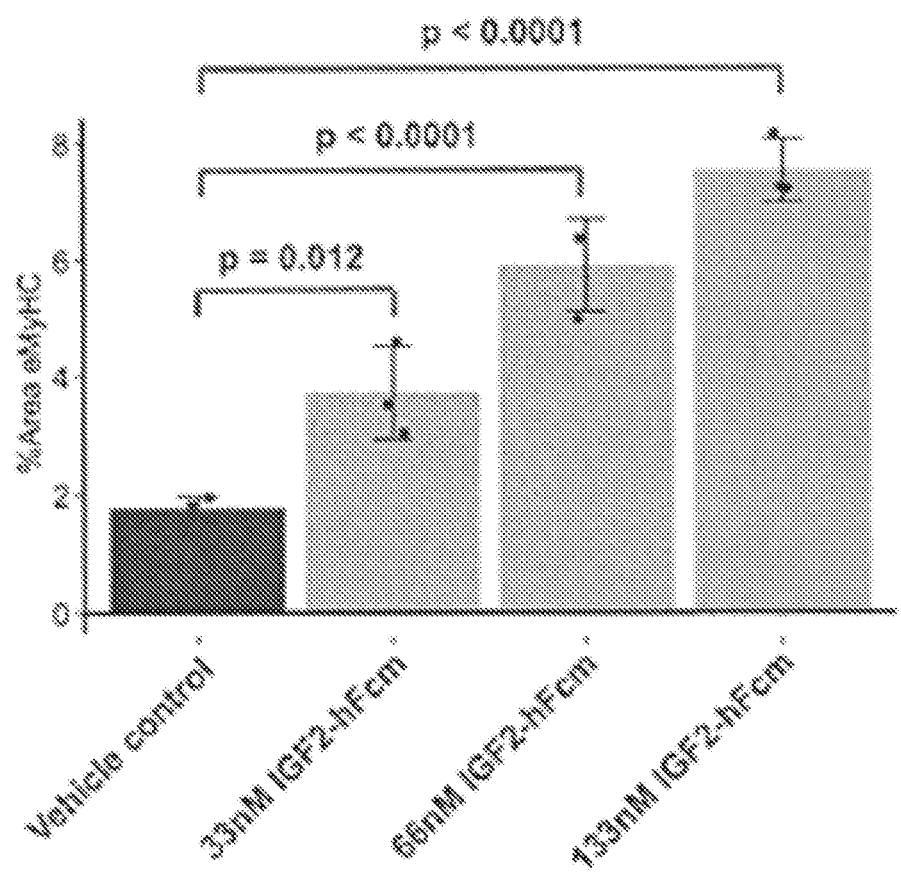
FIG. 1A depicts purified IGF2-hFcm promoted differentiation of human myoblast cells.

In certain aspects disclosed herein is a therapeutically active protein or polypeptide sequence or derivative or fragment thereof that enhances progenitor cell growth or regeneration or function through activation of a cell surface receptor, and one or more of: a secretion signal a multimerizing component, or a stabilizing component. We modify and combined the sequences of certain polypeptides to create secreted, therapeutically active proteins with applications to muscle and soft tissue regeneration useful to treat acute and chronic muscle wasting diseases or conditions, such as sarcopenia, cachexia, muscular dystrophies, and muscle injury. In certain aspects, disclosed herein is a method of treating individuals with acute and chronic muscle wasting diseases or conditions, such as sarcopenia, cachexia, muscular dystrophies, and muscle injury.

In certain aspects, disclosed herein is a polypeptide comprising an FGF8 subfamily amino acid sequence and a heterologous polypeptide amino acid sequence, wherein the heterologous polypeptide increases the stability or biological function of the FGF8 subfamily amino acid sequence. In certain aspects, disclosed herein is a composition comprising an FGFR agonist and a glycosaminoglycan.

In certain aspects, disclosed herein is a polypeptide comprising an IGF2 amino acid sequence and a heterologous polypeptide amino acid sequence, wherein the heterologous polypeptide amino acid sequence increases the stability or biological function of the IGF2 amino acid sequence. In certain aspects, disclosed herein is a composition comprising an IGF1R agonist and a short fatty acid chain.

In certain aspects, disclosed herein is a polypeptide comprising a BMP7 amino acid sequence and a heterologous polypeptide amino acid sequence, wherein the heterologous polypeptide increases the stability or biological function of the BMP7 amino acid sequence. In certain aspects, disclosed herein is a composition comprising a BMP7 receptor agonist and a glycosaminoglycan.

The secretion signal sequence can either be one naturally occurring with a therapeutically active protein or polypeptide sequence or a different one selected, modified, or created to optimize expression yield through secretion efficiency, processing kinetics, or cell line specific processing. Further examples and SEQ IDs are in Table 1. In certain aspects, the polypeptide may comprise a secretory signal peptide. In certain embodiments, the secretory signal peptide is one of SEQ ID NO: 10-16. Production of the fusion polypeptides may be done in heterologous production systems (e.g., bacteria, yeast, mammalian, inset, etc.).

Polypeptides can induce a regenerative effect through membrane receptors in desired cell types. Examples from the stem cell secretome selected for their ability to improve muscle and soft tissue regeneration are listed in Table 2, and include, for example, FGF17, BMP7, IGF2, and variants thereof. Multimerizing components can join two or more other protein components together. A multimerizing component can take the form of a linker sequence of amino acids that joins other components tandemly into a single consecutive amino acid sequence. Or multimerizing components can take the form of proteins or protein domains that dimerize, resulting in covalent disulfide linking or non-covalently associations driving dimerization. Examples are found in Table 3.

Stabilizing components can reduce degradation, increase translational or post-translation folding, reduce unfolding rates, increase half-life, and/or improve other desirable pharmacokinetic parameters (e.g., serum half-life, $C_{max}$, AUC, $T_{max}$, etc.). Examples can include abundant, circulating proteins or fragments thereof such as albumin or the fragment crystallizable (Fc) region from a human antibody. Further examples are in Table 3.

Certain Definitions

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

As used herein the term "about" refers to an amount that is near the stated amount by 10%.

As used herein the terms "individual," "patient," or "subject" are used interchangeably and refer to individuals diagnosed with, suspected of being afflicted with, or at-risk of developing at least one disease for which the described compositions and method are useful for treating. In certain embodiments the individual is a mammal. In certain embodiments, the mammal is a mouse, rat, rabbit, dog, cat, horse, cow, sheep, pig, goat, llama, alpaca, or yak. In certain embodiments, the individual is a human.

As used herein the term "treat" or "treating" refers to interventions to a physiological or disease state of an individual designed or intended to ameliorate at least one sign or symptom associated with said physiological or disease state. The skilled artisan will recognize that given a heterogeneous population of individuals afflicted with a disease, not all individuals will respond equally, or at all, to a given treatment.

As used herein, the term "heterologous" refers to a nucleotide or amino acid sequence that is from a different source (e.g., gene, polypeptide, or organism) compared to the amino acid or nucleotide sequence to which it refers to as being heterologous. Heterologous includes biological sequences derived from different organisms or to sequences derived from different sources (e.g., genes or proteins) of the same organism. Heterologous sequences include recombinant DNA molecules comprising nucleotide sequences from different sources, fusion proteins comprising amino acid sequences from different sources, and epitope or purification tags of natural or synthetic origin.

As used herein, the term "muscle" refers to skeletal muscle, and does not refer to smooth muscle or cardiac muscle.

As used herein, the term "soft tissue" refers to connective tissues, including without limitations, tendons, ligaments, and cartilage.

As used herein, the term "mitogenic activity" refers to an activity that induces cell division or proliferation.

As used herein, the term "fusion promoting activity" refers to activity that promotes the fusion of cells into multinucleated cells, such as the fusion of myocytes into multinucleated myofibers, or advances the differentiation of a terminal differentiating stem or progenitor cells toward a committed cell lineage type, such as the progression of myoblasts into myocytes or the increase in cell size of expanding myofibers.

The terms "polypeptide" and "protein" are used interchangeably to refer to a polymer of amino acid residues, and are not limited to a minimum length. Polypeptides, including the provided antibodies and antibody chains and other peptides, e.g., linkers and binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows. 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The polypeptides described herein can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors and the like. In the expression vectors regulatory elements such as promoters, enhancers, polyadenylation signals for use in controlling transcription can be derived from mammalian, microbial, viral or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (e.g., AttP-AttB recombination). Additionally, vectors can comprise sequences derived from transposable elements.

FGF17 Polypeptides

In certain aspects, described herein, are FGF17 polypeptides that comprise an FGF17 amino acid sequence. The FGF17 amino acid sequence can be a human FGF17. The FGF17 amino acid sequence can have at least about 90%, 95%, 97%, 98%, 99%, or 100% sequence identity to SEQ ID NO: 54. The FGF17 amino acid sequence can be 100% identical to SEQ ID NO: 54. The FGF17 amino acid sequence can be at least about 90%, 95%, 97%, 98%, 99%, or 100% identical to SEQ ID NO: 55. The FGF17 amino acid sequence can be 100% identical to SEQ ID NO: 55. The FGF17 amino acid sequence can be at least about 90%, 95%, 97%, 98%, 99%, or 100% identical to SEQ ID NO: 56. The FGF17 amino acid sequence can be 100% identical to SEQ ID NO: 56. The FGF17 amino acid sequence can be at least about 90%, 95%, 97%, 98%, 99%, or 100% identical to SEQ ID NO: 57, wherein the sequence comprises the R204Q and K207Q mutations. The FGF17 amino acid sequence can be 100% identical to SEQ ID NO: 57. The FGF17 amino acid sequence can be at least about 90%, 95%, 97%, 98%, 99%, or 100% identical to SEQ ID NO: 58. The FGF17 amino acid sequence can be 100% identical to SEQ ID NO: 58. The FGF17 amino acid sequence can be at least about 90%, 95%, 97%, 98%, 99%, or 100% identical to SEQ ID NO: 59, wherein the sequence comprises the K191A, K193A, and S200A mutations. The FGF17 amino acid sequence can be 100% identical to SEQ ID NO: 59.

The FGF17 polypeptides described herein can be fusion proteins or polypeptides that may comprise additional heterologous (non-FGF17) amino acid sequences that enhance the expression, stability or function of the FGF17 polypeptide. These heterologous amino acid sequences may increase the expression of the FGF17 fusion polypeptide from a cell system (e.g., CHO cells or other suitable cell system for bulk production) by 10%, 20%, 25%, 30%, 40%, 50%, 75%, 100%, 150%, 200%, 200%, 400%, 500%, 1,000% or more compared to a polypeptide not comprising the heterologous amino acid sequence. These heterologous amino acid sequences may increase the bioavailability (e.g., increasing the T½) of the FGF17 polypeptide in vivo by 10%, 20%, 25%, 30%, 40%, 50%, 75%, 100%, 150%, 200%, 200%, 400%, 500%, 1,000% or more compared to a polypeptide not comprising the heterologous amino acid sequence. These heterologous amino acid sequences may increase the function (e.g., signaling through an FGF receptor) of the FGF17 polypeptide in vivo by 10%, 20%, 25%, 30%, 40%, 50%, 75%, 100%, 150%, 200%, 200%, 400%, 500%, 1,000% or more compared to a polypeptide not comprising the heterologous amino acid sequence.

The FGF17 amino acid sequence of the FGF17-heterologous polypeptide fusion protein can be at least about 90%, 95%, 97%, 98%, 99%, or 100% identical to SEQ ID NO: 54. The FGF17 amino acid sequence of the fusion protein can be 100% identical to SEQ ID NO: 54. The FGF17 amino acid sequence of the fusion protein can be at least about 90%, 95%, 97%, 98%, 99%, or 100% identical to SEQ ID NO: 55. The FGF17 amino acid sequence of the fusion protein can be 100% identical to SEQ ID NO: 55. The FGF17 amino acid sequence of the fusion protein can be at least about 90%, 95%, 97%, 98%, 99%, or 100% identical to SEQ ID NO: 56. The FGF17 amino acid sequence of the fusion protein can be 100% identical to SEQ ID NO: 56. The FGF17 amino acid sequence of the fusion protein can be at least about 90%, 95%, 97%, 98%, 99%, or 100% identical to SEQ ID NO: 57, wherein the sequence comprises the R204Q and K207Q mutations. The FGF17 amino acid sequence of the fusion protein can be 100% identical to SEQ ID NO: 57. The FGF17 amino acid sequence of the fusion protein can be at least about 90%, 95%, 97%, 98%, 99%, or 100% identical to SEQ ID NO: 58. The FGF17 amino acid sequence of the fusion protein can be 100% identical to SEQ ID NO: 58. The FGF17 amino acid sequence of the fusion protein can be at least about 90%, 95%, 97%, 98%, 99%, or 100% identical to SEQ ID NO: 59, wherein the sequence comprises the K191A, K193A, and S200A mutations. The FGF17 amino acid sequence of the fusion protein can be 100% identical to SEQ ID NO: 59.

An FGF17 fusion polypeptide amino acid sequence can be at least about 90%, 95%, 97%, 98%, 99%, or 100% identical to SEQ ID NO: 60, SEQ ID NO: 61, or SEQ ID NO: 62. The fusion polypeptide amino acid sequence can be at least about 90%, 95%, 97%, 98%, 99%, or 100% identical to SEQ ID NO: 65, wherein the sequence comprises the R204Q and K207Q mutations. The fusion polypeptide amino acid sequence can be 100% identical to SEQ ID NO: 66, SEQ ID NO: 66 or SEQ ID NO: 71, wherein the sequence comprises the K191A, K193A, and S200A mutations. The fusion polypeptide amino acid sequence can be 100% identical to SEQ ID NO: 72. The fusion polypeptide amino acid sequence can be at least about 90%, 95%, 97%, 98%, 99%, or 100% identical to SEQ ID NO: 73, SEQ ID NO: 74, SEQ ID NO: 75, or SEQ ID NO: 69, wherein the sequence comprises the R204Q and K207Q mutations.

The FGF17 amino acid sequence can be at least about 80%, 90%, 95%, 97%, 98%, 99% or 100% identical to one of SEQ ID NO: 54-70 or 74, with 1, 2, 3, 4, 5, 6, 7, 8, 9, or 10 amino acids are deleted from the N- and/or C-terminus of the polypeptide.

IGF2 Fusion Proteins

Described herein are certain therapeutically useful IGF2 polypeptides, including IGF2 fusion polypeptides that promote in vivo stability and function of the IGF2 comprising polypeptides.

In certain aspects described herein are IGF receptor ligand polypeptides. The IGF2 polypeptides can comprise an IGF2 amino acid sequence. The IGF2 amino acid sequence can be that of a human IGF2 polypeptide. The human IGF2 polypeptide can comprise amino acids 25 to 91 of SEQ ID NO. 79 (i.e. SEQ ID NO. 76). The IGF2 amino acid sequence can be at least about 90%, 95%, 97%, 98%, 99%, or 100% identical to one of SEQ ID NO. 76, 79, 81 or 86. The IGF2 amino acid sequence can be 100% identical to SEQ ID NO. 76. The IGF2 amino acid sequence can be at least about 60%, 70%, 80%, 90%, 95%, 97%, 98%, 99% or 100% identical to one of SEQ ID NO: 76, 79-81, 86, or 88 and 1, 2, 3, 4, 5, 6, 7, 8, 9, or 10 amino acids are deleted from the N- and/or C-terminus of the polypeptide.

In certain IGF2 polypeptides described herein are fusion proteins or polypeptides that may comprise additional heterologous (non-IGF2) amino acid sequences that enhance the expression, stability or function of the IGF2 polypeptide compared to a polypeptide not comprising the heterologous amino acid sequence. These heterologous amino acid sequences may increase the expression of the IGF2 fusion polypeptide from a cell system (e.g., CHO cells or other suitable cell system for bulk production) by 10%, 20%, 25%, 30%, 40%, 50%, 75%, 100%, 150%, 200%, 200%, 400%, 500%, 1,000% or more compared to a polypeptide not comprising the heterologous amino acid sequence. These heterologous amino acid sequences may increase the bioavailability or other pharmacokinetic factor (e.g., increasing the $T_{1/2}$, AUC, $C_{max}$, $T_{max}$, etc.) of the IGF2 polypeptide in vivo by 10%, 20%, 25%, 30%, 40%, 50%, 75%, 100%, 150%, 200%, 200%, 400%, 500%, 1,000% or more compared to a polypeptide not comprising the heterologous amino acid sequence. These heterologous amino acid sequences may improve the pharmacodynamics and/or increase the function (e.g., signaling through an IGF receptor) of the IGF2 polypeptide in vivo by 10%, 20%, 25%, 30%, 40%, 50%, 75%, 100%, 150%, 200%, 200%, 400%, 500%, 1,000% or more compared to a polypeptide not comprising the heterologous amino acid sequence.

Also described herein are IGF receptor ligand fusion polypeptides or polypeptides that include an amino acid sequence heterologous to IGF2. The IGF receptor ligand fusion includes a heterologous amino acid sequence that promotes the stability or function of the IGF receptor ligand. The IGF2 amino acid sequence of the IGF2-heterologous polypeptide fusion protein can be at least about 90%, 95%, 97%, 98%, 99%, or 100% identical to SEQ ID NO. 76. The IGF2 amino acid sequence of the fusion protein can be 100% identical to SEQ ID NO. 76. The IGF2 amino acid sequence of the fusion protein can be at least about 90%, 95%, 97%, 98%, 99%, or 100% identical to SEQ ID NO. 80. The IGF2 amino acid sequence of the fusion protein can be 100% identical to SEQ ID NO. 80. The IGF2 amino acid sequence of the fusion protein can be at least about 90%, 95%, 97%, 98%, 99%, or 100% identical to SEQ ID NO. 88. The IGF2 amino acid sequence of the fusion protein can be 100% identical to SEQ ID NO. 88. Additional representative sequences can be found in Table 2.

BMP7 Fusion Proteins

Described herein are certain therapeutically useful BMP7 polypeptides, including BMP7 fusion polypeptides that promote in vivo stability and function of the BMP7 comprising polypeptides.

In one aspect, described herein, are BMP7 polypeptides, that comprise a BMP7 amino acid sequence. The BMP7 amino acid sequence can be a human BMP7 amino acid sequence. The BMP7 amino acid sequence can comprise or consist of amino acids 293 to 431 of BMP7. The BMP7 amino acid sequence can comprise a BMP7 knuckle domain (SEQ ID NO: 92). The BMP7 sequence can be at least about 90%, 95%, 97%, 98%, 99%, or 100% identical to SEQ ID NO: 89. The BMP7 sequence can be 100% identical to SEQ ID NO: 89. The BMP7 sequence can be at least about 90%, 95%, 97%, 98%, 99%, or 100% identical to SEQ ID NO: 92. The BMP7 sequence can be 100% identical to SEQ ID NO: 92. The BMP7 polypeptide sequence can comprise one, two, three, four or more repeats of a BMP7 knuckle domain.

The BMP7 amino acid sequence may be further fused to a heterologous amino acid sequence, either directly or with a linker sequence between the BMP7 amino acid sequence and the heterologous polypeptide amino acid sequence to create a fusion polypeptide. The fusion polypeptide can comprise a human BMP7 amino acid sequence. The fusion polypeptide can comprise or consist of amino acids 293 to 431 of BMP7. The fusion polypeptide can comprise a BMP7 knuckle domain (SEQ ID NO: 92). The fusion polypeptide amino acid sequence can comprise a BMP7 amino acid sequence at least about 90%, 95%, 97%, 98%, 99%, or 100% identical to SEQ ID NO: 89. The fusion polypeptide can comprise a BMP7 amino acid sequence 100% identical to SEQ ID NO: 89. The fusion polypeptide amino acid can comprise a BMP7 amino acid sequence at least about 90%, 95%, 97%, 98%, 99%, or 100% identical to SEQ ID NO: 92. The fusion polypeptide can comprise a BMP7 amino acid sequence 100% identical to SEQ ID NO: 92. The fusion polypeptide amino acid sequence can be at least about 90%, 95%, 97%, 98%, 99%, or 100% identical to SEQ ID NO: 90. The fusion polypeptide amino acid sequence can be 100% identical to SEQ ID NO: 90. The fusion polypeptide amino acid sequence can be at least about 90%, 95%, 97%, 98%, 99%, or 100% identical to SEQ ID NO: 91. The fusion polypeptide amino acid sequence can be 100% identical to SEQ ID NO: 91.

The BMP7 amino acid sequence can be at least about 80%, 90%, 95%, 97%, 98%, 99% or 100% identical to one of SEQ ID NO: 20, 21, 32, or 89, with 1, 2, 3, 4, 5, 6, 7, 8, 9, or 10 amino acids deleted from the N- and/or C-terminus of the polypeptide.

In some aspects, the BMP7 sequence may be a fragment of a BMP7 sequence. The knuckle domain of BMP7 comprises amino acids 98 to 129 of SEQ ID NO: 89 (SEQ ID NO: 32). 15-30 amino acid fragments from the knuckle domain can activate BMP signaling. The BMP7 sequence can comprise a knuckle domain of BMP. The BMP7 sequence can be a 15-30 amino acid fragment of SEQ ID NO: 32. The BMP7 sequence can be at least about 13, 14, 15, 16, 17, 18, 19, 20, 21, 22, 23, 24, 25, 26, 27, 29, 29, 30, 31, 32, 33, 34, or 35 amino acids of SEQ ID NO: 32.

Secretory Signal Peptides

In certain aspects, the fusion polypeptide may comprise a secretory signal peptide. The secretory signal peptide can be SEQ ID NO. 24, SEQ ID NO 25, SEQ ID NO 26, SEQ ID NO 27, SEQ ID NO 28, SEQ ID NO 29, or SEQ ID NO: 30. Production of the fusion polypeptides herein in heterologous production systems (e.g., bacteria, yeast, mammalian, insect, etc.) may involve the use of an appropriate secretory signal sequence for the particular host cell.

Multimerizing components join two or more other protein components. A multimerizing component may comprise a linker sequence of amino acids that joins other components that are identical or different into a single consecutive amino acid sequence. Suitable linkers include polypeptide linkers such as a Gly-Ser linker or spacer described herein. A multimerizing component can take the form of proteins or protein domains that multimerize or dimerize, resulting in covalent disulfide linking (e.g., through the addition of one or more de novo cysteine residues) or non-covalent associations driving dimerization (e.g., a leucine zipper). The multimerizing components may link or multimerize a plurality of IGF2 amino acid sequences. The multimerizing components may link or multimerize two IGF2 amino acid sequences. The two IGF2 amino acid sequences may be the same, or different, and selected from any of the IGF2 sequences described herein. The multimerizing components may link or multimerize two, three, four, five or more IGF2 amino acid sequences. The multimerizing components may link or multimerize an IGF2 amino acid sequence with another polypeptide that provides fusion promoting, proliferation promoting function, increased plasma half-life, or improvement of other pharmacokinetic or pharmacodynamic parameters.

The FGF17, IGF2, or BMP7 amino acid sequence may comprise functional fragments, mutated sequences, or modified polypeptides thereof. Table 2 lists some exemplary fragments, polypeptides and modified polypeptides. The IGF2 or BMP7 sequence can be N-, C-, or O-linked glycosylated. The IGF2 sequence can be glycosylated at one amino acid. The IGF2 sequence can be glycosylated at a site corresponding to Thr96, Thr99, or Thr163 of SEQ ID NO. 31. The BMP7 sequence can comprise at least one glycosylated amino acid. The BMP7 can be glycosylated at residues Asn10, Asn29, or Asn90 of SEQ ID NO. 89.

The FGF17, IGF2, or BMP7 receptor ligand polypeptides and receptor ligand fusion polypeptides described herein may be encoded by nucleic acids to facilitate production of the receptor ligand polypeptide or fusion polypeptide. These nucleic acids can be compatible with bacterial, yeast, insect, or mammalian expression systems. They may comprise promoters/enhancers (either constructive or inducible), polyadenylation signals, selectable markers (such as antibiotic resistance), origins of replication or other accessory nucleic acid sequences. FGF17, IGF2, or BMP7 sequences can be used from many organisms. The FGF17, IGF2, or BMP7 sequence can comprise a human FGF17, IGF2, or BMP7 amino acid sequence. The FGF17, IGF2, or BMP7 sequence can comprise a cat, dog or a horse FGF17, IGF2, or BMP7 sequence. The FGF17, IGF2, or BMP7 sequence can comprise a mouse, rat, rabbit, dog, cat, horse, cow, sheep, pig, goat, llama, alpaca, yak, or monkey sequence.

FGF17 Nucleic Acid Sequences

In certain embodiments, the FGF17 nucleic acid sequence is at least about 90%, 95%, 97%, 98%, 99%, or 100% identical to SEQ ID NO. 17. The FGF17 nucleic acid sequence can be 100% identical to SEQ ID NO. 17. The FGF17 nucleic acid sequence is at least about 90%, 95%, 97%, 98%, 99%, or 100% identical to SEQ ID NO. 22. The FGF17 nucleic acid sequence can be 100% identical to SEQ ID NO. 22. The FGF17 nucleic acid sequence can be at least about 90%, 95%, 97%, 98%, 99%, or 100% identical to SEQ ID NO. 23. The FGF17 nucleic acid sequence can be 100% identical to SEQ ID NO. 23.

IGF2 Nucleic Acid Sequences

The IGF2 nucleic acid sequence can be at least about 90%, 95%, 97%, 98%, 99%, or 100% identical to SEQ ID NO. 39. The IGF2 nucleic acid sequence can be 100% identical to SEQ ID NO. 39. The IGF2 nucleic acid sequence can be at least about 90%, 95%, 97%, 98%, 99%, or 100% identical to SEQ ID NO. 43. The IGF2 nucleic acid sequence can be 100% identical to SEQ ID NO. 43. The IGF2 nucleic acid sequence can be at least about 90%, 95%, 97%, 98%, 99%, or 100% identical to SEQ ID NO. 46. The IGF2 nucleic acid sequence can be 100% identical to SEQ ID NO. 46.

BMP7 Nucleic Acid Sequences

The BMP7 nucleic acid sequence can be at least about 90%, 95%, 97%, 98%, 99%, or 100% identical to SEQ ID NO: 51. The BMP7 nucleic acid sequence can be 100% identical to SEQ ID NO: 51. The BMP7 nucleic acid sequence can be at least about 90%, 95%, 97%, 98%, 99%, or 100% identical to SEQ ID NO: 52. The BMP7 nucleic acid sequence can be 100% identical to SEQ ID NO: 52. The BMP7 nucleic acid sequence can be at least about 90%, 95%, 97%, 98%, 99%, or 100% identical to SEQ ID NO: 53. The BMP7 nucleic acid sequence can be 100% identical to SEQ ID NO: 53.

Heterologous Peptides

The heterologous polypeptide that comprises part of the fusion proteins described herein may comprise, consist, or consist essentially of a fragment of an immunoglobulin molecule, an albumin molecule, a transferrin molecule, an XTEN sequence, a proline-alanine-serine polymer, a homo-amino acid polymer, a glycine-rich sequence, a gelatin-like polymer, an elastin-like peptide, a carboxy-terminal peptide, or combinations thereof.

In one aspect described herein the therapeutic polypeptide is FGF receptor ligand polypeptide or an FGF17 polypeptide. In one aspect described herein the therapeutic polypeptide is IGF receptor ligand polypeptide or an IGF2 polypeptide. In one aspect described herein the therapeutic polypeptide is BMP receptor ligand polypeptide or an BMP7 polypeptide.

In one aspect described herein the therapeutic polypeptide fused to a heterologous polypeptide amino acid sequence, either directly or through a linker, wherein the heterologous amino acid sequence imparts increased function or stability to the therapeutic polypeptide.

The heterologous peptide can improve the pharmacokinetics, pharmacodynamics, stability or biological function of the therapeutic amino acid sequence. The heterologous sequence may be fused to the therapeutic amino acid sequence at the C-terminus or at the N-terminus of the therapeutic amino acid sequence. The therapeutic amino acid sequence can be fused to a heterologous sequence at the N-terminus. The therapeutic amino acid sequence can be fused to a heterologous sequence at the C-terminus. A flexible linker can be used between the therapeutic amino acid sequence and the heterologous sequence at the N terminus. A flexible linker can be used between the therapeutic amino acid sequence and the heterologous sequence at the C terminus. A spacer can be used between the therapeutic amino acid sequence and the heterologous sequence at the N terminus. A spacer can be used between the therapeutic amino acid sequence and the heterologous sequence at the C terminus.

Heterologous peptides can improve the pharmacokinetics, pharmacodynamics, stability, or the biological function of the IGF2 amino acid sequence. Fusion proteins can be used to improve the pharmacokinetics of the biologically active molecules, such as by prolonging the half-life, as discussed in Strohl, "Fusion Proteins for Half-Life Extension of Biologics as a Strategy to Make Biobetters," *BioDrugs* (2015) 29:215-239. Fusing a polypeptide to a molecule or a fragment of a molecule with a long half-life, such as an immunoglobulin, an albumin, or a transferrin increase the half-life of the polypeptide. An XTEN sequence is a repeating amino acid polymer containing the amino acid residues A, E, G, P, S, and T which when fused to a peptide is capable of extending the half-lives of the peptides, while being otherwise inert. Fusing small repeating sequences such as proline-alanine-serine polymers (repeats of proline, alanine and serine), a homo-amino acid polymer sequence such as glycine-rich sequences (G-G-G-S), gelatin-like proteins, and elastin-like sequences (V-P-G-x-G, where x is any amino acid except proline) can also extend the half-life of a polypeptide. Fusing a polypeptide to a carboxy-terminal peptide (CTP) can increase the half-life of the polypeptide in the serum due to the strong negative change of CTP. The heterologous polypeptide can comprise a fragment of an immunoglobulin molecule, an albumin molecule, a transferrin molecule, an XTEN sequence, a proline-alanine-serine polymer, a homo-amino acid polymer, a glycine-rich sequence, a gelatin-like polymer, an elastin-like peptide, a carboxy-terminal peptide, or combinations thereof.

Immunoglobulins are large effector molecules and, for example, IgG immunoglobulins have a plasma half-life of approximately 21 days. When an immunoglobulin fragment is fused to second polypeptide, this can increase the half-life of the second polypeptide. The fragment of the immunoglobulin molecule can comprise the hinge domain of an IgG, the CH2 domain of an IgG, the CH3 domain of an IgG, or any combination thereof. The fragment of the immunoglobulin molecule can comprise the hinge domain of IgG1, the CH2 domain of IgG1, the CH3 domain of IgG1, or any combination thereof. The fragment of the immunoglobulin molecule can comprise the hinge domain of IgG4, the CH2 domain of IgG4, the CH3 domain of IgG4, or any combination thereof.

In some circumstances, mutations of the immunoglobulin molecule or fragment may increase the half-life or stability of the immunoglobulin molecule or fragment. The fragment of the immunoglobulin molecule can comprise the hinge domain of IgG1, the CH2 domain of IgG1, the CH3 domain of IgG1, or any combination thereof with one or more of the following amino acid mutations in the immunoglobulin molecule. P329G, L234A and L235A. The fragment of the immunoglobulin molecule comprises an IgG4 molecule. The fragment of the immunoglobulin molecule can comprise an IgG4 molecule with at least one of the following amino acid mutations in the immunoglobulin molecule: N434A, N434H, T307A/E380A/N434A, M252Y/S254T/T256E, 433K/434F/436H, T250Q, T250F, M428L, M428F, T250Q/ M428L, N434S, V308W, V308Y, V308F, M252Y/M428L, D259I/V308F, M428L/V308F, Q311V/N434S, T307Q/ N434A, E258F/V427T, S228P, L235E, S228P/L235E/ R409K, S228P/L235E, K370Q, K370E, deletion of G446, deletion of K447, and combinations thereof of IgG4 according to the EU numbering system.

Secretory signal sequences are sequence motifs that target proteins to the secretory pathway in the cell. Secretory sequences may be cleaved from the protein to produce the mature, secreted protein. The polypeptide can comprise a secretory signal sequence. The polypeptide can comprise human FGF17, IGF2, or BMP7 secretory sequence (SEQ ID NO 9, SEQ ID NO 11, SEQ ID NO 12). The polypeptide can comprise a secretory signal that is SEQ ID NO. 10, SEQ ID. NO. 13, SEQ ID NO. 14, SEQ ID NO. 15, or SEQ ID NO. 16.

Linkers and Spacers

Linkers or spacers are short amino acid sequences that separate different domains in a single protein, or domains between fusion proteins. As used herein, the term "linker" and spacer" are interchangeable. Linkers can either be rigid or flexible. Rigid linkers may prevent unwanted interactions between different domains. Proline-rich linkers tend to be more rigid, while glycine rich linkers tend to be more flexible. Flexible linkers may allow domains within a single protein to interact. Another use for flexible linkers is to covalently bond protein complexes and binding partners to generate stable protein complexes. Flexible linkers may also be used to promote dimerization. Linkers and spacers are reviewed in Chichili et al, Linkers in the Structural biology of protein-protein interactions, Protein Sci. February 2013. 22(2): 153-167.

The fusion polypeptides described herein may further comprise a linker or a spacer amino acid sequence that separate the therapeutics polypeptide and the heterologous polypeptide. The linker or spacer can be a peptide linker or spacer. The linker or spacer can be a flexible linker or spacer. The linker can be three alanines (AAA). The peptide linker can be a glycine-serine linker. The linker can be (in one-letter amino acid code): GGGGS (4GS) or multimers of the 4GS linker, such as repeats of 2, 3, 4, or 5 4GS linkers. The glycine-serine linker can comprise the amino acid sequence set forth in SEQ ID NO: 94 or 95, or 2, 3, 4, 5, or repeats of SEQ ID NO: 94 or 95. The linker can comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 amino acids derived from neither the polypeptide sequences in Table 2 nor the heterologous polypeptide amino acid sequences of Table 3.

The linker or spacers can be a single amino acid residue or greater in length. In certain embodiments, the peptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 amino acids in length. The peptide linker can have at least one amino acid residue but is no more than 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, or 2 amino acid residues in length.

Combinations of FGFR Agonists and Glycosaminoglycans

In certain aspects, disclosed herein is a composition comprising an FGFR agonist and a glycosaminoglycan. There are four FGF receptors, FGF1R, FGFR2, FGFR3, FGFR4, which are expressed by a variety of tissues throughout the body. Chemical agonists of FGFR include without limitations, PF-05231023 and SUN11602. Other polypeptides, including dekafin and hexafins, are also capable of activating FGFR signaling. These compositions can comprise an unexpected synergistic effect and are useful for treating the muscle and/or soft-tissue conditions or disorders. This synergistic effect may also be promoted by methods comprising separate administration of an FGFR agonist and a glycosaminoglycan. The combinations described herein can impart additional treatment utility and function to each of the individual components of the combination.

FGFR1 can be activated by FGF1, FGF2, FGF3, FGF4, FGF5, FGF6, FGF8, FGF10, FGF17, FGF19, FGF20, FGF21, FGF22, and FGF23. The FGFR1 agonist can be an FGFR1 agonistic antibody, an FGF polypeptide or a functional fragment thereof, FGF17 or a functional fragment thereof, PF-05231023, SUN11602, a dekafin, a hexafin, or combinations thereof.

FGFR2 comprises two alternatively spliced isoforms. FGFR2IIIb binds to FGF1, FGF3, FGF10 and FGF22, while FGFR2IIIc binds to FGF1, FGF2, FGF4, FGF6, FGF8, FGF9, FGF17, and FGF18. The FGFR2 agonist can be an FGFR2 agonistic antibody, an FGF polypeptide or a functional fragment thereof, FGF17 or a functional fragment thereof, PF-05231023, SUN11602, a dekafin, a hexafin, or combinations thereof.

FGFR3 can be activated by at least FGF1, FGF2, FGF4, FGF5, FGF6, FGF8, FGF9, FGF16, FGF17, FGF18, FGF20, FGF9, FGF19, FGF21, and FGF23, and FGF17. Mutations in FGFR3 have been associated with defects in chrondrocyte proliferation and calcification, as well as achondroplasia. The FGFR3 agonist can be an FGFR3 agonistic antibody, an FGF polypeptide or a functional fragment thereof, FGF17 or a functional fragment thereof, PF-05231023, SUN11602, a dekafin, a hexafin, or combinations thereof.

FGFR4 can be activated by at least FGF1, FGF2, FGF4, FGF6, FGF7, FGF8, FGF9, FGF16, FGF17 and FGF18. The FGFR4 agonist can be an FGFR4 agonistic antibody, an FGF polypeptide or a functional fragment thereof, FGF17 or a functional fragment thereof, PF-05231023, SUN11602, a dekafin, a hexafin, or combinations thereof.

The FGFR agonist can be a member of the FGF8 subfamily. The FGFR agonist can be an FGFR1 agonist. The FGFR agonist can be FGF17. The FGF17 polypeptide can be at least about 90%, 95%, 97%, 98%, 99%, or 100% identical to SEQ ID NO: 54. The FGF17 can be 100% identical to SEQ ID NO: 54. The FGF17 polypeptide can be at least about 90%, 95%, 97%, 98%, 99%, or 100% identical to SEQ ID NO: 55. The FGF17 polypeptide can be 100% identical to SEQ ID NO: 55. The FGF17 polypeptide can be at least about 90%, 95%, 97%, 98%, 99%, or 100% identical to SEQ ID NO: 56. The FGF17 can be 100% identical to SEQ ID NO: 56. The FGF17 polypeptide can be at least about 90%, 95%, 97%, 98%, 99%, or 100% identical to SEQ ID NO: 57, wherein the sequence comprises the R204Q and K207Q mutations. In certain embodiments, the FGF17 polypeptide is 100% identical to SEQ ID NO: 57. In certain embodiments, the FGF17 polypeptide is at least about 90%, 95%, 97%, 98%, 99%, or 100% identical to SEQ ID NO: 58. The FGF17 polypeptide can be 100% identical to SEQ ID NO: 58. The FGF17 polypeptide can be at least about 90%, 95%, 97%, 98%, 99%, or 100% identical to SEQ ID NO: 59, wherein the sequence comprises the K191A, K193A, and S200A mutations. The FGF17 polypeptide can be 100% identical to SEQ ID NO: 59.

Glycosaminoglycans are linear polysaccharides containing repeating disaccharide units. There are four glasses of glycosaminoglycans: heparin/heparin sulfate, chondroitin sulfate/dermatan sulfate, keratin sulfate, and hyaluronic acid. The glycosaminoglycan can be a heparin/heparin sulfate, a chondroitin sulfate/dermatan sulfate, a keratin sulfate, or a hyaluronic acid. In some embodiments, the glycosaminoglycan comprises a heparin. The glycosaminoglycan can comprise a hyaluronic acid.

Heparin can be derived from natural sources, often referred to as unfractionated heparin. Heparin can also be defined based upon molecular weight. Low molecular weight heparin includes dalteparin, enoxaparin, certoparin, ardeparin, parnaparin, reviparin, nadroparin, and danaparoid. Heparin can be administered in a mixture with other compounds, such as danaparoid, which is a mixture of heparan sulfate, dermatan sulfate, and chrondriotin sulfate. The composition can comprise low molecular weight heparin, heparin sulfate, unfractionated heparin, heparin tetrasaccharide, dalteparin, tinzaparin, enoxaparin, certoparin, ardeparin, parnaparin, reviparin, nadroparin, heparin flush, danaparoid, fondaparinux, or combinations thereof.

Hyaluronic acid (HA) is a polymeric molecule and can exhibit a range of molecular weights. Hyaluronic acid can be used at almost any average of modal molecular weight formulation of The molecular weight can be, for example, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000 kDa or more, or any range derivable therein. HA can include low molecular weight HA (about 500 to 700 kilodaltons kDa), medium molecular weight HA (700-1000 kDa), and high molecular weight HA (1.0-4.0 million daltons (MDa)). HA includes natural formulations, synthetic formulations, or combinations thereof. In some embodiments, the HA is a low molecular weight, a medium molecular weight, a low molecular weight, or a combination thereof. In some embodiments, the HA is a natural HA, a synthetic HA, or a combination thereof.

The HA may be a hyaluronic acid derivative. Examples of chemical modifications which may be made to HA include any reaction of an agent with the four reactive groups of HA, namely the acetamido, carboxyl, hydroxyl, and the reducing end. HA derivatives include, without limitations, hydrophobized hyaluronan, maleimide modified HA, methacrylated hyaluronic acid, or a sulfated hyaluronic acid. In some embodiments, the HA is modified at an acetamido group, a carboxyl group, a hydroxyl group, a reducing end, or combinations thereof. The HA can comprise a hydrophobized hyaluronan, a maleimide modified HA, a methacrylated hyaluronic acid, a sulfated hyaluronic acid, or a combination thereof. The HA can be covalently cross-linked via proteins or organic molecules into higher molecular weight moieties.

Also described herein are methods comprising administering an FGFR agonist and a glycosaminoglycan. The administration can be in the same composition, separate formulations. When separate formulations are administered they can be administered effectively simultaneously (e.g., during the same treatment) or separately with an interval of at least 1 hour, 12 hours, 24 hours, 2 days, 3 days, 4 days, 5 days, 6 days, 7 days, or more. When separate formulations are administered they can be administered by the same route or different routes selected from intravenous, intradermal, and subcutaneous. The formulations, whether separate or singular can be administered directly to the site of muscle or soft-tissue injury.

Combinations of an IGF1R Agonist and a Short Fatty Acid Chain

In certain aspects, disclosed herein is a composition comprising an IGF1R agonist and a short fatty acid chain. IGF1R signaling activates downstream pathways including pathways involved in cell proliferation, cell differentiation, and cell survival. The two IGF ligands, IGF1 and IGF2, activate IGF1R signaling. Additional peptides that activate IGF1R signaling are INS. Other agonists of IGF1R include, without limitations, demethylasterriquinone B1, Ginsenoside Rg5, and the human antimicrobial peptide LL-37. Tcan he IGF1R agonist comprise an IGF1R agonistic antibody, an IGF polypeptide or a functional fragment thereof, IGF2 or a functional fragment thereof, insulin, demethylasterriquinone B1, Ginsenoside Rg5, LL-37, or combinations thereof. These compositions comprise an unexpected synergistic effect and are useful for treating the muscle and/or soft-tissue conditions or disorders. This synergistic effect may also be promoted by methods comprising separate administration of an IGF1R agonist and a short fatty acid chain.

The IGF2R agonist can be an IGF ligand. The IGF1R agonist can be IGF2. The IGF2 polypeptide can be at least about 90%, 95%, 97%, 98%, 99%, or 100% identical to SEQ ID NO. 76. The IGF2 polypeptide can be 100% identical to SEQ ID NO. 76. The IGF2 polypeptide can be at least about 90%, 95%, 97%, 98%, 99%, or 100% identical to SEQ ID NO. 80. The IGF2 polypeptide can be 100% identical to SEQ ID NO. 80. The IGF2 polypeptide can be at least about 90%, 95%, 97%, 98%, 99%, or 100% identical to SEQ ID NO. 81. The IGF2 polypeptide can be 100% identical to SEQ ID NO. 81.

The composition can comprise an IGF1R agonist and a short fatty acid chain. Short fatty acid chains include, without limitations, butyrates, a phenylbutyrate, valproic acid, propionic acid, methanoic acid, ethanoic acid, 2-methylpropanoic acid, 3-methylbutanoic acid, pentanoic acid, and a multimerized version thereof such as tributyrin. Butyrates include, without limitations, butyric acids, sodium butyrate, methyl butyrate, ethyl butyrate, butyl butyrate, pentyl butyrate, or sodium butyrate. The short chain fatty acid can be a butyrate. The butyrate can be butyric acid. The butyrate can be sodium butyrate. The short chain fatty acid can be a phenylbutyrate, valproic acid, propionic acid, methanoic acid, ethanoic acid, 2-methylpropanoic acid, 3-methylbutanoic acid, pentanoic acid, or a multimerized version thereof such as tributyrin.

Also described herein are methods comprising administering an IGF1R agonist and a short fatty acid chain. The administration can be in the same composition, separate formulations. When separate formulations are administered, they can be administered effectively simultaneously (e.g., during the same treatment) or separately with an interval of at least 1 hour, 12 hours, 24 hours, 2 days, 3 days, 4 days, 5 days, 6 days, 7 days, or more.

Combinations of BMP Receptor Agonists and mTOR Activators

In certain aspects, disclosed herein is a composition comprising a BMP receptor agonist and an mTOR activator. BMP receptors activate downstream signaling through the TGF-beta pathway and are involved in many cell functions including differentiation, proliferation, and migration. There are two classes of BMP receptors: BMP type I (ACVR1, BMPR1A, and BMPR1B), and BMP type II (BMP2R, ACVR2A, and ACVR2B). BMP type 1 receptors bind BMP ligands exclusively, while BMP type II receptors bind BMPs and related proteins, including activin, Gdf9, and GDf11. The BMP receptor agonist can comprise an ACVR1 agonist, a BMPR1A agonist, a BMPR1B agonist, a BMP2R agonist, an ACVR2A agonist, an ACVR2B agonist, or a combination thereof. The BMP receptor agonist can comprise an ACVR1 agonist, an ACVR2A agonist, an ACVR2B agonist, a BMPR1A agonist, or a combination thereof. The BMP receptor can comprise an ACVR1 agonist. The BMP receptor agonist can comprise an ACVR2A agonist. The BMP receptor can comprise an ACRV2B agonist. The BMP receptor can comprise a BMPR1A agonist. The BMP receptor agonist can comprise an ACVR1 agonist antibody, a BMPR1A agonist antibody, a BMPR1B agonist antibody, a BMP2R agonist antibody, a ACVR2A agonist antibody, a ACVR2B agonist antibody, a BMP polypeptide or a functional fragment thereof, a BMP7 or a functional fragment thereof, ventromorphin, SB4, tacrolimus, isoliquiritigeni, alantolactone, PD407824, or combinations thereof. These compositions comprise an unexpected synergistic effect and are useful for treating the muscle and/or soft-tissue conditions or disorders. This synergistic effect may also be promoted by methods comprising separate administration of a BMP receptor agonist and a leucine.

The BMP7 polypeptide can be at least about 90%, 95%, 97%, 98%, 99%, or 100% identical to SEQ ID NO: 89. The BMP7 polypeptide can be 100% identical to SEQ ID NO: 89. The BMP7 polypeptide can be at least about 90%, 95%, 97%, 98%, 99%, or 100% identical to SEQ ID NO: 90. The BMP7 polypeptide can be 100% identical to SEQ ID NO: 90. The BMP7 polypeptide can be at least about 90%, 95%, 97%, 98%, 99%, or 100% identical to SEQ ID NO: 91. The BMP7 polypeptide can be 100% identical to SEQ ID NO: 91. The BMP7 polypeptide can be at least about 90%, 95%, 97%, 98%, 99%, or 100% identical to SEQ ID NO: 93. The BMP7 polypeptide can be 100% identical to SEQ ID NO: 93.

The mammalian target of rapamycin (mTOR) pathway is a key regulator of skeletal muscle mass and growth. mTOR is a serine/threonine kinase involved in diverse cellular processes including cell growth, differentiation, autophagy, survival, and metabolism. mTOR activation through the mTORC1 complex is required both for myofibrillar muscle protein synthesis and skeletal muscle hypertrophy. Inactivation of the mTORC1 complex has been found to be associated with loss of muscle mass and muscle struct during muscle wasting due to old age, cachexia, and atrophy due to physical activity.

The mTOR signaling pathway can be activated by many different signals, including amino acids, polypeptides, and small molecules. The mTOR activator can be an amino acid. The amino acid can be leucine, valine, isoleucine or a combination thereof. The amino acid can be leucine. The mTOR activator can be a polypeptide. The polypeptide can comprise a Ras homolog enriched in brain (Rheb), tuberous sclerosis complex (TSC), protein kinase B (PKB), extracellular-signal-regulated kinase 1/2 (ERK1/2), p90 ribosomal s6 kinase 1 (RSK1), Wnt ligands, or a combination thereof. The mTOR activator can be a small molecule. The mTOR activator can comprise MHY1485, NV-5138, 3-benzyl-5-((2-nitrophenoxy) methyl)-dihydrofuran-2(3H)-one (3BDO), or a combination thereof. The mTOR activator can comprise leucine, valine, isoleucine, Ras homolog enriched in brain (Rheb), tuberous sclerosis complex (TSC), protein kinase B (PKB), extracellular-signal-regulated kinase 1/2 (ERK1/2), p90 ribosomal s6 kinase 1 (RSK1), a Wnt ligand, MHY1485, NV-5138, 3-benzyl-5-((2-nitrophenoxy) methyl)-dihydrofuran-2(3H)-one (3BDO), or a combination thereof.

The mTOR activator can comprise leucine. The amino acid leucine is an important part of mTOR signaling within skeletal muscle. Leucine is a branched chain amino acid that is essential to the human diet. It is the single most common amino acid in human proteins, at a frequency of nearly 1 in 10 amino acids (UniProtKB/Swiss-Prot release 2013_04— April 2013). The circulating and intracellular concentrations of this amino acid are monitored and tightly controlled as part of feedback mechanisms controlling major anabolic and catabolic processes such as cell division, protein synthesis, and autophagy. Part of the regulatory effects of leucine are mediated by the mTORC1 complex whose activation to drive protein synthesis and cell cycle progression are in part driven by intracellular leucine concentration. The combination of a BMP receptor agonist and leucine or another branched chain amino acid demonstrate synergistical mitogenic activity.

Synthetic leucine derivatives may be used. The leucine can comprise 1-leucine, glycyl-1-leucine, acetyl-1-leucine, 1-leucine ethyl ester, and 1-leucine methyl ester, caproic acid, phthaloyl-1-leucine, benzoyl-dl-leucine, or a combination thereof. The leucine can be a salt. The leucine can comprise 1-leucenium hydrogen maleate, leucine hydrochloride, or a combination thereof.

Also described herein are methods comprising administering a BMP receptor agonist and an mTOR activator. The administration can be in the same composition, or separate formulations. When separate formulations are administered, they can be administered effectively simultaneously (e.g., during the same treatment) or separately with an interval of at least 1 hour, 12 hours, 24 hours, 2 days, 3 days, 4 days, 5 days, 6 days, 7 days, or more.

Therapeutic Indications

In certain aspects, the fusion polypeptides comprising an FGF8 subfamily amino acid sequence and a heterologous polypeptide, compositions comprising an FGFR agonist and a glycosaminoglycan, and the methods described herein, are useful for treating diseases and disorders that involve soft-tissue injury, degradation, or destruction, or for use in treating an individual with an aging disorder, a muscle wasting disorder, a muscle injury, an injury to a connective tissue, or an injury to a non-muscle soft-tissue, or any combination thereof.

In certain aspects, the fusion polypeptides comprising an IGF ligand amino acid sequence and a heterologous polypeptide, compositions comprising an IGF1R agonist and a short fatty acid chain, and the methods described herein, are useful for treating diseases and disorders that involve soft-tissue injury, degradation, or destruction, or for use in treating an individual with an aging disorder, a muscle wasting disorder, a muscle injury, an injury to a connective tissue, or an injury to a non-muscle soft-tissue, or any combination thereof.

In certain aspects, the fusion polypeptides comprising a BMP7 amino acid sequence, compositions comprising a BMP receptor agonist and a glycosaminoglycan, compositions comprising a BMP receptor agonist and an mTOR activator, and the methods, described herein, are useful for treating diseases and disorders that involve soft-tissue injury, degradation, or destruction, or for use in treating an individual with an aging disorder, a muscle wasting disorder, a muscle injury, an injury to a connective tissue, or an injury to a non-muscle soft-tissue, or any combination thereof.

Aging disorders that result in the deterioration and loss of muscle tissue are such disorders. Sarcopenia, for example, is the degenerative loss of skeletal muscle mass quality, and strength and can be associated with aging. Injuries that result in acute muscle damage are other muscle disorders, which are treatable by the polypeptides, compositions and methods described herein. The disorders include muscle ruptures, strains, and contusions. A rupture is a separating of the muscle tissues. Muscle strains are contraction-induced injuries in which muscle fibers tear due to extensive mechanical stress, and can be classified as a grade I, II, or III. Muscle contusions are muscle hematomas. Muscle injury can also be caused by non-mechanical stresses such as cachexia. Cachexia may be caused by malnutrition, cancer, AIDS, coeliac disease, chronic obstructive pulmonary disease, multiple sclerosis, rheumatoid arthritis, congestive heart failure, tuberculosis, familial amyloid polyneuropathy, mercury poisoning (acrodynia), Crohn's disease, untreated/severe type 1 diabetes mellitus, anorexia nervosa, chemotherapy, muscular dystrophy or other genetic diseases which cause immobility, and hormonal deficiencies. Certain disorders that are weaknesses of specific muscles such as dysphagia or facioscapulohumeral muscular dystrophy may also be treated by the polypeptides described herein. Additional soft-tissues disorders that may be treated using the polypeptides comprising an FGF8 subfamily amino acid sequence and/or compositions comprising an FGFR agonist and a glycosaminoglycan described herein are those that inflict injury to the tendons, ligaments or cartilage. Additional soft-tissues disorders that may be treated using the polypeptides comprising an IGF ligand amino acid sequence and compositions comprising an IGF1R agonist and a short fatty acid chain described herein are those that inflict injury to the tendons, ligaments or cartilage. Additional soft-tissues disorders that may be treated using the fusion polypeptides comprising a BMP7 amino acid sequence, compositions comprising a BMP receptor agonist and a glycosaminoglycan, and the methods, described herein, are those that inflict injury to the tendons, ligaments or cartilage.

The muscle wasting disease can be a muscular dystrophy. The muscular dystrophy can comprise a myotonic muscular dystrophy, Duchenne muscular dystrophy, Becker muscular dystrophy, Limb-girdle muscular dystrophy, facioscapulohumeral muscular dystrophy, congenital, muscular dystrophy, oculopharyngeal muscular dystrophy, or distal muscular dystrophy. The muscular dystrophy can be myotonic dystrophy.

The aging disorder can be sarcopenia. The muscle wasting disorder can be cachexia. The cachexia can be a result of a cancer, AIDS, end stage kidney disease, or cardiovascular disease. The injury can be a muscle injury. The muscle wasting can be atrophy due to limb immobilization or disuse. The muscle injury can be a strain or a tear. The muscle injury can be a Grade III strain. Sarcopenia can contribute to the incidence of the muscle injury. The injury can be ligament damage. The ligament damage can be a rupture or a tear. The injury can be tendon damage. The tendon damage can be a rupture or a tear. The injury can be cartilage damage.

The compositions described herein, are for use in a method of treating myositis. The myositis can comprise dermatomyositis, polymyositis, necrotizing myopathy (also called necrotizing autoimmune myopathy or immune-mediated necrotizing myopathy), juvenile myositis, or sporadic inclusion-body myositis.

The compositions described herein can be for use in a method of treating cartilage related-disorders. The cartilage related disorder may be due to tears, injuries, or wear. The cartilage-associated disease may be osteoarthritis, osteochondritis dissecans, achondroplasia, or degenerative cartilage lesions.

The compositions described herein can be for use in a method of increasing proliferation or promoting survival of a cell associated with soft-tissue damage. The polypeptides comprising an IGF ligand amino acid sequence and compositions comprising an IGF1R agonist and a short fatty acid chain described herein can be useful in a method of increasing proliferation or promoting survival of any one or more of a muscle cell, a muscle precursor cell, a tenocyte, a tenocyte precursor cell, a chondrocyte, a chondrocyte precursor cell, a mesenchymal stem cell, or a fibroblast.

Muscle fibrosis is an excessive accumulation of extracellular matrix components, including collagen. Muscle fibrosis impairs muscle function, negatively affects muscle regeneration after injury, and increases muscle susceptibility to re-injury. The compositions described herein can be for use in a method of reducing muscle fibrosis. The fibrosis can be associated with aging, muscular dystrophy, or an injury. The IGF ligand can be IGF2.

In order to differentiate into mature muscle cells, myoblasts must fuse and form multinucleated cells. In certain embodiments, the fusion polypeptides comprising an IGF ligand amino acid sequence and a heterologous polypeptide, compositions comprising an IGF1R agonist and a short fatty acid chain, and the methods described herein are for use in a method of increasing myoblast fusion. The IGF ligand can be IGF2.

The fusion polypeptides comprising an IGF ligand amino acid sequence and a heterologous polypeptide, compositions comprising an IGF1R agonist and a short fatty acid chain, and the methods described herein can be for use in a method of increasing muscle mass. Muscle mass can be increased by at least about 1%, 2.5%, 5%, 10%, 20%, 30%, 40%, 50% or more than 50%. The IGF ligand can be IGF2.

The fusion polypeptides comprising an IGF ligand amino acid sequence and a heterologous polypeptide, compositions comprising an IGF1R agonist and a short fatty acid chain, and the methods described herein can be for use in a method of increasing grip strength. Grip strength can be increased by at least about 1%, 2.5%, 5%, 10%, 20%, 30%, 40%, 50% or more than 50%. The IGF ligand can be IGF2.

The fusion polypeptides comprising an IGF ligand amino acid sequence and a heterologous polypeptide, compositions comprising an IGF1R agonist and a short fatty acid chain, and the methods described herein can be for use in a method of increasing muscle endurance. Muscle endurance can be increased by at least about 1%, 2.5%, 5%, 10%, 20%, 30%, 40%, 50% or more than 50%. The IGF ligand can be IGF2.

Methods of Treatment

In certain aspects, disclosed herein is a method of treating an individual with a disorder comprising administering an FGFR agonist and a glycosaminoglycan to the individual with the disorder. The FGFR agonist and the glycosaminoglycan can be administered in separate formulations. The FGFR agonist and the glycosaminoglycan can be administered simultaneously. The FGFR agonist and the glycosaminoglycan can be administered at different times. The glycosaminoglycan can be a heparin. The glycosaminoglycan can be a hyaluronic acid.

In certain aspects, disclosed herein is a method of treating an individual with a disorder comprising administering an FGFR1 agonist and a glycosaminoglycan to the individual the disorder. The FGFR1 agonist and the glycosaminoglycan (e.g., heparin) can be administered in separate formulations.

The FGFR1 agonist and the glycosaminoglycan (e.g., heparin) can be administered simultaneously. The FGFR1 agonist and the glycosaminoglycan (e.g., heparin) can be administered at different times. The glycosaminoglycan can be a heparin. The glycosaminoglycan can be a hyaluronic acid.

In certain aspects, disclosed herein is a method of treating an individual with a disorder comprising administering a polypeptide comprising a FGF8 subfamily amino acid sequence and a glycosaminoglycan (e.g., heparin) or a compound or mixture comprising a glycosaminoglycan to the individual the disorder. The polypeptide comprising a FGF8 subfamily amino acid sequence and the glycosaminoglycan (e.g., heparin) can be administered in separate formulations. The polypeptide comprising a FGF8 subfamily amino acid sequence and the glycosaminoglycan (e.g., heparin) can be administered simultaneously. The polypeptide comprising a FGF8 subfamily amino acid sequence and the glycosaminoglycan (e.g., heparin) can be administered at different times. The glycosaminoglycan can be a hyaluronic acid.

In certain aspects, disclosed herein is a method of treating an individual with a disorder comprising administering a polypeptide comprising a FGF17 amino acid sequence and a glycosaminoglycan (e.g., heparin) or a compound or mixture comprising glycosaminoglycan to the individual the disorder. The polypeptide comprising a FGF17 amino acid sequence and the glycosaminoglycan (e.g., heparin) can be administered in separate formulations. The polypeptide comprising a FGF17 amino acid sequence and the glycosaminoglycan (e.g., heparin) can be administered simultaneously. The polypeptide comprising a FGF17 amino acid sequence and the glycosaminoglycan can be administered at different times. The glycosaminoglycan can be a hyaluronic acid.

In certain aspects, disclosed herein is a method of treating an individual with a disorder comprising administering a polypeptide comprising an FGF8 subfamily amino acid sequence. The polypeptide can comprise a FGF17 amino acid sequence. The polypeptide can comprise a FGF17 fusion protein.

In certain aspects, disclosed herein is a method of treating an individual with a disorder comprising administering an IGF1R agonist and a short fatty acid chain (e.g., butyrate) to the individual. The IGF1R agonist and the short fatty acid chain (e.g., butyrate) can be administered in separate formulations. The IGF1R agonist and the short fatty acid chain (e.g., butyrate) can be administered simultaneously. The IGF1R agonist and the short fatty acid chain (e.g., butyrate) can be administered at different times.

In certain aspects, disclosed herein is a method of treating an individual with a disorder comprising administering a polypeptide comprising an IGF ligand amino acid sequence and a butyrate to the individual the disorder. The polypeptide comprising the IGF ligand amino acid sequence and the butyrate can be administered in separate formulations. The polypeptide comprising the IGF ligand amino acid sequence and the butyrate can be administered simultaneously. The polypeptide comprising the IGF ligand amino acid sequence and the butyrate can be administered at different times.

In certain aspects, disclosed herein is a method of treating an individual with a disorder comprising administering a polypeptide comprising an IGF2 amino acid sequence and a short fatty acid chain (e.g., butyrate) to the individual the disorder. The polypeptide comprising the IGF ligand amino acid sequence and the short fatty acid chain (e.g., butyrate) can be administered in separate formulations. The polypeptide comprising the IGF2 amino acid sequence and the short fatty acid chain (e.g., butyrate) can be administered simultaneously. The polypeptide comprising the IGF2 amino acid sequence and the short fatty acid chain (e.g., butyrate) can be administered at different times.

In certain aspects, disclosed herein is a method of treating an individual with a disorder comprising administering a BMP receptor agonist and a glycosaminoglycan to the individual the disorder. The BMP receptor agonist and a glycosaminoglycan can be administered in separate formulations. The BMP receptor agonist and a glycosaminoglycan can be administered simultaneously. The BMP receptor agonist and a glycosaminoglycan can be administered at different times. The glycosaminoglycan can be a heparin. The glycosaminoglycan can be a hyaluronic acid.

In certain aspects, disclosed herein is a method of treating an individual with a disorder comprising administering a polypeptide comprising a BMP7 amino acid sequence and hyaluronic acid or a compound or mixture comprising hyaluronic acid to the individual the disorder. The polypeptide comprising a BMP7 amino acid sequence and the hyaluronic acid are administered in separate formulations. In some embodiments, the polypeptide comprising a BMP7 amino acid sequence and the hyaluronic acid are administered simultaneously. In some embodiments, the polypeptide comprising a BMP7 amino acid sequence and the hyaluronic acid are administered at different times.

In certain aspects, disclosed herein is a method of treating an individual with a disorder comprising administering a polypeptide comprising a BMP7 amino acid sequence and heparin or a compound or mixture comprising heparin to the individual the disorder. In some embodiments, the polypeptide comprising a BMP7 amino acid sequence and the heparin are administered in separate formulations. In some embodiments, the polypeptide comprising a BMP7 amino acid sequence and the heparin are administered simultaneously. In some embodiments, the polypeptide comprising a BMP7 amino acid sequence and the heparin are administered at different times.

In certain aspects, disclosed herein is a method of treating an individual with a disorder comprising administering a BMP receptor agonist and an mTOR activator to the individual the disorder. In some embodiments, the BMP receptor agonist and an mTOR activator are administered in separate formulations. In some embodiments, the BMP receptor agonist and an mTOR activator are administered simultaneously. In some embodiments, the BMP receptor agonist and an mTOR activator are administered at different times. In certain embodiments, mTOR activator is a leucine.

In certain aspects, disclosed herein is a method of treating an individual with a disorder comprising administering a polypeptide comprising a BMP7 amino acid sequence and leucine or a compound or mixture comprising leucine to the individual the disorder. In some embodiments, the polypeptide comprising a BMP7 amino acid sequence and the leucine are administered in separate formulations. In some embodiments, the polypeptide comprising a BMP7 amino acid sequence and the leucine are administered simultaneously. In some embodiments, the polypeptide comprising a BMP7 amino acid sequence and the leucine are administered at different times.

In certain aspects, disclosed herein is a method of treating an individual with a disorder comprising administering a BMP receptor agonist and a glycosaminoglycan to the individual the disorder. In some embodiments, the BMP receptor agonist and a glycosaminoglycan are administered in separate formulations. In some embodiments, the BMP receptor agonist and a glycosaminoglycan are administered simultaneously. In some embodiments, the BMP receptor agonist and a glycosaminoglycan are administered at different times. In certain embodiments, the glycosaminoglycan is a heparin. In certain embodiments, the glycosaminoglycan is a hyaluronic acid.

In certain aspects, disclosed herein is a method of treating an individual with a disorder comprising administering a polypeptide comprising a BMP7 amino acid sequence and a glycosaminoglycan (e.g., heparin or hyaluronic acid) or a compound or mixture comprising a glycosaminoglycan (e.g., heparin or hyaluronic acid) to the individual the disorder. In some embodiments, the polypeptide comprising a BMP7 amino acid sequence and the glycosaminoglycan (e.g., heparin or hyaluronic acid) are administered in separate formulations. In some embodiments, the polypeptide comprising a BMP7 amino acid sequence and the glycosaminoglycan (e.g., heparin or hyaluronic acid) are administered simultaneously. In some embodiments, the polypeptide comprising a BMP7 amino acid sequence and the glycosaminoglycan (e.g., heparin or hyaluronic acid) are administered at different times.

The treatment can be administered by any suitable route such as, for example, subcutaneous, intravenous, or intramuscular. In certain embodiments, the treatment is administered on a suitable dosage schedule, for example, weekly, twice weekly, monthly, twice monthly, once every three weeks, or once every four weeks. The treatment can be administered in any therapeutically effective amount. The therapeutically effective amount can be about 0.001 mg/kg to about 1 mg/kg. The therapeutically effective amount can be about 0.001 mg/kg to about 0.002 mg/kg, about 0.001 mg/kg to about 0.005 mg/kg, about 0.001 mg/kg to about 0.01 mg/kg, about 0.001 mg/kg to about 0.02 mg/kg, about 0.001 mg/kg to about 0.05 mg/kg, about 0.001 mg/kg to about 0.1 mg/kg, about 0.001 mg/kg to about 0.2 mg/kg, about 0.001 mg/kg to about 0.5 mg/kg, about 0.001 mg/kg to about 1 mg/kg, about 0.002 mg/kg to about 0.005 mg/kg, about 0.002 mg/kg to about 0.01 mg/kg, about 0.002 mg/kg to about 0.02 mg/kg, about 0.002 mg/kg to about 0.05 mg/kg, about 0.002 mg/kg to about 0.1 mg/kg, about 0.002 mg/kg to about 0.2 mg/kg, about 0.002 mg/kg to about 0.5 mg/kg, about 0.002 mg/kg to about 1 mg/kg, about 0.005 mg/kg to about 0.01 mg/kg, about 0.005 mg/kg to about 0.02 mg/kg, about 0.005 mg/kg to about 0.05 mg/kg, about 0.005 mg/kg to about 0.1 mg/kg, about 0.005 mg/kg to about 0.2 mg/kg, about 0.005 mg/kg to about 0.5 mg/kg, about 0.005 mg/kg to about 1 mg/kg, about 0.01 mg/kg to about 0.02 mg/kg, about 0.01 mg/kg to about 0.05 mg/kg, about 0.01 mg/kg to about 0.1 mg/kg, about 0.01 mg/kg to about 0.2 mg/kg, about 0.01 mg/kg to about 0.5 mg/kg, about 0.01 mg/kg to about 1 mg/kg, about 0.02 mg/kg to about 0.05 mg/kg, about 0.02 mg/kg to about 0.1 mg/kg, about 0.02 mg/kg to about 0.2 mg/kg, about 0.02 mg/kg to about 0.5 mg/kg, about 0.02 mg/kg to about 1 mg/kg, about 0.05 mg/kg to about 0.1 mg/kg, about 0.05 mg/kg to about 0.2 mg/kg, about 0.05 mg/kg to about 0.5 mg/kg, about 0.05 mg/kg to about 1 mg/kg, about 0.1 mg/kg to about 0.2 mg/kg, about 0.1 mg/kg to about 0.5 mg/kg, about 0.1 mg/kg to about 1 mg/kg, about 0.2 mg/kg to about 0.5 mg/kg, about 0.2 mg/kg to about 1 mg/kg, or about 0.5 mg/kg to about 1 mg/kg. The therapeutically effective amount can be about 0.001 mg/kg, about 0.002 mg/kg, about 0.005 mg/kg, about 0.01 mg/kg, about 0.02 mg/kg, about 0.05 mg/kg, about 0.1 mg/kg, about 0.2 mg/kg, about 0.5 mg/kg, or about 1 mg/kg. The therapeutically effective amount can be at least about 0.001 mg/kg, about 0.002 mg/kg, about 0.005 mg/kg, about 0.01 mg/kg, about 0.02 mg/kg, about 0.05 mg/kg, about 0.1 mg/kg, about 0.2 mg/kg, or about 0.5 mg/kg. The therapeutically effective amount can be at most about 0.002 mg/kg, about 0.005 mg/kg, about 0.01 mg/kg, about 0.02 mg/kg, about 0.05 mg/kg, about 0.1 mg/kg, about 0.2 mg/kg, about 0.5 mg/kg, or about 1 mg/kg. The therapeutically effective amount can be about 0.1 mg/kg to about 50 mg/kg. The therapeutically effective amount can be about 0.1 mg/kg to about 0.2 mg/kg, about 0.1 mg/kg to about 0.5 mg/kg, about 0.1 mg/kg to about 1 mg/kg, about 0.1 mg/kg to about 2 mg/kg, about 0.1 mg/kg to about 5 mg/kg, about 0.1 mg/kg to about 10 mg/kg, about 0.1 mg/kg to about 20 mg/kg, about 0.1 mg/kg to about 50 mg/kg, about 0.2 mg/kg to about 0.5 mg/kg, about 0.2 mg/kg to about 1 mg/kg, about 0.2 mg/kg to about 2 mg/kg, about 0.2 mg/kg to about 5 mg/kg, about 0.2 mg/kg to about 10 mg/kg, about 0.2 mg/kg to about 20 mg/kg, about 0.2 mg/kg to about 50 mg/kg, about 0.5 mg/kg to about 1 mg/kg, about 0.5 mg/kg to about 2 mg/kg, about 0.5 mg/kg to about 5 mg/kg, about 0.5 mg/kg to about 10 mg/kg, about 0.5 mg/kg to about 20 mg/kg, about 0.5 mg/kg to about 50 mg/kg, about 1 mg/kg to about 2 mg/kg, about 1 mg/kg to about 5 mg/kg, about 1 mg/kg to about 10 mg/kg, about 1 mg/kg to about 20 mg/kg, about 1 mg/kg to about 50 mg/kg, about 2 mg/kg to about 5 mg/kg, about 2 mg/kg to about 10 mg/kg, about 2 mg/kg to about 20 mg/kg, about 2 mg/kg to about 50 mg/kg, about 5 mg/kg to about 10 mg/kg, about 5 mg/kg to about 20 mg/kg, about 5 mg/kg to about 50 mg/kg, about 10 mg/kg to about 20 mg/kg, about 10 mg/kg to about 50 mg/kg, or about 20 mg/kg to about 50 mg/kg. The therapeutically effective amount can be about 0.1 mg/kg, about 0.2 mg/kg, about 0.5 mg/kg, about 1 mg/kg, about 2 mg/kg, about 5 mg/kg, about 10 mg/kg, about 20 mg/kg, or about 50 mg/kg. The therapeutically effective amount can be at least about 0.1 mg/kg, about 0.2 mg/kg, about 0.5 mg/kg, about 1 mg/kg, about 2 mg/kg, about 5 mg/kg, about 10 mg/kg, or about 20 mg/kg. The therapeutically effective amount can be at most about 0.2 mg/kg, about 0.5 mg/kg, about 1 mg/kg, about 2 mg/kg, about 5 mg/kg, about 10 mg/kg, about 20 mg/kg, or about 50 mg/kg.

The individual treated can be a mammal. The mammal can be a mouse, rat, rabbit, dog, cat, horse, cow, sheep, pig, goat, llama, alpaca, or yak. The individual can be a dog, cat, or a horse. The individual to be treated can be a human.

Methods of Production

The polypeptide comprising an FGF17, IGF, or BMP7 ligand amino acid sequence can be purified or synthesized in any suitable manner. A nucleic acid encoding the polypeptide can be cloned into a suitable vector and expressed in a suitable cellular system. The cellular system can be a prokaryotic cell system. The cellular system can be a eukaryotic cell system. The cellular system can be a mammalian cell system. The polypeptide may be expressed from *Escherichia coli*. The polypeptide may be expressed from a yeast cell, including without limitations, *Saccharomyces cerevisiae, Pichia pastoris, Kluyveromyces lactis, Hansenula polymorpha*, or *Yarrowia lipolytica*. The polypeptide may be expressed from a mouse myeloma cell, including without limitations, NS0, Sp2/0, and FO. The polypeptide may be expressed from a chinese hamster ovary (CHO) cell. The polypeptide may be expressed by a mammalian cell, including without limitations, a COS cell, a Vero cell, or a BHK cell. The polypeptide may be expressed from a human cell, including without limitations a HeLa cell, a HEK-293 cell, a CAP cell, a CAP-T cell, a PER.C6® cell.

The supernatants from such an expression system can be subjected to one or more purification steps involving centrifugation, ultracentrifugation, filtration, diafiltration, tangential-flow filtration, dialysis, chromatography (e.g., cation exchange, ion exchange, hydrophobic interaction, reverse phase, affinity, or size exclusion). The polypeptides can be purified to an extent suitable for human administration. Additionally, polypeptides can be synthesized for inclusion in a formulation to be administered to a human individual. The polypeptides can be produced by a suitable peptide synthesis method, such as solid-phase synthesis.

The mammalian expression vector pmax Cloning can be used to make C-terminally 6×His-tagged, StrepII-tagged, and human IgG1 Fc-tagged vectors. The DNA fragments encoding the secreted myogenic factors are amplified by PCR from human open reading frame (ORF) clones, and subsequently inserted into the tagged vectors by In-Fusion cloning technology (Takara Bio Inc.). The expression vectors carrying the secreted myogenic factors are transiently transfected into ExpiCHO-S cells at a density of 6×10$^6$ per ml by using ExpiFectamine CHO transfection kit (Thermo Scientific).

The expressed myogenic factors with different tags in the culture supernatants are affinity-purified by using different purification media. The polypeptide can comprise an Fc region. For these polypeptides a matrix or resin comprising Protein A, Protein G, protein L or any combination thereof can be used. The matrix or resin may suitably be loaded onto a column for ease in batch purification.

Purification of Immunoglobulin Fusion Proteins

The heterologous sequence may comprise an immunoglobulin or a fragment thereof. When the polypeptide comprises an immunoglobulin or a fragment thereof, the polypeptide may be purified by means of protein A, G, or L affinity. Protein A and G are cell surface proteins found in *Staphylococcus aureus*. They have the property of binding the Fc region of a mammalian antibody, in particular of IgG class antibodies. For use in protein A or G affinity chromatography, protein A or G is coupled to a solid matrix such as crosslinked, uncharged agarose (Sepharose, freed from charged fraction of natural agarose), trisacryl, crosslinked dextran or silica-based materials. Methods for such are commonly known in the art, e.g. coupling via primary amino functions of the protein to a CNBr-activated matrix. Protein A binds with high affinity and high specificity to the Fe portion of IgG, that is the Cγ2-Cγ3 interface region of IgG as described in Langone et al., 1982, supra. In particular, it binds strongly to the human allotypes or subclasses IgG1, IgG2, IgG3 and the mouse allotypes or subclasses IgG2a, IgG2b, IgG3.

After purification by Protein A, G, or L the bound fraction can be eluted and passed over or through an additional resin or matrix comprising one or more ion exchange columns. The first ion exchanger is generally an anion exchanger resin. The pH of buffer used for loading and running the first ion exchanger is set as to put opposing total change on the Fc comprising fusion polypeptide and the protein A to be separated by means of the ion exchanger in a flow-through mode according to the present invention, taking the pI's of the Fc comprising fusion polypeptide and protein A into account. The mode of operation of a first anion exchanger according to the present invention requires buffer exchange of the acidic or neutralized eluate from the protein A affinity chromatography step with the equilibrium buffer of the first anion exchanger. After the first anion exchanger, the Fc comprising fusion polypeptide is ready for use in applications or may be deemed to require further polishing by customary purification methods. In a further preferred embodiment, the first ion exchange step is followed by a second ion exchange step in which second step the antibody is loaded and bound by the second ion exchange medium and is eluted with a buffer other than the loading buffer, by means of increased salt and/or pH, as an essentially monomeric, non-aggregated antibody.

In the methods disclosed herein at least 70%, 80%, or 90% of the Fc comprising fusion polypeptide loaded onto the first ion exchanger can be recovered in the flow-through of the ion-exchanger.

Master Cell Bank and Transgenic Cells

Described herein are master cell banks that can comprise a cell that comprises a nucleic acid encoding one or more IGF ligand or IGF2 fusion polypeptides integrated into its genome creating a transgenic cell-line. The master cell bank can comprise a plurality of cells that each comprise a nucleic acid encoding an IGF ligand or IGF2 fusion polypeptide. The nucleic acid can be maintained extrachromosomally on a plasmid or yeast artificial chromosome. The nucleic acid can be integrated into a chromosomal location. The cell can be a yeast cell. The yeast can be *Pichia pastoris* or *Saccharomyces cerevisiae*. The cell can be a mammalian cell. The mammalian cell can be a 293T cell or derivative thereof (e.g., 293T-Rex). The cell can be a bacterial cell.

The transgenic mammalian, yeast, or bacterial cell can be a master cell bank that comprises a cryopreservative suitable for freezing to at least about −80° or below. The master cell bank can comprise glycerol or DMSO at between about 10 and about 30%, and can be suitable for long-term storage at about −80° or below. The master cell bank can preserve a transgenic mammalian, yeast, or bacterial strain for at least 1, 2, 3, 4, 5, 6, 7, 8, 9, 10, or more years.

Pharmaceutically Acceptable Excipients, Carriers, and Diluents

The polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans described herein can be administered in a pharmaceutical composition that comprises one or more pharmaceutically acceptable excipients, carriers, or diluents. The exact components can differ based upon the preferred route of administration. The excipients used in a pharmaceutical composition can provide additional function to the polypeptide by making the polypeptide suitable for a particular route of administration (e.g., intravenous, topical, subcutaneous, or intramuscular), increasing polypeptide stability, increasing penetration of a desired tissue (e.g., muscle or skin), increasing residence time at particular site, increasing solubility, enhancing the efficacy of the polypeptide, and/or reducing inflammatory reactions coincident with administration.

The compositions can be included in a pharmaceutical composition with a solubilizing emulsifying, or dispersing agent. The solubilizing agent can allow high-concentration solutions of fusion polypeptides that exceed at least about 2 mg/mL, 5 mg/mL, 10 mg/mL, 15 mg/mL, or 20 mg/mL. Carbomers in an aqueous pharmaceutical composition serve as emulsifying agents and viscosity modifying agents. The pharmaceutically acceptable excipient can comprise or consist of a carbomer. The carbomer can comprise or consist of carbomer 910, carbomer 934, carbomer 934P, carbomer 940, carbomer 941, carbomer 1342, or combinations thereof. Cyclodextrins in an aqueous pharmaceutical composition serve as solubilizing and stabilizing agents. The pharmaceutically acceptable excipient can comprise or consist of a cyclodextrin. The cyclodextrin can comprise or consist of alpha cyclodextrin, beta cyclodextrin, gamma cyclodextrin, or combinations thereof. Lecithin in a pharmaceutical composition may serve as a solubilizing agent. The solubilizing agent can comprise or consist of lecithin. Poloxamers in a pharmaceutical composition serve as emulsifying agents, solubilizing agents, and dispersing agents. The pharmaceutically acceptable excipient can comprise or consist of a poloxamer. The poloxamer can comprise or consist of poloxamer 124, poloxamer 188, poloxamer 237, poloxamer 338, poloxamer 407, or combinations thereof. Polyoxyethylene sorbitan fatty acid esters in a pharmaceutical composition serve as emulsifying agents, solubilizing agents, surfactants, and dispersing agents. The pharmaceutically acceptable excipient can comprise or consist of a polyoxyethylene sorbitan fatty acid ester. The polyoxyethylene sorbitan fatty acid ester can comprise or consist of polysorbate 20, polysorbate 21, polysorbate 40, polysorbate 60, polysorbate 61, polysorbate 65, polysorbate 80, polysorbate 81, polysorbate 85, polysorbate 120, or combinations thereof. Polyoxyethylene stearates in a pharmaceutical composition serve as emulsifying agents, solubilizing agents, surfactants, and dispersing agents. The pharmaceutically acceptable excipient can comprise or consist of a polyoxyethylene stearate. The polyoxyethylene stearate can comprise or consist of polyoxyl 2 stearate, polyoxyl 4 stearate, polyoxyl 6 stearate, polyoxyl 8 stearate, polyoxyl 12 stearate, polyoxyl 20 stearate, polyoxyl 30 stearate, polyoxyl 40 stearate, polyoxyl 50 stearate, polyoxyl 100 stearate, polyoxyl 150 stearate, polyoxyl 4 distearate, polyoxyl 8 distearate, polyoxyl 12 distearate, polyoxyl 32 distearate, polyoxyl 150 distearate, or combinations thereof. Sorbitan esters in a pharmaceutical composition serve as emulsifying agents, solubilizing agents, and non-ionic surfactants, and dispersing agents. The pharmaceutically acceptable excipient can comprise or consist of a sorbitan ester. The sorbitan ester can comprise or consist of sorbitan laurate, sorbitan oleate, sorbitan palmitate, sorbitan stearate, sorbitan trioleate, sorbitan sesquioleate, or combinations thereof. Solubility can be achieved with a protein carrier. The protein carrier can comprise recombinant human albumin.

The polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans described herein can be formulated to increase stability. Polypeptides in aqueous formulations may require stabilization to prevent degradation. The stabilizer can comprise pH buffers, salts, amino acids, polyols/disaccharides/polysaccharides, liposomes, surfactants, antioxidants, reducing agents, or chelating agents. The stabilizer can comprise or consist of a polyol/non-reducing sugar. The non-reducing sugar can comprise or consist of sucrose, mannitol, trehalose, raffinose, stachyose, xylitol, starch, verbascose, or combinations thereof. Polypeptides can be encapsulated in liposomes to increase stability. The stabilizer can comprise or consist of liposomes. The liposomes can comprise or consist of ipalmitoylphosphatidylcholine (DPPC) liposomes, phosphatidylcholine:cholesterol (PC:Chol) (70:30) liposomes, or dipalmitoylphosphatidylcholine: dipalmitoylphosphatidylserine (DPPC:DPPS) liposomes (70:30). Non-ionic surfactants can increase the stability of a polypeptide. The stabilizer can comprise or consist of a non-ionic surfactant. The non-ionic surfactant can comprise or consist of polysorbates (e.g., poly sorbate 80, poly sorbate 20), alkylsaccharides alkyl ethers and alkyl glyceryl ethers, polyoxyethelene (4) lauryl ether; polyoxyethylene cetyl ethers, polyoxyethylene stearyl ethers, sorbitan fatty acid esters, polyoxyethylene fatty acid esters, or combinations thereof. The polypeptide can be formulated with a protein surfactant, such as recombinant human serum albumin as a stabilizer. Antioxidants or reducing agents can increase the stability of a polypeptide. The stabilizer can comprise or consist of an antioxidant or reducing agent. The reducing agent can comprise or consist of dithiothreitol, ethylenediaminetetraacetic acid, 2-Mercaptoethanol, Tris(2-carboxyethyl)phosphine hydrochloride, Tris(hydroxypropyl)phosphine, or combinations thereof. The antioxidant can comprise or consist of methionine, ascorbic acid, citric acid, alpha tocopherol, sodium bisulfite, ascorbyl palmitate, erythorbic acid, or combinations thereof. Chelating agents can stabilize polypeptides by reducing the activity of proteases. The stabilizer can comprise or consist of a chelating agent. The chelating agent can comprise or consist of ethylenediaminetetraacetic acid (EDTA), ethylene glycol-bis(β-aminoethyl ether)-N,N,N',N'-tetraacetic acid (EGTA), metal complexes (e.g. Zn-protein complexes), or combinations thereof. Buffer agents can stabilize polypeptides by reducing the acid hydrolysis of polypeptides. The stabilizer can comprise or consist of a buffer agent. The buffer agent can comprise or consist of sucrose octa-sulfate, ammonium carbonate, ammonium phosphate, boric acid, sodium citrate, potassium citrate, lactic acid, 3-(N-morpholino)propanesulfonic acid (MOPS), 2-(N-morpholino) ethanesulfonic acid (MES), hydroxymethylaminomethane (Tris), calcium carbonate, calcium phosphate or combinations thereof.

The polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans described herein also may be entrapped in or associated with microcapsules prepared, for example, by coacervation techniques or by interfacial polymerization (for example, hydroxymethylcellulose or gelatin-microcapsules and poly-(methylmethacylate) microcapsules, respectively), in colloidal delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans described herein may be formulated or delivered with an anti-inflammatory agent. The anti-inflammatory agent can comprise or consist of a corticosteroid. The corticosteroid can comprise or consist of hydrocortisone, cortisone, ethamethasoneb (Celestone), prednisone (Prednisone Intensol), prednisolone (Orapred, Prelone), triamcinolone (Aristospan Intra-Articular, Aristospan Intralesional, Kenalog), methylprednisolone (Medrol, Depo-Medrol, Solu-Medrol), or dexamethasone (Dexamethasone Intensol). The anti-inflammatory can comprise or consist of a non-steroidal anti-inflammatory (NSAID). The NSAID can comprise or consist of aspirin, celecoxib, diclofenac, diflunisal, etodolac, ibuprofen, indomethacin, ketoprofen, ketorolac, nabumetone, naproxen, oxaprozin, piroxicam, salsalate, sulindac, or tolmetin.

The polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans described herein can be included in a pharmaceutical composition suitable for intravenous administration comprising one or more pharmaceutically acceptable excipients, carriers, and diluents. The polypeptides of the current disclosure can be administered suspended in a sterile solution. The solution can be one commonly used for administration of biological formulations, and comprises, for example, about 0.9% NaCl or about 5% dextrose. The solution can further comprise one or more of: buffers, for example, acetate, citrate, histidine, succinate, phosphate, potassium phosphate, bicarbonate and hydroxymethylaminomethane (Tris); surfactants, for example, polysorbate 80 (Tween 80), polysorbate 20 (Tween 20), and poloxamer 188; polyol/disaccharide/polysaccharides, for example, glucose, dextrose, mannose, mannitol, sorbitol, sucrose, trehalose, and dextran 40; amino acids, for example, glycine, histidine, leucine, or arginine; antioxidants, for example, ascorbic acid, methionine; or chelating agents, for example, EDTA, or EGTA.

The polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans described herein can be included in a pharmaceutical composition suitable for intramuscular or subcutaneous administration comprising one or more pharmaceutically acceptable excipients, carriers, and diluents. Formulations suitable for intramuscular or subcutaneous injection can include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include ethanol, polyols (inositol, propyleneglycol, polyethylene-glycol, glycerol, cremophor and the like) and suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

The polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans described herein can be formulated for topical administration as a cream, gel, paste, ointment, or emulsion. Excipients in a cream, gel, paste, ointment, or emulsion can comprise gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecyl sulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars, and starches.

The excipient used with the polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans described herein will allow for storage, formulation, or administration of highly concentrated formulations. In certain embodiments, a highly concentrated fusion polypeptide(s) comprises at least about 1, 2, 3, 4, 5, 6, 7, 8, 9, 10, 15, 20, 25, 20, 25, 40, 45, 50 or more milligrams per milliliter.

The polypeptides and/or compositions of the current disclosure can be shipped/stored lyophilized and reconstituted before administration. Lyophilized ligand fusion polypeptide formulations can comprise a bulking agent such as, mannitol, sorbitol, sucrose, trehalose, and dextran 40. The lyophilized formulation can be contained in a vial comprised of glass. The fusion polypeptides when formulated, whether reconstituted or not, can be buffered at a certain pH, generally less than 7.0. In certain embodiments, the pH can be between 4.5 and 6.5, 4.5 and 6.0, 4.5 and 5.5, 4.5 and 5.0, or 5.0 and 6.0.

Kits

Also described herein are kits comprising one or more of the polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans described herein in a suitable container and one or more additional components selected from: instructions for use; a diluent, an excipient, a carrier, and a device for administration.

In an aspect, described herein is a method of preparing a soft tissue or muscle disease or disorder treatment comprising admixing one or more pharmaceutically acceptable excipients, carriers, or diluents and polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans described herein. In an aspect, described herein is a method of preparing a soft tissue or muscle disease or disorder treatment for storage or shipping comprising lyophilizing one or more antibodies of the current disclosure.

The inventions disclosed herein will be better understood from the experimental details which follow. However, one skilled in the art will readily appreciate that the specific methods and results discussed are merely illustrative of the inventions as described more fully in the claims which follow thereafter. Unless otherwise indicated, the disclosure is not limited to specific procedures, materials, or the like, as such may vary. It is also to be understood that the terminology used herein is for the purpose of describing particular embodiments only and is not intended to be limiting.

EXAMPLES

Example 1—Expression and Purification of Recombinant Proteins

Mammalian expression plasmids carrying genes with different tags were transiently transfected into CHO cells. The genes were expressed to produce proteins that were subsequently secreted into the culture medium. The proteins in the culture medium were visualized on polyacrylamide gels and their activities were measured by in vitro functional assays. Then the recombinant proteins in the culture medium were affinity purified. The purified proteins were visualized on polyacrylamide gels to evaluate the purity and assayed by in vitro functional assays to determine their biological activities.

Expression vector engineering: Mammalian expression vector pmax Cloning was used to make C-terminally 6×His-tagged, StrepII-tagged, and human IgG1 and IgG4 Fc-tagged vectors. The DNA fragments encoding the secreted myogenic factors were amplified by PCR from human open reading frame (ORF) clones, and subsequently inserted into the tagged vectors by In-Fusion cloning technology (Takara Bio Inc.).

Expressing secreted myogenic polypeptides: The expression vectors carrying the secreted myogenic factors were transiently transfected into ExpiCHO-S cells at a density of $6 \times 10^6$ per ml by using ExpiFectamine CHO transfection kit (Thermo Scientific). After 18-22 hours, CHO feed and enhancer were added into the transfected culture. Then the expressed proteins were monitored by SDS-PAGE every 24 hours to achieve maximal expression level. In most of the cases, cell culture was collected at day 4, and cells were spun down. The supernatant was spun down again to get rid of cellular debris. The clarified culture supernatant containing the secreted myogenic factors was stored at −80° C. or immediately processed for use.

Measuring expression level of secreted myogenic polypeptides: To measure the improved expression level of the secreted myogenic factors, three protein analytical techniques were applied: sodium dodecyl sulfate polyacrylamide gel electrophoresis (SDS-PAGE), Western blotting, and enzyme-linked immunosorbent assay (ELISA). Western Blots were performed to identify the myogenic factors. ELISAs were used to measure the absolute amount of myogenic factors in the culture supernatant.

Isolation of engineered myogenic polypeptides: The expressed myogenic factors with different tags in the culture supernatants were affinity-purified by using different purification media. For Fc-fusion factors, either Protein A magnetic beads (GenScript) or Protein A membrane column (Takara Bio Inc.) were used to specifically bind to the Fc-fusion factors. For 6×His-tagged factors, NTA-magnetics beads (NEB) were used to isolate the factor.

Example 2—Purified IGF2-hFcm Promoted Differentiation of Human Myoblast Cells

FIG. 1A: The suspension CHO cells were transiently transfected with the IGF2-hFcm encoding plasmid. IGF2-hFcm was affinity-purified by Protein A membrane column. The purified IGF2-hFcm was added into the culture of human myoblast cells for 96 hours. Myosin heavy chain (MyHC) was immunostained and imaged by a fluorescence microscope. The percentage area of MyHC of human myoblasts treated with the purified IGF2-hFcm is significantly higher than the percentage area of MyHC of human myoblasts treated with the vehicle control (One-Way ANOVA Tukey Honest Significant Difference, n=2-6).

| Condition | % MyHC | SD | p-value |
| --- | --- | --- | --- |
| Vehicle control | 1.787 | 0.186 | |
| 33 nM IGF2-hFcm | 3.734 | 0.790 | 0.012 |
| 66 nM IGF2-hFcm | 5.922 | 0.795 | 3.20E−05 |
| 133 nM IGF2-hFcm | 7.568 | 0.538 | 1.46E−06 |

Example 3 IGF2-LhFc4 Promoted Differentiation of Human Myoblast Cells

The suspension CHO cells were transiently transfected with the IGF2-LhFc4 encoding plasmid. IGF2-LhFc4 was affinity-purified by Protein A membrane column. The purified IGF2-LhFc4 was added into the culture of human myoblast cells for 96 hours with daily media change. Myosin heavy chain (MyHC) was immunostained and imaged by a fluorescence microscope. The percentage area of MyHC of human myoblasts treated with the purified IGF2-LhFc4 is significantly higher than the percentage area of MyHC of human myoblasts treated with the vehicle control (One-Way ANOVA Tukey Honest Significant Difference, n=2-6).

| Condition | % MyHC | SD | p-value |
| --- | --- | --- | --- |
| Vehicle control | 1.384 | 0.285 | |
| hFc4L-IGF2 | 5.820 | 0.319 | 0.011 |
| IGF2-hFc4 | 6.901 | 0.537 | 0.004 |
| IGF2-LhFc4 | 6.237 | 1.848 | 0.007 |

Example 4—Purified HSA-L-IGF2R61A Differentiation of Human Myoblast Cells

The suspension CHO cells were transiently transfected with the HSA-L-IGF2R61A encoding plasmid. HSA-L-IGF2R61A was affinity-purified by Protein A membrane column. The purified HSA-L-IGF2R61A was added into the culture of human myoblast cells for 96 hours with daily media change. Myosin heavy chain (MyHC) was immunostained and imaged by a fluorescence microscope. The percentage area of MyHC of human myoblasts treated with the purified HSA-L-IGF2R61A is significantly higher than the percentage area of MyHC of human myoblasts treated with the vehicle control (One-Way ANOVA Tukey Honest Significant Difference, n=2-6).

| Condition | % MyHC | SD | p-value |
| --- | --- | --- | --- |
| Vehicle control | 0.34 | 0.221 | |
| HSA-IGF2 | 7.079 | 2.009 | 0.013 |
| HSA-IGF2R61A | 6.914 | 2.691 | 0.014 |

Example 5 IGF2 and IGF2 Receptors are Expressed in Human Myoblast

Bar graph and quantitation table of IGF2 and IGF2 receptor RNASeq expression in young (17-21 year old caucasian males) and aged human myoblast (68-69 year old caucasian males) cell lines. Myoblast were cultured growth media (GM) or 96h in fusion media (FM). Fresh media was added every 24h. Mean±SEM. n=6. Expression are expressed as FPKM. Significant p-values (Young GM~Aged GM: 3.54E-04).

| n = 6 | IGF2 (FPKM) | SEM | p-val (n = 6) |
|---|---|---|---|
| Young GM | 13.11 | 3.275 | — |
| Aged GM | 3.413 | 1.12 | 3.54E-04 |
| Young FM | 17.68 | 6.42 | — |
| Aged FM | 13.08 | 3.67 | n.s. |

| n = 6 | IGF2R (FPKM) | SEM | P-val (n = 6) |
|---|---|---|---|
| Young GM | 74.93 | 9.45 | — |
| Aged GM | 75.01 | 6.89 | n.s. |
| Young FM | 82.35 | 3.43 | — |
| Aged FM | 88.44 | 9.86 | n.s. |

Example 6 Sodium Butyrate Enhances Muscle Fusion

Figure 2A:
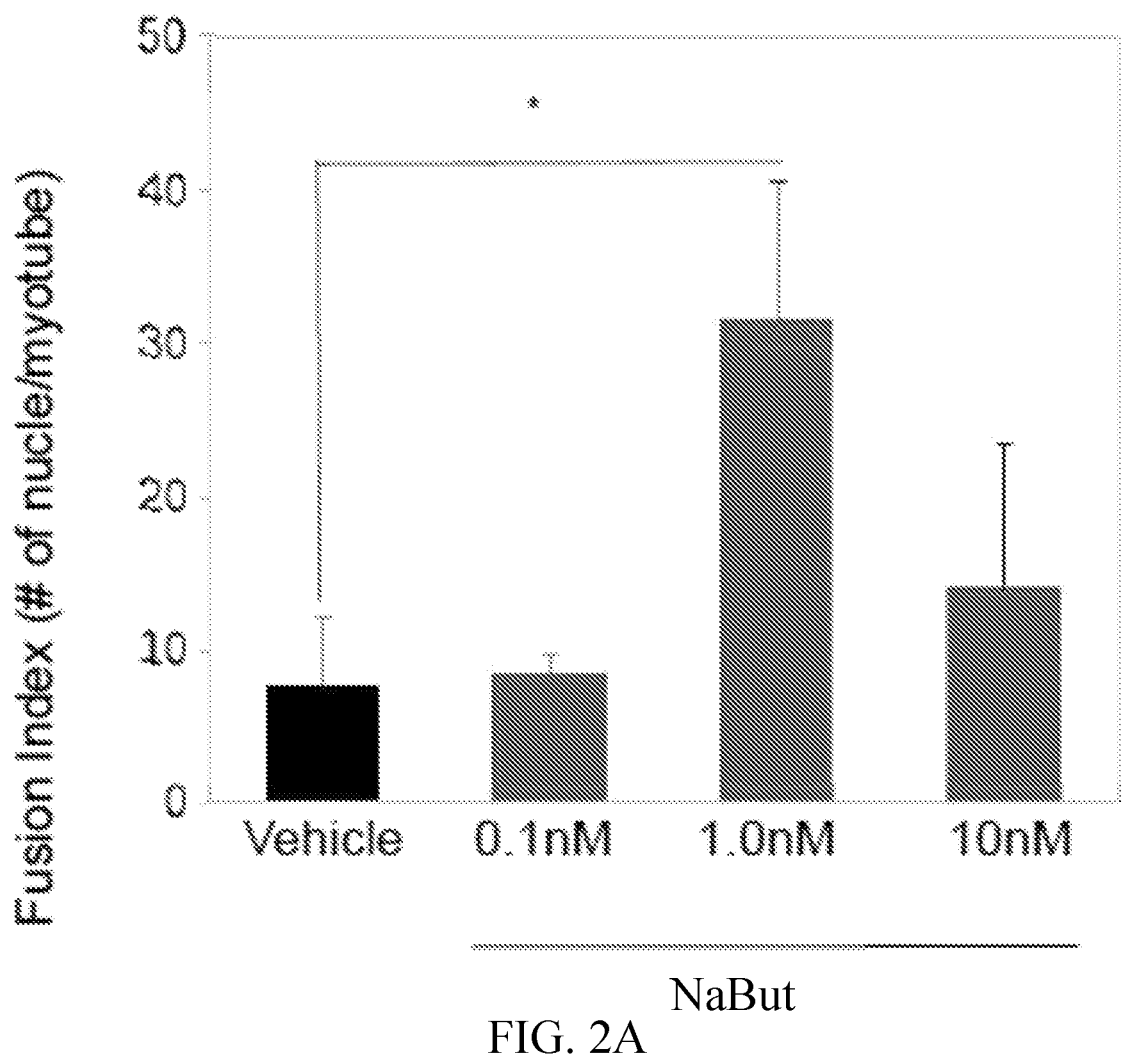
FIG. 2A depicts sodium butyrate enhanced muscle fusion.

Mouse myoblasts were treated with PBS or sodium butyrate at concentrations 0.1 nM, 1 nM, and 10 nM. Myoblasts were cultured for 48 hours, with fresh media added every 24 hours. Cells were pulsed for 2-5 hours with EdU (30 uM), ethanol fixed, stained with Hoescht 3342, immunostained for proliferation—as measured by the percent of cells staining positive for EdU (% EdU)—, and immunostained for differentiation—as measured by the increase in cellular area staining positive for embryonic myosin heavy chain (% eMyHC) relative to the negative controls, which received media and vehicle only. When compared to untreated myoblasts, the cells treated with 1 nM of sodium butyrate had increased rates of fusion, as depicted in FIG. 2A. Significance was determined by a p-value less than 0.05 by the one-way ANOVA Tukey Honest Significant Difference test.

FIG. 2A: Bar graph of fusion index in response to sodium butyrate (NaBut) compared to vehicle. Myoblast were cultured 48h in the presence of NaBut at indicated dose. Fresh media and NaBut were added every 24h. Mean∓S.D. Table quantitation of fusion index and p-values also shown. (*p<0.05 by Student's Two-tailed T-test, n=3-5)

| Condition | Fusion Index (nuclei/myotube) | p-value |
|---|---|---|
| vehicle | 7.56 | — |
| NaBut 0.1 nM | 8.44 | n.s. |
| NaBut 1 nM | 31.60 | 2.02E-3 |
| NaBut 10 nM | 14.00 | n.s. |

Example 7 Sodium Butyrate Enhances IGF2 Activity

Human myoblast cells were treated with either PBS (vehicle), IGF2 (15 ng/mL), sodium butyrate, or IGF2 and sodium butyrate. Fresh media was added every 24 hours. After 96 hours, cells were pulsed for 2-5 hours with EdU (30 uM), ethanol fixed, stained with Hoescht 3342, immunostained for proliferation—as measured by the percent of cells staining positive for EdU (% EdU)—, and immunostained for differentiation—as measured by the increase in cellular area staining positive for embryonic myosin heavy chain (% eMyHC) relative to the negative controls, which received media and vehicle only. The total area of eMyHc positive cells was analyzed, and treated cells were compared to cells treated with the vehicle alone. Cells that had been treated with IGF alone and two conditions in which cells had been treated with IGF2 and sodium butyrate produced a significant increase in the amount of differentiation. There was a significant increase in the total area of eMyHC cells in the cells treated with 1 nM and 100 nM of sodium butyrate and IGF2, compared to the cells treated with IGF2 alone. Significance was determined by a p-value less than 0.05 by the one-way ANOVA Tukey Honest Significant Difference test.

Figure 2B:
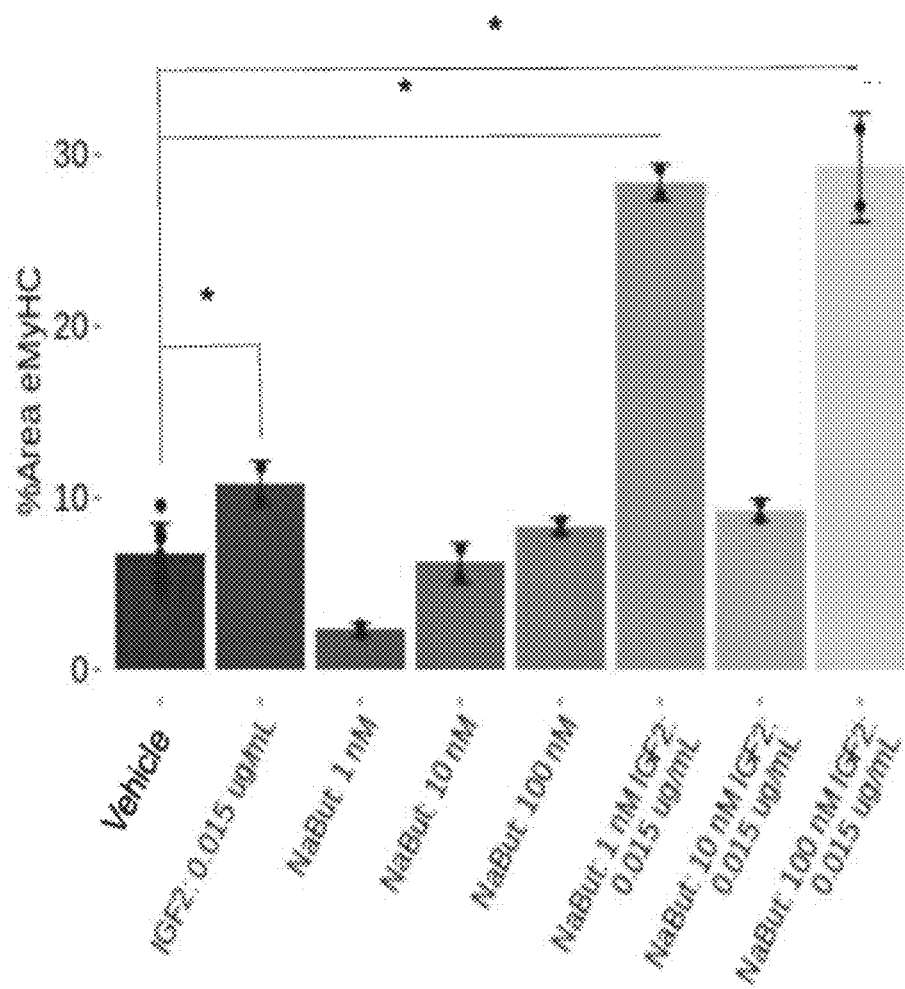
FIG. 2B depicts sodium butyrate enhanced IGF2 activity.

FIG. 2B: Bar graph of fusion index of mouse myoblast in response to sodium butyrate (NaBut) compared to vehicle. Mouse myoblast were cultured 48h in the presence of NaBut at indicated dose. Fresh media and NaBut were added every 24h. Mean∓S.D. Table quantitation of fusion index and p-values shown. (*p<0.05 by Student's Two-tailed T-test, n=3-5). Significant p-values (Vehicle~IGF2: 0.015 ug/mL: 6.33E-06, Vehicle~NaBut: 1 nM IGF2: 0.015 ug/mL: 1.79E-11, Vehicle~NaBut: 100 nM IGF2: 0.015 ug/mL: 1.79E-11)

| Table of data for FIG. 2B | | | |
|---|---|---|---|
| Condition | % eMyHC | SD | p-value |
| Vehicle | 6.813 | 1.695 | — |
| IGF2: 0.015 ug/mL | 10.843 | 1.308 | |
| NaBut: 1 nM | 2.321 | 0.374 | |
| NaBut: 10 nM | 6.199 | 1.174 | |
| NaBut: 100 nM | 8.341 | 0.477 | |
| NaBut: 1 nM IGF2: 0.015 ug/mL | 28.387 | 1.036 | 1.79E-11 |
| NaBut: 10 nM IGF2: 0.015 ug/mL | 9.274 | 0.654 | |
| NaBut: 100 nM IGF2: 0.015 ug/mL | 29.239 | 3.185 | 1.79E-11 |

Figure 2C:
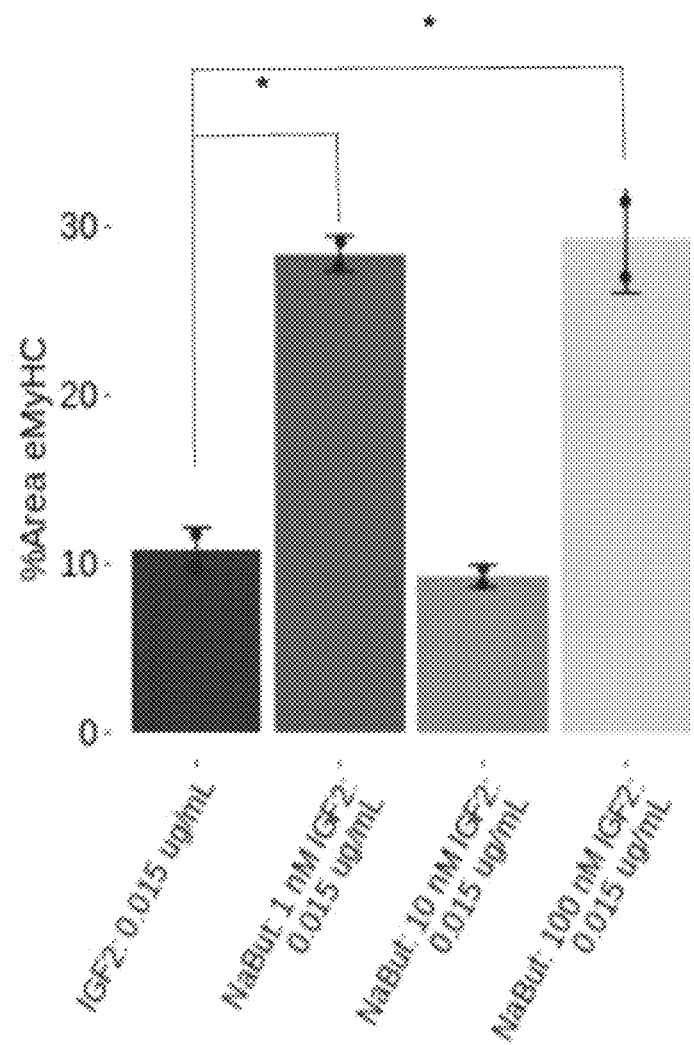
FIG. 2C depicts sodium butyrate enhanced IGF2 activity.

FIG. 2C Bar graph quantitation of % Area eMyHC+ human myoblast in response to indicated treatment compared to IGF2 (15 ng/mL). Myoblast were cultured 96h in the presence of BMP7 at indicated dose. Fresh media and BMP7 was added every 24h. Mean∓S.D. (*p<0.05 by One-Way Anova Tukey Honest Significant Difference, n=2-12)

| Table of data for FIG. 2C | | | |
|---|---|---|---|
| Condition | % eMyHC | SD | p-value |
| IGF2: 0.015 ug/mL | 10.843 | 1.308 | |
| NaBut: 1 nM IGF2: 0.015 ug/mL | 28.387 | 1.036 | 6.18E-8 |
| NaBut: 10 nM IGF2: 0.015 ug/mL | 9.274 | 0.654 | |
| NaBut: 100 nM IGF2: 0.015 ug/mL | 29.239 | 3.185 | 3.50E-3 |

Example 8 Sodium Butyrate Enhances IGF2 Activity

Figure 3A:
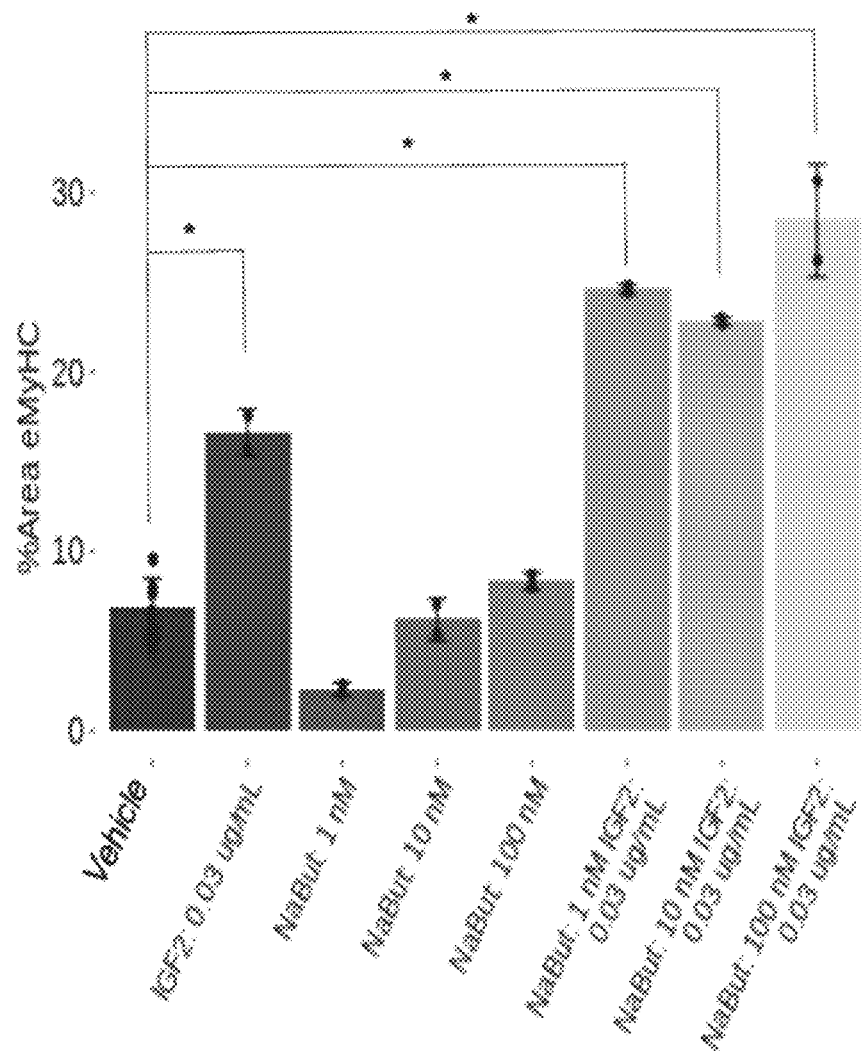
FIG. 3A depicts the change in percent area of eMyHC positive cells treated with additional doses of vehicle, IGF2, sodium butyrate, or IGF2 and sodium butyrate.

Human myoblast cells were treated with either PBS (vehicle), IGF2 (15 ng/mL), sodium butyrate, or IGF2 and sodium butyrate. Fresh media was added every 24 hours. After 48 hours, cells were pulsed for 2-5 hours with EdU (30 uM), ethanol fixed, stained with Hoescht 3342, immunostained for proliferation—as measured by the percent of cells staining positive for EdU (% EdU)—, and immunostained for differentiation—as measured by the increase in cellular area staining positive for embryonic myosin heavy chain (% eMyHC) relative to the negative controls, which received media and vehicle only. The total area of eMyHc positive cells was analyzed, and treated cells were compared to cells treated with the vehicle alone, as seen in FIG. 3A. Myoblasts that had been treated with either 0.03 ug/mL of IGF2 or with IGF2 in combination with sodium butyrate showed a significant increase in the eMyHC+ area when compared to cells cultured with the vehicle alone.

Figure 3B:
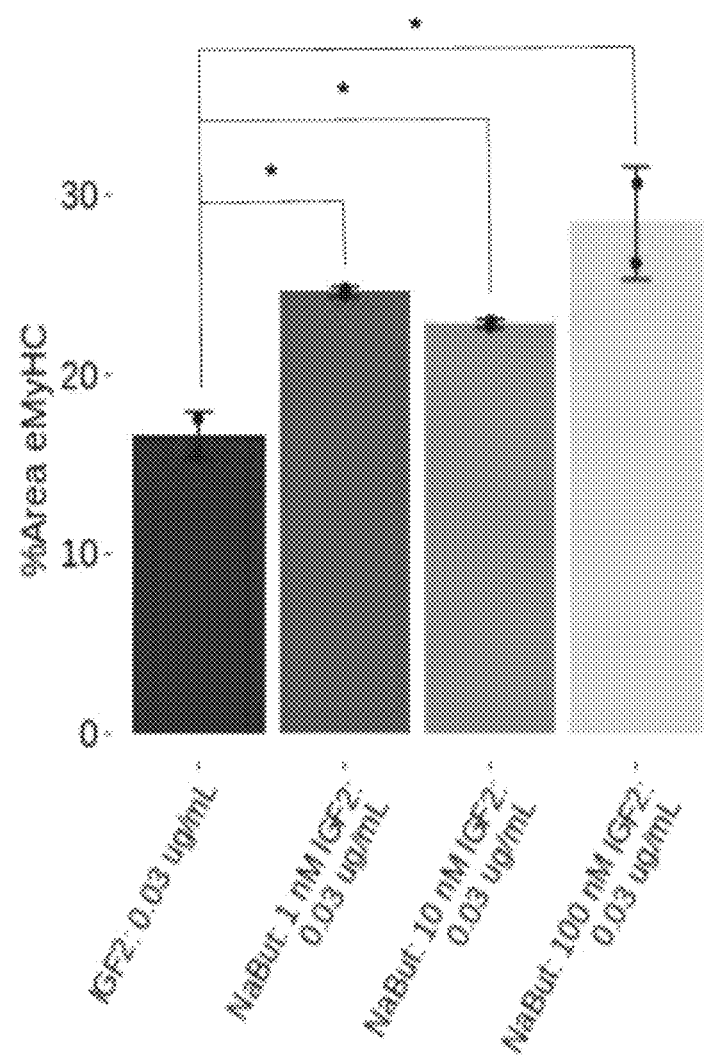
FIG. 3B depict the change in percent area of eMyHC positive cells treated with additional doses of vehicle, IGF2, sodium butyrate, or IGF2 and sodium butyrate.

FIG. 3A: Bar graph of % Area eMyHC+ age human myoblast (68 year old caucasian male) in response to indicated treatment compared to Vehicle (vehicle). Myoblast were cultured 96h in the presence of factors at indicated dose. Fresh media and factors were added every 24h. Mean∓S.D. Significant p-values (Vehicle~IGF2: 0.03 ug/mL: 1.42E-08, Vehicle~NaBut: 1 nM IGF2: 0.03 ug/mL: 1.79E-11, Vehicle~NaBut: 10 nM IGF2: 0.03 ug/mL: 1.80E-11, Vehicle~NaBut: 100 nM IGF2: 0.03 ug/mL: 1.79E-11). FIG. 3B Bar graph quantitation of % Area eMyHC+ human myoblast (68 year old caucasian male) in response to indicated treatment compared to IGF2 (15 ng/mL). Myoblast were cultured 96h in the presence of BMP7 at indicated dose. Mean±S.D. Significant p-values (IGF2~NaBut: 1 nM IGF2: 0.03 ug/mL: 1.88E-3, Vehicle~NaBut: 10 nM IGF2: 0.03 ug/mL: 4.80E-3, Vehicle~NaBut: 100 nM IGF2: 0.03 ug/mL: 1.87E-3) (*p<0.05 by One-Way ANOVA Tukey Honest Significant Difference, n=2-12)

Table of data for FIG. 3A

| Condition | % eMyHC | SD | p-value |
|---|---|---|---|
| Vehicle | 6.813 | 1.695 | — |
| IGF2: 0.03 ug/mL | 16.620 | 1.301 | 1.42E-08 |
| NaBut: 1 nM | 2.321 | 0.374 | |
| NaBut: 10 nM | 6.199 | 1.174 | |
| NaBut: 100 nM | 8.341 | 0.477 | |
| NaBut: 1 nM IGF2: 0.03 ug/mL | 24.615 | 0.258 | 1.79E-11 |
| NaBut: 10 nM IGF2: 0.03 ug/mL | 22.821 | 0.234 | 1.80E-11 |
| NaBut: 100 nM IGF2: 0.03 ug/mL | 28.427 | 3.136 | 1.79E-11 |

The myoblasts that had been treated with a combination of IGF2 and sodium butyrate were compared to the cells treated with IGF2 alone. There was a significant increase in all cells treated with the combination compared to cells treated with IGF2 alone, as depicted in FIG. 3B and Table 12. Significance was determined by a p-value less than 0.05 by the one-way ANOVA Tukey Honest Significant Difference test.

Table of data for FIG. 3B

| Condition | % eMyHC | SD | p-value |
|---|---|---|---|
| IGF2: 0.03 ug/mL | 16.620 | 1.301 | — |
| NaBut: 1 nM IGF2: 0.03 ug/mL | 24.615 | 0.258 | 1.88E-3 |
| NaBut: 10 nM IGF2: 0.03 ug/mL | 22.821 | 0.234 | 4.80E-3 |
| NaBut: 100 nM IGF2: 0.03 ug/mL | 28.427 | 3.136 | 1.87E-3 |

Example 9 IGF2 Enhances MYOG Expression in DM1 Human Myoblast Cells

Bar graph of myogenic gene expression fold change in DM1 human myoblast in response to indicated treatment compared to FM (vehicle). Myoblasts were cultured 48h in the presence of factors (BMP7 50 ng/mL, Butyrate 100 nM, IGF2 200 ng/mL). Mean∓S.D. Significant p-values (FM~IGF2: 4.94E-04, FM~IGF2_NaBut: 6.53E-03) (*p<0.01) Table of mean and p-value of MYF5, MYOD1, and MYOG (n=3).

Table of data

| Condition | MYF5 | MYF5 p-value | MYOD1 | MYOD1 p-value | MYOG | MYOG p-value |
|---|---|---|---|---|---|---|
| FM | 1.000 | | 1.000 | | 1.000 | |
| BMP7 | 0.709 | n.s. | 0.709 | n.s. | 0.361 | n.s. |
| NaBut | 1.128 | n.s. | 1.095 | n.s. | 1.020 | n.s. |
| IGF2 | 0.730 | n.s. | 1.252 | n.s. | 2.972 | 4.94E-04 |
| IGF2 NaBut | 0.820 | n.s. | 1.500 | n.s. | 3.483 | 6.53E-03 |

Example 10 IGF2 Receptor is Expressed on Chondrocyte and Osteocytes

Figure 4A:
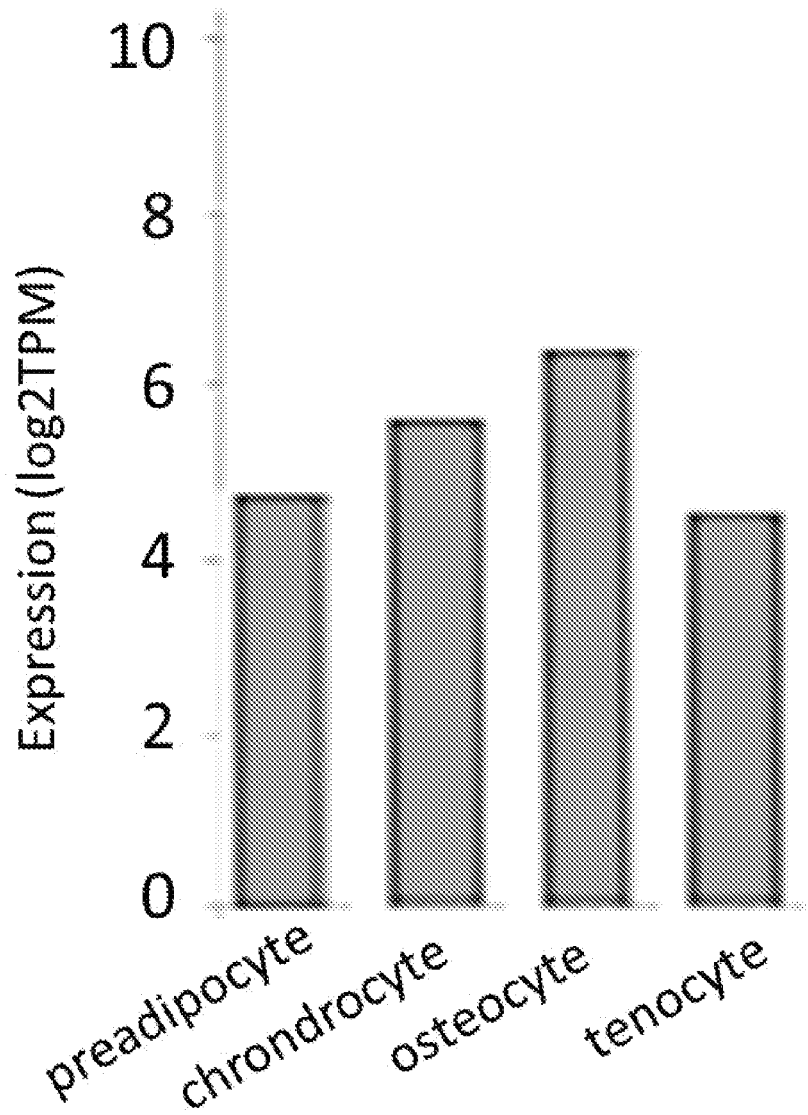
FIG. 4A depicts IGF2 Receptor was expressed on chondrocyte and osteocytes.

FIG. 4A: Bar graph showing IGF2 receptors are expressed on cartilage-associated cells. Data is derived from Ramilowsky et al., Nature 2015.

Table of data for FIG. 4A RNA Expression (TPM)

| Cell Type | IGF2R |
|---|---|
| Preadipocyte (Subcutaneous) | 27.083 |
| Chondrocyte | 47.63 |
| Osteocyte | 83.96 |
| Tenocyte | 23.12 |

Example 11 IGF2 Treatment Promotes Proliferation and Fusion in DM1 Human Myoblast (32 Year Old Caucasian Female) Cells Bar graph of % EdU+ human myoblast (32 year old caucasian female) and % area MyHC in response to IGF2. Myoblast were cultured 72h for proliferation and 96h for fusion in the presence of indicated factor. Mean∓S.D. Mean∓SD. Significant p-values (EdU: Vehicle~IGF2: 6.8E-3, % eMyHC Area: Vehicle~IGF2: 1.9E-4) (*p<0.05 by Students Two-Tailed T-test, n=3-6).

Table of data

| n = 3-6 | EdU FC | s.d. | p-val |
|---|---|---|---|
| Vehicle | 1.0 | 0.02 | |
| IGF2 | 2.18 | 0.32 | 6.8E-3 |

Table of data

| n = 3 | % eMyHC are | s.d. | p-val |
|---|---|---|---|
| Vehicle | 0.45 | 0.02 | |
| IGF2 | 5.49 | 0.54 | 1.9E-4 |

Example 12 IGF2 Enhances MYH3, CKM, and ATP1B1 Expression in DM1 Human Myoblast (32 Year Old Caucasian Female) Cells Bar graph of MYH3 and CKM expression fold change in DM1 human myoblast (32 year old caucasian female) in response to indicated treatment compared to vehicle. Myoblasts were cultured 96h in the presence of factors (IGF2 200 ng/mL). Mean±S.D. Significant p-values (MYH3: Vehicle~IGF2: 1.13E-03, CKM: Vehicle~IGF2: 7.67E-03) Bar graph of ATP1B1 expression fold change in DM1 human myoblast (32 year old caucasian female) in response to indicated treatment compared to FM (vehicle). Myoblasts were cultured 48h in the presence of factors (IGF2 200 ng/mL). Mean±S.D. Significant p-values (Vehicle~IGF2: 3.11E-05) (*p<0.05 by Students Two-Tailed T-test, n=3).

| Table of data | | | | |
|---|---|---|---|---|
| | MYH3 | p-val | CKM | p-val |
| Vehicle | 1 | | 1 | |
| IGF2 | 14.833 | 1.13E-03 | 5.165 | 7.67E-03 |

| Table of data | | |
|---|---|---|
| n = 3 | ATP1B1 | p-val |
| Vehicle | 1 | |
| IGF2 | 3.01789 | 3.11E-05 |

Example 13 Systemic Administration of IGF2/NaB Protects Against Aging Induced Muscle Dysfunction Subcutaneous injection of IGF2 (50 ug/kg) or NaB (1.2 g/kg), IGF2/NaB (150 ug/kg; 1.2 g/kg) or vehicle (PBS) were administered to 21-24M old mice for 14 days. Muscle function was assessed at days 13 and 14. Grip strength force assessed at day 13. The first graph shows Bothlimb grip strength force, **p<0.0001, p=0.0043, p=0.001 (One-way ANOVA, multiple comparisons). Forelimb force, **p<0.0001, *p=0.0368, *p=0.0187 (One-way ANOVA, multiple comparisons). Treadmill performance measured at day 14 using an induced treadmill running model set to progressively increase speed 2 m/min every subsequent 2 min. Distance ran shown. ***p=0.0005, *p=0.0459, **p<0.0001 (One-way ANOVA, multiple comparisons) Time to exhaustion *p=0.0002, p=0.0024 (One-way ANOVA, multiple comparisons) Maximum speed *p=0.0004, p=0.0013 Work in kj p=0.0026, **p=0.0035 (One-way ANOVA, multiple comparisons).

Example 14 Systemic Administration of IGF2/NaB is Safe

Subcutaneous injection of vehicle or IGF2/NaB were administered to 21M old mice for 14 days, blood and serum were collected to assess complete blood count and a metabolic panel for liver, kidney and pancreas function. 4 representative graphs out of 37 readouts measured showing the white blood cell count (Unpaired t-test, p=0.8020), Albumin concentration (Unpaired t-test, p>0.9999), Creatinine concentration (Unpaired t-test, p=0.5490) and Calcium concentration (Unpaired t-test, p=0.811).

Example 15 Systemic Administration of IGF2/but Protects Against Dexamethasone Induced Muscle Atrophy Dexamethasone (25 mg/kg i.p.) was administered to 12 weeks old mice for 14 days simultaneously with a subcutaneous injection of IGF2/NaB (150 ug/kg; 1.2 g/kg) or vehicle (PBS). Muscle function was assessed at day 13-14. Grip strength force assessed at day 13, graphs showing bothlimb force and specific bothlimb force measured on Day 13. Specific bothlimb force calculated as the ratio of bothlimb force in mN over the weight in g, *p=0.0003, *p=0.0004 (Unpaired t-test). Grip strength force assessed at day 13, graphs showing forelimb force and forelimb specific force measured on Day 13. Specific forelimb force calculated as the ratio of forelimb force in mN over the weight in g, p=0.0012, *p=0.0005 (Unpaired t-test). At day 15, mice were euthanized and TAs were collected for histological analysis, graphs showing muscle fiber size distribution assessed using SMASH software. **p=0.054, *p=0.037, and ****p<0.0001 (2-way ANOVA, multiple comparisons).

Example 16 BMP7 Induces Myoblast Proliferation

Figure 5A:
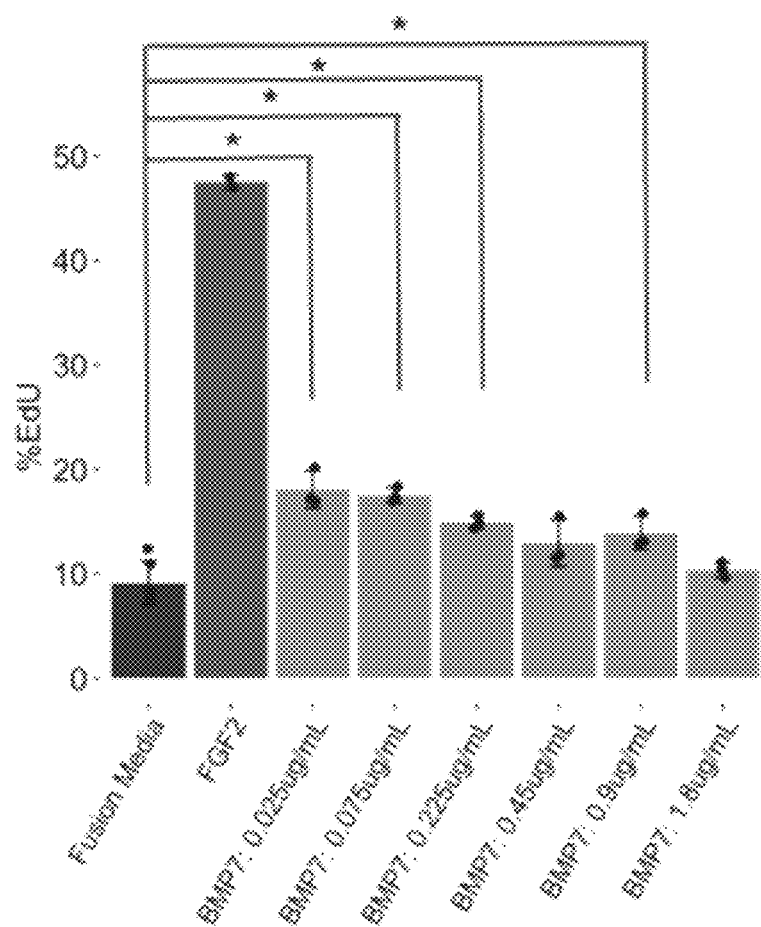
FIG. 5A depicts BMP7 induced myoblast proliferation as measured by newly formed nuclei.
Figure 5B:
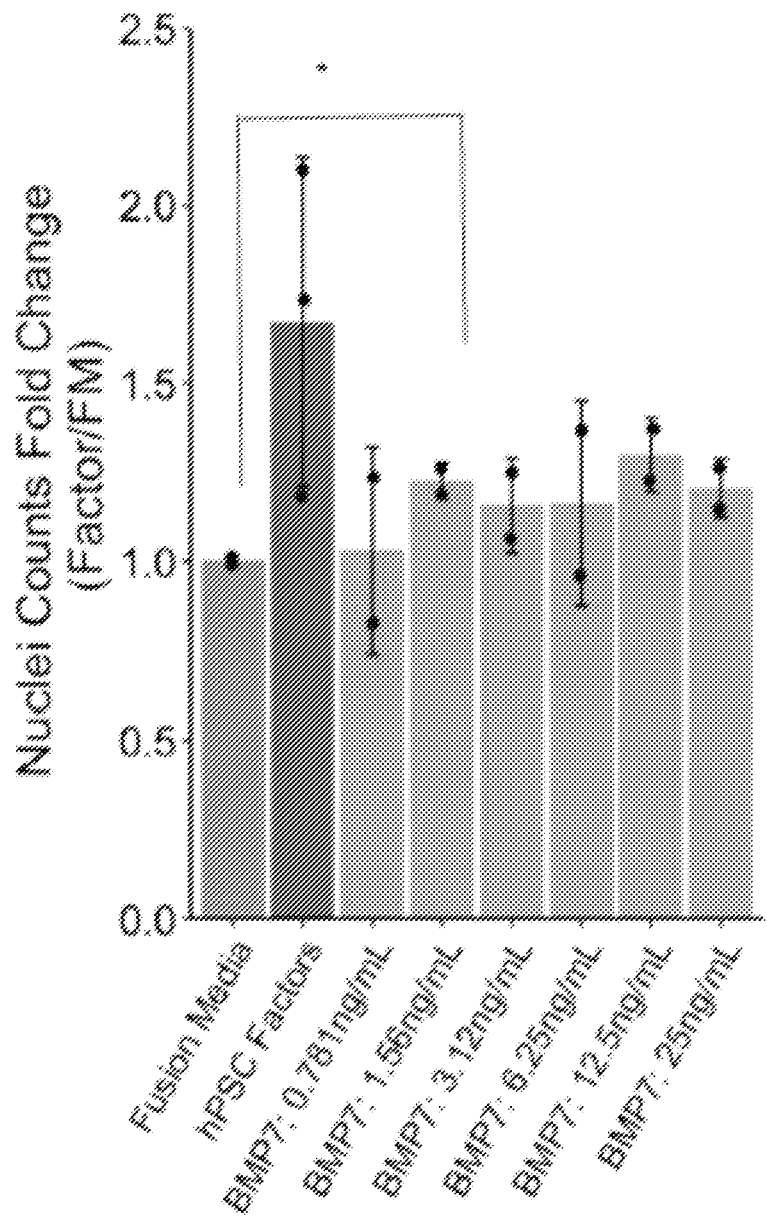
FIG. 5B depicts BMP7 induced myoblast proliferation as measured by total nuclei.

FIG. 5A) Bar graph quantitation of % EdU+ mouse myoblast in response to BMP7. Myoblast were cultured 48h in the presence of BMP7 at indicated dose. Fresh media and BMP7 was added every 24h, followed by 2 hour EdU pulse and fixation. Mean∓S.D. Significant p-values (Vehicle~BMP7 0.025 ug/mL: 1.21E-07, Vehicle~BMP7 0.075 ug/mL: 8.05E-07, Vehicle~BMP7 0.2255 ug/mL: 3.37E-03, Vehicle~BMP7 0.9 ug/mL: 4.99E-02). FIG. 5B) Bar graph quantitation of % EdU+ human myoblast (68 year old caucasian male) in response to BMP7. Myoblast were cultured 72h in the presence of BMP7 at indicated dose. Cells were pulsed with EdU for 4 hours before fixation. Mean∓S.D. Significant p-values (Vehicle~BMP7 1.56 ng/mL: 0.04). (*p<0.05 by Welch's One-Tailed T-test, n=2)

| Table of data for FIG. 5A—BMP7 Mouse Myoblast Proliferation | | |
|---|---|---|
| BMP7 | % EdU | p-value |
| Vehicle | 10.56 | — |
| 0.025 ug/mL | 18.08 | 1.21E-07 |
| 0.075 ug/mL | 17.53 | 8.05E-07 |
| 0.2255 ug/mL | 14.93 | 3.37E-03 |
| 0.45 ug/mL | 12.93 | n.s. |
| 0.9 ug/mL | 13.91 | 4.99E-02 |
| 1.8 ug/mL | 10.37 | n.s. |

| Table of data for FIG. 5B—BMP7 Human Myoblast Proliferation | | |
|---|---|---|
| Human Myoblast | Nuclei Counts | p-value |
| Vehicle | 2083.5 | — |
| 0.78 ng/mL | 2144.5 | n.s. |
| 1.56 ng/mL | 2552.5 | 0.04 |
| 3.12 ng/mL | 2408 | n.s. |
| 6.25 ng/mL | 2422.5 | n.s. |
| 12.5 ng/mL | 2706 | n.s. |
| 25 ng/mL | 2509 | n.s. |

Example 17 Leucine Enhances BMP7 Mitogenic Activity

Figure 6A:
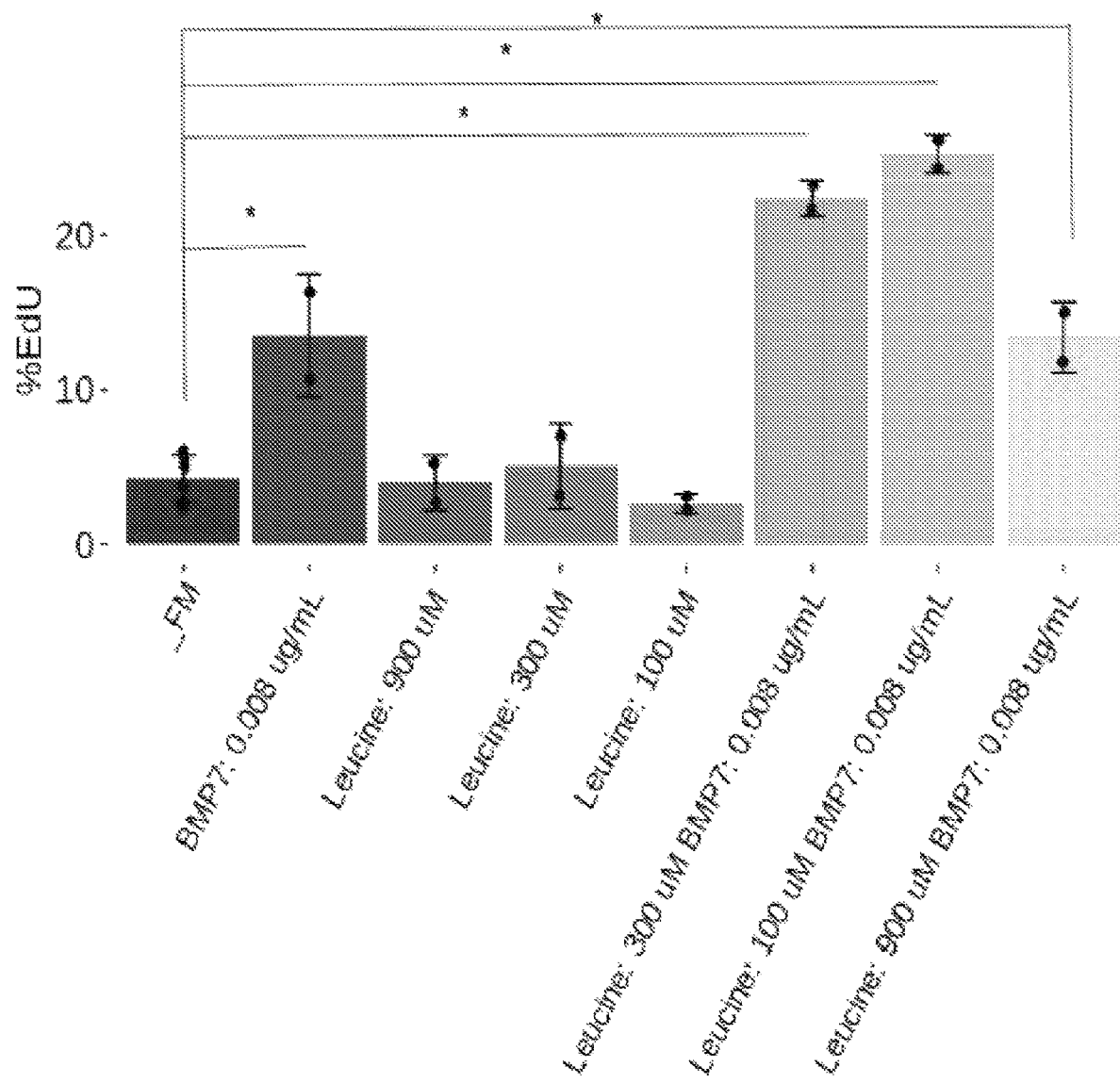
FIG. 6A depicts leucine enhanced BMP7 mitogenic activity.

FIG. 6A) Bar graph of % EdU+ mouse myoblast cells compared to vehicle. Mouse myoblast were cultured 48h in the presence of indicated factors, followed by a 2 hour EdU pulse prior to fixation. Mean∓S.D. Significant p-values (FM~BMP7: 0.008 ug/mL: 3.17E-02, FM~Leucine: 300 uM BMP7: 0.008 ug/mL: 2.77E-03, FM~Leucine: 100 uM
BMP7: 0.008 ug/mL: 3.72E-05, FM~Leucine: 900 uM
BMP7: 0.008 ug/mL: 2.52E-03). (*p<0.05 by One-Way ANOVA Tukey Honest Significant Difference, n=2-6)

Example 18 Hyaluronic Acid (HA) Enhances BMP7 Mitogenic Activity

Figure 7A:
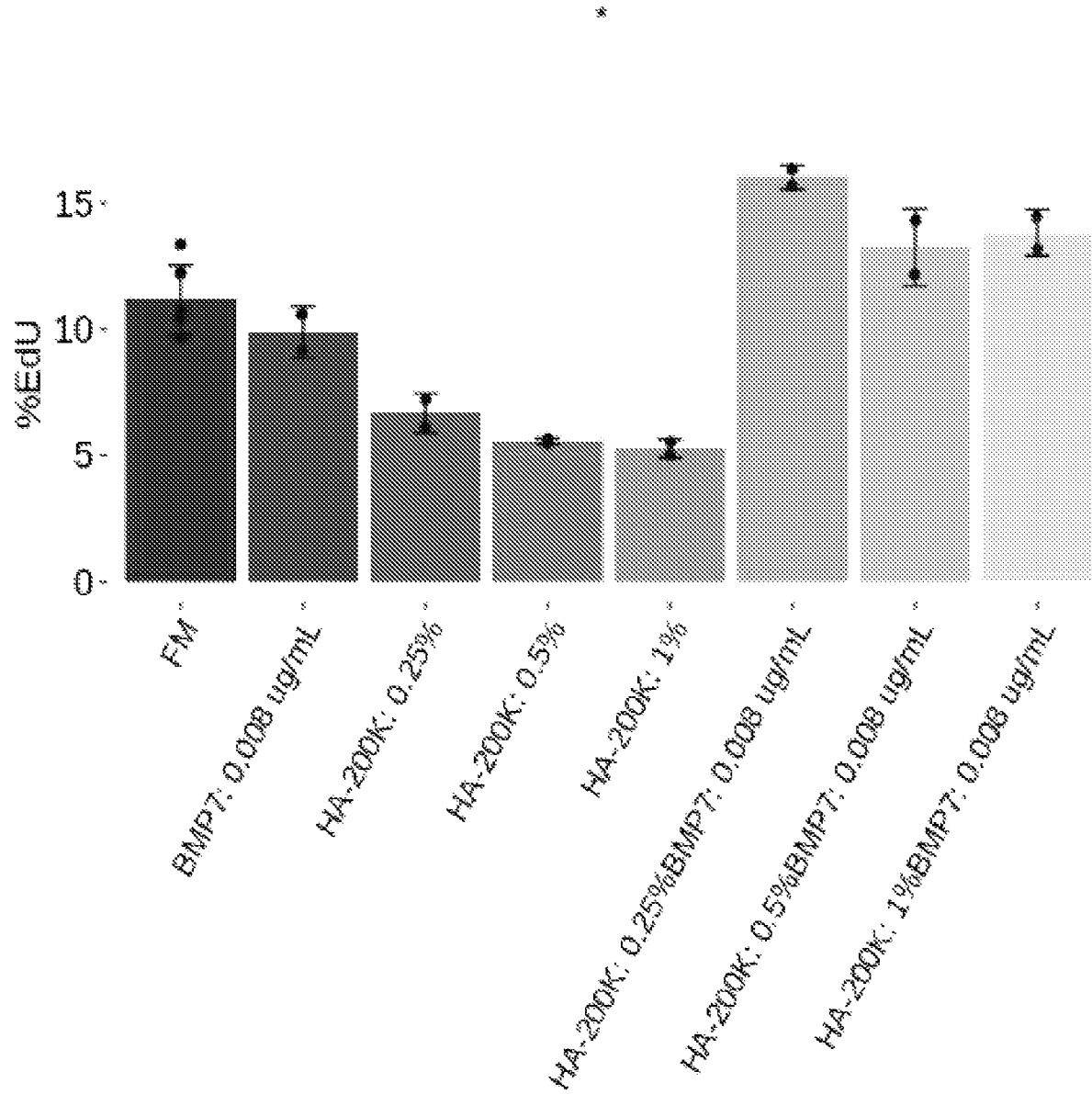
FIG. 7A depicts hyaluronic acid (HA) enhanced BMP7 mitogenic activity.

FIG. 7A: Bar graph of % EdU+ mouse myoblast cells compared to vehicle. Mouse myoblast were cultured 48h in the presence of indicated factors. EdU pulse and fixation. Mean∓S.D. (*p<0.05 by Student's One-Tailed T-Test of increased activity, n=2-6)

Example 19 BMP7 Receptors are Expressed in Human Myoblast

Figure 8A:
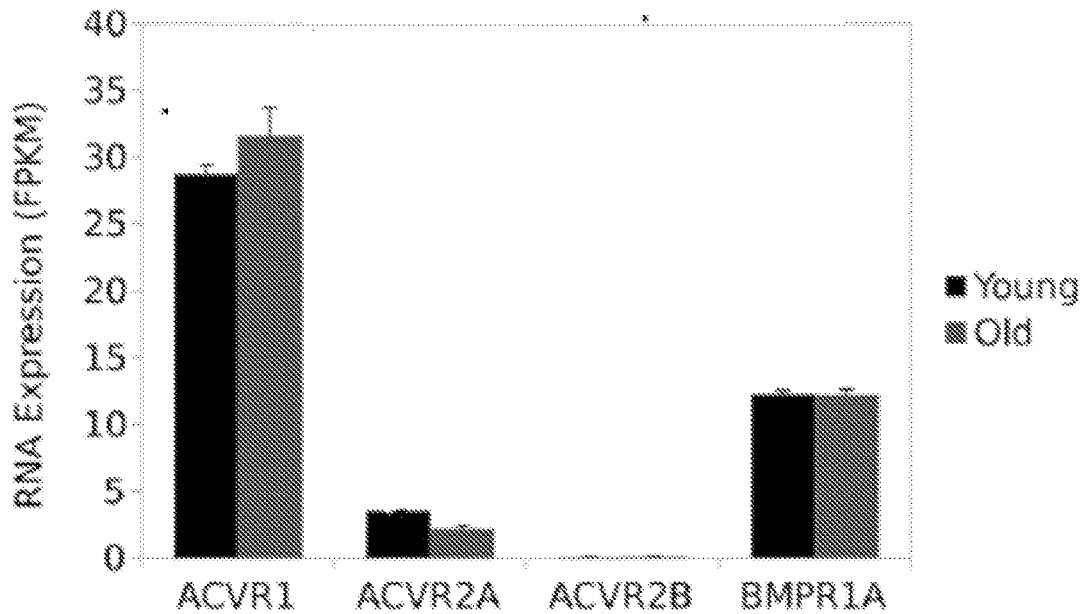
FIG. 8A depicts BMP7 receptors were expressed in human myoblast.

FIG. 8A: Bar graph of BMP7 receptor RNASeq expression in young and aged human myoblast (68-69 year old caucasian males) cell lines. Myoblast were cultured 96h in fusion media. Fresh media was added every 24h, followed by RNA extraction and sequencing. Mean∓SEM. n=3. Expression are expressed as FPKM.

Figure 9A:
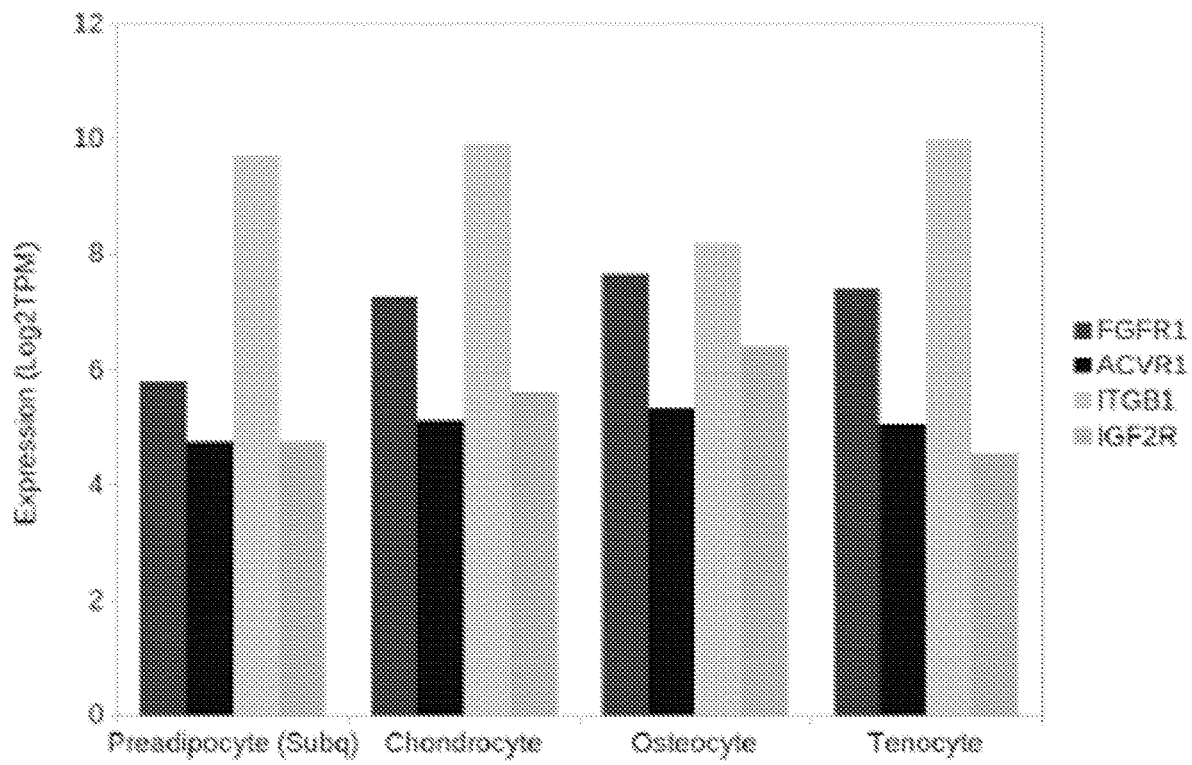
FIG. 9A depicts treatment for chondrocyte proliferation in cartilage injury and osteoarthritis.

Example 20 Treatment for Chondrocyte Proliferation in Cartilage Injury and Osteoarthritis FIG. 9A: Bar graph showing BMP7 receptors are expressed on cartilage-associated cells. Data derived from Ramilowsky et al., Nature, 2015.

Example 21—FGF17-hFcm Promotes Proliferation of Mouse Myoblasts

Figure 10A:
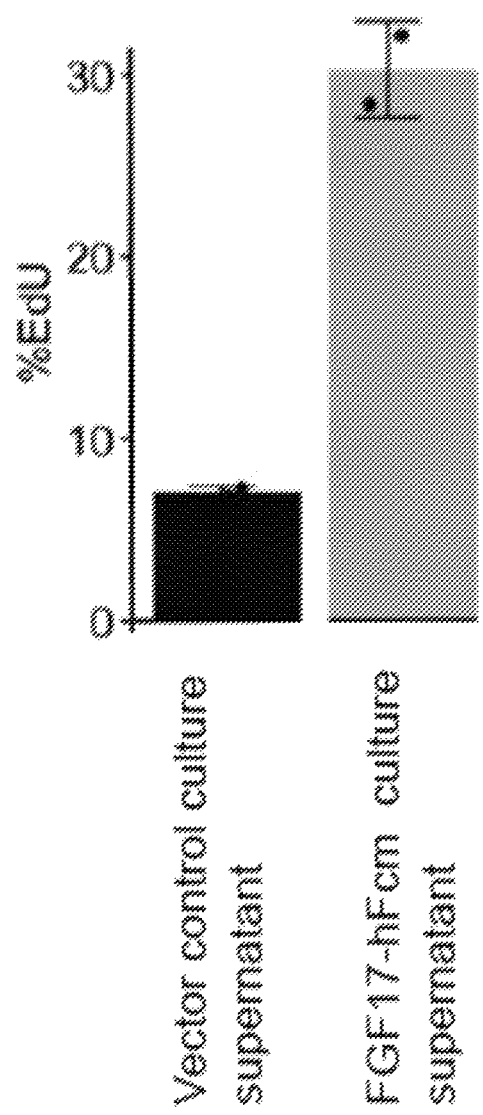
FIG. 10A depicts FGF17-hFcm promoted proliferation of mouse myoblasts as a part of cultured media supernatant, or purified (FIG. 10B).
Figure 10B:
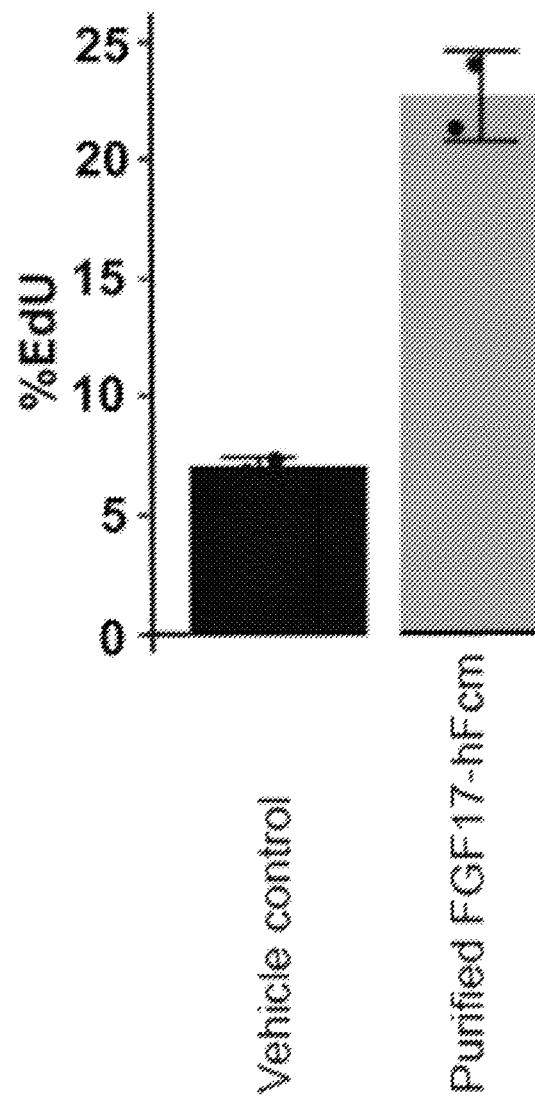

FIG. 10A) The suspension CHO cells were transiently transfected with either the empty control plasmid or the FGF17-hFcm encoding plasmid. After four days, the culture supernatants were collected and added into the culture of mouse myoblast cells for 48 hours, followed by a 2 hour EdU pulse prior to fixation. The percentage of EdU+ mouse myoblasts treated with the culture supernatant of CHO cells expressing FGF17-hFcm is significantly higher than the percentage of EdU+ mouse myoblasts treated with either vehicle control or the culture supernatant of CHO cells expressing the empty control vector (One-Way ANOVA Tukey Honest Significant Difference, n=2-6). FIG. 10B) The suspension CHO cells were transiently transfected with the FGF17-hFcm encoding plasmid. After four days, the culture supernatants were collected and FGF17-hFcm was affinity-purified by Protein A membrane column. The purified FGF17-hFcm was added into the culture of mouse myoblast cells for 48 hours, followed by a 2 hour EdU pulse and fixation. The percentage of EdU+ mouse myoblasts treated with the purified FGF17-hFcm is significantly higher than the percentage of EdU+ mouse myoblasts treated with the culture supernatant of CHO cells expressing the empty control vector (One-Way ANOVA Tukey Honest Significant Difference, n=2-6).

| Table of data for FIG. 10A | | | |
|---|---|---|---|
| Sample | % EdU | SD | p_value |
| Vector control culture supernatant | 7.069 | 0.354 | |
| FGF17-hFcm culture supernatant | 30.285 | 2.650 | 8.88E-6 |

| Table of data for FIG. 10B | | | |
|---|---|---|---|
| Sample | % EdU | SD | p_value |
| Vehicle control | 4.884 | 1.080 | |
| Purified FGF17-hFcm | 22.761 | 1.880 | 2.04E-5 |

Example 22: FGF17 Mutants Improved Protein Expression Levels in CHO Cells

Figure 11A:
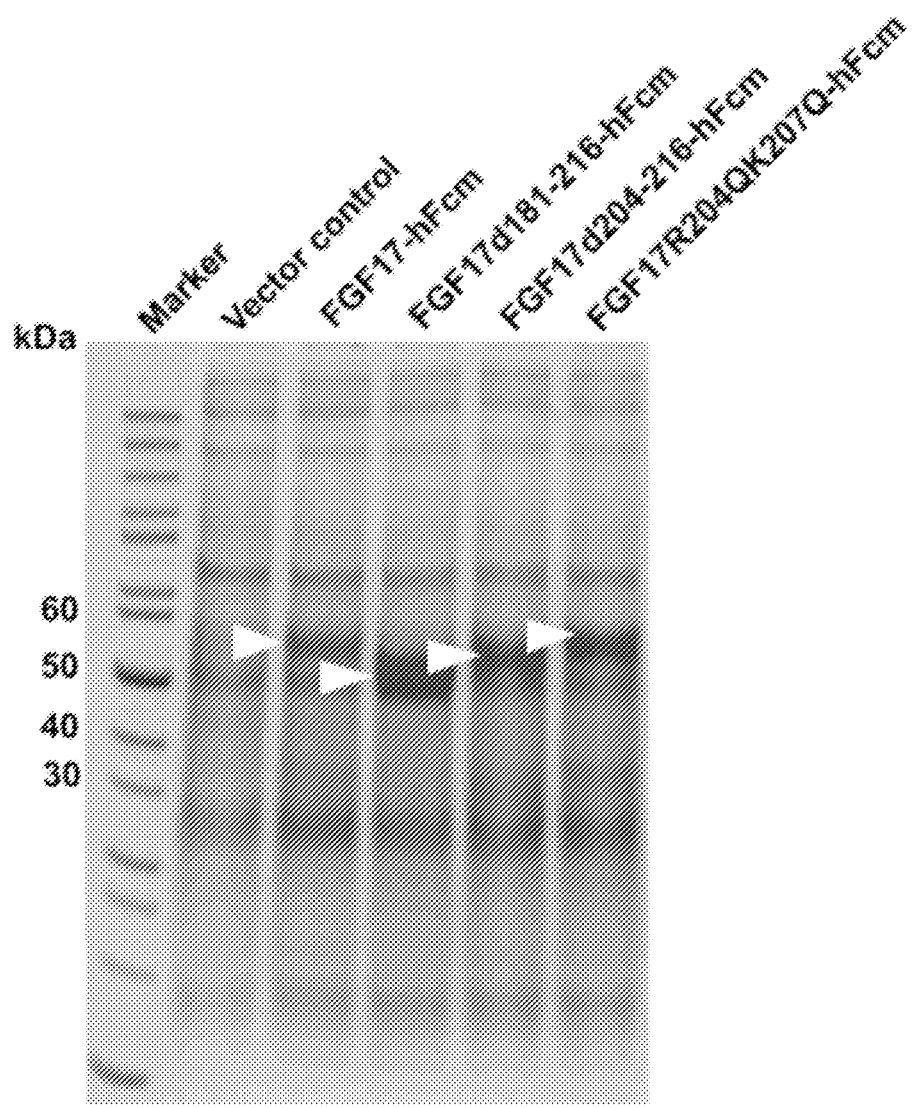
FIG. 11A depicts FGF17 sequence mutations improved protein expression levels in CHO cells.
Figure 11B:
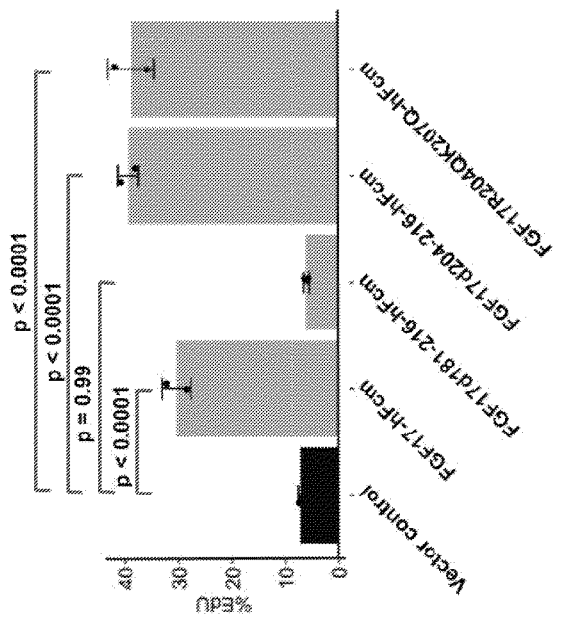
FIG. 11B depicts FGF17 sequence mutations promoted proliferation of mouse myoblasts as a part of cultured media supernatant, or purified.

FIG. 11A: SDS-PAGE of culture supernatants from CHO cells transiently transfected with FGF17-hFcm or its mutants encoding plasmids (FGF17d181-216-hFcm, FGF17d204-216-hFcm, FGF17R204QK207Q-hFcm). The expressed FGF17-hFcm proteins and the mutant proteins were indicated by the white arrowheads. FIG. 11B) The culture supernatants from CHO cells transiently transfected with different FGF17 encoding plasmids were added into the culture of mouse myoblast cells for 48 hours followed by 2 hour EdU pulse and fixation. The percentage of EdU+ mouse myoblasts treated with the culture supernatants of CHO cells expressing wild type FGF17-hFcm or mutants FGF17-hFcm (AA204-216 deletion mutant and R204QK207Q point mutation mutant) is significantly higher than the percentage of EdU+ mouse myoblasts treated with the culture supernatant of CHO cells expressing the empty control vector (One-Way ANOVA Tukey Honest Significant Difference, n=2-6).

| FIG. 11B | | | |
|---|---|---|---|
| Sample | % EdU | SD | p_value |
| Vector control | 7.069 | 0.354 | |
| FGF17-hFcm | 30.285 | 2.650 | 1.08E-4 |
| FGF17d181-216-hFcm | 6.000 | 0.533 | 0.99 |
| FGF17d204-216-hFcm | 39.298 | 2.002 | 1.22E-5 |
| FGF17R204QK207Q-hFcm | 38.831 | 4.343 | 1.35E-5 |

Example 23 FGF17 Mutants Improved Protein Expression Levels in CHO Cells

Figure 12A:
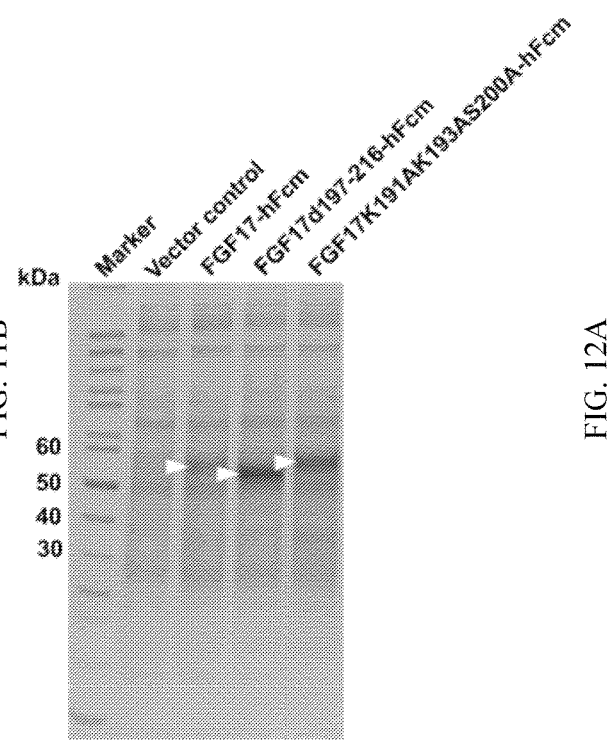
FIG. 12A depicts additional FGF17 mutants improved protein expression levels in CHO cells.
Figure 12B:
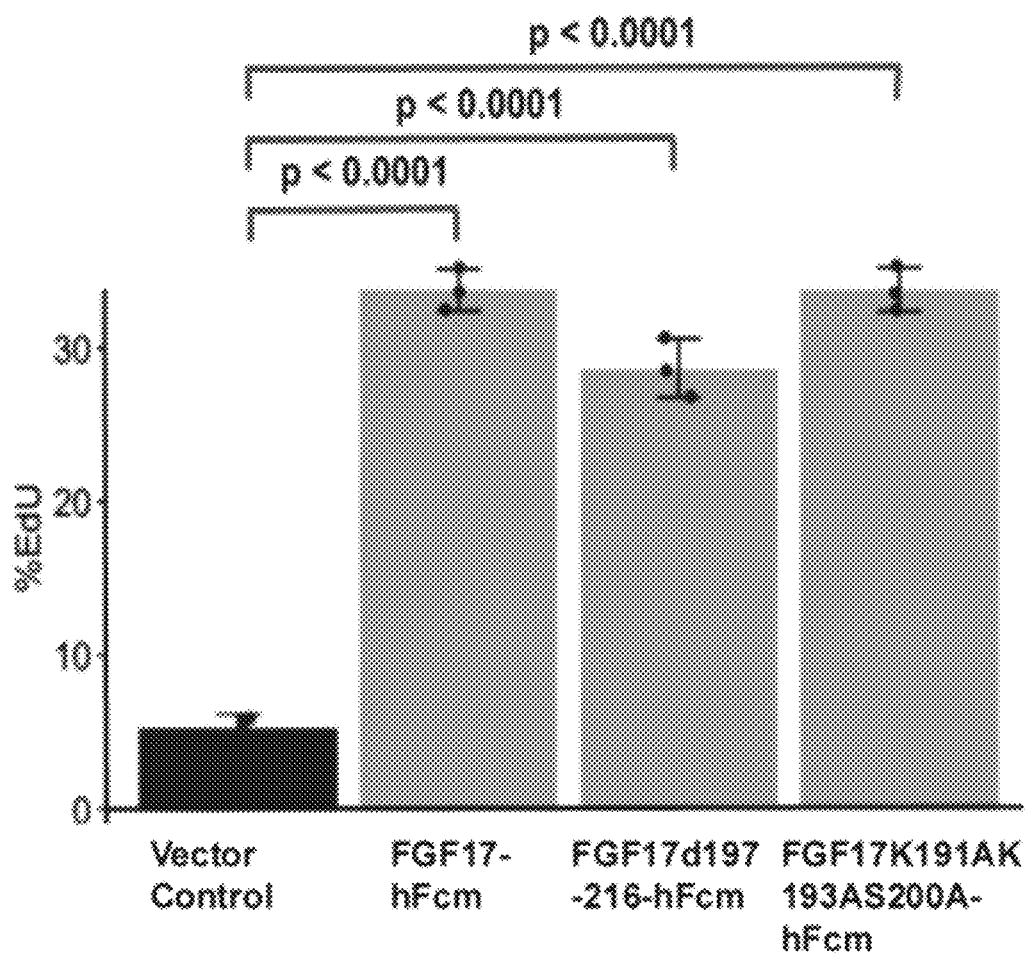
FIG. 12B depicts additional FGF17 sequence mutations promoted proliferation of mouse myoblasts as a part of cultured media supernatant, or purified.

FIG. 12A) SDS-PAGE of culture supernatants from CHO cells transiently transfected with FGF17-hFcm or its mutants encoding plasmids (FGF17d197-216-hFcm, FGF17K191AK193AS200A-hFcm). The expressed FGF17-hFcm proteins and the mutant proteins were indicated by the white arrowheads. FIG. 12B) The culture supernatants from CHO cells transiently transfected with different FGF17 encoding plasmids were added into the culture of mouse myoblast cells for 48 hours, followed by 2 hour EdU pulse and fixation. The percentage of EdU+ mouse myoblasts treated with the culture supernatants of CHO cells expressing wild type FGF17-hFcm or mutants FGF17-hFcm (AA197-216 deletion mutant and K191AK193AS200A point mutation mutant) is significantly higher than mouse myoblasts treated with the culture supernatant of CHO cells expressing the empty control vector (One-Way ANOVA Tukey Honest Significant Difference, n=2-6).

FIG. 12B

| Sample | % EdU | SD | p_value |
|---|---|---|---|
| Vector control | 5.288 | 0.883 | — |
| FGF17-hFcm | 33.806 | 1.351 | 5.46E−10 |
| FGF17d197-216-hFcm | 28.699 | 1.926 | 5.30E−9 |
| FGF17K191AK193AS200A-hFcm | 33.828 | 1.434 | 5.42E−10 |

Example 24 Human Serum Albumin (HSA) Fusion FGF17 is More Stable in Culture Medium than FGF17 without HSA Fusion Tag HSA-FGF17 and FGF17 were incubated in culture medium at 37 deg CO2 incubator. At different time point (day 0, 1, 3, 5, and 7), an aliquot was taken and stored at −80 deg. The activity of each sample was evaluated by mouse myoblast in vitro proliferation assay. The nuclei count at each time point from proliferation assay was normalized to day 0 nuclei count.

Example 25 Differential Induction of Myogenic Gene Expression by FGF17 in Mouse Myoblasts Myogenic gene RNA expression (fold change to FM) in response to vehicle (FM) in mouse myoblast cell lines monitored by real-time qPCR. Myoblast were cultured 48h in fusion media. Mean±SD. n=3. (Y,Z) Differential induction of myogenic gene expression by FGF17 in human myoblast myoblasts. Quantitation table of myogenic gene RNA expression (fold change to FM-fusion media (DMEM+ 2% horse serum)) in response to FM or rh-FGF17 in aged human myoblast cell lines by real-time qPCR. Myoblast were cultured (B) 48 hours or (C) 72 hours in FM. Mean∓SD. n=3.

| Condition | Mean | SD | p-value |
|---|---|---|---|
| Gene: Pax7 | | | |
| FM | 1.011 | 0.185 | — |
| FGF17 | 6.118 | 0.920 | 7.05E−04 |
| Gene: Myf5 | | | |
| FM | 1.002 | 0.071 | — |
| FGF17 | 1.376 | 0.201 | 1.69E−02 |
| Gene: Myod1 | | | |
| FM | 1.002 | 0.086 | — |
| FGF17 | 1.230 | 0.158 | n.s. |
| 48 hr Condition | MYF5 Mean | SD | P-value |
| FM | 1.04 | 0.354 | |
| FGF17 | 1.922 | 0.234 | 6.06E−03 |
| 48 hr Condition | MYOD1 Mean | SD | P-value |
| FM | 1.001 | 0.059 | |
| FGF17 | 0.604 | 0.095 | 2.76E−03 |
| 48 hr Condition | MYOG Mean | SD | P-value |
| FM | 1.013 | 0.193 | |
| FGF17 | 2.353 | 0.016 | 5.77E−03 |
| 72 hr Condition | MYF5 Mean | SD | P-value |
| FM | 1.023 | 0.273 | |
| FGF17 | 0.499 | 0.234 | 1.84E−03 |
| 72 hr Condition | MYOD1 Mean | SD | P-value |
| FM | 1.055 | 0.423 | |
| FGF17 | 1.627 | 0.094 | n.s. |
| 72 hr Condition | MYOG Mean | SD | P-value |
| FM | 1.092 | 0.542 | |
| FGF17 | 13.124 | 0.015 | 6.38E−04 |

Example 26 FGF17 Receptor is Expressed in Human Myoblasts

Figure 13A:
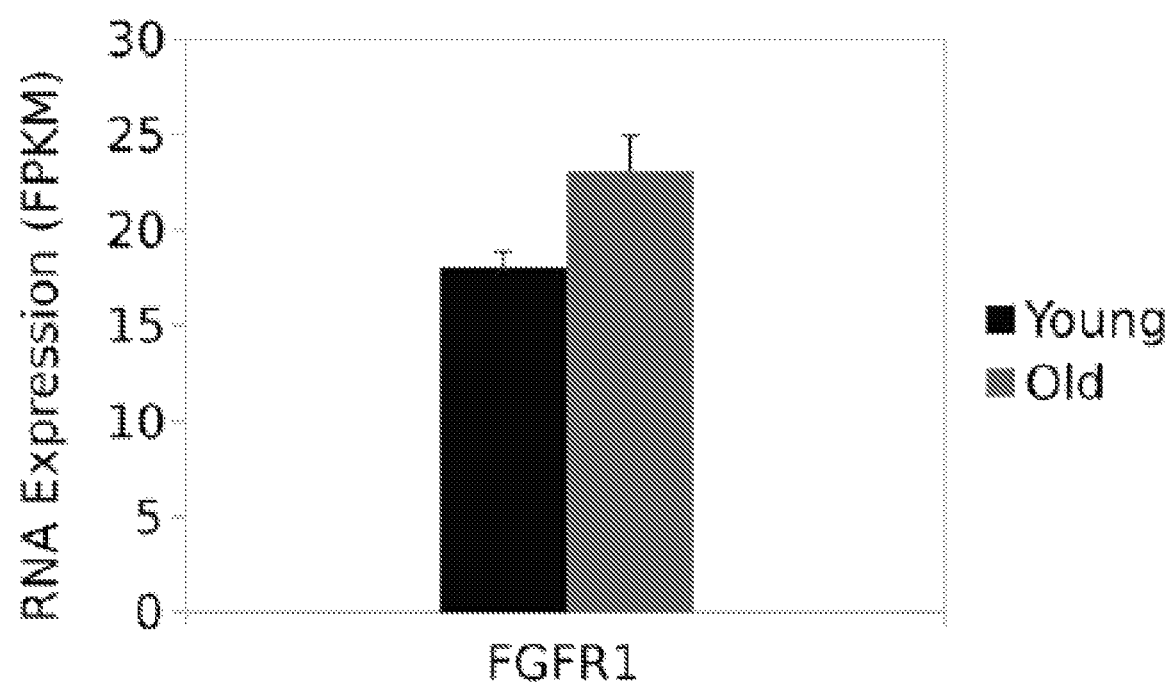
FIG. 13A depicts FGF17 receptor was expressed in human myoblasts.

FIG. 13A: Bar graph of FGF17 receptor RNASeq expression in young and aged human myoblast cell lines. Myoblast were cultured 96h in fusion media with fresh media added every 24h, followed by RNA extraction and sequencing. Mean∓SEM. n=3. Expression values are reported as FPKM.

| GeneName | Young (n = 6) | Old (n = 6) | Young_SEM | Old_SEM |
|---|---|---|---|---|
| FGFR1 | 18.069 | 23.122 | 0.843 | 1.836 |

Example 27 Heparin Enhances FGF17 Mitogenic Activity

Figure 14A:
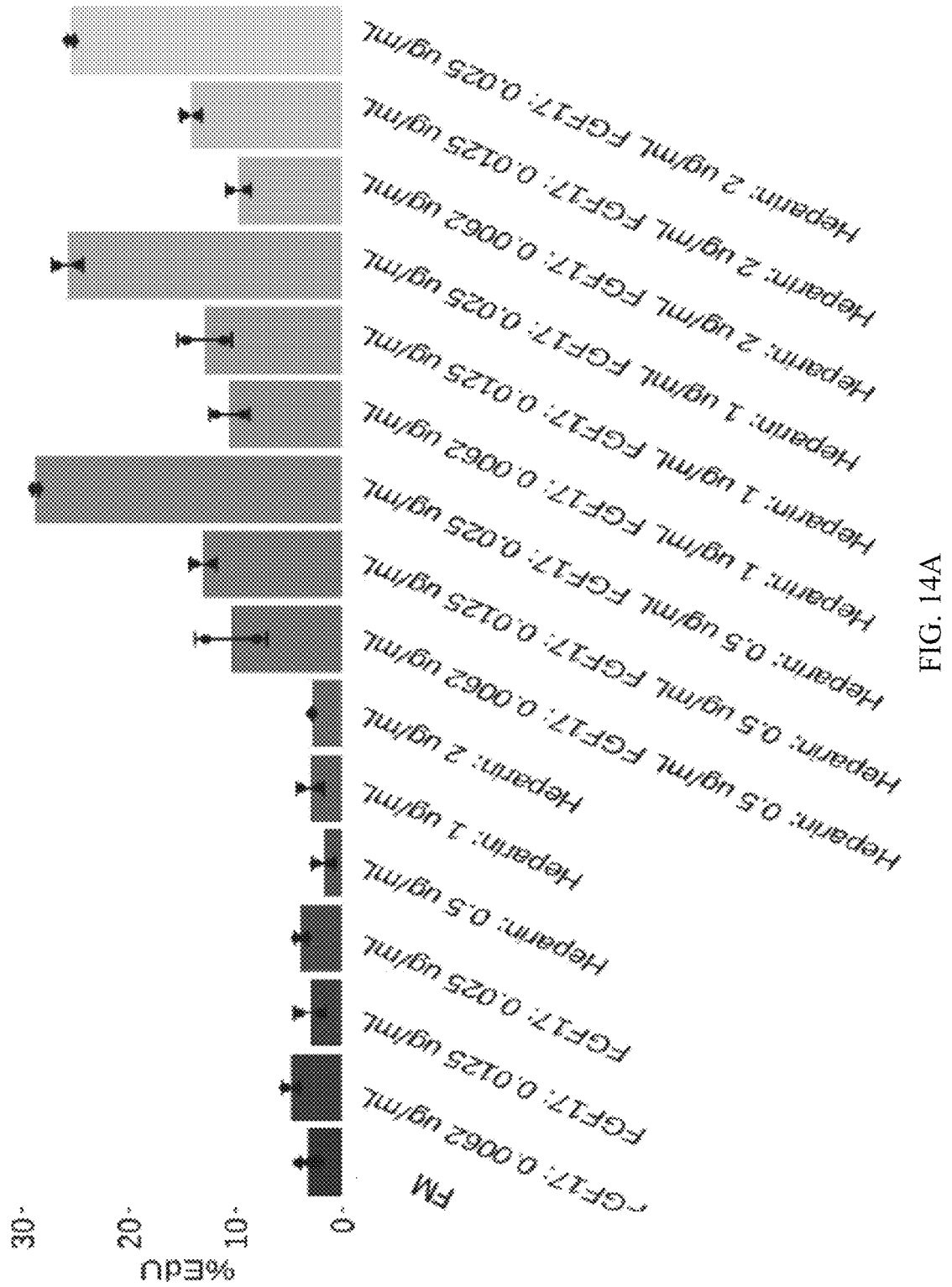
FIG. 14A depicts heparin enhanced FGF17 mitogenic activity.

FIG. 14A: Bar graph of % EdU+ mouse myoblast cells compared to vehicle. Myoblast were cultured 48h in the presence of indicated factors. Fresh media and factors were added every 24h, followed by 2 hour EdU pulse and fixation. Mean∓S.D. Table quantitation of % EdU and p-values ($*p<0.05$ by One-Way ANOVA Tukey Honest Significant Difference, n=2-6)

| Condition | % EdU | SD | p-value |
|---|---|---|---|
| Vehicle | 3.14 | 0.76 | — |
| FGF17: 0.0062 ug/mL | 4.81 | 0.79 | n.s. |
| FGF17: 0.0125 ug/mL | 3.02 | 1.46 | n.s. |
| FGF17: 0.025 ug/mL | 3.85 | 0.59 | n.s. |
| Heparin: 0.5 ug/mL | 1.77 | 1.06 | n.s. |
| Heparin: 1 ug/mL | 3.01 | 1.27 | n.s. |
| Heparin: 2 ug/mL | 2.85 | 0.02 | n.s. |
| Heparin: 0.5 ug/mL FGF17: 0.0062 ug/mL | 10.42 | 3.36 | 9.19E−04 |
| Heparin: 0.5 ug/mL FGF17: 0.0125 ug/mL | 13.01 | 1.24 | 1.09E−06 |
| Heparin: 0.5 ug/mL FGF17: 0.025 ug/mL | 28.73 | 0.29 | p < 0.4E−22 |
| Heparin: 1 ug/mL FGF17: 0.0062 ug/mL | 10.58 | 1.86 | 6.07E−04 |
| Heparin: 1 ug/mL FGF17: 0.0125 ug/mL | 12.88 | 2.50 | 1.54E−06 |
| Heparin: 1 ug/mL FGF17: 0.025 ug/mL | 25.75 | 1.45 | p < 0.4E−22 |
| Heparin: 2 ug/mL FGF17: 0.0062 ug/mL | 9.74 | 1.13 | 4.73E−03 |
| Heparin: 2 ug/mL FGF17: 0.0125 ug/mL | 14.16 | 0.96 | 5.38E−08 |
| Heparin: 2 ug/mL FGF17: 0.025 ug/mL | 25.44 | 0.34 | p < 0.4E−22 |

Example 28 Hyaluronic Acid (HA) Enhances FGF17 Mitogenic Activity

Figure 15A:
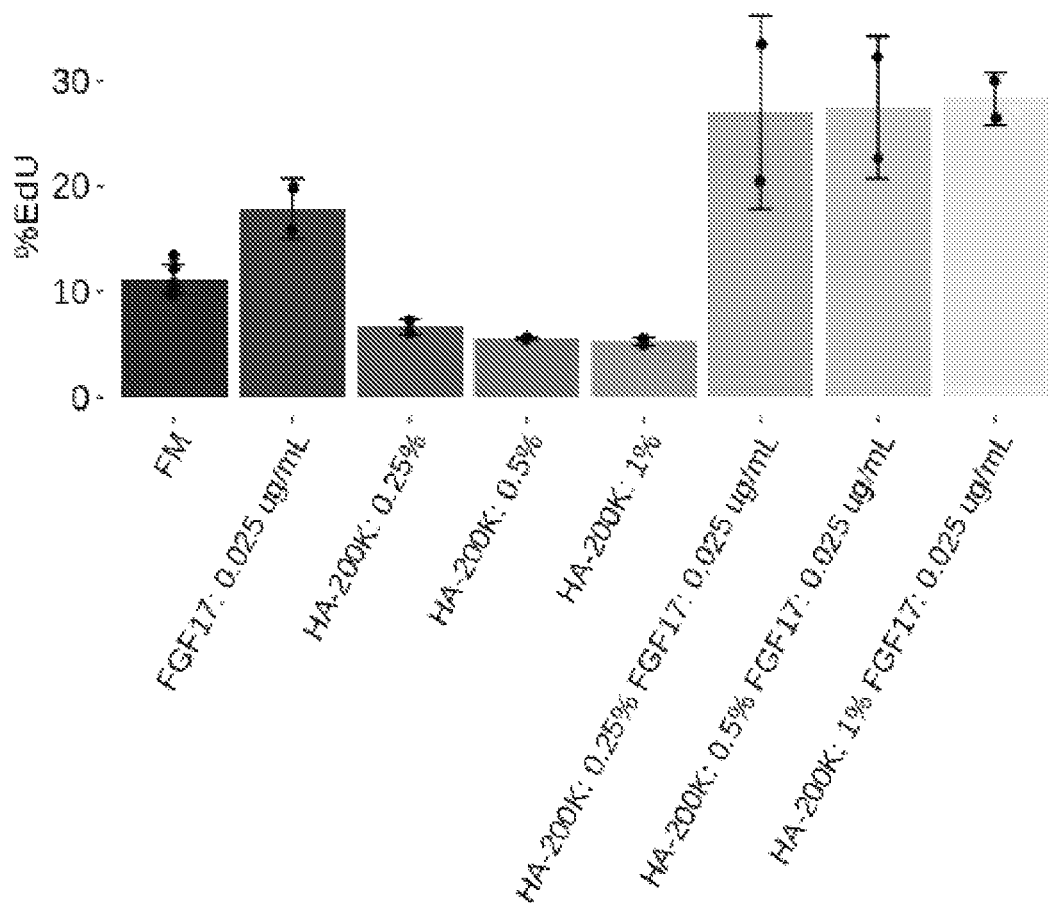
FIG. 15A depicts hyaluronic acid (HA) enhanced FGF17 mitogenic activity.

FIG. 15A: Bar graph of % EdU+ mouse myoblast cells compared to vehicle. Myoblast were cultured 48h in the presence of indicated factors. Fresh media and factors were added every 24h, followed by 2 hour EdU pulse and fixation. Mean∓S.D. Table quantitation of % EdU and p-values shown. ($*p<0.05$ by Student's One-Tailed T-Test of increased activity, n=2-6)

| Condition | N | % Edu | SD | p-value |
|---|---|---|---|---|
| FM | 6 | 11.162 | 1.386 | — |
| FGF17: 0.025 ug/mL | 2 | 17.870 | 2.827 | n.s. |
| HA-200K: 0.25% | 2 | 6.672 | 0.773 | n.s. |
| HA-200K: 0.5% | 2 | 5.561 | 0.116 | n.s. |
| HA-200K: 1% | 2 | 5.276 | 0.366 | n.s. |
| HA-200K: 0.25% FGF17: 0.025 ug/mL | 2 | 26.970 | 9.174 | 2.10E−02 |
| HA-200K: 0.5% FGF17: 0.025 ug/mL | 2 | 27.446 | 6.768 | 7.53E−03 |
| HA-200K: 1% FGF17: 0.025 ug/mL | 2 | 28.252 | 2.511 | 2.49E−04 |

Example 29—Dextran Sulfate (DS) Enhances FGF17 Mitogenic Activity

Bar graph of total EdU+ mouse myoblast cells compared per condition. Myoblast were cultured 48h in the presence of indicated factors. Fresh media and factors were added every 24h, followed by 2 hour EdU pulse and fixation. Mean∓Standard Deviation(SD) Table quantitation of EdU counts per field and p-values for mouse assay (*p<0.05 by Student's One-Tailed T-Test of increased activity, n=3-6, Synergy values <1 are evidence of effect). Bar graph of total EdU+ human myoblast cells per condition. Myoblast were cultured 72h in the presence of indicated factors, followed by 4 hour EdU pulse and fixation. Fresh media and factors were added every 24h. Mean∓Standard Deviation(SD). Table quantitation of +EdU counts and p-values for human assay. (*p<0.05 by Student's One-Tailed T-Test of increased activity, n=3-6, Synergy values <1 are evidence of effect)

Table of data

| Condition- mouse | N | Ave. + EdU Count | SD | p-value | Synergy, Highest Single Agent | Synergy, Response additivity |
|---|---|---|---|---|---|---|
| FM | 6 | 165 | 22 | — | — | — |
| DS10-D3 | 3 | 204 | 23 | — | — | — |
| FGF17 0.01 ug/mL | 3 | 476 | 170 | — | — | — |
| FGF17 0.1 ug/mL | 3 | 1618 | 508 | — | — | — |
| DS10-D3 + 0.01 ug/mL FGF17 | 3 | 3197 | 468 | 3.9E−3 | 0.145 | 0.213 |
| DS10-D3 + 0.1 ug/mL FGF17 | 3 | 6558 | 307 | 3.8E−4 | 0.2247 | 0.278 |

Table of data

| Condition- human | N | Ave. + EdU Counts | SD | p-value | Synergy, Highest Single Agent | Synergy, Response additivity |
|---|---|---|---|---|---|---|
| FM | 3 | 205 | 28 | — | — | — |
| DS10-D2 | 3 | 197 | 18 | — | — | — |
| FGF17 0.1 ug/mL | 3 | 349 | 62 | — | — | — |
| FGF17 0.1 ug/mL + DS10-D2 | 3 | 782 | 85 | 1.9E−3 | 0.45 | 0.70 |

Figure 16A:
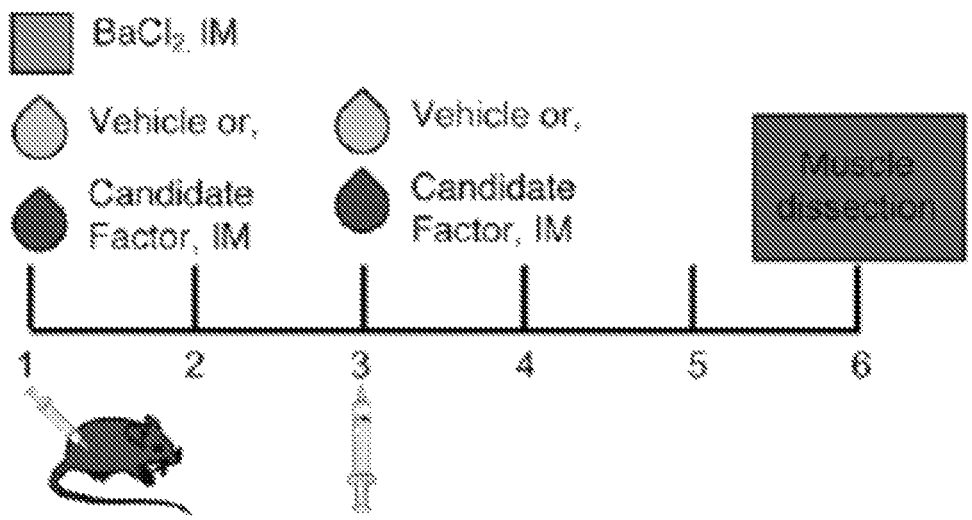
FIG. 16A depicts an experimental overview that demonstrated intramuscular administration of FGF17 promoted the regeneration of muscle in BaCl2 injured old mice model.
Figure 16B:
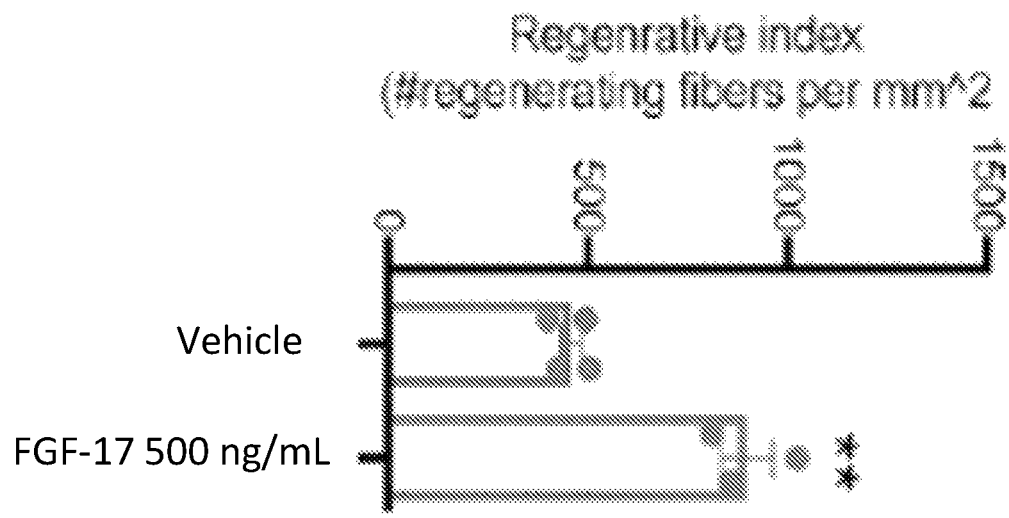
FIG. 16B depicts intramuscular administration of FGF17 promoted the regeneration of muscle in BaCl2 injured old mice model as measured by new fiber formation.
Figure 16C:
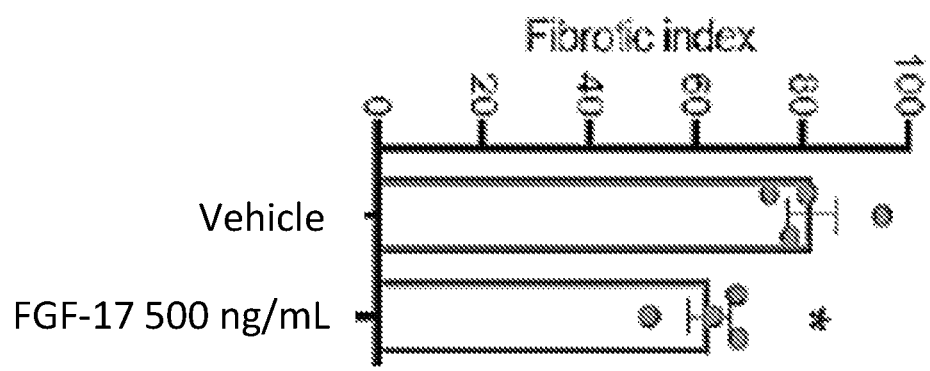
FIG. 16C depicts intramuscular administration of FGF17 promoted the regeneration of muscle in BaCl2 injured old mice model by reducing fibrosis.

Example 30—Intramuscular Administration of FGF17 Promoted the Regeneration of Muscle in BaCl2 Injured Old Mice Model FIG. 16A) Experiment overview. Intramuscular injection of 1.2% of BaCl2 (7 ul/TA) was used to generate chemical injury in the TAs of 78 weeks old mice. FGF17 (500 ng/mL) was administered via intramuscular injection after 2h and 48h of muscle injury. FIG. 16B) Quantification of the regenerative index calculated as the number of newly regenerated fibers per mm 2 of injury area. Regenerated fibers were identified as fibers with central nuclei,****p<0.0001 (unpaired t-test). FIG. 16C) Histogram showing the fibrotic index calculated as the percentage of the fibrotic area. *p=0.0186 (unpaired t-test).

Figure 17A:
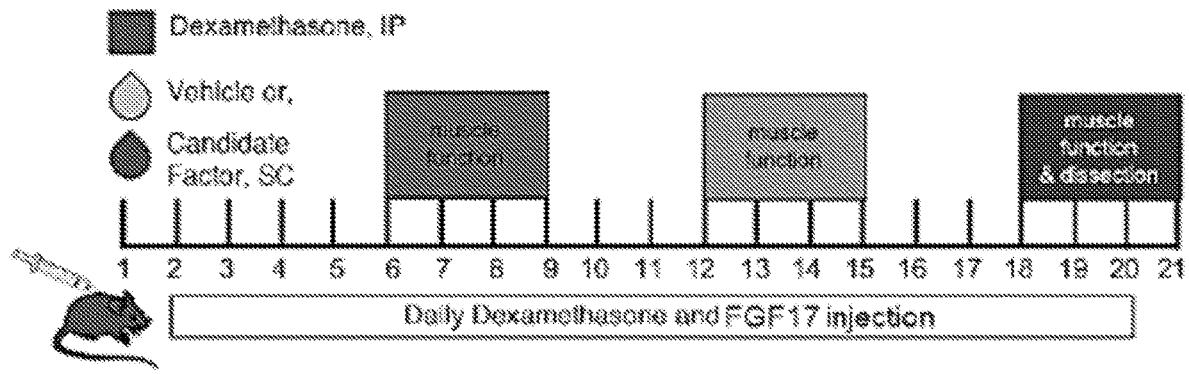
FIG. 17A depicts an experimental overview that demonstrated systemic administration of FGF17 protects against Dexamethasone induced muscle atrophy.
Figure 17B:
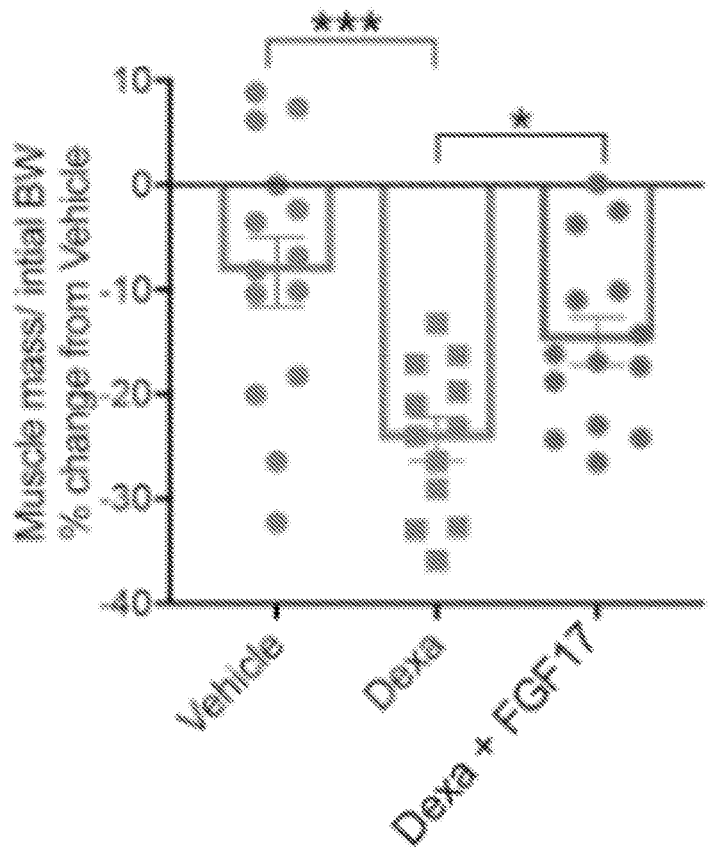
FIG. 17B-D depicts systemic administration of FGF17 protected against Dexamethasone induced muscle atrophy as measured by percent muscle mass change (FIG. 17B), forelimb specific force (FIG. 17C) and bothlimb force (FIG. 17D).
Figure 17C:
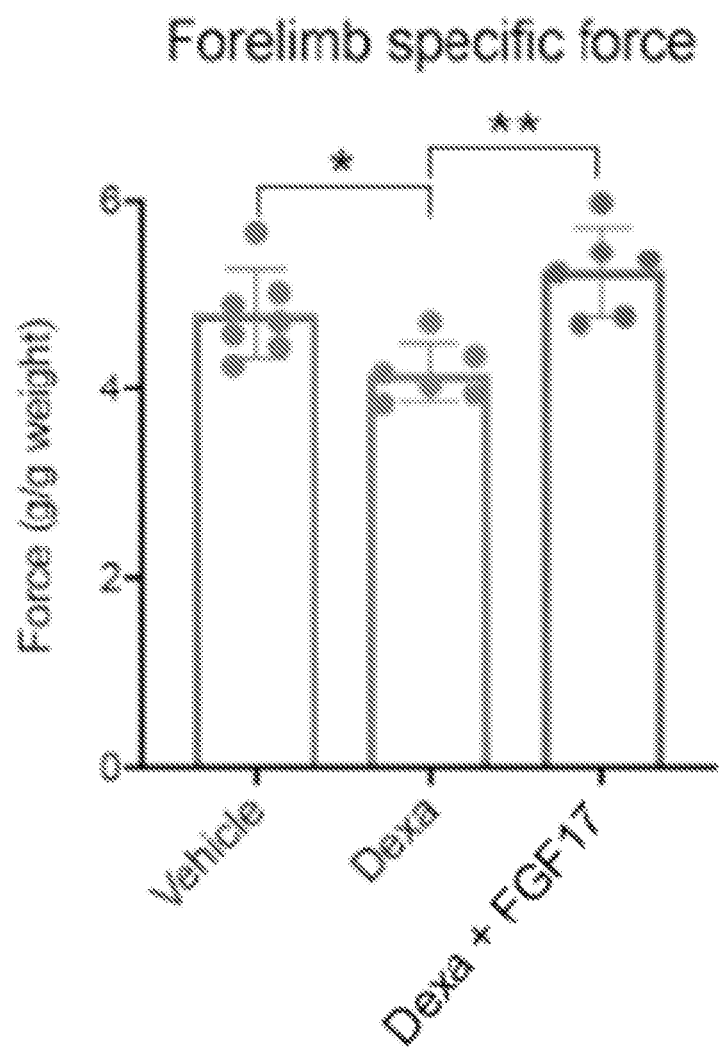
Figure 17D:
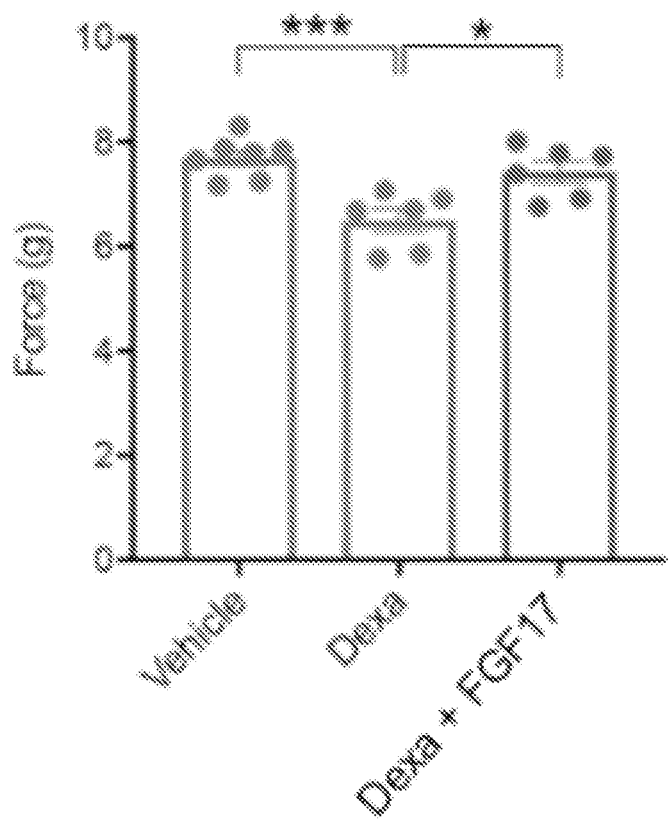

Example 31—Systemic Administration of FGF17 Protects Against Dexamethasone Induced Muscle Atrophy FIG. 17A) Experiment overview and groups. Dexamethasone (25 mg/kg i.p.) was administered to 12 weeks old mice for 20 days simultaneously with a subcutaneous injection of FGF17 (0.5 mg/kg). Muscle weight was assessed on Day 21. Forelimb grip strength and both limb grip strength were measured on Day 7, 13 and 21 FIG. 17B) TAs muscle weight over initial body weight shown as the percentage change from vehicle. ***p=0.0005, *p=0.0499. Forelimb force measured on Day 21, histogram shows the specific forelimb force calculated as the ratio of forelimb force in N over the weight in g, *p=0.0458, p=0.0014 FIG. 17C) Both limb force measured on Day 21 calculated as the ratio of both limb force in N over the weight in g *p=0.001 *p=0.0102. One way Anova corrected for multiple comparisons using Tukey method was used to compare data.

Example 32—Treatment for Chondrocyte Proliferation in Cartilage Injury and Osteoarthritis and FGF17 Induction of Chondrocyte Proliferation RNA expression shows FGF17 receptor was expressed on cartilage-associated cells.) Bar graph quantitation of % EdU+ human chondrocyte in response to FGF17. Chondrocytes were cultured for 48h in the presence of FGF17 at indicated dose. FGF18 was added at 0.1 ug/mL as a positive control. Fresh media and FGF17 was added every 24h. Table of % EdU+ chondrocyte and p-values depicted. Mean∓S.D. (*p<0.05 by Tukey Honest Significant Difference T-test, n=2-3)

TABLE

| FGFR1 RNA Expression (TPM) | |
|---|---|
| Cell Type | FGFR1 |
| Preadipocyte (Subcutaneous) | 54.92 |
| Chondrocyte | 152.59 |
| Osteocyte | 202.57 |
| Tenocyte | 167.01 |

Table of data

| Condition | n | % EdU | sd | adj-p-val |
|---|---|---|---|---|
| Vehicle | 3 | 0.744 | 0.247 | |
| FGF18: 0.1 ug/mL | 3 | 6.039 | 1.637 | 1.29E−03 |
| FGF17: 0.1 ug/mL | 2 | 4.675 | 0.198 | 1.92E−04 |
| FGF17: 0.20 ug/mL | 2 | 9.085 | 0.094 | 7.85E−06 |
| FGF17: 0.40 ug/mL | 2 | 16.773 | 0.621 | 5.42E−07 |

Example 33—Myogenic Activity Measurement Assay In Vitro

Mouse Myoblast Proliferation Assay

Reduced regeneration from an individual's tissue progenitor cells is a hallmark of age or disease related dysfunction, therefore assays that measure mitogenic capacity in tissue progenitor cells serve as a read-out for potential success of a treatment. Measuring the increased proliferation rate, degree of differentiation, and cellular survival of treated mouse or human muscle progenitor cells will provide good basis for potentially therapeutic regenerative factors for treating individuals who have suffered illness, injury, or who possess genetic or developmental defects leading to premature tissue loss, wasting, or weakening.

Mouse muscle progenitor cells (early passage myoblasts) were cultured and expanded in mouse growth medium: Ham's F-10 (Gibco), 20% Bovine Growth Serum (Hyclone), 5 ng/mL FGF2 and 1% penicillin-streptomycin on Matrigel coated plates (1:300 matrigel: PBS), at 37° C. and 5% CO2. For experimental conditions, cells were plated at 40,000 cells/well on Matrigel coated 8-well chamber slides in 250-500 µL medium per well (1:100 matrigel: PBS) in mouse fusion medium: DMEM (Gibco)+2% horse serum (Hyclone). One hour after plating, mouse myoblasts were treated with 50% respective medias: Mouse myoblasts were cultured for 24 hours in the above conditions, at 37° C. in 10% CO2 incubator. BrdU (300 µM) in DMSO was added for 2 hours prior to fixation with cold 70% ethanol and stored at 4° C. until staining.

Quantifying Regenerative Index

Following permeabilization in PBS+0.25% Triton X-100, antigen retrieval was performed. Primary staining was performed with primary antibodies including: a species-specific monoclonal antibody for mouse anti-embryonic Myosin Heavy Chain (eMyHC, hybridoma clone 1.652, Developmental Studies Hybridoma Bank) and Rat-anti-BrdU (Abcam Inc. ab6326). Secondary staining with fluorophore-conjugated, species-specific antibodies (Donkey anti-Rat-488, #712-485-150; Donkey anti-Mouse-488, #715-485-150. Nuclei are visualized by Hoechst staining. Using the Hoechst stain to tally cell numbers, the percent of cells positive for BrdU and eMyHC were tabulated and reported.

FGF17-hFcm Promotes Proliferation of Mouse Myoblasts.

Suspension CHO cells were transiently transfected with either the empty control plasmid or the FGF17-hFcm encoding plasmid. After four days, the culture supernatants were collected and added into the culture of mouse myoblast cells for 48 hours, followed by a 2 hour EdU pulse prior to fixation. The percentage of EdU+ mouse myoblasts treated with the culture supernatant of CHO cells expressing FGF17-hFcm is significantly higher than the percentage of EdU+ mouse myoblasts treated with either vehicle control or the culture supernatant of CHO cells expressing the empty control vector (One-Way ANOVA Tukey Honest Significant Difference, n=2-6).

Suspension CHO cells were transiently transfected with the FGF17-hFcm encoding plasmid. After four days, the culture supernatants were collected and FGF17-hFcm was affinity-purified by Protein A membrane column. The purified FGF17-hFcm was added into the culture of mouse myoblast cells for 48 hours, followed by a 2 hour EdU pulse and fixation. The percentage of EdU+ mouse myoblasts treated with the purified FGF17-hFcm is significantly higher than the percentage of EdU+ mouse myoblasts treated with the culture supernatant of CHO cells expressing the empty control vector (One-Way ANOVA Tukey Honest Significant Difference, n=2-6).

Example 34—Myogenic Gene Profiling for Pro-Regenerative Factors

Expression of myogenic factors Pax7, Myf5, Myod1, and Myog are key indicators of the functional status of muscle progenitor cells. Factors upregulating of Pax7 and Myf5 indicate rejuvenation of proliferative progenitor cells whereas upregulation of Myod1 and Myog are indicative of muscle myofiber regeneration. A read-out of these gene expressions will provide potential success for any given polypeptide comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans described herein. Measuring myogenic genes in mouse or human muscle progenitor cells treated with factors will provide a good characterization of the therapeutic effect for treating individuals who have suffered injury, or who possess genetic or developmental defects leading to premature tissue loss, wasting, or weakening. As a control, the assay will also be performed on proteins purified from differentiated cells, which result in no in myoblast proliferation, cultured in medium conditioned by differentiated cells, or purified heparin-associated fractions.

RNA was isolated from each well (RNeasy Mini Kit, Qiagen) and cDNA was obtained by reverse-transcription (High Capacity Reverse Transcription Kit, Thermo Fisher Scientific). Real-time quantitative PCR was performed using QuantStudio3 (Thermo Fisher).

Aged human myoblasts were cultured in well plates. Culturing the cells with the different medias resulted in differential induction of myogenic gene expression. All factors resulted in changes in at least one myogenic receptor gene at 48 hours and 72 hours when compared to cells cultured in fusion media, as depicted in Table 4. Cells that had been cultured with IGF2 had increases in levels of MYOG at 48 hours and levels of MYOD at 72 hours.

TABLE 4

Myogenic transcription factor fold change increase in myoblasts cultured with IGF2

| Condition | MYF5-48 h | MYOD1-48 h | MYOG-48 h | MYF5-72 h | MYOD1-72 h | MYOG-72 h |
|---|---|---|---|---|---|---|
| FM | 1.04 | 1.001 | 1.013 | 1.023 | 1.055 | 1.092 |
| IGF2 | 0.409 | 0.519 | 5.756 | 0.708 | 5.723 | 0.018 |

Myogenic Gene Profiling in Human or Mouse Progenitor Cells

Human or mouse muscle progenitor cells will be plated and cultured as described above for myogenic activity testing. One hour after plating, myoblasts will be treated with respective factors. Myoblasts are analyzed for expression of Pax7, Myf5, Myod1, and Myog to characterize the regenerative effect of treatment with polypeptides comprising an FGF17, IGF2, or BMP7 amino acid sequence and will be tested to characterize the effects an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans.

Example 35—In Vivo Testing of Stem Cell Secreted Factors

Multiple in vivo models of muscle degeneration will be tested. Given that polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans described herein have regenerative properties in in vitro models, these in vivo models will show that similar regenerative and proliferative effects in the context of intact organ systems.

Acute Injury Model

The experimental groups will be: C57BL/6J male mice, N=18; Young: 12-13 week old (3-month-old) mice, n=6; Aged: 77-78 week old (18-month-old) mice, n=12. This design will be used to test any single factor identified and validated in in vitro assays or polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans.

On Day 0, mice will be weighed and undergo muscle injury with focal injection of barium chloride ($BaCl_2$, 10 µL, 1.2% w/v in saline, Sigma-Aldrich) in the Tibialis anterior (TA; Day 0) of both the right and left hindlegs. Injections of vehicle or factor A (0.1 mg/kg) will be co-administered intramuscularly (i.m) following the $BaCl_2$ into the TA injured hindleg sites, and again 48 hours later on day 2 (i.m.) into the TA injured hindleg sites. Also on day 2, BaCl2 (Ctx; 10 µL, 1.2% w/v in saline, Sigma-Aldrich) was injected into the Gastrocnemius (GA, Day 2, i.m.) muscles of both right and left hind legs. Injections of vehicle or a factor will be sequentially administered (i.m.) following the BaCl2 into the TA hindleg sites post-injury, and again 48 hours later on day 4 (i.m.) into the GA injured hind leg sites. Bromodeoxyuridine (BrdU) was be administered (100 mg/kg, i.p.) once daily for 3 days, day 2-4, before sacrifice to label proliferating cells.

On day 5, animals will be sacrificed, and animal weight recorded followed by collecting 0.5 ml of terminal blood via cardiac puncture which was processed to plasma and stored at 80° C. We then perfuse the animal with 1×PBS, carefully dissect the skin from the GA/TA muscles of each hind leg and took photos (prior to excision). After excision of exclusively the GA or TA muscle, excised tissue is photographed, weighed, then placed into 25% sucrose in PBS at 4° C. for 4 hr rinsed in 1×PBS, immersed in Tissue-TEK OCT and rapidly frozen before storing the muscles tissues frozen at 80° C. Cryosectioning and H&E will be performed to ensure muscle injury site was appropriately visualized. Muscle tissue composition from new skeletal muscle fibers, fibrotic tissue, and adipose (fat), will be measured. Muscle regeneration, as defined as the number of number of new myofibers with centrally located nuclei per millimeter, fibrosis as defined as the area of fibrotic scarring, size of the fibers, as defined as the width and area, adipose tissue, as defined by the amount of fat surrounding the muscle, will be measured to assess level of regeneration.

Sarcopenia/Chronic Administration Model

The experimental design is C57BL/6J male mice, N=18; Young: 12-13 week old (3-month-old) mice, n=6; Aged: 77-78 week old (18-month-old) mice, n=12, as depicted in Table 4. This design can be used to test any single factor identified and validated in in vitro assays or complex mixtures of 2 or more factors or synergistic small molecules.

On Day 0, mice will have the following in vivo healthspan measurements will be performed over 1 day as a baseline for age-based parameters: Weight, running wheel performance, grip strength, and horizontal bar. Each assay should be run for 4 trials per assay per animal. These healthspan assays will be repeated on day −1. After one day of rest on day −9, mice will begin 1× daily injections (0.1 mg/kg) of vehicle or factor A for the remainder of the experiment until sacrifice (days −8 to +5, 13 days of dosing). On day −4, 6 days after dosing begins, mice will undergo a repeat of the healthspan assays. On day 0, 5 days prior to sacrifice, mice will undergo muscle injury with focal injection of cardiotoxin (Ctx; 10 µg, Sigma-Aldrich) in the Tibialis anterior (TA; day 0) of the right hindleg only. On day 2, the Gastrocnemius (GA; day 2) muscle of the right hind leg will then receive cardiotoxin (Ctx; 10 µg, Sigma-Aldrich). BrdU will be administered (100 mg/kg, i.p.) once daily for 3 days, day 2-4, before sacrifice. On day +5, prior to take-down, the animals will have an in vivo incapacitance assay run. On day +5, animals will be sacrificed, and animal weight recorded. We will Collect 0.5 ml of blood via cardiac puncture, process to plasma and store plasma samples at 80° C. The animals will then be perfused with 1×PBS. Carefully dissect the skin from the GA/TA muscles of each hind leg and take photos (prior to excision). After excision of exclusively the GA or TA muscle, we will weigh the muscles, then place muscles into 25% sucrose in PBS at 4° C. for 4 hours, then rinse the muscles in 1×PBS, adding Tissue-TEK OCT and storing the muscles tissues frozen at 80° C. Perform cryosectioning and H&E, ensuring muscle injury site is appropriately visualized. Carefully excising the inguinal white adipose tissue (WAT) will be weighed.

Muscle tissue composition, from new skeletal muscle fibers, fibrotic tissue, and adipose (fat), will be measured. Muscle regeneration, as defined as the number of number of new myofibers with centrally located nuclei per millimeter, fibrosis, as defined as the area of fibrotic scarring, size of the fibers, as defined as the width and area, adipose tissue, as defined by the amount of fat surrounding the muscle, will be measured to assess level of regeneration. Weights of the animals during the duration of treatment, as well as healthspan assays including performance on a running wheel (speed, distance, duration), grip strength, and performance on a horizontal bar will take into account the phenotypic outcomes of treatment of the aged animals systemically with the polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans.

The horizontal bar test will be performed as described previously (Malinowska et al. 2010) at 8 months (n=6 WT, n=7 MPS IIIB) and 10 months (n=3 WT, n=4 MPS IIIB) of age. In brief, a 300-mm metal wire, 2 mm in diameter, was secured between two posts 320 mm above a padded surface. The mouse will be allowed to grip the center of the wire and the time to fall or reach the side was recorded, and after 2 minutes the test was stopped. Crossing the bar in x seconds will be scored as 240−x, remaining on the bar will be scored as 120, and falling off the bar after y seconds will be recorded as the value of y. The test will be repeated three times as a practice run followed by a 10-min rest prior to three tests where the score was recorded.

Animals will also have better healthspan outcomes: reduced weight, fat composition, scar tissue around muscles, increased running speed, duration, and distance, increased grip strength, and enhanced performance on the horizontal bar test.

Genetically Obese Muscle Dystrophy Model

Genetically obese (ob/ob) mice will be injected with BaCl2 on day 0 in the TA muscle. 3 mice will be treated with vehicle only, 3 mice will be injected with the hPSC factors and 3 mice will be treated with FGF19 (positive control) on day 0 and day 2. On day 5, the mice will be euthanized, the TA muscles perfused with PBS, and dissected. Muscles will be then analyzed for regenerative index and fibrotic index.

Atrophy Model

The experimental design is C57BL/6J male mice with daily administration of Vehicle, N=7; dexamethasone (25 mg/kg i.p.), N=6, or dexamethasone+treatment article, N=6, for 20 days. This design can be used to test any single factor identified and validated in in vitro assays or complex mixtures of 2 or more factors.

On day 21, animals are sacrificed, and animal weight recorded. 0.5 ml of blood is collected via cardiac puncture and processed to plasma for storage of plasma samples at −80° C. The animals are perfused with 1×PBS. After carefully dissecting the skin from the GA/TA muscles of each hind leg, photos are taken, followed by excision of exclusively the GA or TA muscle, weighing the muscles, then flash freezing in isopentane at −80 C.

Methods of Testing Muscle Strength, Endurance and Function

Forelimb and Both limb grip strength test: After 30 min acclimation, the mice are introduced to the grip strength meter. For forelimb grip strength, the mice held by the tail are allowed to grasp the grip bar with only its forelimbs. For both limb measurements the mice are placed on the grid and allowed to grasp the grid with both limbs. The force generated by each mouse is calculated as the average of 5-6 measurements.

Limb endurance test: Mice are allowed to discover and acclimate the rodent treadmill environment through 2 training sessions of 10 minutes each at 10m/min on separate days prior to the endurance test. For the endurance test, mice are placed in the individual lanes of the rodent treadmill. The speed is gradually increased at 2m/min until exhaustion is reached. Exhaustion is defined as a mouse staying on a grill electrified to deliver a shock of 2 Hz, intensity 5 for 3-5 seconds.

In vivo tetanic force measurement: Mice are under anesthesia using regulated delivery of isoflurane during the whole process. Following anesthetization, the animal is placed onto a heated chamber with the foot secured on the foot pedal of an Aurora force transducer. The 2 electrodes are placed specifically to stimulate the sciatic nerve. The force generated by the ankle torsion of the animal's hind limb, as opposed to direct force is measured in response to a series of stimulation that includes 50, 100, 150 and 200 Hz.

In situ tetanic force measurement: This experiment is performed using Aurora force measurement. Mice are under anesthesia during the whole process. A small incision in the skin around the Anterior Tibialis exposes the Achilles tendon which is connected via surgical suture to the Aurora force transducer through a hook. The force generated by the muscle in response to a series of stimulation that includes 50, 100, 150 and 200 Hz by 2 electrodes placed on the anterior tibialis is recorded.

Example 36—Mitogenic Polypeptide Stability In Vivo Assayed by Bioavailability and Pharmacokinetics Bioavailability in Tissues The bioavailability of the therapeutic polypeptides will be assessed in the target tissues in young mice (10-12 weeks old) and old mice (78 weeks old). For this experiment, 1 cohort of young mice (10-12 weeks old; N=24) and 1 cohort of old mice (78 weeks old; N=24) will receive 1 subcutaneous (SC) injection of a therapeutic composition. 4 young mice (10-12 weeks old; N=6) and 4 old mice (78 weeks old; N=6) will receive 1 SC injection of Vehicle and used as control. 4 mice from each cohort will be euthanized after 30 minutes, 1 hour, 1.5 hours, 2 hours, or 4 hours. At each time point blood will be collected by heart puncture followed by harvesting select tissues, such as the tibialis anterior, gastrocnemius, quadriceps, heart and diaphragm. The detection and quantitation of the administered therapeutic polypeptides will be detected by enzyme-linked immunosorbent assay (ELISA). The level of therapeutic polypeptides will be compared to the samples collected from mice injected with vehicle to determine tissue level bioavailability.

Pharmacokinetics of Engineered Mitogenic Polypeptides

Murine pharmacokinetics (PK) represents the absorption, distribution, metabolism, and elimination of drugs from the body. The pharmacokinetic profile of the therapeutic polypeptides will be determined in young mice (10-12 weeks old) and old mice (78 weeks old). For this experiment, 2 routes of administration will be investigated, including SC and intravenous (IV) injection in both young (10-12 weeks old) and old mice (78 weeks old). Six time points for each group 5, 15, 30, 60, 90 and 120 minutes will be assessed using end-point or serial sampling. At least 4 animals will be used for each time point/group/route. Engineered mitogenic polypeptides concentrations in the samples will be measured by LC-MS/MS or ELISA. Various pharmacokinetics will be calculated as well as the absorption/elimination dynamics following different routes of administration.

Example 37—Additional Tests for Regenerative Factors

Mechanistic insight into polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans combinations pathway of action will be gained by establishing and screening against a panel of assays for cellular age. Assays include measurements of reactive oxygen species (ROS) production or tolerance cytoplasmically and in the mitochondria, telomerase activity, measurements of proteostasis capacity via lysosomal, autophagy, and proteasomal routes, epigenetic re-patterning, and cellular energy balance (e.g., ATP/ADP and NAD/NADH ratios). Many of these assays leverage high-throughput automated microscopy to make these measurements in a variety of cell types, including fibroblast, endothelial cells, mesenchymal stem cells, and chondrocytes. Collectively these metrics can inform both the pathway and the mechanisms by which the heparin-associated hPSC secretome or its individual components enact their regenerative effects. These deep profile vectors can be crucial for approaching combinations of factors rationally, and for machine learning predictions.

To test the cellular effects of secretomes toward reversing the hallmarks of aging, high-throughput automated imaging and quantification of single cells to achieve deep population level statistical power can be employed. Cellular component state profiles of Young, Aged, and Aged+Treatment in human fibroblasts and epithelial cells, myoblasts, mesenchymal stem cells, chondrocytes, and neural progenitor cells will be compared. Some examples of tests and methods include:

Epigenetic reprogramming: repressive mark H3K9me3, the heterochromatin-associated protein HP1γ, nuclear lamina support protein LAP2α.

Nuclear membrane Folding/Blebbing: immunofluorescence of the nuclear membrane protein Lamin A/C.

Proteolytic Activity: Cleavage of fluorescent-tagged chymotrypsin like substrate corresponds to proteasome 20S core particle activity. Wells will be first stained with PrestoBlue Cell Viability dye (Life Technologies) for 10 minutes. Well signals will be read using a TECAN fluorescence plate reader as a measure of cell count. Then cells will be washed with HBSS/Ca/Mg before switching to original media containing the chymotrypsin like fluorogenic substrate LLVY-R110 (Sigma) which is cleaved by the proteasome 20S core particle. Cells will be then incubated at 37° C. in 5% CO2 for 2 hours before signals will be again read on the TECAN fluorescence plate reader. Readings will be then normalized by PrestoBlue cell count.

Formation of autophagosomes: Autophagosome number and volume will be measured by staining with CellTracker Deep Red (Sigma). The cells will be then incubated at 37° C. in 5% CO2 for 20 minutes, washed 2 times using HBSS/Ca/Mg, and stained for 15 minutes using CellTracker Deep Red cell labeling dye. Cells will be then switched to HBSS/Ca/Mg for single cell imaging using the Operetta High Content Imaging System (Perkin Elmer).

Energy Metabolism: ATP in the cells is measured using colorimetric assay using an ATP assay kit (ab83355; Abcam, Cambridge, MA) following manufacturer's instructions. Cells will be washed in cold phosphate buffered saline and homogenized and centrifuged to collect the supernatant. The samples will be loaded with assay buffer in triplicate. ATP reaction mix and background control (50 μL) is added to the wells and incubated for 30 min in dark. The plate is read at OD 570 nm using SpectraMax M2e (Molecular Devices, Sunnyvale, CA). The mean optical density is used to estimate of the intracellular ATP concentration relative to the standard curve.

Mitochondrial Activity: To measure Mitochondria Membrane Potential, cells will be washed twice with Ham's F10 (no serum or pen/strep). Subsequently, MuSCs will be stained with MitoTracker Green FM (ThermoFisher, M7514) and DAPI for 30 minutes at 37° C., washed three times with Ham's F10, and analyzed using a BD FACSAria III flow cytometer.

Mitochondrial ROS Measurement. Cells will be washed with HBSS/Ca/Mg and then switched to HBSS/Ca/Mg containing MitoSOX (Thermo), a live cell permeant fluorogenic dye that is selectively targeted to mitochondria and fluoresces when oxidized by superoxide. Cells will be incubated for 10 minutes at 37° C. in 5% CO2. Cells will be then washed twice with HBSS/Ca/Mg, and stained for 15 minutes using CellTracker Deep Red. Finally, cells will be imaged in fresh HBSS/Ca/Mg using the Operetta High Content Imaging System (Perkin Elmer).

Deregulated Nutrient Sensing: levels of SIRT1 will be measured.

Senescence: Senescence-associated beta-galactosidase staining is measured in cells washed twice with PBS then fixed with 15% Paraformaldehyde in PBS for 6 minutes. Cells will be rinsed 3 times with PBS before staining with X-gal chromogenic substrate, which is cleaved by endogenous Beta galactosidase. Plates will be kept in the staining solution, Parafilmed, to prevent from drying out, and incubated overnight at 37° C. with ambient CO2. The next day, cells will be washed again with PBS before switching to a 70% glycerol solution for imaging under a Leica brightfield microscope.

Secretome of the cells: Mass-Spec or O-Link for inflammatory cytokines profiles.

Soft Tissue Deposition: Immunofluorescence for SOX9, MMP3, MMP13, and COL2A1 expression, the decrease of which is characterized by cartilage loss, pain, cleft-lip, and joint destruction.

Example 38—the Purified IGF2-hFcm Promoted Differentiation of Myoblast Cells

Suspension CHO cells were transiently transfected with the IGF2-hFcm encoding plasmid. After four days, the culture supernatants were collected and IGF2-hFcm was affinity-purified by Protein A membrane column. The purified IGF2-hFcm was added into the culture of human myoblast cells. Myosin heavy chain (MyHC) was immunostained and imaged by a fluorescent microscope. After quantification of the stained MyHC, the percentage area of MyHC was calculated as the percent of pixels within the field that are illuminated above background in the stained channel. The percentage of EdU of mouse myoblasts treated with the purified IGF2-hFcm is significantly higher than the percentage of EdU of mouse myoblasts treated with the culture supernatant of CHO cells expressing the empty control vector. Significance was determined by a p-value less than 0.05 by the one-way ANOVA Tukey Honest Significant Difference test.

TABLE 5

IGF2 promoted differentiation of myoblast cells

| Condition | % MyHC | SD | p_value |
| --- | --- | --- | --- |
| Vehicle control | 1.787 | 0.186 | |
| 33 nM IGF2-hFcm | 3.734 | 0.790 | 0.012 |
| 66 nM IGF2-hFcm | 5.922 | 0.795 | 3.20E−05 |
| 133 nM IGF2-hFcm | 7.568 | 0.538 | 1.46E−06 |

This example found that the IGF2-fusion protein was able to induce cell proliferation. The IGF2-fusion protein shares in vitro properties with the HAPs, which is suggestive of shared in vivo properties.

Example 39—Modelling Treatment of a Muscular Dystrophy with an IGF2 Composition In Vitro Muscular dystrophies (MD) encompass a variety of muscular degeneration diseases typically due to genetic mutations in genes encoding proteins responsible for forming and stabilizing skeletal muscle. The phenotypic consequence of these genetic mutations is the progressive loss of muscle mass and strength over time, similar to sarcopenia but with different underlying causes. As HAPs provided phenotypic improvements on sarcopenic muscle, we tested for similar improvements in a model for MD.

IGF2 was tested individually for its ability to promote proliferation and/or fusion of human muscle progenitor cells from an individual with myotonic dystrophy type 1 (hMD)—a muscular dystrophy caused by mutations in the DMPK1 gene. The effect of IGF2 on myogenic activity was assayed in biological triplicate across a range of concentrations centered around expected physiological levels by adding each factor to hMD myoblasts for 72 hours with daily media changes (DMEM +2% horse serum) and a second pulse of factors at the first media change. After 72 or 96 hours, cells were pulsed for 2-5 hours with EdU (30 uM), ethanol fixed, stained with Hoescht 3342, immunostained for proliferation—as measured by the percent of cells staining positive for EdU (% EdU)—, and immunostained for differentiation—as measured by the increase in cellular area staining positive for embryonic myosin heavy chain (% eMyHC) relative to the negative controls, which received media and vehicle only. Wells were imaged on a Keyence BZ-100 at 4×, the images quantified in Cell Profiler, and the statistics were computed in R. Additionally, RNA was extracted from myoblast and select transcript abundances quantified by qPCR. depicts IGF2 treatment promoted proliferation and differentiation respectively in DM1 human myoblast (32 year old caucasian female) cells. depict IGF2 enhanced MYH3, CKM, and ATP1B1 expression in DM1 human myoblast (32 year old caucasian female) cells.

Example 40—Systemic Administration of Therapeutic Polypeptides Reverses Sarcopenia and Protects from Muscle Injury A daily subcutaneous injection of therapeutic polypeptides or vehicle only is administered to 78 week old mice for 14 days. IGF2 is injected at a concentration of 100-1000 pg/kg. In some experiments, treatment groups receive a single therapeutic factor while in other experiments, treatment groups receive a combination of factors. At 7 days, muscle function is assessed using forelimb grip strength and both grip strength. On day 12, 13 and 14, groups 1 and 2 are injected with BrdU intraperitoneally. On days 13-15, all mice are assessed for grip strength and an endurance test to determine max distance and max speed and tetanic force.

At 15 days, mice in groups 1 and 2 are euthanized and the muscles are analyzed for markers of proliferation and fibrosis. At 15 days, an intramuscular injection of 1.2% of $BaCl_2$ (7 ul/TA) is used to generate chemical injury in the TAs of group 3 and group 4. Mice from groups 3 and 4 continue to receive a therapeutic polypeptide injected subcutaneously on days 15-21. They also receive BrdU injections intraperitoneally on days 19, 20, and 21. On day 21, the TA muscles are tested for in situ tetanic force. The TA muscles are dissected and assessed for signs of proliferation and fibrosis.

Example 41—Systemic Administration of Fusion Polypeptides Reversed Induced Muscle Atrophy 12-week-old mice are divided into 3 treatment groups: group 1 which receives injections only of the vehicle, group 2 which receives injections of dexamethasone, and group 3 which receives injections of dexamethasone and IGF2 fusion polypeptide. Dexamethasone (25 mg/kg i.p.) is administered for 14 days simultaneously with a subcutaneous injection of IGF2 fusion polypeptide.

At 7 days, mice are assessed for forelimb and both limb grip strength. At days 13-15, mice are assessed for grip strength, in vivo tetanic force, and undergo a treadmill endurance test to determine max speed and max distance.

Example 42—Systemic Administration of IGF2 Fusion Polypeptide Predicted to Improve Muscle Atrophy in Genetically Obese Mice Thirteen-week old genetically obese mice (ob/ob) will be injected subcutaneously with an IGF2 fusion polypeptide for 14 days. At day 7, forelimb and both grip strength will be measured. BrdU is injected on days 12, 13 and 14. On days 13, 14 and 15, forelimb and both limb grip strength and in vivo tetanic force will be tested, and an endurance test to determine max distance and max speed is performed. At 14 days, the mice will be euthanized, and the TA muscles dissected. Muscle weight and proliferation will be analyzed.

Example 43—Systemic Administration of IGF2 Fusion Polypeptide Predicted to Reverse of Slow Down Dystrophic Features in 70 Weeks Old Mdx Mice Another class of human myopathies in need of treatment are the genetic abnormality induced muscular dystrophies, among which Duchenne muscular dystrophy is a rare but fatal case. Old genetically dystrophic (mdx) mice (>15 month old) show similar features to the human Duchenne muscular dystrophy (DMD), notably, a decrease in muscle regeneration leading to muscle wasting. Treatment with IGF2 fusion polypeptide can reverse the dystrophic features of old mdx mice. During the acclimation period, the weight, Forelimb and both limb grip strength as well as in vivo tetanic force will be assessed to determine the baseline strength of each mouse. 70 week dystrophic mice (mdx) are injected with the IGF2 fusion polypeptide subcutaneously for 14 days. At day 7, forelimb and both grip strength are measured. BrdU is injected on days 12, 13 and 14. On days 13, 14, and 15, forelimb and both limb grip strength and in vivo tetanic force are tested, and an endurance test to determine max distance and max speed is performed. The right tibialis anterior and gastrocnemius will be collected, immersed in Tissue-TEK OCT and then flash frozen in chilled isopentane bath precooled in liquid nitrogen and stored at −80° C. Tissue will be sectioned and stained for Laminin to determine the cross sectional area (CSA) of muscle fibers, for eMyHC to measure new fiber formation and for BrdU to assess the proliferation rate. The left anterior tibialis and gastrocnemius will be collected and flash frozen in liquid nitrogen for molecular analysis that include qPCR and western blot.

IGF2 is predicted to be effective at a concentration of 10-200 ug/kg.

Example 44—Systemic Administration of IGF2 Fusion Polypeptide Predicted to Improve the Dystrophic Features in 6 Week Old Mice Between 3-6 weeks old, the skeletal muscle of mdx mice undergoes severe necrosis followed by an increase in the activation of satellite cells to promote muscle regeneration. Treatment with IGF2 fusion polypeptide described herein can improve the regeneration process and therefore muscle health. During the acclimation period, the weight, Forelimb and both limb grip strength as well as in vivo tetanic force will be assessed to determine the baseline strength of each mouse. 6 week old dystrophic mice (mdx) are injected with the IGF2 fusion polypeptide subcutaneously for 14 days. At day 7, forelimb and both grip strength are measured. BrdU is injected on days 12, 13 and 14. On days 13, 14 and 15, forelimb and both limb grip strength and in vivo tetanic force are tested, and an endurance test to determine max distance and max speed is performed.

Mice will be euthanized. The right tibialis anterior and gastrocnemius will be collected, immersed in Tissue-TEK OCT and then flash frozen in chilled isopentane bath precooled in liquid nitrogen and stored at −80° C. Tissue will be sectioned and stained for Laminin to determine the cross sectional area (CSA) of muscle fibers, for eMyHC to measure new fiber formation and for BrdU to assess the proliferation rate. The left anterior tibialis and gastrocnemius will be collected and flash frozen in liquid nitrogen for molecular analysis that include qPCR and western blot.

IGF2 is predicted to be effective at a concentration of 10-200 µg/kg.

Example 45—Treatment for Chondrocyte Proliferation in Cartilage Injury and Osteoarthritis Cartilage can become damaged as a result of a sudden injury or due to gradual wear and tear or inflammation leading to disease states (e.g. osteoarthritis). Chondrocytes secrete the cartilage matrix and preadipocytes, osteocytes and tenocytes are all cell types associated with cartilage.

Preadipocytes, chondrocytes, osteocytes and tenocytes were cultured in well plates. RNA was isolated from each well (RNeasy Mini Kit, Qiagen) and cDNA was obtained by reverse-transcription (High Capacity Reverse Transcription Kit, Thermo Fisher Scientific). Real-time quantitative PCR was performed using QuantStudio3 (Thermo Fisher).

These cartilage-associated cells expressed receptors for polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans. Subcutaneous pre-adipocytes, chondrocytes, osteocytes and tenocytes all expressed one or more receptors, indicating that these polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans may be able to affect cartilage loss and the progression of joint related injury or disease recovery.

Example 46—Clinical Testing of Therapeutic Compositions

The purpose of this study is to determine the safety, tolerability, and pharmacokinetics of repeat dosing with multiple dose levels of polypeptides comprising an FGF17, IGF2, or BMP7 amino acid sequence and an amino acid sequence from a heterologous polypeptide or combinations of an Fibroblast Growth Factor Receptor agonist and a glycosaminoglycan, an Insulin-like Growth Factor 1 Receptor (IGF1R) agonist and a short chain fatty acid, and BMP receptor agonists and mTOR activators and/or glycosaminoglycans in healthy individuals or individuals diagnosed with sarcopenia, a muscular dystrophy, or recovery from surgery. In certain embodiments, the muscular dystrophy is myotonic dystrophy. In addition, this study will generate data on the physical function, skeletal muscle mass and strength resulting from treatment with IGF2 fusion polypeptides in such individuals. Individuals will be administered placebo or IGF2 fusion polypeptide compositions and monitored for 25 weeks of study. The following primary and secondary outcome measures will be assessed:

Primary Outcome Measures:

Safety and tolerability as assessed by various measures such as percent of adverse events per study arm.

Secondary Outcome Measures:

Plasma Pharmacokinetics (Cmax, Tmax, AUC) [Plasma at 0.5, 1, 1.5, 2, 4, 6, 8, 12 and 24 hrs after dosing.]

Short Physical Performance Battery (SPPB). Change from baseline to week 25.

10-meter walk test. Change from baseline to week 25.

Change in total lean body mass and appendicular skeletal muscle index measured by Dual-energy X-ray Absorptiometry (DEXA) from baseline to week 25.

Inclusion Criteria:

Diagnosis of sarcopenia, a muscular dystrophy, or recovery from surgery; Low muscle mass as confirmed by DXA; Low gait speed; SPPB score less than or equal to 9; Weigh at least 35 kg; with adequate dietary intake as determined by patient interview. Independently ambulatory to 10 meters.

Protocol

Patients will be i.v.-administered placebo (5% dextrose solution) or treatment article (in 5% dextrose). Starting on day 1, week 1 and repeated every week (day one of weeks 1 through 25). At the end of week 13 and 25 patients will be assessed by the above methods for improvement. Doses will be selected from a traditional 3+3 design, and selected as the top two-doses that lack dose-limiting toxicity.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

TABLE 1

Secretory Signal Sequences

| Seq ID No | Sequence Name | Description | Sequence |
|---|---|---|---|
| 1 | spFGF-17 | Human FGF-17 secretory signal peptide nucleotide sequence | ATGGGAGCCGCCCGCCTGCTGCCCAACCTCA CTCTGTGCTTACAGCTGCTGATTCTCTGCTGT CAA |
| 2 | spTHBS1 | Human THBS1 secretory signal peptide nucleotide sequence | ATGGGGGCTGGCCTGGGGACTAGGCGTCCTGT TCCTGATGCATGTGTGTGGCACC |

TABLE 1-continued

Secretory Signal Sequences

| Seq ID No | Sequence Name | Description | Sequence |
|---|---|---|---|
| 3 | spIGF-2 | Human IGF-2 secretory signal peptide nucleotide sequence | ATGGGAATCCCAATGGGGAAGTCGATGCTGG TGCTTCTCACCTTCTTGGCCTTCGCCTCGTGC TGCATTGCT |
| 4 | spBMP-7 | Human BMP-7 secretory signal peptide nucleotide sequence | ATGCACGTGCGCTCACTGCGAGCTGCGGCGC CGCACAGCTTCGTGGCGCTCTGGGCACCCCT GTTCCTGCTGCGCTCCGCCCTGGCC |
| 5 | spALB | Human Albumin secretory signal peptide nucleotide sequence | ATGAAGTGGGTAACCTTTATTTCCCTTCTTTT TCTCTTTAGCTCGGCTTATTCC |
| 6 | spAZU1 | Human Azurocidin secretory signal peptide nucleotide sequence | ATGACCCGGCTGACAGTCCTGGCCCTGCTGG CTGGTCTGCTGGCGTCCTCGAGGGCC |
| 7 | spBM40 | Human osteonectin secretory signal peptide nucleotide sequence | ATGAGGGCCTGGATCTTCTTTCTCCTTTGCCT GGCCGGGAGGGCTCTGGCAGCA |
| 8 | spGAU | Gaussia luciferase secretory signal peptide nucleotide sequence | ATGGGAGTCAAAGTTCTGTTTGCCCTGATCTG CATCGCTGTGGCCGAGGCC |
| 9 | spFGF-17 | Human FGF-17 secretory signal peptide amino acid sequence | MGAARLLPNLTLCLQLLILCCQ |
| 10 | spTHBS1 | Human THBS1 secretory signal peptide amino acid sequence | MGLAWGLGVLFLMHVCGT |
| 11 | spIGF-2 | Human IGF-2 secretory signal peptide amino acid sequence | MGIPMGKSMLVLLTFLAFASCCIA |
| 12 | spBMP-7 | Human BMP-7 secretory signal peptide amino acid sequence | MHVRSLRAAAPHSFVALWAPLFLLRSALA |
| 13 | spALB | Human Albumin secretory signal peptide amino acid sequence | MKWVTFISLLFLFSSAYS |
| 14 | spAZU1 | Human Azurocidin secretory signal peptide amino acid sequence | MTRLTVLALLAGLLASSRA |
| 15 | spBM40 | Human osteonectin secretory signal peptide amino acid sequence | MRAWIFFLLCLAGRALAA |
| 16 | spGAU | Gaussia luciferase secretory signal peptide amino acid sequence | MGVKVLFALICIAVAEA |

TABLE 2

Therapeutic Sequences

| Seq ID No | Sequence Name | Description | Sequence |
|---|---|---|---|
| 17 | FGF-17 | Full length of human FGF-17 nucleotide sequence | ACTCAGGGGGAGAATCACCCGTCTCCTAATTTTAACCAG TACGTGAGGGACCAGGGCGCCATGACCGACCAGCTGAG CAGGCGGCAGATCCGCGAGTACCAACTCTACAGCAGGA CCAGTGGCAAGCACGTGCAGGTCACCGGGCGTCGCATCT CCGCCACCGCCGAGGACGGCAACAAGTTTGCCAAGCTC ATAGTGGAGACGGACACGTTTGGCAGCCGGGTTCGCATC AAAGGGGCTGAGAGTGAGAAGTACATCTGTATGAACAA GAGGGGCAAGCTCATCGGGAAGCCCAGCGGGAAGAGCA AGACTGCGTGTTCACGGAGATCGTGCTGGAGAACAAC |

TABLE 2-continued

Therapeutic Sequences

| Seq ID No | Sequence Name | Description | Sequence |
|---|---|---|---|
| | | | TATACGGCCTTCCAGAACGCCCGGCACGAGGGCTGGTTC ATGGCCTTCACGCGGCAGGGGCGGCCCCGCCAGGCTTCC CGCAGCCGCCAGAACCAGCGCGAGGCCCACTTCATCAA GCGCCTCTACCAAGGCCAGCTGCCCTTCCCCAACCACGC CGAGAAGCAGAAGCAGTTCGAGTTTGTGGGCTCCGCCCC CACCCGCCGGACCAAGCGCACACGGCGGCCCCAGCCCC TCACG |
| 18 | FGF-17d204-216 | Human FGF-17 AA204-216 deletion mutant nucleotide sequence | ACTCAGGGGAGAATCACCCGTCTCCTAATTTTAACCAG TACGTGAGGGACCAGGGCGCCATGACCGACCAGCTGAG CAGGCGGCAGATCCGCGAGTACCAACTCTACAGCAGGA CCAGTGGCAAGCACGTGCAGGTCACCGGGCGTCGCATCT CCGCCACCGCCGAGGACGGCAACAAGTTTGCCAAGCTC ATAGTGGAGACGGACACGTTTGGCAGCCGGGTTCGCATC AAAGGGGCTGAGAGTGAGAAGTACATCTGTATGAACAA GAGGGGCAAGCTCATCGGGAAGCCCAGCGGGAAGAGCA AAGACTGCGTGTTCACGGAGATCGTGCTGGAGAACAAC TATACGGCCTTCCAGAACGCCCGGCACGAGGGCTGGTTC ATGGCCTTCACGCGGCAGGGGCGGCCCCGCCAGGCTTCC CGCAGCCGCCAGAACCAGCGCGAGGCCCACTTCATCAA GCGCCTCTACCAAGGCCAGCTGCCCTTCCCCAACCACGC CGAGAAGCAGAAGCAGTTCGAGTTTGTGGGCTCCGCCCC CACC |
| 19 | FGF-17d181-216 | Human FGF-17 AA181-216 deletion mutant nucleotide sequence | ACTCAGGGGAGAATCACCCGTCTCCTAATTTTAACCAG TACGTGAGGGACCAGGGCGCCATGACCGACCAGCTGAG CAGGCGGCAGATCCGCGAGTACCAACTCTACAGCAGGA CCAGTGGCAAGCACGTGCAGGTCACCGGGCGTCGCATCT CCGCCACCGCCGAGGACGGCAACAAGTTTGCCAAGCTC ATAGTGGAGACGGACACGTTTGGCAGCCGGGTTCGCATC AAAGGGGCTGAGAGTGAGAAGTACATCTGTATGAACAA GAGGGGCAAGCTCATCGGGAAGCCCAGCGGGAAGAGCA AAGACTGCGTGTTCACGGAGATCGTGCTGGAGAACAAC TATACGGCCTTCCAGAACGCCCGGCACGAGGGCTGGTTC ATGGCCTTCACGCGGCAGGGGCGGCCCCGCCAGGCTTCC CGCAGCCGCCAGAACCAGCGCGAGGCCCACTTCATCAA GCGCCTCTACCAA |
| 20 | FGF-17R204Q K207Q | Human FGF-17 R204Q K207Q mutant nucleotide sequence | ACTCAGGGGAGAATCACCCGTCTCCTAATTTTAACCAG TACGTGAGGGACCAGGGCGCCATGACCGACCAGCTGAG CAGGCGGCAGATCCGCGAGTACCAACTCTACAGCAGGA CCAGTGGCAAGCACGTGCAGGTCACCGGGCGTCGCATCT CCGCCACCGCCGAGGACGGCAACAAGTTTGCCAAGCTC ATAGTGGAGACGGACACGTTTGGCAGCCGGGTTCGCATC AAAGGGGCTGAGAGTGAGAAGTACATCTGTATGAACAA GAGGGGCAAGCTCATCGGGAAGCCCAGCGGGAAGAGCA AAGACTGCGTGTTCACGGAGATCGTGCTGGAGAACAAC TATACGGCCTTCCAGAACGCCCGGCACGAGGGCTGGTTC ATGGCCTTCACGCGGCAGGGGCGGCCCCGCCAGGCTTCC CGCAGCCGCCAGAACCAGCGCGAGGCCCACTTCATCAA GCGCCTCTACCAAGGCCAGCTGCCCTTCCCCAACCACGC CGAGAAGCAGAAGCAGTTCGAGTTTGTGGGCTCCGCCCC CACCCaGCGGACCCAGCGCACACGGCGGCCCCAGCCCCT CACG |
| 21 | FGF-17d197-216 | Human FGF17 AA197-216 deletion mutant nucleotide sequence | ACTCAGGGGAGAATCACCCGTCTCCTAATTTTAACCAG TACGTGAGGGACCAGGGCGCCATGACCGACCAGCTGAG CAGGCGGCAGATCCGCGAGTACCAACTCTACAGCAGGA CCAGTGGCAAGCACGTGCAGGTCACCGGGCGTCGCATCT CCGCCACCGCCGAGGACGGCAACAAGTTTGCCAAGCTC ATAGTGGAGACGGACACGTTTGGCAGCCGGGTTCGCATC AAAGGGGCTGAGAGTGAGAAGTACATCTGTATGAACAA GAGGGGCAAGCTCATCGGGAAGCCCAGCGGGAAGAGCA AAGACTGCGTGTTCACGGAGATCGTGCTGGAGAACAAC TATACGGCCTTCCAGAACGCCCGGCACGAGGGCTGGTTC ATGGCCTTCACGCGGCAGGGGCGGCCCCGCCAGGCTTCC CGCAGCCGCCAGAACCAGCGCGAGGCCCACTTCATCAA GCGCCTCTACCAAGGCCAGCTGCCCTTCCCCAACCACGC CGAGAAGCAGAAGCAGTTCGAG |
| 22 | FGF-17K191A K193AS200A | Human FGF-17 K191A K193A S200A | ACTCAGGGGAGAATCACCCGTCTCCTAATTTTAACCAG TACGTGAGGGACCAGGGCGCCATGACCGACCAGCTGAG CAGGCGGCAGATCCGCGAGTACCAACTCTACAGCAGGA CCAGTGGCAAGCACGTGCAGGTCACCGGGCGTCGCATCT CCGCCACCGCCGAGGACGGCAACAAGTTTGCCAAGCTC |

TABLE 2-continued

Therapeutic Sequences

| Seq ID No | Sequence Name | Description | Sequence |
|---|---|---|---|
| | | mutant nucleotide sequence | ATAGTGGAGACGGACACGTTTGGCAGCCGGGTTCGCATC<br>AAAGGGGCTGAGAGTGAGAAGTACATCTGTATGAACAA<br>GAGGGGCAAGCTCATCGGGAAGCCCAGCGGGAAGAGCA<br>AAGACTGCGTGTTCACGGAGATCGTGCTGGAGAACAAC<br>TATACGGCCTTCCAGAACGCCCGGCACGAGGGCTGGTTC<br>ATGGCCTTCACGCGGCAGGGGCGGCCCCGCCAGGCTTCC<br>CGCAGCCGCCAGAACCAGCGCGAGGCCCACTTCATCAA<br>GCGCCTCTACCAAGGCCAGCTGCCCTTCCCCAACCACGC<br>CGAGGctCAGGcaCAGTTCGAGTTTGTGGGCgCtGCCCCCA<br>CCCGCCGGACCAAGCGCACACGGCGGCCCCAGCCCCTC<br>ACG |
| 23 | FGF-17-linker1-hFcm | Full length of human FGF-17-linker1-hFcm nucleotide sequence | ACTCAGGGGAGAATCACCCGTCTCCTAATTTTAACCAG<br>TACGTGAGGGACCAGGGCGCCATGACCGACCAGCTGAG<br>CAGGCGGCAGATCCGCGAGTACCAACTCTACAGCAGGA<br>CCAGTGGCAAGCACGTGCAGGTCACCGGGCGTCGCATCT<br>CCGCCACCGCCGAGGACGGCAACAAGTTTGCCAAGCTC<br>ATAGTGGAGACGGACACGTTTGGCAGCCGGGTTCGCATC<br>AAAGGGGCTGAGAGTGAGAAGTACATCTGTATGAACAA<br>GAGGGGCAAGCTCATCGGGAAGCCCAGCGGGAAGAGCA<br>AAGACTGCGTGTTCACGGAGATCGTGCTGGAGAACAAC<br>TATACGGCCTTCCAGAACGCCCGGCACGAGGGCTGGTTC<br>ATGGCCTTCACGCGGCAGGGGCGGCCCCGCCAGGCTTCC<br>CGCAGCCGCCAGAACCAGCGCGAGGCCCACTTCATCAA<br>GCGCCTCTACCAAGGCCAGCTGCCCTTCCCCAACCACGC<br>CGAGAAGCAGAAGCAGTTCGAGTTTGTGGGCTCCGCCCC<br>CACCCGCCGGACCAAGCGCACACGGCGGCCCCAGCCCC<br>TCACGGGATCGGGATCGGACAAAACTCACACATGCCCA<br>CCGTGCCCAGCACCTGAAGCTGCCGGGGGACCGTCAGTC<br>TTCCTCTTCCCCCCAAAACCCAAGGACACCCTCATGATC<br>TCCCGGACCCCTGAGGTCACATGCGTGGTGGTGGACGTG<br>AGCCACGAAGACCCTGAGGTCAAGTTCAACTGGTACGT<br>GGACGGCGTGGAGGTGCATAATGCCAAGACAAAGCCGC<br>GGGAGGAGCAGTACAACAGCACGTACCGTGTGGTCAGC<br>GTCCTCACCGTCCTGCACCAGGACTGGCTGAATGGCAAG<br>GAGTACAAGTGCAAGGTCTCCAACAAAGCCCTCGGCGC<br>CCCCATCGAGAAAACCATCTCCAAAGCCAAAGGGCAGC<br>CCCGAGAACCACAGGTGTACACCCTGCCCCCATCCCGGG<br>ATGAGCTGACCAAGAACCAGGTCAGCCTGACCTGCCTG<br>GTCAAAGGCTTCTATCCCAGCGACATCGCCGTGGAGTGG<br>GAGAGCAATGGGCAGCCGGAGAACAACTACAAGACCAC<br>GCCTCCCGTGCTGGACTCCGACGGCTCCTTCTTCCTCTAC<br>AGCAAGCTCACCGTGGACAAGAGCAGGTGGCAGCAGGG<br>GAACGTCTTCTCATGCTCCGTGATGCATGAGGCTCTGCA<br>CAACCACTACACGCAGAAaAGCCTCTCCCTGTCTCCGGG<br>TAAA |
| 24 | FGF-17d204-216-linker1-hFcm | Human FGF-17 AA204-216 deletion mutant-linker1-hFcm nucleotide sequence | ACTCAGGGGAGAATCACCCGTCTCCTAATTTTAACCAG<br>TACGTGAGGGACCAGGGCGCCATGACCGACCAGCTGAG<br>CAGGCGGCAGATCCGCGAGTACCAACTCTACAGCAGGA<br>CCAGTGGCAAGCACGTGCAGGTCACCGGGCGTCGCATCT<br>CCGCCACCGCCGAGGACGGCAACAAGTTTGCCAAGCTC<br>ATAGTGGAGACGGACACGTTTGGCAGCCGGGTTCGCATC<br>AAAGGGGCTGAGAGTGAGAAGTACATCTGTATGAACAA<br>GAGGGGCAAGCTCATCGGGAAGCCCAGCGGGAAGAGCA<br>AAGACTGCGTGTTCACGGAGATCGTGCTGGAGAACAAC<br>TATACGGCCTTCCAGAACGCCCGGCACGAGGGCTGGTTC<br>ATGGCCTTCACGCGGCAGGGGCGGCCCCGCCAGGCTTCC<br>CGCAGCCGCCAGAACCAGCGCGAGGCCCACTTCATCAA<br>GCGCCTCTACCAAGGCCAGCTGCCCTTCCCCAACCACGC<br>CGAGAAGCAGAAGCAGTTCGAGTTTGTGGGCTCCGCCCC<br>CACCCGGATCGGGATCGGACAAAACTCACACATGCCCAC<br>CGTGCCCAGCACCTGAAGCTGCCGGGGGACCGTCAGTCT<br>TCCTCTTCCCCCCAAAACCCAAGGACACCCTCATGATCT<br>CCCGGACCCCTGAGGTCACATGCGTGGTGGTGGACGTGA<br>GCCACGAAGACCCTGAGGTCAAGTTCAACTGGTACGTG<br>GACGGCGTGGAGGTGCATAATGCCAAGACAAAGCCGCG<br>GGAGGAGCAGTACAACAGCACGTACCGTGTGGTCAGCG<br>TCCTCACCGTCCTGCACCAGGACTGGCTGAATGGCAAGG<br>AGTACAAGTGCAAGGTCTCCAACAAAGCCCTCGGCGCC<br>CCCATCGAGAAAACCATCTCCAAAGCCAAAGGGCAGCC<br>CCGAGAACCACAGGTGTACACCCTGCCCCCATCCCGGGA<br>TGAGCTGACCAAGAACCAGGTCAGCCTGACCTGCCTGGT<br>CAAAGGCTTCTATCCCAGCGACATCGCCGTGGAGTGGGA<br>GAGCAATGGGCAGCCGGAGAACAACTACAAGACCACGC |

TABLE 2-continued

Therapeutic Sequences

| Seq ID No | Sequence Name | Description | Sequence |
|---|---|---|---|
| | | | CTCCCGTGCTGGACTCCGACGGCTCCTTCTTCCTCTACAG CAAGCTCACCGTGGACAAGAGCAGGTGGCAGCAGGGGA ACGTCTTCTCATGCTCCGTGATGCATGAGGCTCTGCACA ACCACTACACGCAGAAaAGCCTCTCCCTGTCTCCGGGTA AA |
| 25 | FGF-17d181-216-linker1-hFcm | Human FGF-17 AA181-216 deletion mutant-linker1-hFcm nucleotide sequence | ACTCAGGGGGAGAATCACCCGTCTCCTAATTTTAACCAG TACGTGAGGGACCAGGGCGCCATGACCGACCAGCTGAG CAGGCGGCAGATCCGCGAGTACCAACTCTACAGCAGGA CCAGTGGCAAGCACGTGCAGGTCACCGGGCGTCGCATCT CCGCCACCGCCGAGGACGGCAACAAGTTTGCCAAGCTC ATAGTGGAGACGGACACGTTTGGCAGCCGGGTTCGCATC AAAGGGGCTGAGAGTGAGAAGTACATCTGTATGAACAA GAGGGGCAAGCTCATCGGGAAGCCCAGCGGGAAGAGCA AAGACTGCGTGTTCACGGAGATCGTGCTGGAGAACAAC TATACGGCCTTCCAGAACGCCCGGCACGAGGGCTGGTTC ATGGCCTTCACGCGGCAGGGGCGGCCCCGCCAGGCTTCC CGCAGCCGCCAGAACCAGCGCGAGGCCCACTTCATCAA GCGCCTCTACCAAGGATCGGGATCGGACAAAACTCACA CATGCCCACCGTGCCCAGCACCTGAAGCTGCCGGGGGA CCGTCAGTCTTCCTCTTCCCCCCAAAACCCAAGGACACC CTCATGATCTCCCGGACCCCTGAGGTCACATGCGTGGTG GTGGACGTGAGCCACGAAGACCCTGAGGTCAAGTTCAA CTGGTACGTGGACGGCGTGGAGGTGCATAATGCCAAGA CAAAGCCGCGGGAGGAGCAGTACAACAGCACGTACCGT GTGGTCAGCGTCCTCACCGTCCTGCACCAGGACTGGCTG AATGGCAAGGAGTACAAGTGCAAGGTCTCCAACAAAGC CCTCGGCGCCCCCATCGAGAAAACCATCTCCAAAGCCAA AGGGCAGCCCCGAGAACCACAGGTGTACACCCTGCCCC CATCCCGGGATGAGCTGACCAAGAACCAGGTCAGCCTG ACCTGCCTGGTCAAAGGCTTCTATCCCAGCGACATCGCC GTGGAGTGGGAGAGCAATGGGCAGCCGGAGAACAACTA CAAGACCACGCCTCCCGTGCTGGACTCCGACGGCTCCTT CTTCCTCTACAGCAAGCTCACCGTGGACAAGAGCAGGTG GCAGCAGGGGAACGTCTTCTCATGCTCCGTGATGCATGA GGCTCTGCACAACCACTACACGCAGAAaAGCCTCTCCCT GTCTCCGGGTAAA |
| 26 | FGF-17R204Q K207Q-linker1-hFcm | Human FGF-17 R204Q K207Q mutant-linker1-hFcm nucleotide sequence | ACTCAGGGGGAGAATCACCCGTCTCCTAATTTTAACCAG TACGTGAGGGACCAGGGCGCCATGACCGACCAGCTGAG CAGGCGGCAGATCCGCGAGTACCAACTCTACAGCAGGA CCAGTGGCAAGCACGTGCAGGTCACCGGGCGTCGCATCT CCGCCACCGCCGAGGACGGCAACAAGTTTGCCAAGCTC ATAGTGGAGACGGACACGTTTGGCAGCCGGGTTCGCATC AAAGGGGCTGAGAGTGAGAAGTACATCTGTATGAACAA GAGGGGCAAGCTCATCGGGAAGCCCAGCGGGAAGAGCA AAGACTGCGTGTTCACGGAGATCGTGCTGGAGAACAAC TATACGGCCTTCCAGAACGCCCGGCACGAGGGCTGGTTC ATGGCCTTCACGCGGCAGGGGCGGCCCCGCCAGGCTTCC CGCAGCCGCCAGAACCAGCGCGAGGCCCACTTCATCAA GCGCCTCTACCAAGGCCAGCTGCCCTTCCCCAACCACG CGAGAAGCAGAAGCAGTTCGAGTTTGTGGGCTCCGCCTC CACCCaGCGGACCcAGCGCACACGGCGGCCCCAGCCCCT CACGGGATCGGGATCGGACAAAACTCACACATGCCCAC CGTGCCCAGCACCTGAAGCTGCCGGGGGACCGTCAGTCT TCCTCTTCCCCCCAAAACCCAAGGACACCCTCATGATCT CCCGGACCCCTGAGGTCACATGCGTGGTGGTGGACGTGA GCCACGAAGACCCTGAGGTCAAGTTCAACTGGTACGTG GACGGCGTGGAGGTGCATAATGCCAAGACAAAGCCGCG GGAGGAGCAGTACAACAGCACGTACCGTGTGGTCAGCG TCCTCACCGTCCTGCACCAGGACTGGCTGAATGGCAAGG AGTACAAGTGCAAGGTCTCCAACAAAGCCCTCGGCGCC CCCATCGAGAAAACCATCTCCAAAGCCAAAGGGCAGCC CCGAGAACCACAGGTGTACACCCTGCCCCCATCCCGGGA TGAGCTGACCAAGAACCAGGTCAGCCTGACCTGCCTGGT CAAAGGCTTCTATCCCAGCGACATCGCCGTGGAGTGGGA GAGCAATGGGCAGCCGGAGAACAACTACAAGACCACGC CTCCCGTGCTGGACTCCGACGGCTCCTTCTTCCTCTACAG CAAGCTCACCGTGGACAAGAGCAGGTGGCAGCAGGGGA ACGTCTTCTCATGCTCCGTGATGCATGAGGCTCTGCACA ACCACTACACGCAGAAaAGCCTCTCCCTGTCTCCGGGTA AA |

TABLE 2-continued

Therapeutic Sequences

| Seq ID No | Sequence Name | Description | Sequence |
|---|---|---|---|
| 27 | FGF-17d197-216-linker1-hFcm | Human FGF17 AA197-216 deletion mutant-linker1-hFcm nucleotide sequence | ACTCAGGGGAGAATCACCCGTCTCCTAATTTTAACCAG<br>TACGTGAGGGACCAGGGCGCCATGACCGACCAGCTGAG<br>CAGGCGGCAGATCCGCGAGTACCAACTCTACAGCAGGA<br>CCAGTGGCAAGCACGTGCAGGTCACCGGGCGTCGCATCT<br>CCGCCACCGCCGAGGACGGCAACAAGTTTGCCAAGCTC<br>ATAGTGGAGACCGGACACGTTTGGCAGCCGGGTTCGCATC<br>AAAGGGGCTGAGAGTGAGAAGTACATCTGTATGAACAA<br>GAGGGGCAAGCTCATCGGGAAGCCCAGCGGGAAGAGCA<br>AAGACTGCGTGTTCACGGAGATCGTGCTGGAGAACAAC<br>TATACGGCCTTCCAGAACGCCCGGCACGAGGGCTGGTTC<br>ATGGCCTTCACGCGGCAGGGGCGGCCCCGCCAGGCTTCC<br>CGCAGCCGCCAGAACCAGCGCGAGGCCCACTTCATCAA<br>GCGCCTCTACCAAGGCCAGCTGCCCTTCCCCAACCACGC<br>CGAGAAGCAGAAGCAGTTCGAGGGATCGGGATCGGACA<br>AAACTCACACATGCCCACCGTGCCCAGCACCTGAAGCTG<br>CCGGGGGACCGTCAGTCTTCCTCTTCCCCCCAAAACCCA<br>AGGACACCCTCATGATCTCCCGGACCCCTGAGGTCACAT<br>GCGTGGTGGTGGACGTGAGCCACGAAGACCCTGAGGTC<br>AAGTTCAACTGGTACGTGGACGGCGTGGAGGTGCATAA<br>TGCCAAGACAAAGCCGCGGGAGGAGCAGTACAACAGCA<br>CGTACCGTGTGGTCAGCGTCCTCACCGTCCTGCACCAGG<br>ACTGGCTGAATGGCAAGGAGTACAAGTGCAAGGTCTCC<br>AACAAAGCCCTCGGCGCCCCCATCGAGAAAACCATCTCC<br>AAAGCCAAAGGGCAGCCCCGAGAACCACAGGTGTACAC<br>CCTGCCCCCATCCCGGGATGAGCTGACCAAGAACCAGGT<br>CAGCCTGACCTGCCTGGTCAAAGGCTTCTATCCCAGCGA<br>CATCGCCGTGGAGTGGGAGAGCAATGGGCAGCCGGAGA<br>ACAACTACAAGACCACGCCTCCCGTGCTGGACTCCGACG<br>GCTCCTTCTTCCTCTACAGCAAGCTCACCGTGGACAAGA<br>GCAGGTGGCAGCAGGGGAACGTCTTCTCATGCTCCGTGA<br>TGCATGAGGCTCTGCACAACCACTACACGCAGAAaAGCC<br>TCTCCCTGTCTCCGGGTAAA |
| 28 | FGF-17K191A K193AS200A-linker1-hFcm | Human FGF-17 K191A K193A S200A mutant-linker1-hFcm nucleotide sequence | ACTCAGGGGAGAATCACCCGTCTCCTAATTTTAACCAG<br>TACGTGAGGGACCAGGGCGCCATGACCGACCAGCTGAG<br>CAGGCGGCAGATCCGCGAGTACCAACTCTACAGCAGGA<br>CCAGTGGCAAGCACGTGCAGGTCACCGGGCGTCGCATCT<br>CCGCCACCGCCGAGGACGGCAACAAGTTTGCCAAGCTC<br>ATAGTGGAGACCGGACACGTTTGGCAGCCGGGTTCGCATC<br>AAAGGGGCTGAGAGTGAGAAGTACATCTGTATGAACAA<br>GAGGGGCAAGCTCATCGGGAAGCCCAGCGGGAAGAGCA<br>AAGACTGCGTGTTCACGGAGATCGTGCTGGAGAACAAC<br>TATACGGCCTTCCAGAACGCCCGGCACGAGGGCTGGTTC<br>ATGGCCTTCACGCGGCAGGGGCGGCCCCGCCAGGCTTCC<br>CGCAGCCGCCAGAACCAGCGCGAGGCCCACTTCATCAA<br>GCGCCTCTACCAAGGCCAGCTGCCCTTCCCCAACCACGC<br>CGAGGctCAGGcaCAGTTCGAGTTTGTGGGCgCtGCCCCCA<br>CCCGCCGGACCAAGCGCACACGGCGGCCCCAGCCCCTC<br>ACGGGATCGGGATCGGACAAAACTCACACATGCCCACC<br>GTGCCCAGCACCTGAAGCTGCCGGGGGACCGTCAGTCTT<br>CCTCTTCCCCCCAAAACCCAAGGACACCCTCATGATCTC<br>CCGGACCCCTGAGGTCACATGCGTGGTGGTGGACGTGA<br>GCCACGAAGACCCTGAGGTCAAGTTCAACTGGTACGTG<br>GACGGCGTGGAGGTGCATAATGCCAAGACAAAGCCGCG<br>GGAGGAGCAGTACAACAGCACGTACCGTGTGGTCAGCG<br>TCCTCACCGTCCTGCACCAGGACTGGCTGAATGGCAAGG<br>AGTACAAGTGCAAGGTCTCCAACAAAGCCCTCGGCGCC<br>CCCATCGAGAAAACCATCTCCAAAGCCAAAGGGCAGCC<br>CCGAGAACCACAGGTGTACACCCTGCCCCCATCCCGGGA<br>TGAGCTGACCAAGAACCAGGTCAGCCTGACCTGCCTGGT<br>CAAAGGCTTCTATCCCAGCGACATCGCCGTGGAGTGGGA<br>GAGCAATGGGCAGCCGGAGAACAACTACAAGACCACGC<br>CTCCCGTGCTGGACTCCGACGGCTCCTTCTTCCTCTACAG<br>CAAGCTCACCGTGGACAAGAGCAGGTGGCAGCAGGGGA<br>ACGTCTTCTCATGCTCCGTGATGCATGAGGCTCTGCACA<br>ACCACTACACGCAGAAaAGCCTCTCCCTGTCTCCGGGTA<br>AA |
| 29 | FGF-17-linker2-hFcm | Full length of human FGF17 linker2-hFcm nucleotide sequence | ACTCAGGGGAGAATCACCCGTCTCCTAATTTTAACCAG<br>TACGTGAGGGACCAGGGCGCCATGACCGACCAGCTGAG<br>CAGGCGGCAGATCCGCGAGTACCAACTCTACAGCAGGA<br>CCAGTGGCAAGCACGTGCAGGTCACCGGGCGTCGCATCT<br>CCGCCACCGCCGAGGACGGCAACAAGTTTGCCAAGCTC<br>ATAGTGGAGACCGGACACGTTTGGCAGCCGGGTTCGCATC<br>AAAGGGGCTGAGAGTGAGAAGTACATCTGTATGAACAA |

TABLE 2-continued

Therapeutic Sequences

| Seq ID No | Sequence Name | Description | Sequence |
|---|---|---|---|
| | | | GAGGGGCAAGCTCATCGGGAAGCCCAGCGGGAAGAGCA AAGACTGCGTGTTCACGGAGATCGTGCTGGAGAACAAC TATACGGCCTTCCAGAACGCCCGGCACGAGGGCTGGTTC ATGGCCTTCACGCGGCAGGGGCGGCCCCGCCAGGCTTCC CGCAGCCGCCAGAACCAGCGCGAGGCCCACTTCATCAA GCGCCTCTACCAAGGCCAGCTGCCCTTCCCCAACCACGC CGAGAAGCAGAAGCAGTTCGAGTTTGTGGGCTCCGCCCC CACCCGCCGGACCAAGCGCACACGGCGGCCCCAGCCCC TCACGGGATCTGGGAGCGCTGACAAAACTCACACATGC CCACCGTGCCCAGCACCTGAAGCTGCCGGGGGACCGTC AGTCTTCCTCTTCCCCCCAAAACCCAAGGACACCCTCAT GATCTCCCGGACCCCTGAGGTCACATGCGTGGTGGTGGA CGTGAGCCACGAAGACCCTGAGGTCAAGTTCAACTGGT ACGTGGACGGCGTGGAGGTGCATAATGCCAAGACAAAG CCGCGGGAGGAGCAGTACAACAGCACGTACCGTGTGGT CAGCGTCCTCACCGTCCTGCACCAGGACTGGCTGAATGG CAAGGAGTACAAGTGCAAGGTCTCCAACAAAGCCCTCG GCGCCCCCATCGAGAAAACCATCTCCAAAGCCAAAGGG CAGCCCCGAGAACCACAGGTGTACACCCTGCCCCCATCC CGGGATGAGCTGACCAAGAACCAGGTCAGCCTGACCTG CCTGGTCAAAGGCTTCTATCCCAGCGACATCGCCGTGGA GTGGGAGAGCAATGGGCAGCCGGAGAACAACTACAAGA CCACGCCTCCCGTGCTGGACTCCGACGGCTCCTTCTTCCT CTACAGCAAGCTCACCGTGGACAAGAGCAGGTGGCAGC AGGGGAACGTCTTCTCATGCTCCGTGATGCATGAGGCTC TGCACAACCACTACACGCAGAAaAGCCTCTCCCTGTCTC CGGGTAAA |
| 30 | FGF-17d204-216 linker2-hFcm | Human FGF17 AA204-216 deletion mutant linker2-hFcm nucleotide sequence | ACTCAGGGGAGAATCACCCGTCTCCTAATTTTAACCAG TACGTGAGGGACCAGGGCGCCATGACCGACCAGCTGAG CAGGCGGCAGATCCGCGAGTACCAACTCTACAGCAGGA CCAGTGGCAAGCACGTGCAGGTCACCGGGCGTCGCATCT CCGCCACCGCCGAGGACGGCAACAAGTTTGCCAAGCTC ATAGTGGAGACGGACACGTTTGGCAGCCGGGTTCGCATC AAAGGGGCTGAGAGTGAGAAGTACATCTGTATGAACAA GAGGGGCAAGCTCATCGGGAAGCCCAGCGGGAAGAGCA AAGACTGCGTGTTCACGGAGATCGTGCTGGAGAACAAC TATACGGCCTTCCAGAACGCCCGGCACGAGGGCTGGTTC ATGGCCTTCACGCGGCAGGGGCGGCCCCGCCAGGCTTCC CGCAGCCGCCAGAACCAGCGCGAGGCCCACTTCATCAA GCGCCTCTACCAAGGCCAGCTGCCCTTCCCCAACCACGC CGAGAAGCAGAAGCAGTTCGAGTTTGTGGGCTCCGCCCC CACCCGGATCTGGGAGCGCTGACAAAACTCACACATGCC CACCGTGCCCAGCACCTGAAGCTGCCGGGGGACCGTCA GTCTTCCTCTTCCCCCCAAAACCCAAGGACACCCTCATG ATCTCCCGGACCCCTGAGGTCACATGCGTGGTGGTGGAC GTGAGCCACGAAGACCCTGAGGTCAAGTTCAACTGGTA CGTGGACGGCGTGGAGGTGCATAATGCCAAGACAAAGC CGCGGGAGGAGCAGTACAACAGCACGTACCGTGTGGTC AGCGTCCTCACCGTCCTGCACCAGGACTGGCTGAATGGC AAGGAGTACAAGTGCAAGGTCTCCAACAAAGCCCTCGG CGCCCCCATCGAGAAAACCATCTCCAAAGCCAAAGGGC AGCCCCGAGAACCACAGGTGTACACCCTGCCCCCATCCC GGGATGAGCTGACCAAGAACCAGGTCAGCCTGACCTGC CTGGTCAAAGGCTTCTATCCCAGCGACATCGCCGTGGAG TGGGAGAGCAATGGGCAGCCGGAGAACAACTACAAGAC CACGCCTCCCGTGCTGGACTCCGACGGCTCCTTCTTCCTC TACAGCAAGCTCACCGTGGACAAGAGCAGGTGGCAGCA GGGGAACGTCTTCTCATGCTCCGTGATGCATGAGGCTCT GCACAACCACTACACGCAGAAaAGCCTCTCCCTGTCTCC GGGTAAA |
| 31 | FGF-17d181-216 linker2-hFcm | Human FGF17 AA181-216 deletion mutant linker2-hFcm nucleotide sequence | ACTCAGGGGAGAATCACCCGTCTCCTAATTTTAACCAG TACGTGAGGGACCAGGGCGCCATGACCGACCAGCTGAG CAGGCGGCAGATCCGCGAGTACCAACTCTACAGCAGGA CCAGTGGCAAGCACGTGCAGGTCACCGGGCGTCGCATCT CCGCCACCGCCGAGGACGGCAACAAGTTTGCCAAGCTC ATAGTGGAGACGGACACGTTTGGCAGCCGGGTTCGCATC AAAGGGGCTGAGAGTGAGAAGTACATCTGTATGAACAA GAGGGGCAAGCTCATCGGGAAGCCCAGCGGGAAGAGCA AAGACTGCGTGTTCACGGAGATCGTGCTGGAGAACAAC TATACGGCCTTCCAGAACGCCCGGCACGAGGGCTGGTTC ATGGCCTTCACGCGGCAGGGGCGGCCCCGCCAGGCTTCC CGCAGCCGCCAGAACCAGCGCGAGGCCCACTTCATCAA GCGCCTCTACCAAGGATCTGGGAGCGCTGACAAAACTC |

TABLE 2-continued

Therapeutic Sequences

| Seq ID No | Sequence Name | Description | Sequence |
|---|---|---|---|
| | | | ACACATGCCCACCGTGCCCAGCACCTGAAGCTGCCGGG<br>GGACCGTCAGTCTTCCTCTTCCCCCCAAAACCCAAGGAC<br>ACCCTCATGATCTCCCGGACCCCTGAGGTCACATGCGTG<br>GTGGTGGACGTGAGCCACGAAGACCCTGAGGTCAAGTT<br>CAACTGGTACGTGGACGGCGTGGAGGTGCATAATGCCA<br>AGACAAAGCCGCGGGAGGAGCAGTACAACAGCACGTAC<br>CGTGTGGTCAGCGTCCTCACCGTCCTGCACCAGGACTGG<br>CTGAATGGCAAGGAGTACAAGTGCAAGGTCTCCAACAA<br>AGCCCTCGGCGCCCCCATCGAGAAAACCATCTCCAAAGC<br>CAAAGGGCAGCCCCGAGAACCACAGGTGTACACCCTGC<br>CCCCATCCCGGGATGAGCTGACCAAGAACCAGGTCAGC<br>CTGACCTGCCTGGTCAAAGGCTTCTATCCCAGCGACATC<br>GCCGTGGAGTGGGAGAGCAATGGGCAGCCGGAGAACAA<br>CTACAAGACCACGCCTCCCGTGCTGGACTCCGACGGCTC<br>CTTCTTCCTCTACAGCAAGCTCACCGTGGACAAGAGCAG<br>GTGGCAGCAGGGGAACGTCTTCTCATGCTCCGTGATGCA<br>TGAGGCTCTGCACAACCACTACACGCAGAAaAGCCTCTC<br>CCTGTCTCCGGGTAAA |
| 32 | FGF-<br>17R204Q<br>K207Q<br>linker2-<br>hFcm | Human<br>FGF-17<br>R204Q<br>K207Q<br>mutant<br>linker2-<br>hFcm<br>nucloetide<br>sequence | ACTCAGGGGAGAATCACCCGTCTCCTAATTTTAACCAG<br>TACGTGAGGGACCAGGGCGCCATGACCGACCAGCTGAG<br>CAGGCGGCAGATCCGCGAGTACCAACTCTACAGCAGGA<br>CCAGTGGCAAGCACGTGCAGGTCACCGGGCGTCGCATCT<br>CCGCCACCGCCGAGGACGGCAACAAGTTTGCCAAGCTC<br>ATAGTGGAGACGGACACGTTTGGCAGCCGGGTTCGCATC<br>AAAGGGGCTGAGAGTGAGAAGTACATCTGTATGAACAA<br>GAGGGGCAAGCTCATCGGGAAGCCCAGCGGGAAGAGCA<br>AAGACTGCGTGTTCACGGAGATCGTGCTGGAGAACAAC<br>TATACGGCCTTCCAGAACGCCCGGCACGAGGGCTGGTTC<br>ATGGCCTTCACGCGGCAGGGCGGCCCCGCCAGGCTTCC<br>CGCAGCCGCCAGAACCAGCGCGAGGCCCACTTCATCAA<br>GCGCCTCTACCAAGGCCAGCTGCCCTTCCCCAACCACGC<br>CGAGAAGCAGAAGCAGTTCGAGTTTGTGGGCTCCGCCCC<br>CACCCaGCGGACCcAGCGCACACGGCGGCCCCAGCCCCT<br>CACGGGATCTGGGAGCGCTGACAAAACTCACACATGCC<br>CACCGTGCCCAGCACCTGAAGCTGCCGGGGGACCGTCA<br>GTCTTCCTCTTCCCCCCAAAACCCAAGGACACCCTCATG<br>ATCTCCCGGACCCCTGAGGTCACATGCGTGGTGGTGGAC<br>GTGAGCCACGAAGACCCTGAGGTCAAGTTCAACTGGTA<br>CGTGGACGGCGTGGAGGTGCATAATGCCAAGACAAAGC<br>CGCGGGAGGAGCAGTACAACAGCACGTACCGTGTGGTC<br>AGCGTCCTCACCGTCCTGCACCAGGACTGGCTGAATGGC<br>AAGGAGTACAAGTGCAAGGTCTCCAACAAAGCCCTCGG<br>CGCCCCCATCGAGAAAACCATCTCCAAAGCCAAAGGGC<br>AGCCCCGAGAACCACAGGTGTACACCCTGCCCCCATCCC<br>GGGATGAGCTGACCAAGAACCAGGTCAGCCTGACCTGC<br>CTGGTCAAAGGCTTCTATCCCAGCGACATCGCCGTGGAG<br>TGGGAGAGCAATGGGCAGCCGGAGAACAACTACAAGAC<br>CACGCCTCCCGTGCTGGACTCCGACGGCTCCTTCTTCCTC<br>TACAGCAAGCTCACCGTGGACAAGAGCAGGTGGCAGCA<br>GGGGAACGTCTTCTCATGCTCCGTGATGCATGAGGCTCT<br>GCACAACCACTACACGCAGAAaAGCCTCTCCCTGTCTCC<br>GGGTAAA |
| 33 | FGF-<br>17d197-<br>216<br>linker2-<br>hFcm | Human<br>FGF17<br>AA197-216<br>deletion<br>mutant<br>linker2-<br>hFcm<br>nucleotide<br>sequence | ACTCAGGGGAGAATCACCCGTCTCCTAATTTTAACCAG<br>TACGTGAGGGACCAGGGCGCCATGACCGACCAGCTGAG<br>CAGGCGGCAGATCCGCGAGTACCAACTCTACAGCAGGA<br>CCAGTGGCAAGCACGTGCAGGTCACCGGGCGTCGCATCT<br>CCGCCACCGCCGAGGACGGCAACAAGTTTGCCAAGCTC<br>ATAGTGGAGACGGACACGTTTGGCAGCCGGGTTCGCATC<br>AAAGGGGCTGAGAGTGAGAAGTACATCTGTATGAACAA<br>GAGGGGCAAGCTCATCGGGAAGCCCAGCGGGAAGAGCA<br>AAGACTGCGTGTTCACGGAGATCGTGCTGGAGAACAAC<br>TATACGGCCTTCCAGAACGCCCGGCACGAGGGCTGGTTC<br>ATGGCCTTCACGCGGCAGGGGCGGCCCCGCCAGGCTTCC<br>CGCAGCCGCCAGAACCAGCGCGAGGCCCACTTCATCAA<br>GCGCCTCTACCAAGGCCAGCTGCCCTTCCCCAACCACGC<br>CGAGAAGCAGAAGCAGTTCGAGGGATCTGGGAGCGCTG<br>ACAAAACTCACACATGCCCACCGTGCCCAGCACCTGAA<br>GCTGCCGGGGGACCGTCAGTCTTCCTCTTCCCCCCAAAA<br>CCCAAGGACACCCTCATGATCTCCCGGACCCCTGAGGTC<br>ACATGCGTGGTGGTGGACGTGAGCCACGAAGACCCTGA<br>GGTCAAGTTCAACTGGTACGTGGACGGCGTGGAGGTGC<br>ATAATGCCAAGACAAAGCCGCGGGAGGAGCAGTACAAC<br>AGCACGTACCGTGTGGTCAGCGTCCTCACCGTCCTGCAC |

TABLE 2-continued

Therapeutic Sequences

| Seq ID No | Sequence Name | Description | Sequence |
|---|---|---|---|
| | | | CAGGACTGGCTGAATGGCAAGGAGTACAAGTGCAAGGT<br>CTCCAACAAAGCCCTCGGCGCCCCCATCGAGAAAACCAT<br>CTCCAAAGCCAAAGGGCAGCCCCGAGAACCACAGGTGT<br>ACACCCTGCCCCCATCCCGGGATGAGCTGACCAAGAACC<br>AGGTCAGCCTGACCTGCCTGGTCAAAGGCTTCTATCCCA<br>GCGACATCGCCGTGGAGTGGGAGAGCAATGGGCAGCCG<br>GAGAACAACTACAAGACCACGCCTCCCGTGCTGGACTCC<br>GACGGCTCCTTCTTCCTCTACAGCAAGCTCACCGTGGAC<br>AAGAGCAGGTGGCAGCAGGGGAACGTCTTCTCATGCTC<br>CGTGATGCATGAGGCTCTGCACAACCACTACACGCAGA<br>AaAGCCTCTCCCTGTCTCCGGGTAAA |
| 34 | FGF-17K191A K193AS200A linker2-hFcm | Human FGF-17 K191A K193A S200A mutant linker2-hFcm nucleotide sequence | ACTCAGGGGAGAATCACCCGTCTCCTAATTTTAACCAG<br>TACGTGAGGGACCAGGGCGCCATGACCGACCAGCTGAG<br>CAGGCGGCAGATCCGCGAGTACCAACTCTACAGCAGGA<br>CCAGTGGCAAGCACGTGCAGGTCACCGGGCGTCGCATCT<br>CCGCCACCGCCGAGGACGGCAACAAGTTTGCCAAGCTC<br>ATAGTGGAGACGGACACGTTTGGCAGCCGGGTTCGCATC<br>AAAGGGGCTGAGAGTGAGAAGTACATCTGTATGAACAA<br>GAGGGGCAAGCTCATCGGGAAGCCCAGCGGGAAGAGCA<br>AAGACTGCGTGTTCACGGAGATCGTGCTGGAGAACAAC<br>TATACGGCCTTCCAGAACGCCCGGCACGAGGGCTGGTTC<br>ATGGGCCTTCACGCGGCAGGGGCGGCCCCGCCAGGCTTCC<br>CGCAGCCGCCAGAACCAGCGCGAGGCCCACTTCATCAA<br>GCGCCTCTACCAAGGCCAGCTGCCCTTCCCCAACCACGC<br>CGAGGCTCAGGCACAGTTCGAGTTTGTGGGCGCTGCCCC<br>CACCCGCCGGACCAAGCGCACACGGCGGCCCCAGCCCC<br>TCACGGGATCTGGGAGCGCTGACAAAACTCACACATGC<br>CCACCGTGCCCAGCACCTGAAGCTGCGGGGGACCCGTC<br>AGTCTTCCTCTTCCCCCCAAAACCCAAGGACACCCTCAT<br>GATCTCCCGGACCCCTGAGGTCACATGCGTGGTGGTGGA<br>CGTGAGCCACGAAGACCCTGAGGTCAAGTTCAACTGGT<br>ACGTGGACGGCGTGGAGGTGCATAATGCCAAGACAAAG<br>CCGCGGGAGGAGCAGTACAACAGCACGTACCGTGTGGT<br>CAGCGTCCTCACCGTCCTGCACCAGGACTGGCTGAATGG<br>CAAGGAGTACAAGTGCAAGGTCTCCAACAAAGCCCTCG<br>GCGCCCCCATCGAGAAAACCATCTCCAAAGCCAAAGGG<br>CAGCCCCGAGAACCACAGGTGTACACCCTGCCCCCATCC<br>CGGGATGAGCTGACCAAGAACCAGGTCAGCCTGACCTG<br>CCTGGTCAAAGGCTTCTATCCCAGCGACATCGCCGTGGA<br>GTGGGAGAGCAATGGGCAGCCGGAGAACAACTACAAGA<br>CCACGCCTCCCGTGCTGGACTCCGACGGCTCCTTCTTCCT<br>CTACAGCAAGCTCACCGTGGACAAGAGCAGGTGGCAGC<br>AGGGGAACGTCTTCTCATGCTCCGTGATGCATGAGGCTC<br>TGCACAACCACTACACGCAGAAaAGCCTCTCCCTGTCTC<br>CGGGTAAA |
| 35 | 6xHis-HSA-linker3-FGF17 | His tagged HSA fusion FGF17 with a long linker nucleotide sequence | CACCATCACCATCACCATAGCGGCGATGCACACAAGAG<br>TGAGGTTGCTCATCGGTTTAAAGATTTGGGAGAAGAAAA<br>TTTCAAAGCCTTGGTGTTGATTGCCTTTGCTCAGTATCTT<br>CAGCAGTGTCCATTTGAAGATCATGTAAAATTAGTGAAT<br>GAAGTAACTGAATTTGCAAAAACATGTGTTGCTGATGAG<br>TCAGCTGAAAATTGTGACAAATCACTTCATACCCTTTTT<br>GGAGACAAATTATGCACAGTTGCAACTCTTCGTGAAACC<br>TATGGTGAAATGGCTGACTGCTGTGCAAAAACAAGAACCT<br>GAGAGAAATGAATGCTTCTTGCAACACAAAGATGACAA<br>CCCAAACCTCCCCCCGATTGGTGAGACCAGAGGTTGATGT<br>GATGTGCACTGCTTTTCATGACAATGAAGAGACATTTTT<br>GAAAAAATACTTATATGAAATTGCCAGAAGACATCCTTA<br>CTTTTATGCCCCGGAACTCCTTTTCTTTGCTAAAAGGTAT<br>AAAGCTGCTTTTACAGAATGTTGCCAAGCTGCTGATAAA<br>GCTGCCTGCCTGTTGCCAAAGCTCGATGAACTTCGGGAT<br>GAAGGGAAGGCTTCGTCTGCCAAACAGAGACTCAAGTG<br>TGCCAGTCTCCAAAAATTTGGAGAAAGAGCTTTCAAAGC<br>ATGGGCAGTAGCTCGCCTGAGCCAGAGATTTCCCAAAGC<br>TGAGTTTGCAGAAGTTTCCAAGTTAGTGACAGATCTTAC<br>CAAAGTCCACACGGAATGCTGCCATGGAGATCTGCTTGA<br>ATGTGCTGATGACAGGGCGGACCTTGCCAAGTATATCTG<br>TGAAAATCAAGATTCGATCTCCAGTAAACTGAAGGAAT<br>GCTGTGAAAAACCTCTGTTGGAAAAATCCCACTGCATTG<br>CCGAAGTGGAAAATGATGAGATGCCTGCTGACTTGCCTT<br>CATTAGCTGCTGATTTTGTTGAAAGTAAGGATGTTTGCA<br>AAAACTATGCTGAGGCAAAGGATGTCTTCCTGGGCATGT<br>TTTTGTATGAATATGCAAGAAGGCATCCTGATTACTCTG<br>TCGTGCTGCTGCTGAGACTTGCCAAGACATATGAAACCA |

TABLE 2-continued

Therapeutic Sequences

| Seq ID No | Sequence Name | Description | Sequence |
|---|---|---|---|
| | | | CTCTAGAGAAGTGCTGTGCCGCTGCAGATCCTCATGAAT
GCTATGCCAAAGTGTTCGATGAATTTAAACCTCTTGTGG
AAGAGCCTCAGAATTTAATCAAACAAAATTGTGAGCTTT
TTGAGCAGCTTGGAGAGTACAAATTCCAGAATGCGCTAT
TAGTTCGTTACACCAAGAAAGTACCCCAAGTGTCAACTC
CAACTCTTGTAGAGGTCTCAAGAAACCTAGGAAAAGTG
GGCAGCAAATGTTGTAAACATCCTGAAGCAAAAAGAAT
GCCCTGTGCAGAAGACTATCTATCCGTGGTCCTGAACCA
GTTATGTGTGTTGCATGAGAAAACGCCAGTAAGTGACAG
AGTCACCAAATGCTGCACAGAATCCTTGGTGAACAGGC
GACCATGCTTTTCAGCTCTGGAAGTCGATGAAACATACG
TTCCCAAAGAGTTTAATGCTGAAACATTCACCTTCCATG
CAGATATATGCACACTTTCTGAGAAGGAGAGACAAATC
AAGAAACAAACTGCACTTGTTGAGCTCGTGAAACACAA
GCCCAAGGCAACAAAAGAGCAACTGAAAGCTGTTATGG
ATGATTTCGCAGCTTTTGTAGAGAAGTGCTGCAAGGCTG
ACGATAAGGAGACCTGCTTTGCCGAGGAGGGTAAAAAA
CTTGTTGCTGCAAGTCAAGCTGCCTTAGGCTTAGGCGGA
GGCGGTAGCGGAGGCGGTGGCTCCGGTGGCGGAGGGTC
TACTCAGGGGGAGAATCACCCGTCTCCTAATTTTAACCA
GTACGTGAGGGACCAGGGCGCCATGACCGACCAGCTGA
GCAGGCGGCAGATCCGCGAGTACCAACTCTACAGCAGG
ACCAGTGGCAAGCACGTGCAGGTCACCGGGCGTCGCAT
CTCCGCCACCGCCGAGGACGGCAACAAGTTTGCCAAGCT
CATAGTGGAGACGGACACGTTTGGCAGCCGGGTTCGCAT
CAAAGGGGCTGAGAGTGAGAAGTACATCTGTATGAACA
AGAGGGGCAAGCTCATCGGGAAGCCCAGCGGGAAGAGC
AAAGACTGCGTGTTCACGGAGATCGTGCTGGAGAACAA
CTATACGGCCTTCCAGAACGCCCGGCACGAGGGCTGGTT
CATGGCCTTCACGCGGCAGGGGCGGCCCCGCCAGGCTTC
CGCAGCCGCCAGAACCAGCGCGAGGCCCACTTCATCA
AGCGCCTCTACCAAGGCCAGCTGCCCTTCCCCAACCACG
CCGAGAAGCAGAAGCAGTTCGAGTTTGTGGGCTCCGCCC
CCACCCGCCGGACCAAGCGCACACGGCGGCCCCAGCCC
CTCACG |
| 36 | FGF17-linker3-hFc4 | Human FGF17-linker3-hFc4 nucleotide sequence | ACTCAGGGGGAGAATCACCCGTCTCCTAATTTTAACCAG
TACGTGAGGGACCAGGGCGCCATGACCGACCAGCTGAG
CAGGCGGCAGATCCGCGAGTACCAACTCTACAGCAGGA
CCAGTGGCAAGCACGTGCAGGTCACCGGGCGTCGCATCT
CCGCCACCGCCGAGGACGGCAACAAGTTTGCCAAGCTC
ATAGTGGAGACGGACACGTTTGGCAGCCGGGTTCGCATC
AAAGGGGCTGAGAGTGAGAAGTACATCTGTATGAACAA
GAGGGGCAAGCTCATCGGGAAGCCCAGCGGGAAGAGCA
AAGACTGCGTGTTCACGGAGATCGTGCTGGAGAACAAC
TATACGGCCTTCCAGAACGCCCGGCACGAGGGCTGGTTC
ATGGCCTTCACGCGGCAGGGGCGGCCCCGCCAGGCTTCC
GCAGCCGCCAGAACCAGCGCGAGGCCCACTTCATCAA
GCGCCTCTACCAAGGCCAGCTGCCCTTCCCCAACCACGC
CGAGAAGCAGAAGCAGTTCGAGTTTGTGGGCTCCGCCCC
CACCCGCCGGACCAAGCGCACACGGCGGCCCCAGCCCC
TCACGGGCGAGGCGGTAGCGGAGGCGGTGGCTCCGGT
GGCGGAGGGTCTGAGTCCAAATATGGTCCCCCATGCCCA
CCCTGCCCAGCACCTGAGTTCCTGGGGGGACCATCAGTC
TTCCTGTTCCCCCCAAAACCCAAGGACACTCTCATGATC
TCCCGGACCCCTGAGGTCACGTGCGTGGTGGTGGACGTG
AGCCAGGAAGACCCCGAGGTCCAGTTCAACTGGTACGT
GGATGGCGTGGAGGTGCATAATGCCAAGACAAAGCCGC
GGGAGGAGCAGTTCAACAGCACGTACCGTGTGGTCAGC
GTCCTCACCGTCCTGCACCAGGACTGGCTGAACGGCAAG
GAGTACAAGTGCAAGGTCTCCAACAAAGGCCTCCCGTCC
TCCATCGAGAAAACCATCTCCAAAGCCAAAGGGCAGCC
CCGAGAGCCACAGGTGTACACCCTGCCCCCATCCCAGGA
GGGAGATGACCAAGAACCAGGTCAGCCTGACCTGCCTGG
TCAAAGGCTTCTACCCCAGCGACATCGCCGTGGAGTGGG
AGAGCAATGGGCAGCCGGAGAACAACTACAAGACCACG
CCTCCCGTGCTGGACTCCGACGGCTCCTTCTTCCTCTACA
GCAGGCTCACCGTGGACAAGAGCAGGTGGCAGGAGGGG
AATGTCTTCTCATGCTCCGTGATGCATGAGGCTCTGCAC
AACCACTACACACAGAAGAGCCTCTCCCTGTCTCTGGGT
AAA |
| 37 | FGF17-hFc4 | Human FGF17-hFc4 | ACTCAGGGGGAGAATCACCCGTCTCCTAATTTTAACCAG
TACGTGAGGGACCAGGGCGCCATGACCGACCAGCTGAG
CAGGCGGCAGATCCGCGAGTACCAACTCTACAGCAGGA |

TABLE 2-continued

Therapeutic Sequences

| Seq ID No | Sequence Name | Description | Sequence |
|---|---|---|---|
| | | nucleotide sequence | CCAGTGGCAAGCACGTGCAGGTCACCGGGCGTCGCATCT CCGCCACCGCCGAGGACGGCAACAAGTTTGCCAAGCTC ATAGTGGAGACGGACACGTTTGGCAGCCGGGTTCGCATC AAAGGGGCTGAGAGTGAGAAGTACATCTGTATGAACAA GAGGGGCAAGCTCATCGGGAAGCCCAGCGGGAAGAGCA AAGACTGCGTGTTCACGGAGATCGTGCTGGAGAACAAC TATACGGCCTTCCAGAACGCCCGGCACGAGGGCTGGTTC ATGGCCTTCACGCGGCAGGGGCGGCCCCGCCAGGCTTCC CGCAGCCGCCAGAACCAGCGCGAGGCCCACTTCATCAA GCGCCTCTACCAAGGCCAGCTGCCCTTCCCCAACCACGC CGAGAAGCAGAAGCAGTTCGAGTTTGTGGGCTCCGCCCC CACCCGCCGGACCAAGCGCACACGGCGGCCCCAGCCCC TCACGGAGTCCAAATATGGTCCCCCATGCCCACCCTGCC CAGCACCTGAGTTCCTGGGGGGACCATCAGTCTTCCTGT TCCCCCCAAAACCCAAGGACACTCTCATGATCTCCCGGA CCCCTGAGGTCACGTGCGTGGTGGTGGACGTGAGCCAG GAAGACCCCGAGGTCCAGTTCAACTGGTACGTGGATGG CGTGGAGGTGCATAATGCCAAGACAAAGCCGCGGGAGG AGCAGTTCAACAGCACGTACCGTGTGGTCAGCGTCCTCA CCGTCCTGCACCAGGACTGGCTGAACGGCAAGGAGTAC AAGTGCAAGGTCTCCAACAAAGGCCTCCCGTCCTCCATC GAGAAAACCATCTCCAAAGCCAAAGGGCAGCCCCGAGA GCCACAGGTGTACACCCTGCCCCCATCCCAGGAGGAGAT GACCAAGAACCAGGTCAGCCTGACCTGCCTGGTCAAAG GCTTCTACCCCAGCGACATCGCCGTGGAGTGGGAGAGC AATGGGCAGCCGGAGAACAACTACAAGACCACGCCTCC CGTGCTGGACTCCGACGGCTCCTTCTTCCTCTACAGCAG GCTCACCGTGGACAAGAGCAGGTGGCAGGAGGGGAATG TCTTCTCATGCTCCGTGATGCATGAGGCTCTGCACAACC ACTACACACAGAAGAGCCTCTCCCTGTCTCTGGGTAAA |
| 38 | FGF17 hFc4L- | hFc4-linker3-human FGF17 nucleotide sequence | GAGTCCAAATATGGTCCCCCATGCCCACCCTGCCCAGCA CCTGAGTTCCTGGGGGGACCATCAGTCTTCCTGTTCCCC CCAAAACCCAAGGACACTCTCATGATCTCCCGGACCCCT GAGGTCACGTGCGTGGTGGTGGACGTGAGCCAGGAAGA CCCCGAGGTCCAGTTCAACTGGTACGTGGATGGCGTGGA GGTGCATAATGCCAAGACAAAGCCGCGGGAGGAGCAGT TCAACAGCACGTACCGTGTGGTCAGCGTCCTCACCGTCC TGCACCAGGACTGGCTGAACGGCAAGGAGTACAAGTGC AAGGTCTCCAACAAAGGCCTCCCGTCCTCCATCGAGAAA ACCATCTCCAAAGCCAAAGGGCAGCCCCGAGAGCCACA GGTGTACACCCTGCCCCCATCCCAGGAGGAGATGACCA AGAACCAGGTCAGCCTGACCTGCCTGGTCAAAGGCTTCT ACCCCAGCGACATCGCCGTGGAGTGGGAGAGCAATGGG CAGCCGGAGAACAACTACAAGACCACGCCTCCCGTGCT GGACTCCGACGGCTCCTTCTTCCTCTACAGCAGGCTCAC CGTGGACAAGAGCAGGTGGCAGGAGGGGAATGTCTTCT CATGCTCCGTGATGCATGAGGCTCTGCACAACCACTACA CACAGAAGAGCCTCTCCCTGTCTCTGGGTAAAGGCGGAG GCGGTAGCGGAGGCGGTGGCTCCGGTGGCGGAGGGTCT ACTCAGGGGGAGAATCACCCGTCTCCTAATTTTAACCAG TACGTGAGGGACCAGGGCGCCATGACCGACCAGCTGAG CAGGCGGCAGATCCGCGAGTACCAACTCTACAGCAGGA CCAGTGGCAAGCACGTGCAGGTCACCGGGCGTCGCATCT CCGCCACCGCCGAGGACGGCAACAAGTTTGCCAAGCTC ATAGTGGAGACGGACACGTTTGGCAGCCGGGTTCGCATC AAAGGGGCTGAGAGTGAGAAGTACATCTGTATGAACAA GAGGGGCAAGCTCATCGGGAAGCCCAGCGGGAAGAGCA AAGACTGCGTGTTCACGGAGATCGTGCTGGAGAACAAC TATACGGCCTTCCAGAACGCCCGGCACGAGGGCTGGTTC ATGGCCTTCACGCGGCAGGGGCGGCCCCGCCAGGCTTCC CGCAGCCGCCAGAACCAGCGCGAGGCCCACTTCATCAA GCGCCTCTACCAAGGCCAGCTGCCCTTCCCCAACCACGC CGAGAAGCAGAAGCAGTTCGAGTTTGTGGGCTCCGCCCC CACCCGCCGGACCAAGCGCACACGGCGGCCCCAGCCCC TCACG |
| 39 | IGF2 | nucleotide sequence | GCTTACCGCCCCAGTGAGACCCTGTGCGGCGGGGAGCTG GTGGACACCCTCCAGTTCGTCTGTGGGGACCGCGGCTTC TACTTCAGCAGGCCCGCAAGCCGTGTGAGCCGTCGCAGC CGTGGCATCGTTGAGGAGTGCTGTTTCCGCAGCTGTGAC CTGGCCCTCCTGGAGACGTACTGTGCTACCCCCGCCAAG TCCGAG |

TABLE 2-continued

Therapeutic Sequences

| Seq ID No | Sequence Name | Description | Sequence |
|---|---|---|---|
| 40 | hFcm IGF2-linker1- | nucleotide sequence | GCTTACCGCCCCAGTGAGACCCTGTGCGGCGGGGAGCTG GTGGACACCCTCCAGTTCGTCTGTGGGGACCGCGGCTTC TACTTCAGCAGGCCCGCAAGCCGTGTGAGCCGTCGCAGC CGTGGCATCGTTGAGGAGTGCTGTTTCCGCAGCTGTGAC CTGGCCCTCCTGGAGACGTACTGTGCTACCCCCGCCAAG TCCGAG GGATCGGGATCGGACAAAACTCACACATGCCCACCGTG CCCAGCACCTGAAGCTGCCGGGGGACCGTCAGTCTTCCT CTTCCCCCCAAAACCCAAGGACACCCTCATGATCTCCCG GACCCCTGAGGTCACATGCGTGGTGGTGGACGTGAGCC ACGAAGACCCTGAGGTCAAGTTCAACTGGTACGTGGAC GGCGTGGAGGTGCATAATGCCAAGACAAAGCCGCGGGA GGAGCAGTACAACAGCACGTACCGTGTGGTCAGCGTCCT CACCGTCCTGCACCAGGACTGGCTGAATGGCAAGGAGT ACAAGTGCAAGGTCTCCAACAAAGCCCTCGGCGCCCCC ATCGAGAAAACCATCTCCAAAGCCAAAGGGCAGCCCCG AGAACCACAGGTGTACACCCTGCCCCCATCCCGGGATGA GCTGACCAAGAACCAGGTCAGCCTGACCTGCCTGGTCAA AGGCTTCTATCCCAGCGACATCGCCGTGGAGTGGGAGA GCAATGGGCAGCCGGAGAACAACTACAAGACCACGCCT CCCGTGCTGGACTCCGACGGCTCCTTCTTCCTCTACAGC AAGCTCACCGTGGACAAGAGCAGGTGGCAGCAGGGGAA CGTCTTCTCATGCTCCGTGATGCATGAGGCTCTGCACAA CCACTACACGCAGAAaAGCCTCTCCCTGTCTCCGGGTAA A |
| 41 | IGF2-linker2-hFcm | nucleotide sequence | GCTTACCGCCCCAGTGAGACCCTGTGCGGCGGGGAGCTG GTGGACACCCTCCAGTTCGTCTGTGGGGACCGCGGCTTC TACTTCAGCAGGCCCGCAAGCCGTGTGAGCCGTCGCAGC CGTGGCATCGTTGAGGAGTGCTGTTTCCGCAGCTGTGAC CTGGCCCTCCTGGAGACGTACTGTGCTACCCCCGCCAAG TCCGAG GGATCTGGGAGCGCTGACAAAACTCACACATGCCCACC GTGCCCAGCACCTGAAGCTGCCGGGGGACCGTCAGTCTT CCTCTTCCCCCCAAAACCCAAGGACACCCTCATGATCTC CCGGACCCCTGAGGTCACATGCGTGGTGGTGGACGTGA GCCACGAAGACCCTGAGGTCAAGTTCAACTGGTACGTG GACGGCGTGGAGGTGCATAATGCCAAGACAAAGCCGCG GGAGGAGCAGTACAACAGCACGTACCGTGTGGTCAGCG TCCTCACCGTCCTGCACCAGGACTGGCTGAATGGCAAGG AGTACAAGTGCAAGGTCTCCAACAAAGCCCTCGGCGCC CCCATCGAGAAAACCATCTCCAAAGCCAAAGGGCAGCC CCGAGAACCACAGGTGTACACCCTGCCCCCATCCCGGGA TGAGCTGACCAAGAACCAGGTCAGCCTGACCTGCCTGGT CAAAGGCTTCTATCCCAGCGACATCGCCGTGGAGTGGGA GAGCAATGGGCAGCCGGAGAACAACTACAAGACCACGC CTCCCGTGCTGGACTCCGACGGCTCCTTCTTCCTCTACAG CAAGCTCACCGTGGACAAGAGCAGGTGGCAGCAGGGGA ACGTCTTCTCATGCTCCGTGATGCATGAGGCTCTGCACA ACCACTACACGCAGAAaAGCCTCTCCCTGTCTCCGGGTA AA |
| 42 | 6xHis-HSA-linker3-IGF2 | His tagged HSA fusion IGF2 with a long linker nucleotide sequence | CACCATCACCATCACCATAGCGGCGATGCACACAAGAG TGAGGTTGCTCATCGGTTTAAAGATTTGGGAGAAGAAAA TTTCAAAGCCTTGGTGTTGATTGCCTTTGCTCAGTATCTT CAGCAGTGTCCATTTGAAGATCATGTAAAATTAGTGAAT GAAGTAACTGAATTTGCAAAAACATGTGTTGCTGATGAG TCAGCTGAAAATTGTGACAAATCACTTCATACCCTTTTT GGAGACAAATTATGCACAGTTGCAACTCTTCGTGAAACC TATGGTGAAATGGCTGACTGCTGTGCAAAACAAGAACCT GAGAGAAATGAATGCTTCTTGCAACACAAAGATGACAA CCCAAACCTCCCCCGATTGGTGAGACCAGAGGTTGATGT GATGTGCACTGCTTTTCATGACAATGAAGAGACATTTTT GAAAAAATACTTATATGAAATTGCCAGAAGACATCCTTA CTTTTATGCCCCGGAACTCCTTTTCTTTGCTAAAAGGTAT AAAGCTGCTTTTACAGAATGTTGCCAAGCTGCTGATAAA GCTGCCTGCCTGTTGCCAAAGCTCGATGAACTTCGGGAT GAAGGGAAGGCTTCGTCTGCCAAACAGAGACTCAAGTG TGCCAGTCTCCAAAAATTTGGAGAAAGAGCTTTCAAAGC ATGGGCAGTAGCTCGCCTGAGCCAGAGATTTCCCAAAGC TGAGTTTGCAGAAGTTTCCAAGTTAGTGACAGATCTTAC CAAAGTCCACACGGAATGCTGCCATGGAGATCTGCTTGA ATGTGCTGATGACAGGGCGGACCTTGCCAAGTATATCTG TGAAAATCAAGATTCGATCTCCAGTAAACTGAAGGAAT GCTGTGAAAAACCTCTGTTGGAAAAATCCCACTGCATTG |

TABLE 2-continued

Therapeutic Sequences

| Seq ID No | Sequence Name | Description | Sequence |
|---|---|---|---|
| | | | CCGAAGTGGAAAATGATGAGATGCCTGCTGACTTGCCTT
CATTAGCTGCTGATTTTGTTGAAAGTAAGGATGTTTGCA
AAAACTATGCTGAGGCAAAGGATGTCTTCCTGGGCATGT
TTTTGTATGAATATGCAAGAAGGCATCCTGATTACTCTG
TCGTGCTGCTGCTGAGACTTGCCAAGACATATGAAACCA
CTCTAGAGAAGTGCTGTGCCGCTGCAGATCCTCATGAAT
GCTATGCCAAAGTGTTCGATGAATTTAAACCTCTTGTGG
AAGAGCCTCAGAATTTAATCAAACAAAATTGTGAGCTTT
TTGAGCAGCTTGGAGAGTACAAATTCCAGAATGCGCTAT
TAGTTCGTTACACCAAGAAAGTACCCCAAGTGTCAACTC
CAACTCTTGTAGAGGTCTCAAGAAACCTAGGAAAAGTG
GGCAGCAAATGTTGTAAACATCCTGAAGCAAAAAGAAT
GCCCTGTGCAGAAGACTATCTATCCGTGGTCCTGAACCA
GTTATGTGTTGCATGAGAAACGCCAGTAAGTGACAG
AGTCACCAAATGCTGCACAGAATCCTTGGTGAACAGGC
GACCATGCTTTTCAGCTCTGGAAGTCGATGAAACATACG
TTCCCAAAGAGTTTAATGCTGAAACATTCACCTTCCATG
CAGATATATGCACACTTTCTGAGAAGGAGAGACAAATC
AAGAAACAAACTGCACTTGTTGAGCTCGTGAAACACAA
GCCCAAGGCAACAAAAGAGCAACTGAAAGCTGTTATGG
ATGATTTCGCAGCTTTTGTAGAGAAGTGCTGCAAGGCTG
ACGATAAGGAGACCTGCTTTGCCGAGGAGGGTAAAAAA
CTTGTTGCTGCAAGTCAAGCTGCCTTAGGCTTAGGCGGA
GGCGGTAGCGGAGGCGGTGGCTCCGGTGGCGGAGGGTC
TGCTTACCGCCCCAGTGAGACCCTGTGCGGCGGGGAGCT
GGTGGACACCCTCCAGTTCGTCTGTGGGGACCGCGGCTT
CTACTTCAGCAGGCCCGCAAGCCGTGTGAGCCGTCGCAG
CCGTGGCATCGTTGAGGAGTGCTGTTTCCGCAGCTGTGA
CCTGGCCCTCCTGGAGACGTACTGTGCTACCCCCGCCAA
GTCCGAG |
| 43 | 6xHis-HSA-linker3-IGF2R61A | His tagged HSA fusion IGF2 R61A mutant with a long linker nucleotide sequence | CACCATCACCATCACCATAGCGGCGATGCACACAAGAG
TGAGGTTGCTCATCGGTTTAAAGATTTGGGAGAAGAAAA
TTTCAAAGCCTTGGTGTTGATTGCCTTTGCTCAGTATCTT
CAGCAGTGTCCATTTGAAGATCATGTAAAATTAGTGAAT
GAAGTAACTGAATTTGCAAAAACATGTGTTGCTGATGAG
TCAGCTGAAAATTGTGACAAATCACTTCATACCCTTTTT
GGAGACAAATTATGCACAGTTGCAACTCTTCGTGAAACC
TATGGTGAAATGGCTGACTGCTGTGCAAAACAAGAACCT
GAGAGAAATGAATGCTTCTTGCAACACAAAGATGACAA
CCCAAACCTCCCCCGATTGGTGAGACCAGAGGTTGATGT
GATGTGCACTGCTTTTCATGACAATGAAGAGACATTTTT
GAAAAAATACTTATATGAAATTGCCAGAAGACATCCTTA
CTTTTATGCCCCGGAACTCCTTTTCTTTGCTAAAAGGTAT
AAAGCTGCTTTTACAGAATGTTGCCAAGCTGCTGATAAA
GCTGCCTGCCTGTTGCCAAAGCTCGATGAACTTCGGGAT
GAAGGGAAGGCTTCGTCTGCCAAACAGAGACTCAAGTG
TGCCAGTCTCCAAAAATTTGGAGAAAGAGCTTTCAAAGC
ATGGGCAGTAGCTCGCCTGAGCCAGAGATTTCCCAAAGC
TGAGTTTGCAGAAGTTTCCAAGTTAGTGACAGATCTTAC
CAAAGTCCACACGGAATGCTGCCATGGAGATCTGCTTGA
ATGTGCTGATGACAGGGCGGACCTTGCCAAGTATATCTG
TGAAAATCAAGATTCGATCTCCAGTAAACTGAAGGAAT
GCTGTGAAAAACCTCTGTTGGAAAAATCCCACTGCATTG
CCGAAGTGGAAAATGATGAGATGCCTGCTGACTTGCCTT
CATTAGCTGCTGATTTTGTTGAAAGTAAGGATGTTTGCA
AAAACTATGCTGAGGCAAAGGATGTCTTCCTGGGCATGT
TTTTGTATGAATATGCAAGAAGGCATCCTGATTACTCTG
TCGTGCTGCTGCTGAGACTTGCCAAGACATATGAAACCA
CTCTAGAGAAGTGCTGTGCCGCTGCAGATCCTCATGAAT
GCTATGCCAAAGTGTTCGATGAATTTAAACCTCTTGTGG
AAGAGCCTCAGAATTTAATCAAACAAAATTGTGAGCTTT
TTGAGCAGCTTGGAGAGTACAAATTCCAGAATGCGCTAT
TAGTTCGTTACACCAAGAAAGTACCCCAAGTGTCAACTC
CAACTCTTGTAGAGGTCTCAAGAAACCTAGGAAAAGTG
GGCAGCAAATGTTGTAAACATCCTGAAGCAAAAAGAAT
GCCCTGTGCAGAAGACTATCTATCCGTGGTCCTGAACCA
GTTATGTGTTGCATGAGAAACGCCAGTAAGTGACAG
AGTCACCAAATGCTGCACAGAATCCTTGGTGAACAGGC
GACCATGCTTTTCAGCTCTGGAAGTCGATGAAACATACG
TTCCCAAAGAGTTTAATGCTGAAACATTCACCTTCCATG
CAGATATATGCACACTTTCTGAGAAGGAGAGACAAATC
AAGAAACAAACTGCACTTGTTGAGCTCGTGAAACACAA
GCCCAAGGCAACAAAAGAGCAACTGAAAGCTGTTATGG
ATGATTTCGCAGCTTTTGTAGAGAAGTGCTGCAAGGCTG |

TABLE 2-continued

Therapeutic Sequences

| Seq ID No | Sequence Name | Description | Sequence |
|---|---|---|---|
| | | | ACGATAAGGAGACCTGCTTTGCCGAGGAGGGTAAAAAA<br>CTTGTTGCTGCAAGTCAAGCTGCCTTAGGCTTAGGCGGA<br>GGCGGTAGCGGAGGCGGTGGCTCCGGTGGCGGAGGGTC<br>TGCTTACCGCCCCAGTGAGACCCTGTGCGGCGGGGAGCT<br>GGTGGACACCCTCCAGTTCGTCTGTGGGGACCGCGGCTT<br>CTACTTCAGCAGGCCCGCAAGCCGTGTGAGCGcTCGCAG<br>CCGTGGCATCGTTGAGGAGTGCTGTTTCCGCAGCTGTGA<br>CCTGGCCCTCCTGGAGACGTACTGTGCTACCCCCGCCAA<br>GTCCGAG |
| 44 | 6xHis-HSA-linker3-IGF2R61Q | His tagged HSA fusion IGF2 R61Q mutant with a long linker nucleotide sequence | CACCATCACCATCACCATAGCGGCGATGCACACAAGAG<br>TGAGGTTGCTCATCGGTTTAAAGATTTGGGAGAAGAAAA<br>TTTCAAAGCCTTGGTGTTGATTGCCTTTGCTCAGTATCTT<br>CAGCAGTGTCCATTTGAAGATCATGTAAAATTAGTGAAT<br>GAAGTAACTGAATTTGCAAAAACATGTGTTGCTGATGAG<br>TCAGCTGAAAATTGTGACAAATCACTTCATACCCTTTTT<br>GGAGACAAATTATGCACAGTTGCAACTCTTCGTGAAACC<br>TATGGTGAAATGGCTGACTGCTGTGCAAAACAAGAACCT<br>GAGAGAAATGAATGCTTCTTGCAACACAAAGATGACAA<br>CCCAAACCTCCCCCGATTGGTGAGACCAGAGGTTGATGT<br>GATGTGCACTGCTTTTCATGACAATGAAGAGACATTTTT<br>GAAAAAATACTTATATGAAATTGCCAGAAGACATCCTTA<br>CTTTTATGCCCCGGAACTCCTTTTCTTTGCTAAAAGGTAT<br>AAAGCTGCTTTTACAGAATGTTGCCAAGCTGCTGATAAA<br>GCTGCCTGCCTGTTGCCAAAGCTCGATGAACTTCGGGAT<br>GAAGGGAAGGCTTCGTCTGCCAAACAGAGACTCAAGTG<br>TGCCAGTCTCCAAAAATTTGGAGAAAGAGCTTTCAAAGC<br>ATGGGCAGTAGCTCGCCTGAGCCAGAGATTTCCCAAAGC<br>TGAGTTTGCAGAAGTTTCCAAGTTAGTGACAGATCTTAC<br>CAAAGTCCACACGGAATGCTGCCATGGAGATCTGCTTGA<br>ATGTGCTGATGACAGGGCGGACCTTGCCAAGTATATCTG<br>TGAAAATCAAGATTCGATCTCCAGTAAACTGAAGGAAT<br>GCTGTGAAAAACCTCTGTTGGAAAAATCCCACTGCATTG<br>CCGAAGTGGAAAATGATGAGATGCCTGCTGACTTGCCTT<br>CATTAGCTGCTGATTTTGTTGAAAGTAAGGATGTTTGCA<br>AAAACTATGCTGAGGCAAAGGATGTCTTCCTGGGCATGT<br>TTTTGTATGAATATGCAAGAAGGCATCCTGATTACTCTG<br>TCGTGCTGCTGCTGAGACTTGCCAAGACATATGAAACCA<br>CTCTAGAGAAGTGCTGTGCCGCTGCAGATCCTCATGAAT<br>GCTATGCCAAAGTGTTCGATGAATTTAAACCTCTTGTGG<br>AAGAGCCTCAGAATTTAATCAAACAAAATTGTGAGCTTT<br>TTGAGCAGCTTGGAGAGTACAAATTCCAGAATGCGCTAT<br>TAGTTCGTTACACCAAGAAAGTACCCCAAGTGTCAACTC<br>CAACTCTTGTAGAGGTCTCAAGAAACCTAGGAAAAGTG<br>GGCAGCAAATGTTGTAAACATCCTGAAGCAAAAAGAAT<br>GCCCTGTGCAGAAGACTATCTATCCGTGGTCCTGAACCA<br>GTTATGTGTGTTGCATGAGAAACGCCAGTAAGTGACAG<br>AGTCACCAAATGCTGCACAGAATCCTTGGTGAACAGGC<br>GACCATGCTTTTCAGCTCTGGAAGTCGATGAAACATACG<br>TTCCCAAAGAGTTTAATGCTGAAACATTCACCTTCCATG<br>CAGATATATGCACACTTTCTGAGAAGGAGAGACAAATC<br>AAGAAACAAACTGCACTTGTTGAGCTCGTGAAACACAA<br>GCCCAAGGCAACAAAAGAGCAACTGAAAGCTGTTATGG<br>ATGATTTCGCAGCTTTTGTAGAGAAGTGCTGCAAGGCTG<br>ACGATAAGGAGACCTGCTTTGCCGAGGAGGGTAAAAAA<br>CTTGTTGCTGCAAGTCAAGCTGCCTTAGGCTTAGGCGGA<br>GGCGGTAGCGGAGGCGGTGGCTCCGGTGGCGGAGGGTC<br>TGCTTACCGCCCCAGTGAGACCCTGTGCGGCGGGGAGCT<br>GGTGGACACCCTCCAGTTCGTCTGTGGGGACCGCGGCTT<br>CTACTTCAGCAGGCCCGCAAGCCGTGTGAGCCaGCGCAG<br>CCGTGGCATCGTTGAGGAGTGCTGTTTCCGCAGCTGTGA<br>CCTGGCCCTCCTGGAGACGTACTGTGCTACCCCCGCCAA<br>GTCCGAG |
| 45 | 6xHis-HSA-linker3-IGF2R64A | His tagged HSA fusion IGF2 R64A mutant with a long linker nucleotide sequence | CACCATCACCATCACCATAGCGGCGATGCACACAAGAG<br>TGAGGTTGCTCATCGGTTTAAAGATTTGGGAGAAGAAAA<br>TTTCAAAGCCTTGGTGTTGATTGCCTTTGCTCAGTATCTT<br>CAGCAGTGTCCATTTGAAGATCATGTAAAATTAGTGAAT<br>GAAGTAACTGAATTTGCAAAAACATGTGTTGCTGATGAG<br>TCAGCTGAAAATTGTGACAAATCACTTCATACCCTTTTT<br>GGAGACAAATTATGCACAGTTGCAACTCTTCGTGAAACC<br>TATGGTGAAATGGCTGACTGCTGTGCAAAACAAGAACCT<br>GAGAGAAATGAATGCTTCTTGCAACACAAAGATGACAA<br>CCCAAACCTCCCCCGATTGGTGAGACCAGAGGTTGATGT<br>GATGTGCACTGCTTTTCATGACAATGAAGAGACATTTTT |

TABLE 2-continued

Therapeutic Sequences

| Seq ID No | Sequence Name | Description | Sequence |
|---|---|---|---|
| | | | GAAAAAATACTTATATGAAATTGCCAGAAGACATCCTTA CTTTTATGCCCCGGAACTCCTTTTCTTTGCTAAAAGGTAT AAAGCTGCTTTTACAGAATGTTGCCAAGCTGCTGATAAA GCTGCCTGCCTGTTGCCAAAGCTCGATGAACTTCGGGAT GAAGGGAAGGCTTCGTCTGCCAAACAGAGACTCAAGTG TGCCAGTCTCCAAAAATTTGGAGAAAGAGCTTTCAAAGC ATGGGCAGTAGCTCGCCTGAGCCAGAGATTTCCCAAAGC TGAGTTTGCAGAAGTTTCCAAGTTAGTGACAGATCTTAC CAAAGTCCACACGGAATGCTGCCATGGAGATCTGCTTGA ATGTGCTGATGACAGGGCGGACCTTGCCAAGTATATCTG TGAAAATCAAGATTCGATCTCCAGTAAACTGAAGGAAT GCTGTGAAAAACCTCTGTTGGAAAAATCCCACTGCATTG CCGAAGTGGAAAATGATGAGATGCCTGCTGACTTGCCTT CATTAGCTGCTGATTTTGTTGAAAGTAAGGATGTTTGCA AAAACTATGCTGAGGCAAAGGATGTCTTCCTGGGCATGT TTTTGTATGAATATGCAAGAAGGCATCCTGATTACTCTG TCGTGCTGCTGCTGAGACTTGCCAAGACATATGAAACCA CTCTAGAGAAGTGCTGTGCCGCTGCAGATCCTCATGAAT GCTATGCCAAAGTGTTCGATGAATTTAAACCTCTTGTGG AAGAGCCTCAGAATTTAATCAAACAAAATTGTGAGCTTT TTGAGCAGCTTGGAGAGTACAAATTCCAGAATGCGCTAT TAGTTCGTTACACCAAGAAAGTACCCCAAGTGTCAACTC CAACTCTTGTAGAGGTCTCAAGAAACCTAGGAAAAGTG GGCAGCAAATGTTGTAAACATCCTGAAGCAAAAAGAAT GCCCTGTGCAGAAGACTATCTATCCGTGGTCCTGAACCA GTTATGTGTGTTGCATGAGAAAACGCCAGTAAGTGACAG AGTCACCAAATGCTGCACAGAATCCTTGGTGAACAGGC GACCATGCTTTTCAGCTCTGGAAGTCGATGAAACATACG TTCCCAAAGAGTTTAATGCTGAAACATTCACCTTCCATG CAGATATATGCACACTTTCTGAGAAGGAGAGACAAATC AAGAAACAAACTGCACTTGTTGAGCTCGTGAAACACAA GCCCAAGGCAACAAAAGAGCAACTGAAAGCTGTTATGG ATGATTTCGCAGCTTTTGTAGAGAAGTGCTGCAAGGCTG ACGATAAGGAGACCTGCTTTGCCGAGGAGGGTAAAAAA CTTGTTGCTGCAAGTCAAGCTGCCTTAGGCTTAGGCGGA GGCGGTAGCGGAGGCGGTGGCTCCGGTGGCGGAGGGTC TGCTTACCGCCCCAGTGAGACCCTGTGCGGCGGGAGCT GGTGGACACCCTCCAGTTCGTCTGTGGGGACCGCGGCTT CTACTTCAGCAGGCCCGCAAGCCGTGTGAGCCGTCGCAG CGCTGGCATCGTTGAGGAGTGCTGTTTCCGCAGCTGTGA CCTGGCCCTCCTGGAGACGTACTGTGCTACCCCCGCCAA GTCCGAG |
| 46 | 6xHis-HSA-linker3-IGF2R64Q | His tagged HSA fusion IGF2 R64Q mutant with a long linker nucleotide sequence | CACCATCACCATCACCATAGCGGCGATGCACACAAGAG TGAGGTTGCTCATCGGTTTAAAGATTTGGGAGAAGAAAA TTTCAAAGCCTTGGTGTTGATTGCCTTTGCTCAGTATCTT CAGCAGTGTCCATTTGAAGATCATGTAAAATTAGTGAAT GAAGTAACTGAATTTGCAAAAACATGTGTTGCTGATGAG TCAGCTGAAAATTGTGACAAATCACTTCATACCCTTTTT GGAGACAAATTATGCACAGTTGCAACTCTTCGTGAAACC TATGGTGAAATGGCTGACTGCTGTGCAAAACAAGAACCT GAGAGAAATGAATGCTTCTTGCAACACAAAGATGACAA CCCAAACCTCCCCCGATTGGTGAGACCAGAGGTTGATGT GATGTGCACTGCTTTTCATGACAATGAAGAGACATTTTT GAAAAAATACTTATATGAAATTGCCAGAAGACATCCTTA CTTTTATGCCCCGGAACTCCTTTTCTTTGCTAAAAGGTAT AAAGCTGCTTTTACAGAATGTTGCCAAGCTGCTGATAAA GCTGCCTGCCTGTTGCCAAAGCTCGATGAACTTCGGGAT GAAGGGAAGGCTTCGTCTGCCAAACAGAGACTCAAGTG TGCCAGTCTCCAAAAATTTGGAGAAAGAGCTTTCAAAGC ATGGGCAGTAGCTCGCCTGAGCCAGAGATTTCCCAAAGC TGAGTTTGCAGAAGTTTCCAAGTTAGTGACAGATCTTAC CAAAGTCCACACGGAATGCTGCCATGGAGATCTGCTTGA ATGTGCTGATGACAGGGCGGACCTTGCCAAGTATATCTG TGAAAATCAAGATTCGATCTCCAGTAAACTGAAGGAAT GCTGTGAAAAACCTCTGTTGGAAAAATCCCACTGCATTG CCGAAGTGGAAAATGATGAGATGCCTGCTGACTTGCCTT CATTAGCTGCTGATTTTGTTGAAAGTAAGGATGTTTGCA AAAACTATGCTGAGGCAAAGGATGTCTTCCTGGGCATGT TTTTGTATGAATATGCAAGAAGGCATCCTGATTACTCTG TCGTGCTGCTGCTGAGACTTGCCAAGACATATGAAACCA CTCTAGAGAAGTGCTGTGCCGCTGCAGATCCTCATGAAT GCTATGCCAAAGTGTTCGATGAATTTAAACCTCTTGTGG AAGAGCCTCAGAATTTAATCAAACAAAATTGTGAGCTTT TTGAGCAGCTTGGAGAGTACAAATTCCAGAATGCGCTAT |

TABLE 2-continued

Therapeutic Sequences

| Seq ID No | Sequence Name | Description | Sequence |
|---|---|---|---|
| | | | TAGTTCGTTACACCAAGAAAGTACCCCAAGTGTCAACTC CAACTCTTGTAGAGGTCTCAAGAAACCTAGGAAAAGTG GGCAGCAAATGTTGTAAACATCCTGAAGCAAAAAGAAT GCCCTGTGCAGAAGACTATCTATCCGTGGTCCTGAACCA GTTATGTGTGTTGCATGAGAAAACGCCAGTAAGTGACAG AGTCACCAAATGCTGCACAGAATCCTTGGTGAACAGGC GACCATGCTTTTCAGCTCTGGAAGTCGATGAAACATACG TTCCCAAAGAGTTTAATGCTGAAACATTCACCTTCCATG CAGATATATGCACACTTTCTGAGAAGGAGAGACAAATC AAGAAACAAACTGCACTTGTTGAGCTCGTGAAACACAA GCCCAAGGCAACAAAAGAGCAACTGAAAGCTGTTATGG ATGATTTCGCAGCTTTTGTAGAGAAGTGCTGCAAGGCTG ACGATAAGGAGACCTGCTTTGCCGAGGAGGGTAAAAAA CTTGTTGCTGCAAGTCAAGCTGCCTTAGGCTTAGGCGGA GGCGGTAGCGGAGGCGGTGGCTCCGGTGGCGGAGGGTC TGCTTACCGCCCCAGTGAGACCCTGTGCGGCGGGGAGCT GGTGGACACCCTCCAGTTCGTCTGTGGGGACCGCGGCTT CTACTTCAGCAGGCCCGCAAGCCGTGTGAGCCGTCGCAG CCaGGGCATCGTTGAGGAGTGCTGTTTCCGCAGCTGTGA CCTGGCCCTCCTGGAGACGTACTGTGCTACCCCCGCCAA GTCCGAG |
| 47 | IGF2-linker3-hFc4 | Human IGF2-linker3-hFc4 nucleotide sequence | GCTTACCGCCCCAGTGAGACCCTGTGCGGCGGGGAGCTG GTGGACACCCTCCAGTTCGTCTGTGGGGACCGCGGCTTC TACTTCAGCAGGCCCGCAAGCCGTGTGAGCCGTCGCAGC CGTGGCATCGTTGAGGAGTGCTGTTTCCGCAGCTGTGAC CTGGCCCTCCTGGAGACGTACTGTGCTACCCCCGCCAAG TCCGAGGGCGGAGGCGGTAGCGGAGGCGGTGGCTCCGG TGGCGGAGGGTCTGAGTCCAAATATGGTCCCCCATGCCC ACCCTGCCCAGCACCTGAGTTCCTGGGGGGACCATCAGT CTTCCTGTTCCCCCCAAAACCCAAGGACACTCTCATGAT CTCCCGGACCCCTGAGGTCACGTGCGTGGTGGTGGACGT GAGCCAGGAAGACCCCGAGGTCCAGTTCAACTGGTACG TGGATGGCGTGGAGGTGCATAATGCCAAGACAAAGCCG CGGGAGGAGCAGTTCAACAGCACGTACCGTGTGGTCAG CGTCCTCACCGTCCTGCACCAGGACTGGCTGAACGGCAA GGAGTACAAGTGCAAGGTCTCCAACAAAGGCCTCCCGT CCTCCATCGAGAAAACCATCTCCAAAGCCAAAGGGCAG CCCCGAGAGCCACAGGTGTACACCCTGCCCCCATCCCAG GAGGAGATGACCAAGAACCAGGTCAGCCTGACCTGCCT GGTCAAAGGCTTCTACCCCAGCGACATCGCCGTGGAGTG GGAGAGCAATGGGCAGCCGGAGAACAACTACAAGACCA CGCCTCCCGTGCTGGACTCCGACGGCTCCTTCTTCCTCTA CAGCAGGCTCACCGTGGACAAGAGCAGGTGGCAGGAGG GGAATGTCTTCTCATGCTCCGTGATGCATGAGGCTCTGC ACAACCACTACACACAGAAGAGCCTCTCCCTGTCTCTGG GTAAA |
| 48 | IGF2-hFc4 | Human IGF2-hFc4 nucleotide sequence | GCTTACCGCCCCAGTGAGACCCTGTGCGGCGGGGAGCTG GTGGACACCCTCCAGTTCGTCTGTGGGGACCGCGGCTTC TACTTCAGCAGGCCCGCAAGCCGTGTGAGCCGTCGCAGC CGTGGCATCGTTGAGGAGTGCTGTTTCCGCAGCTGTGAC CTGGCCCTCCTGGAGACGTACTGTGCTACCCCCGCCAAG TCCGAGGAGTCCAAATATGGTCCCCCATGCCCACCCTGC CCAGCACCTGAGTTCCTGGGGGGACCATCAGTCTTCCTG TTCCCCCCAAAACCCAAGGACACTCTCATGATCTCCCGG ACCCCTGAGGTCACGTGCGTGGTGGTGGACGTGAGCCA GGAAGACCCCGAGGTCCAGTTCAACTGGTACGTGGATG GCGTGGAGGTGCATAATGCCAAGACAAAGCCGCGGGAG GAGCAGTTCAACAGCACGTACCGTGTGGTCAGCGTCCTC ACCGTCCTGCACCAGGACTGGCTGAACGGCAAGGAGTA CAAGTGCAAGGTCTCCAACAAAGGCCTCCCGTCCTCCAT CGAGAAAACCATCTCCAAAGCCAAAGGGCAGCCCCGAG AGCCACAGGTGTACACCCTGCCCCCATCCCAGGAGGAG ATGACCAAGAACCAGGTCAGCCTGACCTGCCTGGTCAA AGGCTTCTACCCCAGCGACATCGCCGTGGAGTGGGAGA GCAATGGGCAGCCGGAGAACAACTACAAGACCACGCCT CCCGTGCTGGACTCCGACGGCTCCTTCTTCCTCTACAGC AGGCTCACCGTGGACAAGAGCAGGTGGCAGGAGGGGAA TGTCTTCTCATGCTCCGTGATGCATGAGGCTCTGCACAA CCACTACACACAGAAGAGCCTCTCCCTGTCTCTGGGTAA A |

TABLE 2-continued

Therapeutic Sequences

| Seq ID No | Sequence Name | Description | Sequence |
|---|---|---|---|
| 49 | hFc4-linker3-IGF2 | hFc4-linker3-human IGF2 nucleotide sequence | GAGTCCAAATATGGTCCCCCATGCCCACCCTGCCCAGCA CCTGAGTTCCTGGGGGGACCATCAGTCTTCCTGTTCCCC CCAAAACCCAAGGACACTCTCATGATCTCCCGGACCCCT GAGGTCACGTGCGTGGTGGTGGACGTGAGCCAGGAAGA CCCCGAGGTCCAGTTCAACTGGTACGTGGATGGCGTGGA GGTGCATAATGCCAAGACAAAGCCGCGGGAGGAGCAGT TCAACAGCACGTACCGTGTGGTCAGCGTCCTCACCGTCC TGCACCAGGACTGGCTGAACGGCAAGGAGTACAAGTGC AAGGTCTCCAACAAAGGCCTCCCGTCCTCCATCGAGAAA ACCATCTCCAAAGCCAAAGGGCAGCCCCGAGAGCCACA GGTGTACACCCTGCCCCCATCCCAGGAGGAGATGACCA AGAACCAGGTCAGCCTGACCTGCCTGGTCAAAGGCTTCT ACCCCAGCGACATCGCCGTGGAGTGGGAGAGCAATGGG CAGCCGGAGAACAACTACAAGACCACGCCTCCCGTGCT GGACTCCGACGGCTCCTTCTTCCTCTACAGCAGGCTCAC CGTGGACAAGAGCAGGTGGCAGGAGGGGAATGTCTTCT CATGCTCCGTGATGCATGAGGCTCTGCACAACCACTACA CACAGAAGAGCCTCTCCCTGTCTCTGGGTAAAGGCGGAG GCGGTAGCGGAGGCGGTGGCTCCGGTGGCGGAGGGTCT GCTTACCGCCCCAGTGAGACCCTGTGCGGCGGGGAGCTG GTGGACACCCTCCAGTTCGTCTGTGGGGACCGCGGCTTC TACTTCAGCAGGCCCGCAAGCCGTGTGAGCCGTCGCAGC CGTGGCATCGTTGAGGAGTGCTGTTTCCGCAGCTGTGAC CTGGCCCTCCTGGAGACGTACTGTGCTACCCCCGCCAAG TCCGAG |
| 50 | IGF2R61A-linker3-hFc4 | Human IGF2 R61A point mutant-linker3-hFc4 nucleotide sequence | GCTTACCGCCCCAGTGAGACCCTGTGCGGCGGGGAGCTG GTGGACACCCTCCAGTTCGTCTGTGGGGACCGCGGCTTC TACTTCAGCAGGCCCGCAAGCCGTGTGAGCGcTCGCAGC CGTGGCATCGTTGAGGAGTGCTGTTTCCGCAGCTGTGAC CTGGCCCTCCTGGAGACGTACTGTGCTACCCCCGCCAAG TCCGAGGGCGGAGGCGGTAGCGGAGGCGGTGGCTCCGG TGGCGGAGGGTCTGAGTCCAAATATGGTCCCCCATGCCC ACCCTGCCCAGCACCTGAGTTCCTGGGGGGACCATCAGT CTTCCTGTTCCCCCCAAAACCCAAGGACACTCTCATGAT CTCCCGGACCCCTGAGGTCACGTGCGTGGTGGTGGACGT GAGCCAGGAAGACCCCGAGGTCCAGTTCAACTGGTACG TGGATGGCGTGGAGGTGCATAATGCCAAGACAAAGCCG CGGGAGGAGCAGTTCAACAGCACGTACCGTGTGGTCAG CGTCCTCACCGTCCTGCACCAGGACTGGCTGAACGGCAA GGAGTACAAGTGCAAGGTCTCCAACAAAGGCCTCCCGT CCTCCATCGAGAAAACCATCTCCAAAGCCAAAGGGCAG CCCCGAGAGCCACAGGTGTACACCCTGCCCCCATCCCAG GAGGAGATGACCAAGAACCAGGTCAGCCTGACCTGCCT GGTCAAAGGCTTCTACCCCAGCGACATCGCCGTGGAGTG GGAGAGCAATGGGCAGCCGGAGAACAACTACAAGACCA CGCCTCCCGTGCTGGACTCCGACGGCTCCTTCTTCCTCTA CAGCAGGCTCACCGTGGACAAGAGCAGGTGGCAGGAGG GGAATGTCTTCTCATGCTCCGTGATGCATGAGGCTCTGC ACAACCACTACACACAGAAGAGCCTCTCCCTGTCTCTGG GTAAA |
| 51 | BMP-7 | Mature form of human BMP-7 (AA293-431) nucleotide sequence | TCCACGGGGAGCAAACAGCGCAGCCAGAACCGCTCCAA GACGCCCAAGAACCAGGAAGCCCTGCGGATGGCCAACG TGGCAGAGAACAGCAGCAGCGACCAGAGGCAGGCCTGT AAGAAGCACGAGCTGTATGTCAGCTTCCGAGACCTGGG CTGGCAGGACTGGATCATCGCGCCTGAAGGCTACGCCGC CTACTACTGTGAGGGGGAGTGTGCCTTCCCTCTGAACTC CTACATGAACGCCACCAACCACGCCATCGTGCAGACGCT GGTCCACTTCATCAACCCGGAAACGGTGCCCAAGCCCTG CTGTGCGCCCACGCAGCTCAATGCCATCTCCGTCCTCTA CTTCGATGACAGCTCCAACGTCATCCTGAAGAAATACAG AAACATGGTGGTCCGGGCCTGTGGCTGCCAC |
| 52 | BMP-7-linker1-hFcm | BMP7 fusion protein nucleotide sequence | TCCACGGGGAGCAAACAGCGCAGCCAGAACCGCTCCAA GACGCCCAAGAACCAGGAAGCCCTGCGGATGGCCAACG TGGCAGAGAACAGCAGCAGCGACCAGAGGCAGGCCTGT AAGAAGCACGAGCTGTATGTCAGCTTCCGAGACCTGGG CTGGCAGGACTGGATCATCGCGCCTGAAGGCTACGCCGC CTACTACTGTGAGGGGGAGTGTGCCTTCCCTCTGAACTC CTACATGAACGCCACCAACCACGCCATCGTGCAGACGCT GGTCCACTTCATCAACCCGGAAACGGTGCCCAAGCCCTG CTGTGCGCCCACGCAGCTCAATGCCATCTCCGTCCTCTA CTTCGATGACAGCTCCAACGTCATCCTGAAGAAATACAG AAACATGGTGGTCCGGGCCTGTGGCTGCCAC |

TABLE 2-continued

Therapeutic Sequences

| Seq ID No | Sequence Name | Description | Sequence |
|---|---|---|---|
| | | | GGATCGGGATCGGACAAAACTCACACATGCCCACCGTG
CCCAGCACCTGAAGCTGCCGGGGGACCGTCAGTCTTCCT
CTTCCCCCCAAAACCCAAGGACACCCTCATGATCTCCCG
GACCCCTGAGGTCACATGCGTGGTGGTGGACGTGAGCC
ACGAAGACCCTGAGGTCAAGTTCAACTGGTACGTGGAC
GGCGTGGAGGTGCATAATGCCAAGACAAAGCCGCGGGA
GGAGCAGTACAACAGCACGTACCGTGTGGTCAGCGTCCT
CACCGTCCTGCACCAGGACTGGCTGAATGGCAAGGAGT
ACAAGTGCAAGGTCTCCAACAAAGCCCTCGGCGCCCCC
ATCGAGAAAACCATCTCCAAAGCCAAAGGGCAGCCCCG
AGAACCACAGGTGTACACCCTGCCCCCATCCCGGGATGA
GCTGACCAAGAACCAGGTCAGCCTGACCTGCCTGGTCAA
AGGCTTCTATCCCAGCGACATCGCCGTGGAGTGGGAGA
GCAATGGGCAGCCGGAGAACAACTACAAGACCACGCCT
CCCGTGCTGGACTCCGACGGCTCCTTCTTCCTCTACAGC
AAGCTCACCGTGGACAAGAGCAGGTGGCAGCAGGGGAA
CGTCTTCTCATGCTCCGTGATGCATGAGGCTCTGCACAA
CCACTACACGCAGAAaAGCCTCTCCCTGTCTCCGGGTAA
A |
| 53 | BMP-7-linker2-hFcm | BMP7 fusion protein nucleotide sequence | TCCACGGGGAGCAAACAGCGCAGCCAGAACCGCTCCAA
GACGCCCAAGAACCAGGAAGCCCTGCGGATGGCCAACG
TGGCAGAGAACAGCAGCAGCGACCAGAGGCAGGCCTGT
AAGAAGCACGAGCTGTATGTCAGCTTCCGAGACCTGGG
CTGGCAGGACTGGATCATCGCGCCTGAAGGCTACGCCGC
CTACTACTGTGAGGGGGAGTGTGCCTTCCCTCTGAACTC
CTACATGAACGCCACCAACCACGCCATCGTGCAGACGCT
GGTCCACTTCATCAACCCGGAAACGGTGCCCAAGCCCTG
CTGTGCGCCCACGCAGCTCAATGCCATCTCCGTCCTCTA
CTTCGATGACAGCTCCAACGTCATCCTGAAGAAATACAG
AAACATGGTGGTCCGGGCCTGTGGCTGCCAC
GGATCTGGGAGCGCTGACAAAACTCACACATGCCCACC
GTGCCCAGCACCTGAAGCTGCCGGGGGACCGTCAGTCTT
CCTCTTCCCCCCAAAACCCAAGGACACCCTCATGATCTC
CCGGACCCCTGAGGTCACATGCGTGGTGGTGGACGTGA
GCCACGAAGACCCTGAGGTCAAGTTCAACTGGTACGTG
GACGGCGTGGAGGTGCATAATGCCAAGACAAAGCCGCG
GGAGGAGCAGTACAACAGCACGTACCGTGTGGTCAGCG
TCCTCACCGTCCTGCACCAGGACTGGCTGAATGGCAAGG
AGTACAAGTGCAAGGTCTCCAACAAAGCCCTCGGCGCC
CCCATCGAGAAAACCATCTCCAAAGCCAAAGGGCAGCC
CCGAGAACCACAGGTGTACACCCTGCCCCCATCCCGGGA
TGAGCTGACCAAGAACCAGGTCAGCCTGACCTGCCTGGT
CAAAGGCTTCTATCCCAGCGACATCGCCGTGGAGTGGGA
GAGCAATGGGCAGCCGGAGAACAACTACAAGACCACGC
CTCCCGTGCTGGACTCCGACGGCTCCTTCTTCCTCTACAG
CAAGCTCACCGTGGACAAGAGCAGGTGGCAGCAGGGGA
ACGTCTTCTCATGCTCCGTGATGCATGAGGCTCTGCACA
ACCACTACACGCAGAAaAGCCTCTCCCTGTCTCCGGGTA
AA |
| 54 | FGF-17 | Full length of human FGF-17 amino acid sequence | TQGENHPSPNFNQYVRDQGAMTDQLSRRQIREYQLYSRTS
GKHVQVTGRRISATAEDGNKFAKLIVETDTFGSRVRIKGAE
SEKYICMNKRGKLIGKPSGKSKDCVFTEIVLENNYTAFQNA
RHEGWFMAFTRQGRPRQASRSRQNQREAHFIKRLYQGQLP
FPNHAEKQKQFEFVGSAPTRRTKRTRRPQPLT |
| 55 | FGF-17d204-216 | Human FGF-17 AA204-216 deletion mutant amino acid sequence | TQGENHPSPNFNQYVRDQGAMTDQLSRRQIREYQLYSRTS
GKHVQVTGRRISATAEDGNKFAKLIVETDTFGSRVRIKGAE
SEKYICMNKRGKLIGKPSGKSKDCVFTEIVLENNYTAFQNA
RHEGWFMAFTRQGRPRQASRSRQNQREAHFIKRLYQGQLP
FPNHAEKQKQFEFVGSAPT |
| 56 | FGF-17d181-216 | Human FGF-17 AA181-216 deletion mutant amino acid sequence | TQGENHPSPNFNQYVRDQGAMTDQLSRRQIREYQLYSRTS
GKHVQVTGRRISATAEDGNKFAKLIVETDTFGSRVRIKGAE
SEKYICMNKRGKLIGKPSGKSKDCVFTEIVLENNYTAFQNA
RHEGWFMAFTRQGRPRQASRSRQNQREAHFIKRLYQ |

TABLE 2-continued

Therapeutic Sequences

| Seq ID No | Sequence Name | Description | Sequence |
|---|---|---|---|
| 57 | FGF-17R204Q K207Q | Human FGF-17 R204Q K207Q mutant amino acid sequence | TQGENHPSPNFNQYVRDQGAMTDQLSRRQIREYQLYSRTS GKHVQVTGRRISATAEDGNKFAKLIVETDTFGSRVRIKGAE SEKYICMNKRGKLIGKPSGKSKDCVFTEIVLENNYTAFQNA RHEGWFMAFTRQGRPRQASRSRQNQREAHFIKRLYQGQLP FPNHAEKQKQFEFVGSAPTQRTQRTRRPQPLT |
| 58 | FGF-17d197-216 | Human FGF-17 AA197-216 deletion mutant amino acid sequence | TQGENHPSPNFNQYVRDQGAMTDQLSRRQIREYQLYSRTS GKHVQVTGRRISATAEDGNKFAKLIVETDTFGSRVRIKGAE SEKYICMNKRGKLIGKPSGKSKDCVFTEIVLENNYTAFQNA RHEGWFMAFTRQGRPRQASRSRQNQREAHFIKRLYQGQLP FPNHAEKQKQFE |
| 59 | FGF-17K191A K193AS200A | Human FGF-17 K191A K193A S200A mutant amino acid sequence | TQGENHPSPNFNQYVRDQGAMTDQLSRRQIREYQLYSRTS GKHVQVTGRRISATAEDGNKFAKLIVETDTFGSRVRIKGAE SEKYICMNKRGKLIGKPSGKSKDCVFTEIVLENNYTAFQNA RHEGWFMAFTRQGRPRQASRSRQNQREAHFIKRLYQGQLP FPNHAEAQAQFEFVGAAPTRRTKRTRRPQPLT |
| 60 | FGF-17-linker1-hFcm | Full length of human FGF-17-linker1-hFcm amino acid sequence | TQGENHPSPNFNQYVRDQGAMTDQLSRRQIREYQLYSRTS GKHVQVTGRRISATAEDGNKFAKLIVETDTFGSRVRIKGAE SEKYICMNKRGKLIGKPSGKSKDCVFTEIVLENNYTAFQNA RHEGWFMAFTRQGRPRQASRSRQNQREAHFIKRLYQGQLP FPNHAEKQKQFEFVGSAPTRRTKRTRRPQPLTGSGSDKTHT CPPCPAPEAAGGPSVFLFPPKPKDTLMISRTPEVTCVVVDVS HEDPEVKFNWYVDGVEVHNAKTKPREEQYNSTYRVVSVL TVLHQDWLNGKEYKCKVSNKALGAPIEKTISKAKGQPREP QVYTLPPSRDELTKNQVSLTCLVKGFYPSDIAVEWESNGQP ENNYKTTPPVLDSDGSFFLYSKLTVDKSRWQQGNVFSCSV MHEALHNHYTQKSLSLSPGK |
| 61 | FGF-17d204-216-linker1-hFcm | Human FGF-17 AA204-216 deletion mutant-linker1-hFcm amino acid sequence | TQGENHPSPNFNQYVRDQGAMTDQLSRRQIREYQLYSRTS GKHVQVTGRRISATAEDGNKFAKLIVETDTFGSRVRIKGAE SEKYICMNKRGKLIGKPSGKSKDCVFTEIVLENNYTAFQNA RHEGWFMAFTRQGRPRQASRSRQNQREAHFIKRLYQGQLP FPNHAEKQKQFEFVGSAPTGSGSDKTHTCPPCPAPEAAGGP SVFLFPPKPKDTLMISRTPEVTCVVVDVSHEDPEVKFNWYV DGVEVHNAKTKPREEQYNSTYRVVSVLTVLHQDWLNGKE YKCKVSNKALGAPIEKTISKAKGQPREPQVYTLPPSRDELT KNQVSLTCLVKGFYPSDIAVEWESNGQPENNYKTTPPVLD SDGSFFLYSKLTVDKSRWQQGNVFSCSVMHEALHNHYTQ KSLSLSPGK |
| 62 | FGF-17d181-216-linker1-hFcm | Human FGF-17 AA181-216 deletion mutant-linker1-hFcm amino acid sequence | TQGENHPSPNFNQYVRDQGAMTDQLSRRQIREYQLYSRTS GKHVQVTGRRISATAEDGNKFAKLIVETDTFGSRVRIKGAE SEKYICMNKRGKLIGKPSGKSKDCVFTEIVLENNYTAFQNA RHEGWFMAFTRQGRPRQASRSRQNQREAHFIKRLYQGSGS DKTHTCPPCPAPEAAGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALGAPIEKTISKAKG QPREPQVYTLPPSRDELTKNQVSLTCLVKGFYPSDIAVEWE SNGQPENNYKTTPPVLDSDGSFFLYSKLTVDKSRWQQGNV FSCSVMHEALHNHYTQKSLSLSPGK |
| 63 | FGF-17R204Q K207Q-linker1-hFcm | Human FGF-17 R204Q K207Q mutant-linker1-hFcm amino acid sequence | TQGENHPSPNFNQYVRDQGAMTDQLSRRQIREYQLYSRTS GKHVQVTGRRISATAEDGNKFAKLIVETDTFGSRVRIKGAE SEKYICMNKRGKLIGKPSGKSKDCVFTEIVLENNYTAFQNA RHEGWFMAFTRQGRPRQASRSRQNQREAHFIKRLYQGQLP FPNHAEKQKQFEFVGSAPTQRTQRTRRPQPLTGSGSDKTHT CPPCPAPEAAGGPSVFLFPPKPKDTLMISRTPEVTCVVVDVS HEDPEVKFNWYVDGVEVHNAKTKPREEQYNSTYRVVSVL TVLHQDWLNGKEYKCKVSNKALGAPIEKTISKAKGQPREP QVYTLPPSRDELTKNQVSLTCLVKGFYPSDIAVEWESNGQP ENNYKTTPPVLDSDGSFFLYSKLTVDKSRWQQGNVFSCSV MHEALHNHYTQKSLSLSPGK |
| 64 | FGF-17d197-216- | Human FGF17 AA197-216 | TQGENHPSPNFNQYVRDQGAMTDQLSRRQIREYQLYSRTS GKHVQVTGRRISATAEDGNKFAKLIVETDTFGSRVRIKGAE SEKYICMNKRGKLIGKPSGKSKDCVFTEIVLENNYTAFQNA |

TABLE 2-continued

Therapeutic Sequences

| Seq ID No | Sequence Name | Description | Sequence |
|---|---|---|---|
| | linker1-hFcm | deletion mutant-linker1-hFcm | RHEGWFMAFTRQGRPRQASRSRQNQREAHFIKRLYQGQLP FPNHAEKQKQFEGSGSDKTHTCPPCPAPEAAGGPSVFLFPP KPKDTLMISRTPEVTCVVVDVSHEDPEVKFNWYVDGVEV HNAKTKPREEQYNSTYRVVSVLTVLHQDWLNGKEYKCKV SNKALGAPIEKTISKAKGQPREPQVYTLPPSRDELTKNQVS LTCLVKGFYPSDIAVEWESNGQPENNYKTTPPVLDSDGSFF LYSKLTVDKSRWQQGNVFSCSVMHEALHNHYTQKSLSLSP GK |
| 65 | FGF-17K191A K193AS200A-linker1-hFcm | Human FGF-17 K191A K193A S200A mutant-linker1-hFcm | TQGENHPSPNFNQYVRDQGAMTDQLSRRQIREYQLYSRTS GKHVQVTGRRISATAEDGNKFAKLIVETDTFGSRVRIKGAE SEKYICMNKRGKLIGKPSGKSKDCVFTEIVLENNYTAFQNA RHEGWFMAFTRQGRPRQASRSRQNQREAHFIKRLYQGQLP FPNHAEAQAQFEFVGAAPTRRTKRTRRPQPLTGSGSDKTH TCPPCPAPEAAGGPSVFLFPPKPKDTLMISRTPEVTCVVVD VSHEDPEVKFNWYVDGVEVHNAKTKPREEQYNSTYRVVS VLTVLHQDWLNGKEYKCKVSNKALGAPIEKTISKAKGQPR EPQVYTLPPSRDELTKNQVSLTCLVKGFYPSDIAVEWESNG QPENNYKTTPPVLDSDGSFFLYSKLTVDKSRWQQGNVFSC SVMHEALHNHYTQKSLSLSPGK |
| 66 | FGF-17-linker2-hFcm | Full length of human FGF17-linker2-hFcm | TQGENHPSPNFNQYVRDQGAMTDQLSRRQIREYQLYSRTS GKHVQVTGRRISATAEDGNKFAKLIVETDTFGSRVRIKGAE SEKYICMNKRGKLIGKPSGKSKDCVFTEIVLENNYTAFQNA RHEGWFMAFTRQGRPRQASRSRQNQREAHFIKRLYQGQLP FPNHAEKQKQFEFVGSAPTRRTKRTRRPQPLTGSGSADKTH TCPPCPAPEAAGGPSVFLFPPKPKDTLMISRTPEVTCVVVD VSHEDPEVKFNWYVDGVEVHNAKTKPREEQYNSTYRVVS VLTVLHQDWLNGKEYKCKVSNKALGAPIEKTISKAKGQPR EPQVYTLPPSRDELTKNQVSLTCLVKGFYPSDIAVEWESNG QPENNYKTTPPVLDSDGSFFLYSKLTVDKSRWQQGNVFSC SVMHEALHNHYTQKSLSLSPGK |
| 67 | FGF-17d204-216-linker2-hFcm | Human FGF17 AA204-216 deletion mutant-linker2-hFcm | TQGENHPSPNFNQYVRDQGAMTDQLSRRQIREYQLYSRTS GKHVQVTGRRISATAEDGNKFAKLIVETDTFGSRVRIKGAE SEKYICMNKRGKLIGKPSGKSKDCVFTEIVLENNYTAFQNA RHEGWFMAFTRQGRPRQASRSRQNQREAHFIKRLYQGQLP FPNHAEKQKQFEFVGSAPTGSGSADKTHTCPPCPAPEAAG GPSVFLFPPKPKDTLMISRTPEVTCVVVDVSHEDPEVKFNW YVDGVEVHNAKTKPREEQYNSTYRVVSVLTVLHQDWLNG KEYKCKVSNKALGAPIEKTISKAKGQPREPQVYTLPPSRDE LTKNQVSLTCLVKGFYPSDIAVEWESNGQPENNYKTTPPV LDSDGSFFLYSKLTVDKSRWQQGNVFSCSVMHEALHNHY TQKSLSLSPGK |
| 68 | FGF-17d181-216-linker2-hFcm | Human FGF17 AA181-216 deletion mutant-linker2-hFcm | TQGENHPSPNFNQYVRDQGAMTDQLSRRQIREYQLYSRTS GKHVQVTGRRISATAEDGNKFAKLIVETDTFGSRVRIKGAE SEKYICMNKRGKLIGKPSGKSKDCVFTEIVLENNYTAFQNA RHEGWFMAFTRQGRPRQASRSRQNQREAHFIKRLYQGSGS ADKTHTCPPCPAPEAAGGPSVFLFPPKPKDTLMISRTPEVTC VVVDVSHEDPEVKFNWYVDGVEVHNAKTKPREEQYNSTY RVVSVLTVLHQDWLNGKEYKCKVSNKALGAPIEKTISKAK GQPREPQVYTLPPSRDELTKNQVSLTCLVKGFYPSDIAVEW ESNGQPENNYKTTPPVLDSDGSFFLYSKLTVDKSRWQQGN VFSCSVMHEALHNHYTQKSLSLSPGK |
| 69 | FGF-17R204Q K207Q-linker2-hFcm | Human FGF-17 R204Q K207Q mutant-linker2-hFcm | TQGENHPSPNFNQYVRDQGAMTDQLSRRQIREYQLYSRTS GKHVQVTGRRISATAEDGNKFAKLIVETDTFGSRVRIKGAE SEKYICMNKRGKLIGKPSGKSKDCVFTEIVLENNYTAFQNA RHEGWFMAFTRQGRPRQASRSRQNQREAHFIKRLYQGQLP FPNHAEKQKQFEFVGSAPTQRTQRTRRPQPLTGSGSADKT HTCPPCPAPEAAGGPSVFLFPPKPKDTLMISRTPEVTCVVV DVSHEDPEVKFNWYVDGVEVHNAKTKPREEQYNSTYRVV SVLTVLHQDWLNGKEYKCKVSNKALGAPIEKTISKAKGQP REPQVYTLPPSRDELTKNQVSLTCLVKGFYPSDIAVEWESN GQPENNYKTTPPVLDSDGSFFLYSKLTVDKSRWQQGNVFS CSVMHEALHNHYTQKSLSLSPGK |
| 70 | FGF-17d197-216-linker2-hFcm | Human FGF17 AA197-216 deletion mutant-linker2-hFcm | TQGENHPSPNFNQYVRDQGAMTDQLSRRQIREYQLYSRTS GKHVQVTGRRISATAEDGNKFAKLIVETDTFGSRVRIKGAE SEKYICMNKRGKLIGKPSGKSKDCVFTEIVLENNYTAFQNA RHEGWFMAFTRQGRPRQASRSRQNQREAHFIKRLYQGQLP FPNHAEKQKQFEGSGSADKTHTCPPCPAPEAAGGPSVFLFP PKPKDTLMISRTPEVTCVVVDVSHEDPEVKFNWYVDGVEV HNAKTKPREEQYNSTYRVVSVLTVLHQDWLNGKEYKCKV |

TABLE 2-continued

Therapeutic Sequences

| Seq ID No | Sequence Name | Description | Sequence |
|---|---|---|---|
| | | | SNKALGAPIEKTISKAKGQPREPQVYTLPPSRDELTKNQVS
LTCLVKGFYPSDIAVEWESNGQPENNYKTTPPVLDSDGSFF
LYSKLTVDKSRWQQGNVFSCSVMHEALHNHYTQKSLSLSP
GK |
| 71 | FGF-17K191A K193AS200A-linker2-hFcm | Human FGF-17 K191A K193A S200A mutant-linker2-hFcm | TQGENHPSPNFNQYVRDQGAMTDQLSRRQIREYQLYSRTS
GKHVQVTGRRISATAEDGNKFAKLIVETDTFGSRVRIKGAE
SEKYICMNKRGKLIGKPSGKSKDCVFTEIVLENNYTAFQNA
RHEGWFMAFTRQGRPRQASRSRQNQREAHFIKRLYQGQLP
FPNHAEAQAQFEFVGAAPTRRTKRTRRPQPLTGSGSADKT
HTCPPCPAPEAAGGPSVFLFPPKPKDTLMISRTPEVTCVVV
DVSHEDPEVKFNWYVDGVEVHNAKTKPREEQYNSTYRVV
SVLTVLHQDWLNGKEYKCKVSNKALGAPIEKTISKAKGQP
REPQVYTLPPSRDELTKNQVSLTCLVKGFYPSDIAVEWESN
GQPENNYKTTPPVLDSDGSFFLYSKLTVDKSRWQQGNVFS
CSVMHEALHNHYTQKSLSLSPGK |
| 72 | 6xHis-HSA-linker3-FGF17 | His tagged HSA fusion FGF17 with a long linker | HHHHHHSGDAHKSEVAHRFKDLGEENFKALVLIAFAQYL
QQCPFEDHVKLVNEVTEFAKTCVADESAENCDKSLHTLFG
DKLCTVATLRETYGEMADCCAKQEPERNECFLQHKDDNP
NLPRLVRPEVDVMCTAFHDNEETFLKKYLYEIARRHPYFY
APELLFFAKRYKAAFTECCQAADKAACLLPKLDELRDEGK
ASSAKQRLKCASLQKFGERAFKAWAVARLSQRFPKAEFAE
VSKLVTDLTKVHTECCHGDLLECADDRADLAKYICENQDS
ISSKLKECCEKPLLEKSHCIAEVENDEMPADLPSLAADFVES
KDVCKNYAEAKDVFLGMFLYEYARRHPDYSVVLLLRLAK
TYETTLEKCCAAADPHECYAKVFDEFKPLVEEPQNLIKQN
CELFEQLGEYKFQNALLVRYTKKVPQVSTPTLVEVSRNLG
KVGSKCCKHPEAKRMPCAEDYLSVVLNQLCVLHEKTPVS
DRVTKCCTESLVNRRPCFSALEVDETYVPKEFNAETFTFHA
DICTLSEKERQIKKQTALVELVKHKPKATKEQLKAVMDDF
AAFVEKCCKADDKETCFAEEGKKLVAASQAALGLGGGGS
GGGGSGGGGSTQGENHPSPNFNQYVRDQGAMTDQLSRRQ
IREYQLYSRTSGKHVQVTGRRISATAEDGNKFAKLIVETDT
FGSRVRIKGAESEKYICMNKRGKLIGKPSGKSKDCVFTEIV
LENNYTAFQNARHEGWFMAFTRQGRPRQASRSRQNQREA
HFIKRLYQGQLPFPNHAEKQKQFEFVGSAPTRRTKRTRRPQ
PLT |
| 73 | FGF17-linker3-hFc4 | Human FGF17-linker3-hFc4 | TQGENHPSPNFNQYVRDQGAMTDQLSRRQIREYQLYSRTS
GKHVQVTGRRISATAEDGNKFAKLIVETDTFGSRVRIKGAE
SEKYICMNKRGKLIGKPSGKSKDCVFTEIVLENNYTAFQNA
RHEGWFMAFTRQGRPRQASRSRQNQREAHFIKRLYQGQLP
FPNHAEKQKQFEFVGSAPTRRTKRTRRPQPLTGGGGSGGG
GSGGGGSESKYGPPCPPCPAPEFLGGPSVFLFPPKPKDTLMI
SRTPEVTCVVVDVSQEDPEVQFNWYVDGVEVHNAKTKPR
EEQFNSTYRVVSVLTVLHQDWLNGKEYKCKVSNKGLPSSI
EKTISKAKGQPREPQVYTLPPSQEEMTKNQVSLTCLVKGFY
PSDIAVEWESNGQPENNYKTTPPVLDSDGSFFLYSRLTVDK
SRWQEGNVFSCSVMHEALHNHYTQKSLSLSLGK |
| 74 | FGF17-hFc4 | Human FGF17-hFc4 | TQGENHPSPNFNQYVRDQGAMTDQLSRRQIREYQLYSRTS
GKHVQVTGRRISATAEDGNKFAKLIVETDTFGSRVRIKGAE
SEKYICMNKRGKLIGKPSGKSKDCVFTEIVLENNYTAFQNA
RHEGWFMAFTRQGRPRQASRSRQNQREAHFIKRLYQGQLP
FPNHAEKQKQFEFVGSAPTRRTKRTRRPQPLTESKYGPPCP
PCPAPEFLGGPSVFLFPPKPKDTLMISRTPEVTCVVVDVSQE
DPEVQFNWYVDGVEVHNAKTKPREEQFNSTYRVVSVLTV
LHQDWLNGKEYKCKVSNKGLPSSIEKTISKAKGQPREPQV
YTLPPSQEEMTKNQVSLTCLVKGFYPSDIAVEWESNGQPE
NNYKTTPPVLDSDGSFFLYSRLTVDKSRWQEGNVFSCSVM
HEALHNHYTQKSLSLSLGK |
| 75 | hFc4L-FGF17 | hFc4-linker3-human FGF17 | ESKYGPPCPPCPAPEFLGGPSVFLFPPKPKDTLMISRTPEVTC
VVVDVSQEDPEVQFNWYVDGVEVHNAKTKPREEQFNSTY
RVVSVLTVLHQDWLNGKEYKCKVSNKGLPSSIEKTISKAK
GQPREPQVYTLPPSQEEMTKNQVSLTCLVKGFYPSDIAVE
WESNGQPENNYKTTPPVLDSDGSFFLYSRLTVDKSRWQEG
NVFSCSVMHEALHNHYTQKSLSLSLGKGGGGSGGGGSGG
GGSTQGENHPSPNFNQYVRDQGAMTDQLSRRQIREYQLYS
RTSGKHVQVTGRRISATAEDGNKFAKLIVETDTFGSRVRIK
GAESEKYICMNKRGKLIGKPSGKSKDCVFTEIVLENNYTAF
QNARHEGWFMAFTRQGRPRQASRSRQNQREAHFIKRLYQ
GQLPFPNHAEKQKQFEFVGSAPTRRTKRTRRPQPLT |

TABLE 2-continued

Therapeutic Sequences

| Seq ID No | Sequence Name | Description | Sequence |
|---|---|---|---|
| 76 | IGF2 | human IGF2 amino acid sequence | AYRPSETLCGGELVDTLQFVCGDRGFYFSRPASRVSRRSRG IVEECCFRSCDLALLETYCATPAKSE |
| 77 | IGF2-linker1-hFcm | | AYRPSETLCGGELVDTLQFVCGDRGFYFSRPASRVSRRSRG IVEECCFRSCDLALLETYCATPAKSEGSGSDKTHTCPPCPAP EAAGGPSVFLFPPKPKDTLMISRTPEVTCVVVDVSHEDPEV KFNWYVDGVEVHNAKTKPREEQYNSTYRVVSVLTVLHQD WLNGKEYKCKVSNKALGAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSCSVMHEAL HNHYTQKSLSLSPGK |
| 78 | IGF2-linker2-hFcm | | AYRPSETLCGGELVDTLQFVCGDRGFYFSRPASRVSRRSRG IVEECCFRSCDLALLETYCATPAKSEGSGSADKTHTCPPCP APEAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALGAPIEKTISKAKGQPREPQVYT LPPSRDELTKNQVSLTCLVKGFYPSDIAVEWESNGQPENNY KTTPPVLDSDGSFFLYSKLTVDKSRWQQGNVFSCSVMHEA LHNHYTQKSLSLSPGK |
| 79 80 | IGF2 Big | Full-length human IGF2 | MGIPMGKSMLVLLTFLAFASCCIAAYRPSETLCGGELVDTL QFVCGDRGFYFSRPASRVSRRSRGIVEECCFRSCDLALLET YCATPAKSERDVSTPPTVLPDNFPRYPVGKFFQYDTWKQS TQRLRRGLPALLRARRGHVLAKELEAFREAKRHRPLIALPT QDPAHGGAPPEMASNRK |
| 80 | 6xHis-HSA-linker3-IGF2 | His tagged HSA fusion IGF2 with a long linker | HHHHHHSGDAHKSEVAHRFKDLGEENFKALVLIAFAQYL QQCPFEDHVKLVNEVTEFAKTCVADESAENCDKSLHTLFG DKLCTVATLRETYGEMADCCAKQEPERNECFLQHKDDNP NLPRLVRPEVDVMCTAFHDNEETFLKKYLYEIARRHPYFY APELLFFAKRYKAAFTECCQAADKAACLLPKLDELRDEGK ASSAKQRLKCASLQKFGERAFKAWAVARLSQRFPKAEFAE VSKLVTDLTKVHTECCHGDLLECADDRADLAKYICENQDS ISSKLKECCEKPLLEKSHCIAEVENDEMPADLPSLAADFVES KDVCKNYAEAKDVFLGMFLYEYARRHPDYSVVLLLRLAK TYETTLEKCCAAADPHECYAKVFDEFKPLVEEPQNLIKQN CELFEQLGEYKFQNALLVRYTKKVPQVSTPTLVEVSRNLG KVGSKCCKHPEAKRMPCAEDYLSVVLNQLCVLHEKTPVS DRVTKCCTESLVNRRPCFSALEVDETYVPKEFNAETFTFHA DICTLSEKERQIKKQTALVELVKHKPKATKEQLKAVMDDF AAFVEKCCKADDKETCFAEEGKKLVAASQAALGLGGGGS GGGGSGGGGSAYRPSETLCGGELVDTLQFVCGDRGFYFSR PASRVSRRSRGIVEECCFRSCDLALLETYCATPAKSE |
| 81 | 6xHis-HSA-linker3-IGF2R61A | His tagged HSA fusion IGF2 R61A mutant with a long linker | HHHHHHSGDAHKSEVAHRFKDLGEENFKALVLIAFAQYL QQCPFEDHVKLVNEVTEFAKTCVADESAENCDKSLHTLFG DKLCTVATLRETYGEMADCCAKQEPERNECFLQHKDDNP NLPRLVRPEVDVMCTAFHDNEETFLKKYLYEIARRHPYFY APELLFFAKRYKAAFTECCQAADKAACLLPKLDELRDEGK ASSAKQRLKCASLQKFGERAFKAWAVARLSQRFPKAEFAE VSKLVTDLTKVHTECCHGDLLECADDRADLAKYICENQDS ISSKLKECCEKPLLEKSHCIAEVENDEMPADLPSLAADFVES KDVCKNYAEAKDVFLGMFLYEYARRHPDYSVVLLLRLAK TYETTLEKCCAAADPHECYAKVFDEFKPLVEEPQNLIKQN CELFEQLGEYKFQNALLVRYTKKVPQVSTPTLVEVSRNLG KVGSKCCKHPEAKRMPCAEDYLSVVLNQLCVLHEKTPVS DRVTKCCTESLVNRRPCFSALEVDETYVPKEFNAETFTFHA DICTLSEKERQIKKQTALVELVKHKPKATKEQLKAVMDDF AAFVEKCCKADDKETCFAEEGKKLVAASQAALGLGGGGS GGGGSGGGGSAYRPSETLCGGELVDTLQFVCGDRGFYFSR PASRVSARSRGIVEECCFRSCDLALLETYCATPAKSE |
| 82 | 6xHis-HSA-linker3-IGF2R61Q | His tagged HSA fusion IGF2 R61Q mutant with a long linker | HHHHHHSGDAHKSEVAHRFKDLGEENFKALVLIAFAQYL QQCPFEDHVKLVNEVTEFAKTCVADESAENCDKSLHTLFG DKLCTVATLRETYGEMADCCAKQEPERNECFLQHKDDNP NLPRLVRPEVDVMCTAFHDNEETFLKKYLYEIARRHPYFY APELLFFAKRYKAAFTECCQAADKAACLLPKLDELRDEGK ASSAKQRLKCASLQKFGERAFKAWAVARLSQRFPKAEFAE VSKLVTDLTKVHTECCHGDLLECADDRADLAKYICENQDS ISSKLKECCEKPLLEKSHCIAEVENDEMPADLPSLAADFVES KDVCKNYAEAKDVFLGMFLYEYARRHPDYSVVLLLRLAK TYETTLEKCCAAADPHECYAKVFDEFKPLVEEPQNLIKQN |

TABLE 2-continued

Therapeutic Sequences

| Seq ID No | Sequence Name | Description | Sequence |
|---|---|---|---|
| | | | CELFEQLGEYKFQNALLVRYTKKVPQVSTPTLVEVSRNLG KVGSKCCKHPEAKRMPCAEDYLSVVLNQLCVLHEKTPVS DRVTKCCTESLVNRRPCFSALEVDETYVPKEFNAETFTFHA DICTLSEKERQIKKQTALVELVKHKPKATKEQLKAVMDDF AAFVEKCCKADDKETCFAEEGKKLVAASQAALGLGGGGS GGGGSGGGGSAYRPSETLCGGELVDTLQFVCGDRGFYFSR PASRVSQRSRGIVEECCFRSCDLALLETYCATPAKSE |
| 83 | 6xHis-HSA-linker3-IGF2R64A | His tagged HSA fusion IGF2 R64A mutant with a long linker | HHHHHHSGDAHKSEVAHRFKDLGEENFKALVLIAFAQYL QQCPFEDHVKLVNEVTEFAKTCVADESAENCDKSLHTLFG DKLCTVATLRETYGEMADCCAKQEPERNECFLQHKDDNP NLPRLVRPEVDVMCTAFHDNEETFLKKYLYEIARRHPYFY APELLFFAKRYKAAFTECCQAADKAACLLPKLDELRDEGK ASSAKQRLKCASLQKFGERAFKAWAVARLSQRFPKAEFAE VSKLVTDLTKVHTECCHGDLLECADDRADLAKYICENQDS ISSKLKECCEKPLLEKSHCIAEVENDEMPADLPSLAADFVES KDVCKNYAEAKDVFLGMFLYEYARRHPDYSVVLLLRLAK TYETTLEKCCAAADPHECYAKVFDEFKPLVEEPQNLIKQN CELFEQLGEYKFQNALLVRYTKKVPQVSTPTLVEVSRNLG KVGSKCCKHPEAKRMPCAEDYLSVVLNQLCVLHEKTPVS DRVTKCCTESLVNRRPCFSALEVDETYVPKEFNAETFTFHA DICTLSEKERQIKKQTALVELVKHKPKATKEQLKAVMDDF AAFVEKCCKADDKETCFAEEGKKLVAASQAALGLGGGGS GGGGSGGGGSAYRPSETLCGGELVDTLQFVCGDRGFYFSR PASRVSRRSAGIVEECCFRSCDLALLETYCATPAKSE |
| 84 | 6xHis-HSA-linker3-IGF2R64Q | His tagged HSA fusion IGF2 R64Q mutant with a long linker | HHHHHHSGDAHKSEVAHRFKDLGEENFKALVLIAFAQYL QQCPFEDHVKLVNEVTEFAKTCVADESAENCDKSLHTLFG DKLCTVATLRETYGEMADCCAKQEPERNECFLQHKDDNP NLPRLVRPEVDVMCTAFHDNEETFLKKYLYEIARRHPYFY APELLFFAKRYKAAFTECCQAADKAACLLPKLDELRDEGK ASSAKQRLKCASLQKFGERAFKAWAVARLSQRFPKAEFAE VSKLVTDLTKVHTECCHGDLLECADDRADLAKYICENQDS ISSKLKECCEKPLLEKSHCIAEVENDEMPADLPSLAADFVES KDVCKNYAEAKDVFLGMFLYEYARRHPDYSVVLLLRLAK TYETTLEKCCAAADPHECYAKVFDEFKPLVEEPQNLIKQN CELFEQLGEYKFQNALLVRYTKKVPQVSTPTLVEVSRNLG KVGSKCCKHPEAKRMPCAEDYLSVVLNQLCVLHEKTPVS DRVTKCCTESLVNRRPCFSALEVDETYVPKEFNAETFTFHA DICTLSEKERQIKKQTALVELVKHKPKATKEQLKAVMDDF AAFVEKCCKADDKETCFAEEGKKLVAASQAALGLGGGGS GGGGSGGGGSAYRPSETLCGGELVDTLQFVCGDRGFYFSR PASRVSRRSQGIVEECCFRSCDLALLETYCATPAKSE |
| 85 | IGF2-linker3-hFc4 | Human IGF2-linker3-hFc4 | AYRPSETLCGGELVDTLQFVCGDRGFYFSRPASRVSRRSRG IVEECCFRSCDLALLETYCATPAKSEGGGGSGGGGSGGGGS ESKYGPPCPPCPAPEFLGGPSVFLFPPKPKDTLMISRTPEVTC VVVDVSQEDPEVQFNWYVDGVEVHNAKTKPREEQFNSTY RVVSVLTVLHQDWLNGKEYKCKVSNKGLPSSIEKTISKAK GQPREPQVYTLPPSQEEMTKNQVSLTCLVKGFYPSDIAVE WESNGQPENNYKTTPPVLDSDGSFFLYSRLTVDKSRWQEG NVFSCSVMHEALHNHYTQKSLSLSLGK |
| 86 | IGF2-hFc4 | Human IGF2-hFc4 | AYRPSETLCGGELVDTLQFVCGDRGFYFSRPASRVSRRSRG IVEECCFRSCDLALLETYCATPAKSEESKYGPPCPPCPAPEF LGGPSVFLFPPKPKDTLMISRTPEVTCVVVDVSQEDPEVQF NWYVDGVEVHNAKTKPREEQFNSTYRVVSVLTVLHQDW LNGKEYKCKVSNKGLPSSIEKTISKAKGQPREPQVYTLPPS QEEMTKNQVSLTCLVKGFYPSDIAVEWESNGQPENNYKTT PPVLDSDGSFFLYSRLTVDKSRWQEGNVFSCSVMHEALHN HYTQKSLSLSLGK |
| 87 | hFc4-linker3-IGF2 | hFc4-linker3-human IGF2 | ESKYGPPCPPCPAPEFLGGPSVFLFPPKPKDTLMISRTPEVTC VVVDVSQEDPEVQFNWYVDGVEVHNAKTKPREEQFNSTY RVVSVLTVLHQDWLNGKEYKCKVSNKGLPSSIEKTISKAK GQPREPQVYTLPPSQEEMTKNQVSLTCLVKGFYPSDIAVE WESNGQPENNYKTTPPVLDSDGSFFLYSRLTVDKSRWQEG NVFSCSVMHEALHNHYTQKSLSLSLGKGGGGSGGGGSGG GGSAYRPSETLCGGELVDTLQFVCGDRGFYFSRPASRVSRR SRGIVEECCFRSCDLALLETYCATPAKSE |
| 88 | IGF2R61A-linker3-hFc4 | Human IGF2 R61A point mutant- | AYRPSETLCGGELVDTLQFVCGDRGFYFSRPASRVSARSRG IVEECCFRSCDLALLETYCATPAKSEGGGGSGGGGSGGGGS ESKYGPPCPPCPAPEFLGGPSVFLFPPKPKDTLMISRTPEVTC VVVDVSQEDPEVQFNWYVDGVEVHNAKTKPREEQFNSTY |

TABLE 2-continued

Therapeutic Sequences

| Seq ID No | Sequence Name | Description | Sequence |
|---|---|---|---|
| | | linker3-hFc4 | RVVSVLTVLHQDWLNGKEYKCKVSNKGLPSSIEKTISKAK GQPREPQVYTLPPSQEEMTKNQVSLTCLVKGFYPSDIAVE WESNGQPENNYKTTPPVLDSDGSFFLYSRLTVDKSRWQEG NVFSCSVMHEALHNHYTQKSLSLSLGK |
| 89 | BMP-7 | Mature form of human BMP-7 (AA293-431) | STGSKQRSQNRSKTPKNQEALRMANVAENSSSDQRQACK KHELYVSFRDLGWQDWIIAPEGYAAYYCEGECAFPLNSYM NATNHAIVQTLVHFINPETVPKPCCAPTQLNAISVLYFDDSS NVILKKYRNMVVRACGCH |
| 90 | BMP-7-linker1-hFcm | BMP7 fusion protein | STGSKQRSQNRSKTPKNQEALRMANVAENSSSDQRQACK KHELYVSFRDLGWQDWIIAPEGYAAYYCEGECAFPLNSYM NATNHAIVQTLVHFINPETVPKPCCAPTQLNAISVLYFDDSS NVILKKYRNMVVRACGCHGSGSDKTHTCPPCPAPEAAGGP SVFLFPPKPKDTLMISRTPEVTCVVVDVSHEDPEVKFNWYV DGVEVHNAKTKPREEQYNSTYRVVSVLTVLHQDWLNGKE YKCKVSNKALGAPIEKTISKAKGQPREPQVYTLPPSRDELT KNQVSLTCLVKGFYPSDIAVEWESNGQPENNYKTTPPVLD SDGSFFLYSKLTVDKSRWQQGNVFSCSVMHEALHNHYTQ KSLSLSPGK |
| 91 | BMP-7-linker2-hFcm | BMP7 fusion protein | STGSKQRSQNRSKTPKNQEALRMANVAENSSSDQRQACK KHELYVSFRDLGWQDWIIAPEGYAAYYCEGECAFPLNSYM NATNHAIVQTLVHFINPETVPKPCCAPTQLNAISVLYFDDSS NVILKKYRNMVVRACGCHGSGSADKTHTCPPCPAPEAAG GPSVFLFPPKPKDTLMISRTPEVTCVVVDVSHEDPEVKFNW YVDGVEVHNAKTKPREEQYNSTYRVVSVLTVLHQDWLNG KEYKCKVSNKALGAPIEKTISKAKGQPREPQVYTLPPSRDE LTKNQVSLTCLVKGFYPSDIAVEWESNGQPENNYKTTPPV LDSDGSFFLYSKLTVDKSRWQQGNVFSCSVMHEALHNHY TQKSLSLSPGK |
| 92 | BMP7 | BMP7 knuckle | ACGGTGCCCAAGCCCTGCTGTGCGCCCACGCAGCTCAAT GCCATCTCCGTCCTCTACTTCGATGACAGCTCCAACGTC ATCCTGAAGAAATACAGA |
| 93 | BMP7 | BMP7 knuckle[A1][A2] | TVPKPCCAPTQLNAISVLYFDDSSNVILKKYR |

TABLE 3

Linker and Heterologous Sequences

| Seq ID No | Sequence Name | Description | Sequence |
|---|---|---|---|
| 94 | Linker 1 | A short flexible linker nucleotide sequence | GGATCGGGATCG |
| 95 | Linker 2 | A short flexible linker nucleotide sequence | GGATCTGGGAGCGCT |
| 96 | Linker 3 | A long flexible linker nucleotide sequence | GGCGGAGGCGGTAGCGGAGGCGGTGGCTCCGGTGGC GGAGGGTCT |
| 97 | hFcm IgG1 | Human IgG1 Fc mutant (L234A L235A P329G) nucleotide sequence | GACAAAACTCACACATGCCCACCGTGCCCAGCACCT GAAGCTGCCGGGGACCGTCAGTCTTCCTCTTCCCC CCAAAACCCAAGGACACCCTCATGATCTCCCGGACC CCTGAGGTCACATGCGTGGTGGTGGACGTGAGCCAC GAAGACCCTGAGGTCAAGTTCAACTGGTACGTGGAC GGCGTGGAGGTGCATAATGCCAAGACAAAGCCGCG GAGGAGCAGTACAACAGCACGTACCGTGTGGTCAGC GTCCTCACCGTCCTGCACCAGGACTGGCTGAATGGC AAGGAGTACAAGTGCAAGGTCTCCAACAAAGCCCTC GGCGCCCCCATCGAGAAAACCATCTCCAAAGCCAAA GGGCAGCCCCGAGAACCACAGGTGTACACCCTGCCC |

TABLE 3-continued

Linker and Heterologous Sequences

| Seq ID No | Sequence Name | Description | Sequence |
|---|---|---|---|
| | | | CCATCCCGGGATGAGCTGACCAAGAACCAGGTCAGC<br>CTGACCTGCCTGGTCAAAGGCTTCTATCCCAGCGAC<br>ATCGCCGTGGAGTGGGAGAGCAATGGGCAGCCGGAG<br>AACAACTACAAGACCACGCCTCCCGTGCTGGACTCC<br>GACGGCTCCTTCTTCCTCTACAGCAAGCTCACCGTG<br>GACAAGAGCAGGTGGCAGCAGGGGAACGTCTTCTCA<br>TGCTCCGTGATGCATGAGGCTCTGCACAACCACTAC<br>ACGCAGAAaAGCCTCTCCCTGTCTCCGGGTAAA |
| 98 | hFc4 | Human IgG4 Fc with S228P point mutation nucleotide sequence | GAGTCCAAATATGGTCCCCCATGCCCACCCTGCCCA<br>GCACCTGAGTTCCTGGGGGGACCATCAGTCTTCCTG<br>TTCCCCCCAAAACCCAAGGACACTCTCATGATCTCC<br>CGGACCCCTGAGGTCACGTGCGTGGTGGTGGACGTG<br>AGCCAGGAAGACCCCGAGGTCCAGTTCAACTGGTAC<br>GTGGATGGCGTGGAGGTGCATAATGCCAAGACAAAG<br>CCGCGGGAGGAGCAGTTCAACAGCACGTACCGTGTG<br>GTCAGCGTCCTCACCGTCCTGCACCAGGACTGGCTG<br>AACGGCAAGGAGTACAAGTGCAAGGTCTCCAACAAA<br>GGCCTCCCGTCCTCCATCGAGAAAACCATCTCCAAA<br>GCCAAAGGGCAGCCCCGAGAGCCACAGGTGTACACC<br>CTGCCCCCATCCCAGGAGGAGATGACCAAGAACCAG<br>GTCAGCCTGACCTGCCTGGTCAAAGGCTTCTACCCC<br>AGCGACATCGCCGTGGAGTGGGAGAGCAATGGGCAG<br>CCGGAGAACAACTACAAGACCACGCCTCCCGTGCTG<br>GACTCCGACGGCTCCTTCTTCCTCTACAGCAGGCTC<br>ACCGTGGACAAGAGCAGGTGGCAGGAGGGGAATGTC<br>TTCTCATGCTCCGTGATGCATGAGGCTCTGCACAAC<br>CACTACACACAGAAGAGCCTCTCCCTGTCTCTGGGT<br>AAA |
| 99 | 6xHis | Six Histidine short peptide nucleotide sequence | CACCATCACCATCACCAT |
| 100 | StrepII | Strep-Tactin binding peptide nucleotide sequence | TGGAGCCACCCGCAGTTCGAAAAA |
| 101 | HSA | Full length of Human Serum Albumin nucleotide sequence | GATGCACACAAGAGTGAGGTTGCTCATCGGTTTAAA<br>GATTTGGGAGAAGAAAATTTCAAAGCCTTGGTGTTG<br>ATTGCCTTTGCTCAGTATCTTCAGCAGTGTCCATTT<br>GAAGATCATGTAAAATTAGTGAATGAAGTAACTGAA<br>TTTGCAAAAACATGTGTTGCTGATGAGTCAGCTGAA<br>AATTGTGACAAATCACTTCATACCCTTTTTGGAGAC<br>AAATTATGCACAGTTGCAACTCTTCGTGAAACCTAT<br>GGTGAAATGGCTGACTGCTGTGCAAAACAAGAACCT<br>GAGAGAAATGAATGCTTCTTGCAACACAAAGATGAC<br>AACCCAAACCTCCCCCGATTGGTGAGACCAGAGGTT<br>GATGTGATGTGCACTGCTTTTCATGACAATGAAGAG<br>ACATTTTTGAAAAAATACTTATATGAAATTGCCAGA<br>AGACATCCTTACTTTTATGCCCCGGAACTCCTTTTC<br>TTTGCTAAAAGGTATAAAGCTGCTTTTACAGAATGT<br>TGCCAAGCTGCTGATAAAGCTGCCTGCCTGTTGCCA<br>AAGCTCGATGAACTTCGGGATGAAGGGAAGGCTTCG<br>TCTGCCAAACAGAGACTCAAGTGTGCCAGTCTCCAA<br>AAATTTGGAGAAAGAGCTTTCAAAGCATGGGCAGTA<br>GCTCGCCTGAGCCAGAGATTTCCCAAAGCTGAGTTT<br>GCAGAAGTTTCCAAGTTAGTGACAGATCTTACCAAA<br>GTCCACACGGAATGCTGCCATGGAGATCTGCTTGAA<br>TGTGCTGATGACAGGGCGGACCTTGCCAAGTATATC<br>TGTGAAAATCAAGATTCGATCTCCAGTAAACTGAAG<br>GAATGCTGTGAAAAACCTCTGTTGGAAAAATCCCAC<br>TGCATTGCCGAAGTGGAAAATGATGAGATGCCTGCT<br>GACTTGCCTTCATTAGCTGCTGATTTTGTTGAAAGT<br>AAGGATGTTTGCAAAAACTATGCTGAGGCAAAGGAT<br>GTCTTCCTGGGCATGTTTTTGTATGAATATGCAAGA<br>AGGCATCCTGATTACTCTGTCGTGCTGCTGCTGAGA<br>CTTGCCAAGACATATGAAACCACTCTAGAGAAGTGC<br>TGTGCCGCTGCAGATCCTCATGAATGCTATGCCAAA<br>GTGTTCGATGAATTTAAACCTCTTGTGGAAGAGCCT<br>CAGAATTTAATCAAACAAAATTGTGAGCTTTTTGAG<br>CAGCTTGGAGAGTACAAATTCCAGAATGCGCTATTA<br>GTTCGTTACACCAAGAAAGTACCCCAAGTGTCAACT |

TABLE 3-continued

Linker and Heterologous Sequences

| Seq ID No | Sequence Name | Description | Sequence |
|---|---|---|---|
| | | | CCAACTCTTGTAGAGGTCTCAAGAAACCTAGGAAAA GTGGGCAGCAAATGTTGTAAACATCCTGAAGCAAAA AGAATGCCCTGTGCAGAAGACTATCTATCCGTGGTC CTGAACCAGTTATGTGTGTTGCATGAGAAAACGCCA GTAAGTGACAGAGTCACCCAAATGCTGCACAGAATCC TTGGTGAACAGGCGACCATGCTTTTCAGCTCTGGAA GTCGATGAAACATACGTTCCCAAAGAGTTTAATGCT GAAACATTCACCTTCCATGCAGATATATGCACACTT TCTGAGAAGGAGAGACAAATCAAGAAACAAACTGCA CTTGTTGAGCTCGTGAAACACAAGCCCAAGGCAACA AAAGAGCAACTGAAAGCTGTTATGGATGATTTCGCA GCTTTTGTAGAGAAGTGCTGCAAGGCTGACGATAAG GAGACCTGCTTTGCCGAGGAGGGTAAAAAACTTGTT GCTGCAAGTCAAGCTGCCTTAGGCTTA |
| 102 | Linker 1 | A short flexible linker amino acid sequence | GSGS |
| 103 | Linker 2 | A short flexible linker amino acid sequence | GSGSA |
| 104 | Linker 3 | A long flexible linker amino acid sequence | GGGGSGGGGSGGGGS |
| 105 | hFcm IgG1 | Human IgG1 Fc mutant (L234A L235A P329G) amino acid sequence | DKTHTCPPCPAPEAAGGPSVFLFPPKPKDTLMISRT PEVTCVVVDVSHEDPEVKFNWYVDGVEVHNAKTKPR EEQYNSTYRVVSVLTVLHQDWLNGKEYKCKVSNKAL GAPIEKTISKAKGQPREPQVYTLPPSRDELTKNQVS LTCLVKGFYPSDIAVEWESNGQPENNYKTTPPVLDS DGSFFLYSKLTVDKSRWQQGNVFSCSVMHEALHNHY TQKSLSLSPGK |
| 106 | hFc4 | Human IgG4 Fc with S228P point mutation amino acid sequence | ESKYGPPCPPCPAPEFLGGPSVFLFPPKPKDTLMIS RTPEVTCVVVDVSQEDPEVQFNWYVDGVEVHNAKTK PREEQFNSTYRVVSVLTVLHQDWLNGKEYKCKVSNK GLPSSIEKTISKAKGQPREPQVYTLPPSQEEMTKNQ VSLTCLVKGFYPSDIAVEWESNGQPENNYKTTPPVL DSDGSFFLYSRLTVDKSRWQEGNVFSCSVMHEALHN HYTQKSLSLSLGK |
| 107 | 6xHis | Six Histidine short peptide amino acid sequence | HHHHHH |
| 108 | StrepII | Strep-Tactin binding peptide amino acid sequence | WSHPQFEK |
| 109 | HSA | Full length of Human Serum Albumin amino acid sequence | DAHKSEVAHRFKDLGEENFKALVLIAFAQYLQQCPF EDHVKLVNEVTEFAKTCVADESAENCDKSLHTLFGD KLCTVATLRETYGEMADCCAKQEPERNECFLQHKDD NPNLPRLVRPEVDVMCTAFHDNEETFLKKYLYEIAR RHPYFYAPELLFFAKRYKAAFTECCQAADKAACLLP KLDELRDEGKASSAKQRLKCASLQKFGERAFKAWAV ARLSQRFPKAEFAEVSKLVTDLTKVHTECCHGDLLE CADDRADLAKYICENQDSISSKLKECCEKPLLEKSH CIAEVENDEMPADLPSLAADFVESKDVCKNYAEAKD VFLGMFLYEYARRHPDYSVVLLLRLAKTYETTLEKC CAAADPHECYAKVFDEFKPLVEEPQNLIKQNCELFE QLGEYKFQNALLVRYTKKVPQVSTPTLVEVSRNLGK VGSKCCKHPEAKRMPCAEDYLSVVLNQLCVLHEKTP VSDRVTKCCTESLVNRRPCFSALEVDETYVPKEFNA ETFTFHADICTLSEKERQIKKQTALVELVKHKPKAT KEQLKAVMDDFAAFVEKCCKADDKETCFAEEGKKLV AASQAALGL |

What is claimed is:

1. A method of treating a muscle wasting disease or condition in an individual comprising administering to the individual a therapeutically effective amount of a polypeptide comprising an Insulin-like growth factor 2 (IGF-2) amino acid sequence and an N-terminal human serum albumin (HSA) heterologous polypeptide amino acid sequence, wherein the N-terminal HSA heterologous polypeptide amino acid sequence and the IGF2 amino acid sequence are separated by a flexible peptide linker, wherein the N-terminal HSA heterologous polypeptide amino acid sequence increases the stability or biological function of the IGF-2 amino acid sequence, and wherein the administering increases differentiation of myoblast cells by increasing fusion of myoblasts into multinucleated muscle fibers.

2. The method of claim 1, wherein the muscle wasting disease or condition comprises a muscular dystrophy.

3. The method of claim 1, further comprising the step of administering a short chain fatty acid.

4. The method of claim 3, wherein the short chain fatty acid is a butyrate.

5. The method of claim 1, wherein the IGF2 amino acid sequence comprises a human IGF2 amino acid sequence.

6. The method of claim 5, wherein the human IGF2 amino acid sequence consists of an amino acid sequence at least about 98% identical to the amino acid sequence set forth in SEQ ID NO: 76.

7. The method of claim 5, wherein the IGF2 sequence comprises at least one amino acid that is N-, C-, or O-linked glycosylated.

8. The method of claim 1, wherein the N-terminal HSA heterologous polypeptide amino acid sequence comprises SEQ ID NO: 109, and wherein the flexible peptide linker comprises a glycine-serine linker or multimers of a glycine-serine linker.

9. The method of claim 8, wherein the heterologous polypeptide amino acid sequence comprises a fragment of an immunoglobulin molecule and wherein the fragment of the immunoglobulin molecule comprises the hinge domain of an IgG, the CH2 domain of an IgG, the CH3 domain of an IgG, or any combination thereof.

10. The method of claim 9, wherein the fragment of the immunoglobulin molecule comprises one or more mutations that reduce the effector function of the fragment of the immunoglobulin molecule.

11. The method of claim 10, wherein the fragment of the immunoglobulin molecule comprises a fragment of an IgG4 molecule.

12. The method of claim 11, wherein the fragment of the immunoglobulin molecule comprises a fragment of an IgG4 molecule with at least one of the following amino acid mutations or sets of mutations in the fragment of the immunoglobulin molecule: N434A, N434H, T307A/E380A/N434A, M252Y/S254T/T256E, 433K/434F/436H, T250Q, T250F, M428L, M428F, T250Q/M428L, N434S, V308W, V308Y, V308F, M252Y/M428L, D2591/V308F, M428L/V308F, Q311V/N434S, T307Q/N434A, E258F/V427T, S228P, L235E, S228P/L235E/R409K, S228P/L235E, K370Q, K370E, deletion of G446, deletion of K447, and combinations thereof of IgG4 according to the EU numbering system.

13. The method of claim 1, further comprising the step of increasing a regenerative capability of myoblast cells in the subject by administering the polypeptide according to a dosage schedule, wherein the dosage schedule comprises repeated administrations of the therapeutically effective amount of the polypeptide to the subject.

14. The method of claim 13, wherein the regenerative capability is a proliferation of the myoblast cells, a degree of differentiation of the myoblast cells, or a cellular survival of the myoblast cells.

15. The method of claim 14, wherein increasing a proliferation of the myoblast cells produces an increase in new myofibers.

16. The method of claim 14, wherein the subject has an increase in a muscle regeneration.

17. The method of claim 13, wherein a grip strength of the subject is increased.

18. The method of claim 13, wherein a weight of muscle in the subject is increased.

19. The method of claim 13, wherein a lean body mass of the subject is increased.

20. The method of claim 13, wherein an appendicular skeletal muscle index of the subject is increased.

* * * * *

SEQUENCE LISTING

<160> NUMBER OF SEQ ID NOS: 109

<210> SEQ ID NO 1
<211> LENGTH: 66
<212> TYPE: DNA
<213> ORGANISM: Homo sapiens

<400> SEQUENCE: 1
atgggagccg cccgcctgct gcccaacctc actctgtgct tacagctgct gattctctgc    60
tgtcaa                                                                66

<210> SEQ ID NO 2
<211> LENGTH: 54
<212> TYPE: DNA
<213> ORGANISM: Homo sapiens

<400> SEQUENCE: 2
atggggctgg cctggggact aggcgtcctg ttcctgatgc atgtgtgtgg cacc          54

<210> SEQ ID NO 3
<211> LENGTH: 72
<212> TYPE: DNA
<213> ORGANISM: Homo sapiens

<400> SEQUENCE: 3
atgggaatcc caatggggaa gtcgatgctg gtgcttctca ccttcttggc cttcgcctcg    60
tgctgcattg ct                                                         72

<210> SEQ ID NO 4
<211> LENGTH: 87
<212> TYPE: DNA
<213> ORGANISM: Homo sapiens

<400> SEQUENCE: 4
atgcacgtgc gctcactgcg agctgcggcg ccgcacagct tcgtggcgct ctgggcaccc    60
ctgttcctgc tgcgctccgc cctggcc                                         87

<210> SEQ ID NO 5
<211> LENGTH: 54
<212> TYPE: DNA
<213> ORGANISM: Homo sapiens

<400> SEQUENCE: 5
atgaagtggg taacctttat ttcccttctt tttctcttta gctcggctta ttcc          54

<210> SEQ ID NO 6
<211> LENGTH: 57
<212> TYPE: DNA
<213> ORGANISM: Homo sapiens

<400> SEQUENCE: 6
atgacccggc tgacagtcct ggccctgctg gctggtctgc tggcgtcctc gagggcc       57

<210> SEQ ID NO 7
<211> LENGTH: 54
<212> TYPE: DNA
<213> ORGANISM: Homo sapiens

<400> SEQUENCE: 7
atgagggcct ggatcttctt tctcctttgc ctggccggga gggctctggc agca          54

-continued

<210> SEQ ID NO 8
<211> LENGTH: 51
<212> TYPE: DNA
<213> ORGANISM: Artificial Sequence
<220> FEATURE:
<223> OTHER INFORMATION: Gaussia princeps signal sequence for luciferase

<400> SEQUENCE: 8
atgggagtca aagttctgtt tgccctgatc tgcatcgctg tggccgaggc c         51

<210> SEQ ID NO 9
<211> LENGTH: 22
<212> TYPE: PRT
<213> ORGANISM: Homo sapiens

<400> SEQUENCE: 9

Met Gly Ala Ala Arg Leu Leu Pro Asn Leu Thr Leu Cys Leu Gln Leu
1               5                   10                  15

Leu Ile Leu Cys Cys Gln
            20

<210> SEQ ID NO 10
<211> LENGTH: 18
<212> TYPE: PRT
<213> ORGANISM: Homo sapiens

<400> SEQUENCE: 10

Met Gly Leu Ala Trp Gly Leu Gly Val Leu Phe Leu Met His Val Cys
1               5                   10                  15

Gly Thr

<210> SEQ ID NO 11
<211> LENGTH: 24
<212> TYPE: PRT
<213> ORGANISM: Homo sapiens

<400> SEQUENCE: 11

Met Gly Ile Pro Met Gly Lys Ser Met Leu Val Leu Leu Thr Phe Leu
1               5                   10                  15

Ala Phe Ala Ser Cys Cys Ile Ala
            20

<210> SEQ ID NO 12
<211> LENGTH: 29
<212> TYPE: PRT
<213> ORGANISM: Homo sapiens

<400> SEQUENCE: 12

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala
            20                  25

<210> SEQ ID NO 13
<211> LENGTH: 18
<212> TYPE: PRT
<213> ORGANISM: Homo sapiens

<400> SEQUENCE: 13

Met Lys Trp Val Thr Phe Ile Ser Leu Leu Phe Leu Phe Ser Ser Ala
1               5                   10                  15

Tyr Ser

<210> SEQ ID NO 14
<211> LENGTH: 19
<212> TYPE: PRT
<213> ORGANISM: Homo sapiens

<400> SEQUENCE: 14

Met Thr Arg Leu Thr Val Leu Ala Leu Leu Ala Gly Leu Leu Ala Ser
1               5                   10                  15

Ser Arg Ala

<210> SEQ ID NO 15
<211> LENGTH: 18
<212> TYPE: PRT
<213> ORGANISM: Homo sapiens

<400> SEQUENCE: 15

Met Arg Ala Trp Ile Phe Phe Leu Leu Cys Leu Ala Gly Arg Ala Leu
1               5                   10                  15

Ala Ala

<210> SEQ ID NO 16
<211> LENGTH: 17
<212> TYPE: PRT
<213> ORGANISM: Artificial Sequence
<220> FEATURE:
<223> OTHER INFORMATION: Gaussia princeps signal sequence for luciferase

<400> SEQUENCE: 16

Met Gly Val Lys Val Leu Phe Ala Leu Ile Cys Ile Ala Val Ala Glu
1               5                   10                  15

Ala

<210> SEQ ID NO 17
<211> LENGTH: 582
<212> TYPE: DNA
<213> ORGANISM: Homo sapiens

<400> SEQUENCE: 17
actcaggggg agaatcaccc gtctcctaat tttaaccagt acgtgaggga ccagggcgcc      60
atgaccgacc agctgagcag gcggcagatc cgcgagtacc aactctacag caggaccagt     120
ggcaagcacg tgcaggtcac cgggcgtcgc atctccgcca ccgccgagga cggcaacaag     180
tttgccaagc tcatagtgga cacggacacg tttggcagcc gggttcgcat caaaggggct     240
gagagtgaga agtacatctg tatgaacaag agggggcaagc tcatcgggaa gcccagcggg     300
aagagcaaag actgcgtgtt cacggagatc gtgctggaga caactatac ggccttccag     360 aacgcccggc acgagggctg gttcatggcc ttcacgcggc aggggcggcc ccgccaggct     420
tcccgcagcc gccagaacca gcgcgaggcc cacttcatca gcgcctcta ccaaggccag     480 ctgccctccc ccaaccacgc cgagaagcag aagcagttcg agtttgtggg ctccgccccc     540
acccgccgga ccaagcgcac acggcggccc cagcccctca cg                        582

<210> SEQ ID NO 18
<211> LENGTH: 543
<212> TYPE: DNA
<213> ORGANISM: Artificial Sequence
<220> FEATURE:
<223> OTHER INFORMATION: FGF17 deletion mutant

<400> SEQUENCE: 18

```
actcaggggg agaatcaccc gtctcctaat tttaaccagt acgtgaggga ccagggcgcc    60
atgaccgacc agctgagcag gcggcagatc cgcgagtacc aactctacag caggaccagt   120
ggcaagcacg tgcaggtcac cgggcgtcgc atctccgcca ccgccgagga cggcaacaag   180
tttgccaagc tcatagtgga gacggacacg tttggcagcc gggttcgcat caaaggggct   240
gagagtgaga agtacatctg tatgaacaag aggggcaagc tcatcgggaa gcccagcggg   300
aagagcaaag actgcgtgtt cacggagatc gtgctggaga caactatac ggccttccag    360
aacgcccggc acgagggctg gttcatggcc ttcacgcggc aggggcggcc ccgccaggct   420
tcccgcagcc gccagaacca gcgcgaggcc cacttcatca gcgcctcta ccaaggccag    480
ctgccccttcc ccaaccacgc cgagaagcag aagcagttcg agtttgtggg ctccgccccc  540
acc                                                                 543
```

<210> SEQ ID NO 19
<211> LENGTH: 474
<212> TYPE: DNA
<213> ORGANISM: Artificial Sequence
<220> FEATURE:
<223> OTHER INFORMATION: FGF17 deletion mutant

<400> SEQUENCE: 19

```
actcaggggg agaatcaccc gtctcctaat tttaaccagt acgtgaggga ccagggcgcc    60
atgaccgacc agctgagcag gcggcagatc cgcgagtacc aactctacag caggaccagt   120
ggcaagcacg tgcaggtcac cgggcgtcgc atctccgcca ccgccgagga cggcaacaag   180
tttgccaagc tcatagtgga gacggacacg tttggcagcc gggttcgcat caaaggggct   240
gagagtgaga agtacatctg tatgaacaag aggggcaagc tcatcgggaa gcccagcggg   300
aagagcaaag actgcgtgtt cacggagatc gtgctggaga caactatac ggccttccag    360
aacgcccggc acgagggctg gttcatggcc ttcacgcggc aggggcggcc ccgccaggct   420
tcccgcagcc gccagaacca gcgcgaggcc cacttcatca gcgcctcta ccaa          474
```

<210> SEQ ID NO 20
<211> LENGTH: 582
<212> TYPE: DNA
<213> ORGANISM: Artificial Sequence
<220> FEATURE:
<223> OTHER INFORMATION: FGF17 mutant

<400> SEQUENCE: 20

```
actcaggggg agaatcaccc gtctcctaat tttaaccagt acgtgaggga ccagggcgcc    60
atgaccgacc agctgagcag gcggcagatc cgcgagtacc aactctacag caggaccagt   120
ggcaagcacg tgcaggtcac cgggcgtcgc atctccgcca ccgccgagga cggcaacaag   180
tttgccaagc tcatagtgga gacggacacg tttggcagcc gggttcgcat caaaggggct   240
gagagtgaga agtacatctg tatgaacaag aggggcaagc tcatcgggaa gcccagcggg   300
aagagcaaag actgcgtgtt cacggagatc gtgctggaga caactatac ggccttccag    360
aacgcccggc acgagggctg gttcatggcc ttcacgcggc aggggcggcc ccgccaggct   420
tcccgcagcc gccagaacca gcgcgaggcc cacttcatca gcgcctcta ccaaggccag    480
ctgccccttcc ccaaccacgc cgagaagcag aagcagttcg agtttgtggg ctccgccccc  540
acccagcgga cccagcgcac acggcggccc cagcccctca cg                      582
```

<210> SEQ ID NO 21
<211> LENGTH: 522

-continued

```
<212> TYPE: DNA
<213> ORGANISM: Artificial Sequence
<220> FEATURE:
<223> OTHER INFORMATION: FGF17 deletion mutant

<400> SEQUENCE: 21
actcaggggg agaatcaccc gtctcctaat tttaaccagt acgtgaggga ccagggcgcc      60
atgaccgacc agctgagcag gcggcagatc cgcgagtacc aactctacag caggaccagt    120
ggcaagcacg tgcaggtcac cgggcgtcgc atctccgcca ccgccgagga cggcaacaag    180
tttgccaagc tcatagtgga gacggacacg tttggcagcc gggttcgcat caaaggggct    240
gagagtgaga agtacatctg tatgaacaag aggggcaagc tcatcgggaa gcccagcggg    300
aagagcaaag actgcgtgtt cacggagatc gtgctggaga caactatac ggccttccag     360 aacgcccggc acgagggctg gttcatggcc ttcacgcggc aggggcggcc ccgccaggct    420
tcccgcagcc gccagaacca gcgcgaggcc cacttcatca gcgcctcta ccaaggccag     480 ctgcccttcc ccaaccacgc cgagaagcag aagcagttcg ag                       522

<210> SEQ ID NO 22
<211> LENGTH: 582
<212> TYPE: DNA
<213> ORGANISM: Artificial Sequence
<220> FEATURE:
<223> OTHER INFORMATION: FGF17 mutant

<400> SEQUENCE: 22
actcaggggg agaatcaccc gtctcctaat tttaaccagt acgtgaggga ccagggcgcc      60
atgaccgacc agctgagcag gcggcagatc cgcgagtacc aactctacag caggaccagt    120
ggcaagcacg tgcaggtcac cgggcgtcgc atctccgcca ccgccgagga cggcaacaag    180
tttgccaagc tcatagtgga gacggacacg tttggcagcc gggttcgcat caaaggggct    240
gagagtgaga agtacatctg tatgaacaag aggggcaagc tcatcgggaa gcccagcggg    300
aagagcaaag actgcgtgtt cacggagatc gtgctggaga caactatac ggccttccag     360 aacgcccggc acgagggctg gttcatggcc ttcacgcggc aggggcggcc ccgccaggct    420
tcccgcagcc gccagaacca gcgcgaggcc cacttcatca gcgcctcta ccaaggccag     480 ctgcccttcc ccaaccacgc cgaggctcag gcacagttcg agtttgtggg cgctgccccc    540
acccgccgga ccaagcgcac acggcggccc cagcccctca cg                       582

<210> SEQ ID NO 23
<211> LENGTH: 1275
<212> TYPE: DNA
<213> ORGANISM: Artificial Sequence
<220> FEATURE:
<223> OTHER INFORMATION: FGF17 fusion

<400> SEQUENCE: 23
actcaggggg agaatcaccc gtctcctaat tttaaccagt acgtgaggga ccagggcgcc      60
atgaccgacc agctgagcag gcggcagatc cgcgagtacc aactctacag caggaccagt    120
ggcaagcacg tgcaggtcac cgggcgtcgc atctccgcca ccgccgagga cggcaacaag    180
tttgccaagc tcatagtgga gacggacacg tttggcagcc gggttcgcat caaaggggct    240
gagagtgaga agtacatctg tatgaacaag aggggcaagc tcatcgggaa gcccagcggg    300
aagagcaaag actgcgtgtt cacggagatc gtgctggaga caactatac ggccttccag     360 aacgcccggc acgagggctg gttcatggcc ttcacgcggc aggggcggcc ccgccaggct    420
```

| | |
|---|---|
| tcccgcagcc gccagaacca gcgcgaggcc cacttcatca agcgcctcta ccaaggccag | 480 |
| ctgcccttcc ccaaccacgc cgagaagcag aagcagttcg agtttgtggg ctccgccccc | 540 |
| acccgccgga ccaagcgcac acggcggccc cagcccctca cgggatcggg atcggacaaa | 600 |
| actcacacat gcccaccgtg cccagcacct gaagctgccg ggggaccgtc agtcttcctc | 660 |
| ttccccccaa acccaagga caccctcatg atctcccgga cccctgaggt cacatgcgtg | 720 |
| gtggtggacg tgagccacga agaccctgag gtcaagttca actggtacgt ggacggcgtg | 780 |
| gaggtgcata atgccaagac aaagccgcgg gaggagcagt acaacagcac gtaccgtgtg | 840 |
| gtcagcgtcc tcaccgtcct gcaccaggac tggctgaatg gcaaggagta caagtgcaag | 900 |
| gtctccaaca aagccctcgg cgcccccatc gagaaaacca tctccaaagc caagggcag | 960 |
| ccccgagaac acaggtgta caccctgccc ccatcccggg atgagctgac caagaaccag | 1020 |
| gtcagcctga cctgcctggt caaaggcttc tatcccagcg acatcgccgt ggagtgggag | 1080 |
| agcaatgggc agccggagaa caactacaag accacgcctc ccgtgctgga ctccgacggc | 1140 |
| tccttcttcc tctacagcaa gctcaccgtg gacaagagca ggtggcagca ggggaacgtc | 1200 |
| ttctcatgct ccgtgatgca tgaggctctg cacaaccact acacgcagaa aagcctctcc | 1260 |
| ctgtctccgg gtaaa | 1275 |

<210> SEQ ID NO 24
<211> LENGTH: 1236
<212> TYPE: DNA
<213> ORGANISM: Artificial Sequence
<220> FEATURE:
<223> OTHER INFORMATION: FGF17 deletion mutant

<400> SEQUENCE: 24

| | |
|---|---|
| actcaggggg agaatcaccc gtctcctaat tttaaccagt acgtgaggga ccagggcgcc | 60 |
| atgaccgacc agctgagcag gcggcagatc cgcgagtacc aactctacag caggaccagt | 120 |
| ggcaagcacg tgcaggtcac cgggcgtcgc atctccgcca ccgccgagga cggcaacaag | 180 |
| tttgccaagc tcatagtgga gacggacacg tttggcagcc gggttcgcat caaaggggct | 240 |
| gagagtgaga agtacatctg tatgaacaag aggggcaagc tcatcgggaa gcccagcggg | 300 |
| aagagcaaag actgcgtgtt cacggagatc gtgctggaga caactatac ggccttccag | 360 |
| aacgcccggc acgagggctg gttcatggcc ttcacgcggc aggggcggcc ccgccaggct | 420 |
| tcccgcagcc gccagaacca gcgcgaggcc cacttcatca agcgcctcta ccaaggccag | 480 |
| ctgcccttcc ccaaccacgc cgagaagcag aagcagttcg agtttgtggg ctccgccccc | 540 |
| accggatcgg gatcggacaa aactcacaca tgcccaccgt gcccagcacc tgaagctgcc | 600 |
| ggggaccgt cagtcttcct cttccccccc aaacccaagg acaccctcat gatctcccgg | 660 |
| acccctgagg tcacatgcgt ggtggtggac gtgagccacg aagaccctga ggtcaagttc | 720 |
| aactggtacg tggacggcgt ggaggtgcat aatgccaaga caaagccgcg ggaggagcag | 780 |
| tacaacagca cgtaccgtgt ggtcagcgtc ctcaccgtcc tgcaccagga ctggctgaat | 840 |
| ggcaaggagt acaagtgcaa ggtctccaac aaagccctcg gcgcccccat cgagaaaacc | 900 |
| atctccaaag ccaagggca gccccgagaa cacaggtgt acaccctgcc cccatcccgg | 960 |
| gatgagctga ccaagaacca ggtcagcctg acctgcctgg tcaaaggctt ctatcccagc | 1020 |
| gacatcgccg tggagtggga gagcaatggg cagccggaga caactacaa gaccacgcct | 1080 |
| cccgtgctga ctccgacgg ctccttcttc tctacagca gctcaccgt ggacaagagc | 1140 |
| aggtggcagc aggggaacgt cttctcatgc tccgtgatgc atgaggctct gcacaaccac | 1200 | tacacgcaga aaagcctctc cctgtctccg ggtaaa                        1236

<210> SEQ ID NO 25
<211> LENGTH: 1167
<212> TYPE: DNA
<213> ORGANISM: Artificial Sequence
<220> FEATURE:
<223> OTHER INFORMATION: FGF17 deletion mutant

<400> SEQUENCE: 25
actcaggggg agaatcaccc gtctcctaat tttaaccagt acgtgaggga ccagggcgcc    60
atgaccgacc agctgagcag gcggcagatc cgcgagtacc aactctacag caggaccagt   120
ggcaagcacg tgcaggtcac cgggcgtcgc atctccgcca ccgccgagga cggcaacaag   180
tttgccaagc tcatagtgga gacggacacg tttggcagcc gggttcgcat caaaggggct   240
gagagtgaga agtacatctg tatgaacaag aggggcaagc tcatcgggaa gcccagcggg   300
aagagcaaag actgcgtgtt cacggagatc gtgctggaga caactatacg gccttccag   360
aacgcccggc acgagggctg gttcatggcc ttcacgcggc aggggcggcc ccgccaggct   420
tcccgcagcc gccagaacca gcgcgaggcc cacttcatca gcgcctcta ccaaggatcg   480
ggatcggaca aaactcacac atgcccaccg tgcccagcac ctgaagctgc gggggaccg    540
tcagtcttcc tcttcccccc aaaacccaag gacaccctca tgatctcccg gacccctgag   600
gtcacatgcg tggtggtgga cgtgagccac gaagaccctg aggtcaagtt caactggtac   660
gtggacggcg tggaggtgca taatgccaag acaaagccgc gggaggagca gtacaacagc   720
acgtaccgtg tggtcagcgt cctcaccgtc ctgcaccagg actggctgaa tggcaaggag   780
tacaagtgca aggtctccaa caaagccctc ggcgccccca tcgagaaaac catctccaaa   840
gccaaagggc agccccgaga accacaggtg tacaccctgc ccccatcccg ggatgagctg   900
accaagaacc aggtcagcct gacctgcctg gtcaaaggct tctatcccag cgacatcgcc   960
gtggagtggg agagcaatgg gcagccggag aacaactaca agaccacgcc tcccgtgctg  1020
gactccgacg gctccttctt cctctacagc aagctcaccg tggacaagag caggtggcag  1080
caggggaacg tcttctcatg ctccgtgatg catgaggctc tgcacaacca ctacacgcag  1140
aaaagcctct ccctgtctcc gggtaaa                                       1167

<210> SEQ ID NO 26
<211> LENGTH: 1275
<212> TYPE: DNA
<213> ORGANISM: Artificial Sequence
<220> FEATURE:
<223> OTHER INFORMATION: FGF17 mutant

<400> SEQUENCE: 26
actcaggggg agaatcaccc gtctcctaat tttaaccagt acgtgaggga ccagggcgcc    60
atgaccgacc agctgagcag gcggcagatc cgcgagtacc aactctacag caggaccagt   120
ggcaagcacg tgcaggtcac cgggcgtcgc atctccgcca ccgccgagga cggcaacaag   180
tttgccaagc tcatagtgga gacggacacg tttggcagcc gggttcgcat caaaggggct   240
gagagtgaga agtacatctg tatgaacaag aggggcaagc tcatcgggaa gcccagcggg   300
aagagcaaag actgcgtgtt cacggagatc gtgctggaga caactatacg gccttccag   360
aacgcccggc acgagggctg gttcatggcc ttcacgcggc aggggcggcc ccgccaggct   420
tcccgcagcc gccagaacca gcgcgaggcc cacttcatca gcgcctcta ccaaggccag   480

```
ctgcccttcc ccaaccacgc cgagaagcag aagcagttcg agtttgtggg ctccgccccc      540
acccagcgga cccagcgcac acggcggccc cagcccctca cgggatcggg atcggacaaa      600
actcacacat gcccaccgtg cccagcacct gaagctgccg ggggaccgtc agtcttcctc      660
ttccccccaa aacccaagga caccctcatg atctcccgga cccctgaggt cacatgcgtg      720
gtggtggacg tgagccacga agaccctgag gtcaagttca actggtacgt ggacggcgtg      780
gaggtgcata atgccaagac aaagccgcgg gaggagcagt acaacagcac gtaccgtgtg      840
gtcagcgtcc tcaccgtcct gcaccaggac tggctgaatg gcaaggagta caagtgcaag      900
gtctccaaca aagccctcgg cgcccccatc gagaaaacca tctccaaagc caaagggcag      960
ccccgagaac cacaggtgta caccctgccc ccatcccggg atgagctgac caagaaccag     1020
gtcagcctga cctgcctggt caaaggcttc tatcccagcg acatcgccgt ggagtgggag     1080
agcaatgggc agccggagaa caactacaag accacgcctc ccgtgctgga ctccgacggc     1140
tccttcttcc tctacagcaa gctcaccgtg gacaagagca ggtggcagca ggggaacgtc     1200
ttctcatgct ccgtgatgca tgaggctctg cacaaccact acacgcagaa aagcctctcc     1260
ctgtctccgg gtaaa                                                      1275

<210> SEQ ID NO 27
<211> LENGTH: 1215
<212> TYPE: DNA
<213> ORGANISM: Artificial Sequence
<220> FEATURE:
<223> OTHER INFORMATION: FGF17 deletion mutant

<400> SEQUENCE: 27 actcagggg agaatcaccc gtctcctaat tttaaccagt acgtgaggga ccagggcgcc       60
atgaccgacc agctgagcag gcggcagatc cgcgagtacc aactctacag caggaccagt      120
ggcaagcacg tgcaggtcac cgggcgtcgc atctccgcca ccgccgagga cggcaacaag      180
tttgccaagc tcatagtgga gacggacacg tttggcagcc gggttcgcat caaagggggct     240
gagagtgaga agtacatctg tatgaacaag aggggcaagc tcatcgggaa gcccagcggg      300
aagagcaaag actgcgtgtt cacggagatc gtgctggaga caactatac ggccttccag       360
aacgcccggc acgagggctg gttcatggcc ttcacgcggc aggggcggcc ccgccaggct      420
tcccgcagcc gccagaacca gcgcgaggcc cacttcatca gcgcctcta ccaaggccag       480
ctgcccttcc ccaaccacgc cgagaagcag aagcagttcg agggatcggg atcggacaaa      540
actcacacat gcccaccgtg cccagcacct gaagctgccg ggggaccgtc agtcttcctc      600
ttccccccaa aacccaagga caccctcatg atctcccgga cccctgaggt cacatgcgtg      660
gtggtggacg tgagccacga agaccctgag gtcaagttca actggtacgt ggacggcgtg      720
gaggtgcata atgccaagac aaagccgcgg gaggagcagt acaacagcac gtaccgtgtg      780
gtcagcgtcc tcaccgtcct gcaccaggac tggctgaatg gcaaggagta caagtgcaag      840
gtctccaaca aagccctcgg cgcccccatc gagaaaacca tctccaaagc caaagggcag      900
ccccgagaac cacaggtgta caccctgccc ccatcccggg atgagctgac caagaaccag      960
gtcagcctga cctgcctggt caaaggcttc tatcccagcg acatcgccgt ggagtgggag     1020
agcaatgggc agccggagaa caactacaag accacgcctc ccgtgctgga ctccgacggc     1080
tccttcttcc tctacagcaa gctcaccgtg gacaagagca ggtggcagca ggggaacgtc     1140
ttctcatgct ccgtgatgca tgaggctctg cacaaccact acacgcagaa aagcctctcc     1200
ctgtctccgg gtaaa                                                     1215
```

<210> SEQ ID NO 28
<211> LENGTH: 1275
<212> TYPE: DNA
<213> ORGANISM: Artificial Sequence
<220> FEATURE:
<223> OTHER INFORMATION: FGF17 mutant

<400> SEQUENCE: 28

| | |
|---|---|
| actcagggggg agaatcaccc gtctcctaat tttaaccagt acgtgaggga ccagggcgcc | 60 |
| atgaccgacc agctgagcag gcggcagatc cgcgagtacc aactctacag caggaccagt | 120 |
| ggcaagcacg tgcaggtcac cgggcgtcgc atctccgcca ccgccgagga cggcaacaag | 180 |
| tttgccaagc tcatagtgga gacggacacg tttggcagcc gggttcgcat caaaggggct | 240 |
| gagagtgaga agtacatctg tatgaacaag aggggcaagc tcatcgggaa gcccagcggg | 300 |
| aagagcaaag actgcgtgtt cacggagatc gtgctggaga acaactatac ggccttccag | 360 |
| aacgcccggc acgagggctg gttcatggcc ttcacgcggc aggggcggcc ccgccaggct | 420 |
| tcccgcagcc gccagaacca gcgcgaggcc cacttcatca gcgcctcta ccaaggccag | 480 |
| ctgcccttcc caaccacgc cgaggctcag gcacagttcg agtttgtggg cgctgccccc | 540 |
| acccgccgga ccaagcgcac acggcggccc cagcccctca cgggatcggg atcggacaaa | 600 |
| actcacacat gcccaccgtg cccagcacct gaagctgccg ggggaccgtc agtcttcctc | 660 |
| ttccccccaa acccaagga caccctcatg atctcccgga cccctgaggt cacatgcgtg | 720 |
| gtggtggacg tgagccacga agaccctgag gtcaagttca actggtacgt ggacggcgtg | 780 |
| gaggtgcata atgccaagac aaagccgcgg gaggagcagt acaacagcac gtaccgtgtg | 840 |
| gtcagcgtcc tcaccgtcct gcaccaggac tggctgaatg gcaaggagta caagtgcaag | 900 |
| gtctccaaca aagccctcgg cgcccccatc gagaaaacca tctccaaagc caaagggcag | 960 |
| ccccgagaac cacaggtgta caccctgccc ccatcccggg atgagctgac caagaaccag | 1020 |
| gtcagcctga cctgcctggt caaaggcttc tatcccagcg acatcgccgt ggagtgggag | 1080 |
| agcaatgggc agccggagaa caactacaag accacgcctc ccgtgctgga ctccgacggc | 1140 |
| tccttcttcc tctacagcaa gctcaccgtg gacaagagca ggtggcagca ggggaacgtc | 1200 |
| ttctcatgct ccgtgatgca tgaggctctg cacaaccact acacgcagaa aagcctctcc | 1260 |
| ctgtctccgg gtaaa | 1275 |

<210> SEQ ID NO 29
<211> LENGTH: 1278
<212> TYPE: DNA
<213> ORGANISM: Artificial Sequence
<220> FEATURE:
<223> OTHER INFORMATION: FGF17 fusion

<400> SEQUENCE: 29

| | |
|---|---|
| actcagggggg agaatcaccc gtctcctaat tttaaccagt acgtgaggga ccagggcgcc | 60 |
| atgaccgacc agctgagcag gcggcagatc cgcgagtacc aactctacag caggaccagt | 120 |
| ggcaagcacg tgcaggtcac cgggcgtcgc atctccgcca ccgccgagga cggcaacaag | 180 |
| tttgccaagc tcatagtgga gacggacacg tttggcagcc gggttcgcat caaaggggct | 240 |
| gagagtgaga agtacatctg tatgaacaag aggggcaagc tcatcgggaa gcccagcggg | 300 |
| aagagcaaag actgcgtgtt cacggagatc gtgctggaga acaactatac ggccttccag | 360 |
| aacgcccggc acgagggctg gttcatggcc ttcacgcggc aggggcggcc ccgccaggct | 420 |

```
tcccgcagcc gccagaacca gcgcgaggcc cacttcatca agcgcctcta ccaaggccag    480
ctgcccttcc ccaaccacgc cgagaagcag aagcagttcg agtttgtggg ctccgccccc    540
acccgccgga ccaagcgcac acggcggccc cagcccctca cgggatctgg gagcgctgac    600
aaaactcaca catgcccacc gtgcccagca cctgaagctg ccgggggacc gtcagtcttc    660
ctcttccccc caaaacccaa ggacaccctc atgatctccc ggaccectga ggtcacatgc    720
gtggtggtgg acgtgagcca cgaagaccct gaggtcaagt tcaactggta cgtggacggc    780
gtggaggtgc ataatgccaa gacaaagccg cgggaggagc agtacaacag cacgtaccgt    840
gtggtcagcg tcctcaccgt cctgcaccag gactggctga atggcaagga gtacaagtgc    900
aaggtctcca acaaagccct cggcgccccc atcgagaaaa ccatctccaa agccaaaggg    960
cagccccgag aaccacaggt gtacaccctg cccccatccc gggatgagct gaccaagaac   1020
caggtcagcc tgacctgcct ggtcaaaggc ttctatccca gcgacatcgc cgtggagtgg   1080
gagagcaatg ggcagccgga gaacaactac aagaccacgc ctcccgtgct ggactccgac   1140
ggctccttct cctctacag caagctcacc gtggacaaga gcaggtggca gcaggggaac   1200
gtcttctcat gctccgtgat gcatgaggct ctgcacaacc actacacgca gaaaagcctc   1260
tccctgtctc cgggtaaa                                                 1278
```

<210> SEQ ID NO 30
<211> LENGTH: 1239
<212> TYPE: DNA
<213> ORGANISM: Artificial Sequence
<220> FEATURE:
<223> OTHER INFORMATION: FGF17 deletion mutant

<400> SEQUENCE: 30

```
actcaggggg agaatcaccc gtctcctaat tttaaccagt acgtgaggga ccagggcgcc     60
atgaccgacc agctgagcag gcggcagatc cgcgagtacc aactctacag caggaccagt    120
ggcaagcacg tgcaggtcac cggccgtcgc atctccgcca ccgccgagga cggcaacaag    180
tttgccaagc tcatagtgga gacggacacg tttggcagcc gggttcgcat caaaggggct    240
gagagtgaga agtacatctg tatgaacaag aggggcaagc tcatcgggaa gcccagcggg    300
aagagcaaag actgcgtgtt cacggagatc gtgctggaga caactatac ggccttccag     360
aacgcccggc acgagggctg gttcatggcc ttcacgcggc aggggcggcc ccgccaggct    420
tcccgcagcc gccagaacca gcgcgaggcc cacttcatca agcgcctcta ccaaggccag    480
ctgcccttcc ccaaccacgc cgagaagcag aagcagttcg agtttgtggg ctccgccccc    540
accggatctg ggagcgctga caaaactcac acatgcccac cgtgcccagc acctgaagct    600
gccgggggac cgtcagtctt cctcttcccc ccaaaaccca aggacaccct catgatctcc    660
cggacccctg aggtcacatg cgtggtggtg gacgtgagcc acgaagaccc tgaggtcaag    720
ttcaactggt acgtggacgg cgtggaggtg cataatgcca agacaaagcc gcgggaggag    780
cagtacaaca gcacgtaccg tgtggtcagc gtcctcaccg tcctgcacca ggactggctg    840
aatggcaagg agtacaagtg caaggtctcc aacaaagccc tcggcgcccc catcgagaaa    900
accatctcca aagccaaagg gcagccccga gaaccacagg tgtacaccct gcccccatcc    960
cgggatgagc tgaccaagaa ccaggtcagc ctgacctgcc tggtcaaagg cttctatccc   1020
agcgacatcg ccgtggagtg ggagagcaat gggcagccgg agaacaacta caagaccacg   1080
cctcccgtgc tggactccga cggctccttc ttcctctaca gcaagctcac cgtggacaag   1140
agcaggtggc agcaggggaa cgtcttctca tgctccgtga tgcatgaggc tctgcacaac   1200
```

| | |
|---|---|
| cactacacgc agaaaagcct ctccctgtct ccgggtaaa | 1239 |

<210> SEQ ID NO 31
<211> LENGTH: 1170
<212> TYPE: DNA
<213> ORGANISM: Artificial Sequence
<220> FEATURE:
<223> OTHER INFORMATION: FGF17 deletion mutant
<400> SEQUENCE: 31

| | |
|---|---|
| actcaggggg agaatcaccc gtctcctaat tttaaccagt acgtgaggga ccagggcgcc | 60 |
| atgaccgacc agctgagcag gcggcagatc cgcgagtacc aactctacag caggaccagt | 120 |
| ggcaagcacg tgcaggtcac cgggcgtcgc atctccgcca ccgccgagga cggcaacaag | 180 |
| tttgccaagc tcatagtgga gacggacacg tttggcagcc gggttcgcat caaaggggct | 240 |
| gagagtgaga agtacatctg tatgaacaag aggggcaagc tcatcgggaa gcccagcggg | 300 |
| aagagcaaag actgcgtgtt cacggagatc gtgctggaga caactatac ggccttccag | 360 |
| aacgcccggc acgagggctg gttcatggcc ttcacgcggc aggggcggcc ccgccaggct | 420 |
| tcccgcagcc gccagaacca gcgcgaggcc cacttcatca agcgcctcta ccaaggatct | 480 |
| gggagcgctg acaaaactca cacatgccca ccgtgcccag cacctgaagc tgccggggga | 540 |
| ccgtcagtct tcctcttccc cccaaaaccc aaggacaccc tcatgatctc ccggacccct | 600 |
| gaggtcacat gcgtggtggt ggacgtgagc cacgaagacc ctgaggtcaa gttcaactgg | 660 |
| tacgtggacg gcgtggaggt gcataatgcc aagacaaagc cgcgggagga gcagtacaac | 720 |
| agcacgtacc gtgtggtcag cgtcctcacc gtcctgcacc aggactggct gaatggcaag | 780 |
| gagtacaagt gcaaggtctc caacaaagcc ctcggcgccc ccatcgagaa aaccatctcc | 840 |
| aaagccaaag gcagccccg agaaccacag gtgtacaccc tgcccccatc ccgggatgag | 900 |
| ctgaccaaga accaggtcag cctgacctgc ctggtcaaag gcttctatcc cagcgacatc | 960 |
| gccgtggagt gggagagcaa tgggcagccg gagaacaact acaagaccac gcctcccgtg | 1020 |
| ctggactccg acggctcctt cttcctctac agcaagctca ccgtggacaa gagcaggtgg | 1080 |
| cagcagggga acgtcttctc atgctccgtg atgcatgagg ctctgcacaa ccactacacg | 1140 |
| cagaaaagcc tctccctgtc tccgggtaaa | 1170 |

<210> SEQ ID NO 32
<211> LENGTH: 1278
<212> TYPE: DNA
<213> ORGANISM: Artificial Sequence
<220> FEATURE:
<223> OTHER INFORMATION: FGF17 mutant
<400> SEQUENCE: 32

| | |
|---|---|
| actcaggggg agaatcaccc gtctcctaat tttaaccagt acgtgaggga ccagggcgcc | 60 |
| atgaccgacc agctgagcag gcggcagatc cgcgagtacc aactctacag caggaccagt | 120 |
| ggcaagcacg tgcaggtcac cgggcgtcgc atctccgcca ccgccgagga cggcaacaag | 180 |
| tttgccaagc tcatagtgga gacggacacg tttggcagcc gggttcgcat caaaggggct | 240 |
| gagagtgaga agtacatctg tatgaacaag aggggcaagc tcatcgggaa gcccagcggg | 300 |
| aagagcaaag actgcgtgtt cacggagatc gtgctggaga caactatac ggccttccag | 360 |
| aacgcccggc acgagggctg gttcatggcc ttcacgcggc aggggcggcc ccgccaggct | 420 |
| tcccgcagcc gccagaacca gcgcgaggcc cacttcatca agcgcctcta ccaaggccag | 480 |

```
ctgcccttcc ccaaccacgc cgagaagcag aagcagttcg agtttgtggg ctccgccccc    540
acccagcgga cccagcgcac acggcggccc cagcccctca cgggatctgg gagcgctgac    600
aaaactcaca catgcccacc gtgcccagca cctgaagctg ccgggggacc gtcagtcttc    660
ctcttccccc caaaacccaa ggacaccctc atgatctccc ggacccctga ggtcacatgc    720
gtggtggtgg acgtgagcca cgaagaccct gaggtcaagt tcaactggta cgtggacggc    780
gtggaggtgc ataatgccaa gacaaagccg cgggaggagc agtacaacag cacgtaccgt    840
gtggtcagcg tcctcaccgt cctgcaccag gactggctga atggcaagga gtacaagtgc    900
aaggtctcca acaaagccct cggcgccccc atcgagaaaa ccatctccaa agccaaaggg    960
cagccccgag aaccacaggt gtacaccctg cccccatccc gggatgagct gaccaagaac   1020
caggtcagcc tgacctgcct ggtcaaaggc ttctatccca gcgacatcgc cgtggagtgg   1080
gagagcaatg ggcagccgga gaacaactac aagaccacgc ctcccgtgct ggactccgac   1140
ggctccttct cctctacag caagctcacc gtggacaaga gcaggtggca gcaggggaac   1200
gtcttctcat gctccgtgat gcatgaggct ctgcacaacc actacacgca gaaaagcctc   1260
tccctgtctc cgggtaaa                                                1278
```

<210> SEQ ID NO 33
<211> LENGTH: 1218
<212> TYPE: DNA
<213> ORGANISM: Artificial Sequence
<220> FEATURE:
<223> OTHER INFORMATION: FGF17 deletion mutant

<400> SEQUENCE: 33

```
actcaggggg agaatcaccc gtctcctaat tttaaccagt acgtgaggga ccagggcgcc     60
atgaccgacc agctgagcag gcggcagatc cgcgagtacc aactctacag caggaccagt    120
ggcaagcacg tgcaggtcac cgggcgtcgc atctccgcca ccgccgagga cggcaacaag    180
tttgccaagc tcatagtgga gacggacacg tttggcagcc gggttcgcat caaaggggct    240
gagagtgaga agtacatctg tatgaacaag aggggcaagc tcatcgggaa gcccagcggg    300
aagagcaaag actgcgtgtt cacggagatc gtgctggaga caactatac ggccttccag    360 aacgcccggc acgagggctg gttcatggcc ttcacgcggc aggggcggcc ccgccaggct    420
tcccgcagcc gccagaacca gcgcgaggcc cacttcatca gcgcctcta ccaaggccag    480 ctgccctc ccaaccacgc cgagaagcag aagcagttcg agggatctgg gagcgctgac    540
aaaactcaca catgcccacc gtgcccagca cctgaagctg ccgggggacc gtcagtcttc    600
ctcttccccc caaaacccaa ggacaccctc atgatctccc ggacccctga ggtcacatgc    660
gtggtggtgg acgtgagcca cgaagaccct gaggtcaagt tcaactggta cgtggacggc    720
gtggaggtgc ataatgccaa gacaaagccg cgggaggagc agtacaacag cacgtaccgt    780
gtggtcagcg tcctcaccgt cctgcaccag gactggctga atggcaagga gtacaagtgc    840
aaggtctcca acaaagccct cggcgccccc atcgagaaaa ccatctccaa agccaaaggg    900
cagccccgag aaccacaggt gtacaccctg cccccatccc gggatgagct gaccaagaac    960
caggtcagcc tgacctgcct ggtcaaaggc ttctatccca gcgacatcgc cgtggagtgg   1020
gagagcaatg ggcagccgga gaacaactac aagaccacgc ctcccgtgct ggactccgac   1080
ggctccttct cctctacag caagctcacc gtggacaaga gcaggtggca gcaggggaac   1140
gtcttctcat gctccgtgat gcatgaggct ctgcacaacc actacacgca gaaaagcctc   1200
tccctgtctc cgggtaaa                                                1218
```

<210> SEQ ID NO 34
<211> LENGTH: 1278
<212> TYPE: DNA
<213> ORGANISM: Artificial Sequence
<220> FEATURE:
<223> OTHER INFORMATION: FGF17 mutant

<400> SEQUENCE: 34

```
actcagggggg agaatcaccc gtctcctaat tttaaccagt acgtgaggga ccagggcgcc      60
atgaccgacc agctgagcag gcggcagatc cgcgagtacc aactctacag caggaccagt     120
ggcaagcacg tgcaggtcac cgggcgtcgc atctccgcca ccgccgagga cggcaacaag     180
tttgccaagc tcatagtgga gacggacacg tttggcagcc gggttcgcat caaaggggct     240
gagagtgaga agtacatctg tatgaacaag aggggcaagc tcatcgggaa gcccagcggg     300
aagagcaaag actgcgtgtt cacggagatc gtgctggaga caactatac ggccttccag      360
aacgcccggc acgagggctg gttcatggcc ttcacgcggc aggggcggcc ccgccaggct     420
tcccgcagcc gccagaacca gcgcgaggcc cacttcatca gcgcctcta ccaaggccag      480
ctgcccttcc ccaaccacgc cgaggctcag gcacagttcg agtttgtggg cgctgccccc     540
acccgccgga ccaagcgcac acggcggccc cagcccctca cgggatctgg gagcgctgac    600
aaaactcaca catgcccacc gtgcccagca cctgaagctg ccggggggacc gtcagtcttc    660
ctcttccccc caaaacccaa ggacaccctc atgatctccc ggacccctga ggtcacatgc     720
gtggtggtgg acgtgagcca cgaagaccct gaggtcaagt tcaactggta cgtggacggc    780
gtggaggtgc ataatgccaa gacaaagccg cgggaggagc agtacaacag cacgtaccgt    840
gtggtcagcg tcctcaccgt cctgcaccag gactggctga atggcaagga gtacaagtgc    900
aaggtctcca acaaagccct cggcgccccc atcgagaaaa ccatctccaa agccaaaggg    960
cagccccgag aaccacaggt gtacaccctg ccccccatccc gggatgagct gaccaagaac   1020
caggtcagcc tgacctgcct ggtcaaaggc ttctatccca gcgacatcgc cgtggagtgg   1080
gagagcaatg ggcagccgga gaacaactac aagaccacgc ctcccgtgct ggactccgac   1140
ggctccttct tcctctacag caagctcacc gtggacaaga gcaggtggca gcaggggaac   1200
gtcttctcat gctccgtgat gcatgaggct ctgcacaacc actacacgca gaaaagcctc   1260
tccctgtctc cgggtaaa                                                 1278
```

<210> SEQ ID NO 35
<211> LENGTH: 2406
<212> TYPE: DNA
<213> ORGANISM: Artificial Sequence
<220> FEATURE:
<223> OTHER INFORMATION: FGF17 fusion

<400> SEQUENCE: 35

```
caccatcacc atcaccatag cggcgatgca cacaagagtg aggttgctca tcggtttaaa     60
gatttgggag aagaaaattt caaagccttg gtgttgattg cctttgctca gtatcttcag    120
cagtgtccat ttgaagatca tgtaaaatta gtgaatgaag taactgaatt tgcaaaaaca    180
tgtgttgctg atgagtcagc tgaaaattgt gacaaatcac ttcataccct ttttggagac    240
aaattatgca cagttgcaac tcttcgtgaa accttatggtg aaatggctga ctgctgtgca    300
aaacaagaac ctgagagaaa tgaatgcttc ttgcaacaca aagatgacaa cccaaacctc    360
ccccgattgg tgagaccaga ggttgatgtg atgtgcactg cttttcatga caatgaagag    420
```

```
acatttttga aaaatacttt atatgaaatt gccagaagac atccttactt ttatgccccg    480
gaactccttt tctttgctaa aaggtataaa gctgctttta cagaatgttg ccaagctgct    540
gataaagctg cctgcctgtt gccaaagctc gatgaacttc gggatgaagg aaggcttcg    600 tctgccaaac agagactcaa gtgtgccagt ctccaaaaat ttggagaaag agctttcaaa    660
gcatgggcag tagctcgcct gagccagaga tttcccaaag ctgagtttgc agaagtttcc    720
aagttagtga cagatcttac caaagtccac acggaatgct gccatggaga tctgcttgaa    780
tgtgctgatg acagggcgga ccttgccaag tatatctgtg aaaatcaaga ttcgatctcc    840
agtaaactga aggaatgctg tgaaaaacct ctgttggaaa atcccactg cattgccgaa     900 gtggaaaatg atgagatgcc tgctgacttg ccttcattag ctgctgattt tgttgaaagt    960
aaggatgttt gcaaaaacta tgctgaggca aaggatgtct tcctgggcat gttttttgtat   1020 gaatatgcaa gaaggcatcc tgattactct gtcgtgctgc tgctgagact tgccaagaca   1080
tatgaaacca ctctagagaa gtgctgtgcc gctgcagatc ctcatgaatg ctatgccaaa   1140
gtgttcgatg aatttaaacc tcttgtggaa gagcctcaga atttaatcaa acaaaattgt   1200 gagcttttг agcagcttgg agagtacaaa ttccagaatg cgctattagt tcgttacacc    1260
aagaaagtac cccaagtgtc aactccaact cttgtagagg tctcaagaaa cctaggaaaa    1320
gtgggcagca atgttgtaa acatcctgaa gcaaaagaa tgccctgtgc agaagactat      1380
ctatccgtgg tcctgaacca gttatgtgtg ttgcatgaga aaacgccagt aagtgacaga    1440
gtcaccaaat gctgcacaga atccttggtg aacaggcgac catgcttttc agctctggaa   1500
gtcgatgaaa catacgttcc caaagagttt aatgctgaaa cattcacctt ccatgcagat    1560
atatgcacac tttctgagaa ggagagacaa atcaagaaac aaactgcact tgttgagctc   1620
gtgaaacaca gcccaaggc aacaaaagag caactgaaag ctgttatgga tgatttcgca     1680
gcttttgtag agaagtgctg caaggctgac gataaggaga cctgctttgc cgaggagggt    1740
aaaaaacttg ttgctgcaag tcaagctgcc ttaggcttag gcggaggcgg tagcggaggc    1800
ggtggctccg gtggcggagg gtctactcag ggggagaatc acccgtctcc taattttaac    1860
cagtacgtga gggaccaggg cgccatgacc gaccagctga gcaggcggca gatccgcgag    1920
taccaactct acagcaggac cagtggcaag cacgtgcagg tcaccgggcg tcgcatctcc    1980
gccaccgccg aggacggcaa caagtttgcc aagctcatag tggagacgga cacgtttggc    2040
agccgggttc gcatcaaagg ggctgagagt gagaagtaca tctgtatgaa caagagggc    2100 aagctcatcg ggaagcccag cgggaagagc aaagactgcg tgttcacgga gatcgtgctg    2160
gagaacaact atacggcctt ccagaacgcc cggcacgagg gctggttcat ggccttcacg    2220
cggcaggggc ggccccgcca ggcttcccgc agccgccaga accagcgcga ggcccacttc    2280
atcaagcgcc tctaccaagg ccagctgccc ttccccaacc acgccgagaa gcagaagcag    2340

ttcgagtttg tgggctccgc ccccacccgc cggaccaagc gcacacggcg gccccagccc   2400
ctcacg                                                                2406
```

<210> SEQ ID NO 36
<211> LENGTH: 1314
<212> TYPE: DNA
<213> ORGANISM: Artificial Sequence
<220> FEATURE:
<223> OTHER INFORMATION: FGF17 fusion

<400> SEQUENCE: 36

```
actcagggg agaatcaccc gtctcctaat tttaaccagt acgtgaggga ccagggcgcc    60
```

| | |
|---|---|
| atgaccgacc agctgagcag gcggcagatc cgcgagtacc aactctacag caggaccagt | 120 |
| ggcaagcacg tgcaggtcac cgggcgtcgc atctccgcca ccgccgagga cggcaacaag | 180 |
| tttgccaagc tcatagtgga cacggacacg tttggcagcc gggttcgcat caaaggggct | 240 |
| gagagtgaga agtacatctg tatgaacaag aggggcaagc tcatcgggaa gcccagcggg | 300 |
| aagagcaaag actgcgtgtt cacggagatc gtgctggaga caactatac ggccttccag | 360 |
| aacgccggc acgagggctg gttcatggcc ttcacgcgc aggggcggcc ccgccaggct | 420 |
| tcccgcagcc gccagaacca gcgcgaggcc cacttcatca gcgcctcta ccaaggccag | 480 |
| ctgcccttcc ccaaccacgc cgagaagcag aagcagttcg agtttgtggg ctccgccccc | 540 |
| acccgccgga ccaagcgcac acggcggccc cagcccctca cgggcggagg cggtagcgga | 600 |
| ggcggtggct ccgtggcgg agggtctgag tccaaatatg gtcccccatg cccaccctgc | 660 |
| ccagcacctg agttcctggg gggaccatca gtcttcctgt tccccccaaa acccaaggac | 720 |
| actctcatga tctcccggac ccctgaggtc acgtgcgtgg tggtggacgt gagccaggaa | 780 |
| gaccccgagg tccagttcaa ctggtacgtg gatggcgtgg aggtgcataa tgccaagaca | 840 |
| aagccgcggg aggagcagtt caacagcacg taccgtgtgg tcagcgtcct caccgtcctg | 900 |
| caccaggact ggctgaacgg caaggagtac aagtgcaagg tctccaacaa aggcctcccg | 960 |
| tcctccatcg agaaaaccat ctccaaagcc aaagggcagc ccgagagcc acaggtgtac | 1020 |
| accctgcccc catcccagga ggagatgacc aagaaccagg tcagcctgac ctgcctggtc | 1080 |
| aaaggcttct accccagcga catcgccgtg gagtgggaga gcaatgggca gccggagaac | 1140 |
| aactacaaga ccacgcctcc cgtgctggac tccgacggct ccttcttcct ctacagcagg | 1200 |
| ctcaccgtgg acaagagcag gtggcaggag gggaatgtct tctcatgctc cgtgatgcat | 1260 |
| gaggctctgc acaaccacta cacacagaag agcctctccc tgtctctggg taaa | 1314 |

<210> SEQ ID NO 37
<211> LENGTH: 1269
<212> TYPE: DNA
<213> ORGANISM: Artificial Sequence
<220> FEATURE:
<223> OTHER INFORMATION: FGF17 fusion

<400> SEQUENCE: 37

| | |
|---|---|
| actcaggggg agaatcaccc gtctcctaat tttaaccagt acgtgaggga ccagggcgcc | 60 |
| atgaccgacc agctgagcag gcggcagatc cgcgagtacc aactctacag caggaccagt | 120 |
| ggcaagcacg tgcaggtcac cgggcgtcgc atctccgcca ccgccgagga cggcaacaag | 180 |
| tttgccaagc tcatagtgga cacggacacg tttggcagcc gggttcgcat caaaggggct | 240 |
| gagagtgaga agtacatctg tatgaacaag aggggcaagc tcatcgggaa gcccagcggg | 300 |
| aagagcaaag actgcgtgtt cacggagatc gtgctggaga caactatac ggccttccag | 360 |
| aacgccggc acgagggctg gttcatggcc ttcacgcgc aggggcggcc ccgccaggct | 420 |
| tcccgcagcc gccagaacca gcgcgaggcc cacttcatca gcgcctcta ccaaggccag | 480 |
| ctgcccttcc ccaaccacgc cgagaagcag aagcagttcg agtttgtggg ctccgccccc | 540 |
| acccgccgga ccaagcgcac acggcggccc cagcccctca cgggagtccaa atatggtccc | 600 |
| ccatgcccac cctgcccagc acctgagttc ctgggggac catcagtctt cctgttcccc | 660 |
| ccaaaaccca aggacactct catgatctcc cggacccctg aggtcacgtg cgtggtggtg | 720 |
| gacgtgagcc aggaagaccc cgaggtccag ttcaactggt acgtggatgg cgtggaggtg | 780 |

```
cataatgcca agacaaagcc gcgggaggag cagttcaaca gcacgtaccg tgtggtcagc    840
gtcctcaccg tcctgcacca ggactggctg aacggcaagg agtacaagtg caaggtctcc    900
aacaaaggcc tcccgtcctc catcgagaaa accatctcca agccaaagg gcagccccga    960 gagccacagg tgtacaccct gcccccatcc caggaggaga tgaccaagaa ccaggtcagc    1020
ctgacctgcc tggtcaaagg cttctacccc agcgacatcg ccgtggagtg ggagagcaat    1080
gggcagccgg agaacaacta caagaccacg cctcccgtgc tggactccga cggctccttc    1140
ttcctctaca gcaggctcac cgtggacaag agcaggtggc aggaggggaa tgtcttctca    1200
tgctccgtga tgcatgaggc tctgcacaac cactacacac agaagagcct ctccctgtct    1260
ctgggtaaa                                                             1269

<210> SEQ ID NO 38
<211> LENGTH: 1314
<212> TYPE: DNA
<213> ORGANISM: Artificial Sequence
<220> FEATURE:
<223> OTHER INFORMATION: FGF17 fusion

<400> SEQUENCE: 38
gagtccaaat atggtccccc atgcccaccc tgcccagcac ctgagttcct ggggggacca    60
tcagtcttcc tgttcccccc aaaacccaag gacactctca tgatctcccg gacccctgag    120
gtcacgtgcg tggtggtgga cgtgagccag gaagaccccg aggtccagtt caactggtac    180
gtggatggcg tggaggtgca taatgccaag acaaagccgc gggaggagca gttcaacagc    240
acgtaccgtg tggtcagcgt cctcaccgtc ctgcaccagg actggctgaa cggcaaggag    300
tacaagtgca aggtctccaa caaaggcctc ccgtcctcca tcgagaaaac catctccaaa    360
gccaaagggc agccccgaga gccacaggtg tacaccctgc ccccatccca ggaggagatg    420
accaagaacc aggtcagcct gacctgcctg gtcaaaggct tctacccag cgacatcgcc    480 gtggagtggg agagcaatgg gcagccggag aacaactaca agaccacgcc tcccgtgctg    540
gactccgacg gctccttctt cctctacagc aggctcaccg tggacaagag caggtggcag    600
gaggggaatg tcttctcatg ctccgtgatg catgaggctc tgcacaacca ctacacacag    660
aagagcctct ccctgtctct gggtaaaggc ggaggcggta gcggaggcgg tggctccggt    720
ggcggagggt ctactcaggg ggagaatcac ccgtctccta attttaacca gtacgtgagg    780
gaccagggcg ccatgaccga ccagctgagc aggcggcaga tccgcgagta ccaactctac    840
agcaggacca gtggcaagca cgtgcaggtc accggcgtc gcatctccgc caccgccgag    900
gacggcaaca agtttgccaa gctcatagtg gagacggaca cgtttggcag ccgggttcgc    960
atcaaagggg ctgagagtga agtacatc tgtatgaaca gaggggcaa gctcatcggg    1020 aagcccagcg ggaagagcaa agactgcgtg ttcacggaga tcgtgctgga aacaactat    1080 acggccttcc agaacgcccg gcacgagggc tggttcatgg ccttcacgcg gcaggggcgg    1140
ccccgccagg cttcccgcag ccgccagaac cagcgcgagg cccacttcat caagcgcctc    1200
taccaaggcc agctgcccct tcccaaccac gccgagaagc agaagcagtt cgagtttgtg    1260
ggctccgccc ccacccgccg gaccaagcgc acacggcggc cccagcccct cacg          1314

<210> SEQ ID NO 39
<211> LENGTH: 201
<212> TYPE: DNA
<213> ORGANISM: Homo sapiens

<400> SEQUENCE: 39
```

| | |
|---|---|
| gcttaccgcc ccagtgagac cctgtgcggc ggggagctgg tggacaccct ccagttcgtc | 60 |
| tgtggggacc gcggcttcta cttcagcagg cccgcaagcc gtgtgagccg tcgcagccgt | 120 |
| ggcatcgttg aggagtgctg tttccgcagc tgtgacctgg ccctcctgga gacgtactgt | 180 |
| gctaccccg ccaagtccga g | 201 |

```
<210> SEQ ID NO 40
<211> LENGTH: 894
<212> TYPE: DNA
<213> ORGANISM: Artificial Sequence
<220> FEATURE:
<223> OTHER INFORMATION: IGF2 fusion

<400> SEQUENCE: 40
```

| | |
|---|---|
| gcttaccgcc ccagtgagac cctgtgcggc ggggagctgg tggacaccct ccagttcgtc | 60 |
| tgtggggacc gcggcttcta cttcagcagg cccgcaagcc gtgtgagccg tcgcagccgt | 120 |
| ggcatcgttg aggagtgctg tttccgcagc tgtgacctgg ccctcctgga gacgtactgt | 180 |
| gctaccccg ccaagtccga gggatcggga tcggacaaaa ctcacacatg cccaccgtgc | 240 |
| ccagcacctg aagctgccgg gggaccgtca gtcttcctct tccccccaaa acccaaggac | 300 |
| accctcatga tctcccggac ccctgaggtc acatgcgtgg tggtggacgt gagccacgaa | 360 |
| gaccctgagg tcaagttcaa ctggtacgtg gacggcgtgg aggtgcataa tgccaagaca | 420 |
| aagccgcggg aggagcagta caacagcacg taccgtgtgg tcagcgtcct caccgtcctg | 480 |
| caccaggact ggctgaatgg caaggagtac aagtgcaagg tctccaacaa agccctcggc | 540 |
| gcccccatcg agaaaaccat ctccaaagcc aaagggcagc ccgagaacca caggtgtac | 600 |
| accctgcccc catcccggga tgagctgacc aagaaccagg tcagcctgac ctgcctggtc | 660 |
| aaaggcttct atcccagcga catcgccgtg gagtgggaga gcaatgggca gccggagaac | 720 |
| aactacaaga ccacgcctcc cgtgctggac tccgacggct ccttcttcct ctacagcaag | 780 |
| ctcaccgtgg acaagagcag gtggcagcag gggaacgtct tctcatgctc cgtgatgcat | 840 |
| gaggctctgc acaaccacta cacgcagaaa agcctctccc tgtctccggg taaa | 894 |

```
<210> SEQ ID NO 41
<211> LENGTH: 897
<212> TYPE: DNA
<213> ORGANISM: Artificial Sequence
<220> FEATURE:
<223> OTHER INFORMATION: IGF2 fusion

<400> SEQUENCE: 41
```

| | |
|---|---|
| gcttaccgcc ccagtgagac cctgtgcggc ggggagctgg tggacaccct ccagttcgtc | 60 |
| tgtggggacc gcggcttcta cttcagcagg cccgcaagcc gtgtgagccg tcgcagccgt | 120 |
| ggcatcgttg aggagtgctg tttccgcagc tgtgacctgg ccctcctgga gacgtactgt | 180 |
| gctaccccg ccaagtccga gggatctggg agcgctgaca aaactcacac atgcccaccg | 240 |
| tgcccagcac ctgaagctgc cggggaccg tcagtcttcc tcttcccccc aaaacccaag | 300 |
| gacacccctca tgatctcccg gacccctgag gtcacatgcg tggtggtgga cgtgagccac | 360 |
| gaagaccctg aggtcaagtt caactggtac gtggacggcg tggaggtgca taatgccaag | 420 |
| acaaagccgc gggaggagca gtacaacagc acgtaccgtg tggtcagcgt cctcaccgtc | 480 |
| ctgcaccagg actggctgaa tggcaaggag tacaagtgca aggtctccaa caaagccctc | 540 |
| ggcgccccca tcgagaaaac catctccaaa gccaagggc agccccgaga accacaggtg | 600 |

```
tacaccctgc ccccatcccg ggatgagctg accaagaacc aggtcagcct gacctgcctg    660
gtcaaaggct tctatcccag cgacatcgcc gtggagtggg agagcaatgg gcagccggag    720
aacaactaca agaccacgcc tcccgtgctg gactccgacg gctccttctt cctctacagc    780
aagctcaccg tggacaagag caggtggcag caggggaacg tcttctcatg ctccgtgatg    840
catgaggctc tgcacaacca ctacacgcag aaaagcctct ccctgtctcc gggtaaa      897
```

<210> SEQ ID NO 42
<211> LENGTH: 2025
<212> TYPE: DNA
<213> ORGANISM: Artificial Sequence
<220> FEATURE:
<223> OTHER INFORMATION: IGF2 fusion

<400> SEQUENCE: 42

```
caccatcacc atcaccatag cggcgatgca cacaagagtg aggttgctca tcggtttaaa     60
gatttgggag aagaaaattt caaagccttg gtgttgattg cctttgctca gtatcttcag    120
cagtgtccat ttgaagatca tgtaaaatta gtgaatgaag taactgaatt tgcaaaaaca    180
tgtgttgctg atgagtcagc tgaaaattgt gacaaatcac ttcataccct ttttggagac    240
aaattatgca cagttgcaac tcttcgtgaa acctatggtg aaatggctga ctgctgtgca    300
aaacaagaac ctgagagaaa tgaatgcttc ttgcaacaca agatgacaa  cccaaacctc    360 ccccgattgg tgagaccaga ggttgatgtg atgtgcactg cttttcatga caatgaagag    420 acattttga aaaatactt atatgaaatt gccagaagac atccttactt ttatgccccg      480
gaactccttt tctttgctaa aaggtataaa gctgctttta cagaatgttg ccaagctgct    540
gataaagctg cctgcctgtt gccaaagctc gatgaacttc gggatgaagg gaaggcttcg    600
tctgccaaac agagactcaa gtgtgccagt ctccaaaaat ttggagaaag agctttcaaa    660
gcatgggcag tagctcgcct gagccagaga tttcccaaag ctgagtttgc agaagtttcc    720
aagttagtga cagatcttac caaagtccac acggaatgct gccatggaga tctgcttgaa    780
tgtgctgatg acagggcgga ccttgccaag tatatctgtg aaaatcaaga ttcgatctcc    840
agtaaactga aggaatgctg tgaaaaacct ctgttggaaa atccccactg cattgccgaa    900
gtggaaaatg atgagatgcc tgctgacttg ccttcattag ctgctgattt tgttgaaagt    960
aaggatgttt gcaaaaacta tgctgaggca aaggatgtct tcctgggcat gttttttgtat  1020 gaatatgcaa gaaggcatcc tgattactct gtcgtgctgc tgctgagact tgccaagaca  1080
tatgaaacca ctctagagaa gtgctgtgcc gctgcagatc ctcatgaatg ctatgccaaa  1140
gtgttcgatg aatttaaacc tcttgtggaa gagcctcaga atttaatcaa acaaaattgt  1200 gagcttttg agcagcttgg agagtacaaa ttccagaatg cgctattagt tcgttacacc  1260
aagaaagtac cccaagtgtc aactccaact cttgtagagg tctcaagaaa cctaggaaaa  1320
gtgggcagca aatgttgtaa acatcctgaa gcaaaaagaa tgccctgtgc agaagactat  1380
ctatccgtgg tcctgaacca gttatgtgtg ttgcatgaga aaacgccagt aagtgacaga  1440
gtcaccaaat gctgcacaga atccttggtg aacaggcgac catgcttttc agctctggaa  1500
gtcgatgaaa catacgttcc caaagagttt aatgctgaaa cattcacctt ccatgcagat  1560
atatgcacac tttctgagaa ggagagacaa atcaagaaac aaactgcact tgttgagctc  1620
gtgaaacaca gcccaaggc aacaaaagag caactgaaag ctgttatgga tgatttcgca  1680
gcttttgtag agaagtgctg caaggctgac gataaggaga cctgctttgc cgaggagggt  1740
aaaaaacttg ttgctgcaag tcaagctgcc ttaggcttag gcggaggcgg tagcggaggc  1800
```

```
ggtggctccg gtggcggagg gtctgcttac cgccccagtg agaccctgtg cggcggggag    1860
ctggtggaca ccctccagtt cgtctgtggg gaccgcggct tctacttcag caggcccgca    1920
agccgtgtga gccgtcgcag ccgtggcatc gttgaggagt gctgtttccg cagctgtgac    1980
ctggccctcc tggagacgta ctgtgctacc cccgccaagt ccgag                    2025

<210> SEQ ID NO 43
<211> LENGTH: 2025
<212> TYPE: DNA
<213> ORGANISM: Artificial Sequence
<220> FEATURE:
<223> OTHER INFORMATION: IGF2 mutant

<400> SEQUENCE: 43
caccatcacc atcaccatag cggcgatgca cacaagagtg aggttgctca tcggtttaaa      60
gatttgggag aagaaaattt caaagccttg gtgttgattg cctttgctca gtatcttcag     120
cagtgtccat ttgaagatca tgtaaaatta gtgaatgaag taactgaatt tgcaaaaaca     180
tgtgttgctg atgagtcagc tgaaaattgt gacaaatcac ttcataccct ttttggagac     240
aaattatgca cagttgcaac tcttcgtgaa acctatggtg aaatggctga ctgctgtgca     300
aaacaagaac ctgagagaaa tgaatgcttc ttgcaacaca agatgacaa cccaaacctc      360 ccccgattgg tgagaccaga ggttgatgtg atgtgcactg cttttcatga caatgaagag     420 acattttga aaaaatactt atatgaaatt gccagaagac atccttactt ttatgccccg      480
gaactccttt tctttgctaa aaggtataaa gctgctttta cagaatgttg ccaagctgct     540
gataaagctg cctgcctgtt gccaaagctc gatgaacttc gggatgaagg aaggcttcg     600 tctgccaaac agagactcaa gtgtgccagt ctccaaaaat ttggagaaag agctttcaaa    660
gcatgggcag tagctcgcct gagccagaga tttcccaaag ctgagtttgc agaagtttcc     720
aagttagtga cagatcttac caaagtccac acggaatgct gccatggaga tctgcttgaa     780
tgtgctgatg acagggcgga ccttgccaag tatatctgtg aaaatcaaga ttcgatctcc     840
agtaaactga aggaatgctg tgaaaaacct ctgttggaaa atcccactg cattgccgaa      900 gtggaaaatg atgagatgcc tgctgacttg ccttcattag ctgctgattt tgttgaaagt    960
aaggatgttt gcaaaaacta tgctgaggca aggatgtct tcctgggcat gttttgtat     1020 gaatatgcaa gaaggcatcc tgattactct gtcgtgctgc tgctgagact tgccaagaca    1080
tatgaaacca ctctagagaa gtgctgtgcc gctgcagatc tcatgaatg ctatgccaaa     1140 gtgttcgatg aatttaaacc tcttgtggaa gagcctcaga atttaatcaa acaaaattgt    1200 gagcttttg agcagcttgg agagtacaaa ttccagaatg cgctattagt tcgttacacc     1260
aagaaagtac cccaagtgtc aactccaact cttgtagagg tctcaagaaa cctaggaaaa    1320
gtgggcagca atgttgtaa acatcctgaa gcaaaagaa tgccctgtgc agaagactat      1380
ctatccgtgg tcctgaacca gttatgtgtg ttgcatgaga aaacgccagt aagtgacaga    1440
gtcaccaaat gctgcacaga atccttggtg aacaggcgac catgcttttc agctctggaa    1500
gtcgatgaaa catacgttcc caaagagttt aatgctgaaa cattcacctt ccatgcagat    1560
atatgcacac tttctgagaa ggagagacaa atcaagaaac aaactgcact tgttgagctc    1620
gtgaaacaca gcccaaggc aacaaaagag caactgaaag ctgttatgga tgatttcgca    1680
gcttttgtag agaagtgctg caaggctgac gataaggaga cctgctttgc cgaggagggt    1740
aaaaaacttg ttgctgcaag tcaagctgcc ttaggcttag gcggaggcgg tagcggaggc    1800
```

| ggtggctccg gtggcggagg gtctgcttac cgccccagtg agaccctgtg cggcggggag | 1860 |
| ctggtggaca ccctccagtt cgtctgtggg gaccgcggct tctacttcag caggcccgca | 1920 |
| agccgtgtga gcgctcgcag ccgtggcatc gttgaggagt gctgtttccg cagctgtgac | 1980 |
| ctggccctcc tggagacgta ctgtgctacc cccgccaagt ccgag | 2025 |

<210> SEQ ID NO 44
<211> LENGTH: 2025
<212> TYPE: DNA
<213> ORGANISM: Artificial Sequence
<220> FEATURE:
<223> OTHER INFORMATION: IGF2 mutant

<400> SEQUENCE: 44

| caccatcacc atcaccatag cggcgatgca cacaagagtg aggttgctca tcggtttaaa | 60 |
| gatttgggag aagaaaattt caaagccttg gtgttgattg cctttgctca gtatcttcag | 120 |
| cagtgtccat ttgaagatca tgtaaaatta gtgaatgaag taactgaatt tgcaaaaaca | 180 |
| tgtgttgctg atgagtcagc tgaaaattgt gacaaatcac ttcatacccct ttttggagac | 240 |
| aaattatgca cagttgcaac tcttcgtgaa acctatggtg aaatggctga ctgctgtgca | 300 |
| aaacaagaac ctgagagaaa tgaatgcttc ttgcaacaca agatgacaa cccaaacctc | 360 |
| ccccgattgg tgagaccaga ggttgatgtg atgtgcactg cttttcatga caatgaagag | 420 |
| acattttga aaaatacctt atatgaaatt gccagaagac atccttactt ttatgccccg | 480 |
| gaactccttt tctttgctaa aaggtataaa gctgctttta cagaatgttg ccaagctgct | 540 |
| gataaagctg cctgcctgtt gccaaagctc gatgaacttc gggatgaagg gaaggcttcg | 600 |
| tctgccaaac agagactcaa gtgtgccagt ctccaaaaat ttggagaaag agctttcaaa | 660 |
| gcatgggcag tagctcgcct gagccagaga tttcccaaag ctgagtttgc agaagtttcc | 720 |
| aagttagtga cagatcttac caaagtccac acggaatgct gccatggaga tctgcttgaa | 780 |
| tgtgctgatg acagggcgga ccttgccaag tatatctgtg aaaatcaaga ttcgatctcc | 840 |
| agtaaactga aggaatgctg tgaaaaacct ctgttggaaa atccactg cattgccgaa | 900 |
| gtggaaaatg atgagatgcc tgctgacttg ccttcattag ctgctgattt tgttgaaagt | 960 |
| aaggatgttt gcaaaaacta tgctgaggca aaggatgtct tcctgggcat gtttttgtat | 1020 |
| gaatatgcaa gaaggcatcc tgattactct gtcgtgctgc tgctgagact tgccaagaca | 1080 |
| tatgaaacca ctctagagaa gtgctgtgcc gctgcagatc ctcatgaatg ctatgccaaa | 1140 |
| gtgttcgatg aatttaaacc tcttgtggaa gagcctcaga atttatcaa acaaaattgt | 1200 |
| gagcttttg agcagcttgg agagtacaaa ttccagaatg cgctattagt tcgttacacc | 1260 |
| aagaaagtac cccaagtgtc aactccaact cttgtagagg tctcaagaaa cctaggaaaa | 1320 |
| gtgggcagca aatgttgtaa acatcctgaa gcaaaaagaa tgccctgtgc agaagactat | 1380 |
| ctatccgtgg tcctgaacca gttatgtgtg ttgcatgaga aaacgccagt aagtgacaga | 1440 |
| gtcaccaaat gctgcacaga atccttggtg aacaggcgac catgcttttc agctctggaa | 1500 |
| gtcgatgaaa catacgttcc caaagagttt aatgctgaaa cattcacctt ccatgcagat | 1560 |
| atatgcacac tttctgagaa ggagagacaa atcaagaaac aaactgcact tgttgagctc | 1620 |
| gtgaaacaca agcccaaggc aacaaaagag caactgaaag ctgttatgga tgatttcgca | 1680 |
| gcttttgtag agaagtgctg caaggctgac gataaggaga cctgctttgc cgaggagggt | 1740 |
| aaaaaacttg ttgctgcaag tcaagctgcc ttaggcttag cggaggcgg tagcggaggc | 1800 |
| ggtggctccg gtggcggagg gtctgcttac cgccccagtg agaccctgtg cggcggggag | 1860 |

-continued

| | |
|---|---|
| ctggtggaca cccctccagtt cgtctgtggg gaccgcggct tctacttcag caggcccgca | 1920 |
| agccgtgtga gccagcgcag ccgtggcatc gttgaggagt gctgtttccg cagctgtgac | 1980 |
| ctggccctcc tggagacgta ctgtgctacc cccgccaagt ccgag | 2025 |

<210> SEQ ID NO 45
<211> LENGTH: 2025
<212> TYPE: DNA
<213> ORGANISM: Artificial Sequence
<220> FEATURE:
<223> OTHER INFORMATION: IGF2 mutant

<400> SEQUENCE: 45

| | |
|---|---|
| caccatcacc atcaccatag cggcgatgca cacaagagtg aggttgctca tcggtttaaa | 60 |
| gatttgggag aagaaaattt caaagccttg gtgttgattg cctttgctca gtatcttcag | 120 |
| cagtgtccat ttgaagatca tgtaaaatta gtgaatgaag taactgaatt tgcaaaaaca | 180 |
| tgtgttgctg atgagtcagc tgaaaattgt gacaaatcac ttcatacect ttttggagac | 240 |
| aaattatgca cagttgcaac tcttcgtgaa acctatggtg aaatggctga ctgctgtgca | 300 |
| aaacaagaac ctgagagaaa tgaatgcttc ttgcaacaca agatgacaa cccaaacctc | 360 |
| ccccgattgg tgagaccaga ggttgatgtg atgtgcactg cttttcatga caatgaagag | 420 |
| acatttttga aaaatactt atatgaaatt gccagaagac atccttactt ttatgccccg | 480 |
| gaactccttt tctttgctaa aaggtataaa gctgctttta cagaatgttg ccaagctgct | 540 |
| gataaagctg cctgcctgtt gccaaagctc gatgaacttc gggatgaagg gaaggcttcg | 600 |
| tctgccaaac agagactcaa gtgtgccagt ctccaaaaat ttggagaaag agctttcaaa | 660 |
| gcatgggcag tagctcgcct gagccagaga tttcccaaag ctgagtttgc agaagtttcc | 720 |
| aagttagtga cagatcttac caaagtccac acggaatgct gccatggaga tctgcttgaa | 780 |
| tgtgctgatg acagggcgga ccttgccaag tatatctgtg aaaatcaaga ttcgatctcc | 840 |
| agtaaactga aggaatgctg tgaaaaacct ctgttggaaa atcccactg cattgccgaa | 900 |
| gtggaaaatg atgagatgcc tgctgacttg ccttcattag ctgctgattt tgttgaaagt | 960 |
| aaggatgttt gcaaaaacta tgctgaggca aaggatgtct tcctgggcat gttttttgtat | 1020 |
| gaatatgcaa gaaggcatcc tgattactct gtcgtgctgc tgctgagact tgccaagaca | 1080 |
| tatgaaacca ctctagagaa gtgctgtgcc gctgcagatc ctcatgaatg ctatgccaaa | 1140 |
| gtgttcgatg aatttaaacc tcttgtggaa gagcctcaga atttaatcaa acaaaattgt | 1200 |
| gagcttttg agcagcttgg agagtacaaa ttccagaatg cgctattagt tcgttacacc | 1260 |
| aagaaagtac cccaagtgtc aactccaact cttgtagagg tctcaagaaa cctaggaaaa | 1320 |
| gtgggcagca atgttgtaa acatcctgaa gcaaaagaa tgccctgtgc agaagactat | 1380 |
| ctatccgtgg tcctgaacca gttatgtgtg ttgcatgaga aaacgccagt aagtgacaga | 1440 |
| gtcaccaaat gctgcacaga atccttggtg aacaggcgac catgcttttc agctctggaa | 1500 |
| gtcgatgaaa catacgttcc caaagagttt aatgctgaaa cattcaccctt ccatgcagat | 1560 |
| atatgcacac tttctgagaa ggagagacaa atcaagaaac aaactgcact tgttgagctc | 1620 |
| gtgaaacaca gcccaaggc aacaaaagag caactgaaag ctgttatgga tgatttcgca | 1680 |
| gcttttgtag agaagtgctg caaggctgac gataaggaga cctgctttgc cgaggagggt | 1740 |
| aaaaaacttg ttgctgcaag tcaagctgcc ttaggcttag gcggaggcgg tagcggaggc | 1800 |
| ggtggctccg gtggcggagg gtctgcttac cgccccagtg agaccctgtg cggcggggag | 1860 |

```
ctggtggaca ccctccagtt cgtctgtggg gaccgcggct tctacttcag caggcccgca    1920
agccgtgtga gccgtcgcag cgctggcatc gttgaggagt gctgtttccg cagctgtgac    1980
ctggccctcc tggagacgta ctgtgctacc cccgccaagt ccgag                    2025

<210> SEQ ID NO 46
<211> LENGTH: 2025
<212> TYPE: DNA
<213> ORGANISM: Artificial Sequence
<220> FEATURE:
<223> OTHER INFORMATION: IGF2 mutant

<400> SEQUENCE: 46
caccatcacc atcaccatag cggcgatgca cacaagagtg aggttgctca tcggtttaaa      60
gatttgggag aagaaaattt caaagccttg gtgttgattg cctttgctca gtatcttcag     120
cagtgtccat ttgaagatca tgtaaaatta gtgaatgaag taactgaatt tgcaaaaaca     180
tgtgttgctg atgagtcagc tgaaaattgt gacaaatcac ttcatacccc ttttggagac     240
aaattatgca cagttgcaac tcttcgtgaa acctatggtg aaatggctga ctgctgtgca     300
aaacaagaac ctgagagaaa tgaatgcttc ttgcaacaca agatgacaa cccaaacctc     360 ccccgattgg tgagaccaga ggttgatgtg atgtgcactg cttttcatga caatgaagag     420
acatttttga aaaaatactt atatgaaatt gccagaagac atccttactt ttatgccccg     480
gaactccttt tctttgctaa aaggtataaa gctgctttta cagaatgttg ccaagctgct     540
gataaagctg cctgcctgtt gccaaagctc gatgaacttc gggatgaagg gaaggcttcg     600
tctgccaaac agagactcaa gtgtgccagt ctccaaaaat tggagaaag agctttcaaa     660 gcatgggcag tagctcgcct gagccagaga tttcccaaag ctgagtttgc agaagtttcc     720
aagttagtga cagatcttac caaagtccac acggaatgct gccatggaga tctgcttgaa     780
tgtgctgatg acagggcgga ccttgccaag tatatctgtg aaaatcaaga ttcgatctcc     840
agtaaactga aggaatgctg tgaaaaacct ctgttggaaa atcccactg cattgccgaa     900 gtggaaaatg atgagatgcc tgctgacttg ccttcattag ctgctgattt tgttgaaagt     960
aaggatgttt gcaaaaacta tgctgaggca aaggatgtct tcctgggcat gttttttgtat    1020 gaatatgcaa gaaggcatcc tgattactct gtcgtgctgc tgctgagact tgccaagaca    1080
tatgaaacca ctctagagaa gtgctgtgcc gctgcagatc ctcatgaatg ctatgccaaa    1140
gtgttcgatg aatttaaacc tcttgtggaa gagcctcaga atttaatcaa acaaaattgt    1200 gagcttttg agcagcttgg agagtacaaa ttccagaatg cgctattagt tcgttacacc    1260
aagaaagtac cccaagtgtc aactccaact cttgtagagg tctcaagaaa cctaggaaaa    1320
gtgggcagca aatgttgtaa acatcctgaa gcaaaaagaa tgccctgtgc agaagactat    1380
ctatccgtgg tcctgaacca gttatgtgtg ttgcatgaga aaacgccagt aagtgacaga    1440
gtcaccaaat gctgcacaga atccttggtg aacaggcgac catgctttc agctctggaa    1500 gtcgatgaaa catacgttcc caaagagttt aatgctgaaa cattcacctt ccatgcagat    1560
atatgcacac tttctgagaa ggagagacaa atcaagaaac aaactgcact tgttgagctc    1620
gtgaaacaca gcccaaggc aacaaaagag caactgaaag ctgttatgga tgatttcgca    1680
gcttttgtag agaagtgctg caaggctgac gataaggaga cctgctttgc cgaggagggt    1740
aaaaaacttg ttgctgcaag tcaagctgcc ttaggcttag gcggaggcgg tagcggaggc    1800
ggtggctccg gtgcggaggg gtctgcttac cgccccagtg agaccctgtg cggcggggag    1860
ctggtggaca ccctccagtt cgtctgtggg gaccgcggct tctacttcag caggcccgca    1920
```

```
agccgtgtga gccgtcgcag ccagggcatc gttgaggagt gctgtttccg cagctgtgac   1980
ctggccctcc tggagacgta ctgtgctacc cccgccaagt ccgag                   2025

<210> SEQ ID NO 47
<211> LENGTH: 933
<212> TYPE: DNA
<213> ORGANISM: Artificial Sequence
<220> FEATURE:
<223> OTHER INFORMATION: IGF2 fusion

<400> SEQUENCE: 47
gcttaccgcc ccagtgagac cctgtgcggc ggggagctgg tggacaccct ccagttcgtc     60
tgtggggacc gcggcttcta cttcagcagg cccgcaagcc gtgtgagccg tcgcagccgt    120
ggcatcgttg aggagtgctg tttccgcagc tgtgacctgg ccctcctgga gacgtactgt    180 gctaccccg ccaagtccga gggcggaggc ggtagcggag gcggtggctc cggtggcgga    240
gggtctgagt ccaaatatgg tccccatgc cacccctgcc cagcacctga gttcctgggg    300
ggaccatcag tcttcctgtt ccccccaaaa cccaaggaca ctctcatgat ctcccggacc    360
cctgaggtca cgtgcgtggt ggtggacgtg agccaggaag accccgaggt ccagttcaac    420
tggtacgtgg atggcgtgga ggtgcataat gccaagacaa agccgcggga ggagcagttc    480
aacagcacgt accgtgtggt cagcgtcctc accgtcctgc accaggactg gctgaacggc    540
aaggagtaca agtgcaaggt ctccaacaaa ggcctcccgt cctccatcga gaaaaccatc    600
tccaaagcca agggcagcc cgagagcca caggtgtaca ccctgccccc atcccaggag    660
gagatgacca agaaccaggt cagcctgacc tgcctggtca aaggcttcta ccccagcgac    720
atcgccgtgg agtgggagag caatgggcag ccggagaaca actacaagac cacgcctccc    780
gtgctggact ccgacggctc cttcttcctc tacagcaggc tcaccgtgga caagagcagg    840
tggcaggagg ggaatgtctt ctcatgctcc gtgatgcatg aggctctgca caaccactac    900
acacagaaga gcctctccct gtctctgggt aaa                                933

<210> SEQ ID NO 48
<211> LENGTH: 888
<212> TYPE: DNA
<213> ORGANISM: Artificial Sequence
<220> FEATURE:
<223> OTHER INFORMATION: IGF2 fusion

<400> SEQUENCE: 48
gcttaccgcc ccagtgagac cctgtgcggc ggggagctgg tggacaccct ccagttcgtc     60
tgtggggacc gcggcttcta cttcagcagg cccgcaagcc gtgtgagccg tcgcagccgt    120
ggcatcgttg aggagtgctg tttccgcagc tgtgacctgg ccctcctgga gacgtactgt    180 gctaccccg ccaagtccga ggagtccaaa tatggtcccc catgcccacc ctgcccagca    240
cctgagttcc tggggggacc atcagtcttc ctgttccccc caaaacccaa ggacactctc    300
atgatctccc ggacccctga ggtcacgtgc gtggtggtgg acgtgagcca ggaagacccc    360
gaggtccagt tcaactggta cgtggatggc gtggaggtgc ataatgccaa gacaaagccg    420
cgggaggagc agttcaacag cacgtaccgt gtggtcagcg tcctcaccgt cctgcaccag    480
gactggctga acggcaagga gtacaagtgc aaggtctcca acaaaggcct cccgtcctcc    540
atcgagaaaa ccatctccaa agccaaggg cagccccgag agccacaggt gtacaccctg    600
cccccatccc aggaggagat gaccaagaac caggtcagcc tgacctgcct ggtcaaaggc    660
```

| | |
|---|---|
| ttctacccca gcgacatcgc cgtggagtgg gagagcaatg ggcagccgga gaacaactac | 720 |
| aagaccacgc ctcccgtgct ggactccgac ggctccttct tcctctacag caggctcacc | 780 |
| gtggacaaga gcaggtggca ggaggggaat gtcttctcat gctccgtgat gcatgaggct | 840 |
| ctgcacaacc actacacaca gaagagcctc tccctgtctc tgggtaaa | 888 |

<210> SEQ ID NO 49
<211> LENGTH: 933
<212> TYPE: DNA
<213> ORGANISM: Artificial Sequence
<220> FEATURE:
<223> OTHER INFORMATION: IGF2 fusion

<400> SEQUENCE: 49

| | |
|---|---|
| gagtccaaat atggtccccc atgcccaccc tgcccagcac ctgagttcct ggggggacca | 60 |
| tcagtcttcc tgttcccccc aaaacccaag gacactctca tgatctcccg gacccctgag | 120 |
| gtcacgtgcg tggtggtgga cgtgagccag gaagaccccg aggtccagtt caactggtac | 180 |
| gtggatggcg tggaggtgca taatgccaag acaaagccgc gggaggagca gttcaacagc | 240 |
| acgtaccgtg tggtcagcgt cctcaccgtc ctgcaccagg actggctgaa cggcaaggag | 300 |
| tacaagtgca aggtctccaa caaaggcctc ccgtcctcca tcgagaaaac catctccaaa | 360 |
| gccaaagggc agccccgaga gccacaggtg tacaccctgc ccccatccca ggaggagatg | 420 |
| accaagaacc aggtcagcct gacctgcctg gtcaaaggct tctacccag cgacatcgcc | 480 |
| gtggagtggg agagcaatgg gcagccggag aacaactaca agaccacgcc tcccgtgctg | 540 |
| gactccgacg gctccttctt cctctacagc aggctcaccg tggacaagag caggtggcag | 600 |
| gaggggaatg tcttctcatg ctccgtgatg catgaggctc tgcacaacca ctacacacag | 660 |
| aagagcctct ccctgtctct gggtaaaggc ggaggcggta gcggaggcgg tggctccggt | 720 |
| ggcggagggt ctgcttaccg ccccagtgag accctgtgcg gcggggagct ggtggacacc | 780 |
| ctccagttcg tctgtgggga ccgcggcttc tacttcagca ggcccgcaag ccgtgtgagc | 840 |
| cgtcgcagcc gtggcatcgt tgaggagtgc tgtttccgca gctgtgacct ggccctcctg | 900 |
| gagacgtact gtgctacccc cgccaagtcc gag | 933 |

<210> SEQ ID NO 50
<211> LENGTH: 933
<212> TYPE: DNA
<213> ORGANISM: Artificial Sequence
<220> FEATURE:
<223> OTHER INFORMATION: IGF2 mutant

<400> SEQUENCE: 50

| | |
|---|---|
| gcttaccgcc ccagtgagac cctgtgcggc ggggagctgg tggacaccct ccagttcgtc | 60 |
| tgtggggacc gcggcttcta cttcagcagg cccgcaagcc gtgtgagcgc tcgcagccgt | 120 |
| ggcatcgttg aggagtgctg tttccgcagc tgtgacctgg ccctcctgga gacgtactgt | 180 |
| gctaccccg ccaagtccga gggcggaggc ggtagcggag cggtggctc cggtggcgga | 240 |
| gggtctgagt ccaaatatgg tccccatgc ccaccctgcc cagcacctga gttcctgggg | 300 |
| ggaccatcag tcttcctgtt ccccccaaaa cccaaggaca ctctcatgat ctcccggacc | 360 |
| cctgaggtca cgtgcgtggt ggtggacgtg agccaggaag accccgaggt ccagttcaac | 420 |
| tggtacgtgg atggcgtgga ggtgcataat gccaagacaa agccgcggga ggagcagttc | 480 |
| aacagcacgt accgtgtggt cagcgtcctc accgtcctgc accaggactg gctgaacggc | 540 |
| aaggagtaca agtgcaaggt ctccaacaaa ggcctcccgt cctccatcga gaaaaccatc | 600 |

```
tccaaagcca aagggcagcc ccgagagcca caggtgtaca ccctgccccc atcccaggag     660
gagatgacca agaaccaggt cagcctgacc tgcctggtca aaggcttcta ccccagcgac     720
atcgccgtgg agtgggagag caatgggcag ccggagaaca actacaagac cacgcctccc     780
gtgctggact ccgacggctc cttcttcctc tacagcaggc tcaccgtgga caagagcagg     840
tggcaggagg ggaatgtctt ctcatgctcc gtgatgcatg aggctctgca caaccactac     900
acacagaaga gcctctccct gtctctgggt aaa                                 933

<210> SEQ ID NO 51
<211> LENGTH: 417
<212> TYPE: DNA
<213> ORGANISM: Homo sapiens

<400> SEQUENCE: 51
tccacgggga gcaaacagcg cagccagaac cgctccaaga cgcccaagaa ccaggaagcc      60
ctgcggatgg ccaacgtggc agagaacagc agcagcgacc agaggcaggc ctgtaagaag     120
cacgagctgt atgtcagctt ccgagacctg ggctggcagg actggatcat cgcgcctgaa     180
ggctacgccg cctactactg tgaggggag tgtgccttcc ctctgaactc ctacatgaac     240
gccaccaacc acgccatcgt gcagacgctg gtccacttca tcaacccgga aacggtgccc     300
aagccctgct gtgcgcccac gcagctcaat gccatctccg tcctctactt cgatgacagc     360
tccaacgtca tcctgaagaa atacagaaac atggtggtcc gggcctgtgg ctgccac       417

<210> SEQ ID NO 52
<211> LENGTH: 1110
<212> TYPE: DNA
<213> ORGANISM: Artificial Sequence
<220> FEATURE:
<223> OTHER INFORMATION: BMP7 fusion

<400> SEQUENCE: 52
tccacgggga gcaaacagcg cagccagaac cgctccaaga cgcccaagaa ccaggaagcc      60
ctgcggatgg ccaacgtggc agagaacagc agcagcgacc agaggcaggc ctgtaagaag     120
cacgagctgt atgtcagctt ccgagacctg ggctggcagg actggatcat cgcgcctgaa     180
ggctacgccg cctactactg tgaggggag tgtgccttcc ctctgaactc ctacatgaac     240
gccaccaacc acgccatcgt gcagacgctg gtccacttca tcaacccgga aacggtgccc     300
aagccctgct gtgcgcccac gcagctcaat gccatctccg tcctctactt cgatgacagc     360
tccaacgtca tcctgaagaa atacagaaac atggtggtcc gggcctgtgg ctgccacgga     420
tcgggatcgg acaaaactca cacatgccca ccgtgcccag cacctgaagc tgccggggga     480
ccgtcagtct tcctcttccc cccaaaaccc aaggacaccc tcatgatctc ccggacccct     540
gaggtcacat gcgtggtggt ggacgtgagc cacgaagacc ctgaggtcaa gttcaactgg     600
tacgtggacg gcgtggaggt gcataatgcc aagacaaagc cgcgggagga gcagtacaac     660
agcacgtacc gtgtggtcag cgtcctcacc gtcctgcacc aggactggct gaatggcaag     720
gagtacaagt gcaaggtctc caacaaagcc ctcggcgccc ccatcgagaa aaccatctcc     780
aaagccaaag gcagccccg agaaccacag gtgtacaccc tgcccccatc ccgggatgag     840
ctgaccaaga accaggtcag cctgacctgc ctggtcaaag gcttctatcc cagcgacatc     900
gccgtggagt gggagagcaa tgggcagccg gagaacaact acaagaccac gcctcccgtg     960
ctggactccg acggctcctt cttcctctac agcaagctca ccgtggacaa gagcaggtgg    1020
```

-continued

| cagcagggga acgtcttctc atgctccgtg atgcatgagg ctctgcacaa ccactacacg | 1080 |
| cagaaaagcc tctccctgtc tccgggtaaa | 1110 |

<210> SEQ ID NO 53
<211> LENGTH: 1113
<212> TYPE: DNA
<213> ORGANISM: Artificial Sequence
<220> FEATURE:
<223> OTHER INFORMATION: BMP7 fusion

<400> SEQUENCE: 53

| tccacgggga gcaaacagcg cagccagaac cgctccaaga cgcccaagaa ccaggaagcc | 60 |
| ctgcggatgg ccaacgtggc agagaacagc agcagcgacc agaggcaggc ctgtaagaag | 120 |
| cacgagctgt atgtcagctt ccgagacctg ggctggcagg actggatcat cgcgcctgaa | 180 |
| ggctacgccg cctactactg tgagggggag tgtgccttcc ctctgaactc ctacatgaac | 240 |
| gccaccaacc acgccatcgt gcagacgctg gtccacttca tcaacccgga aacggtgccc | 300 |
| aagccctgct gtgcgcccac gcagctcaat gccatctccg tcctctactt cgatgacagc | 360 |
| tccaacgtca tcctgaagaa atacagaaac atggtggtcc gggcctgtgg ctgccacgga | 420 |
| tctgggagcg ctgacaaaac tcacacatgc ccaccgtgcc cagcacctga gctgccgggg | 480 |
| ggaccgtcag tcttcctctt ccccccaaaa cccaaggaca ccctcatgat ctcccggacc | 540 |
| cctgaggtca catgcgtggt ggtggacgtg agccacgaag accctgaggt caagttcaac | 600 |
| tggtacgtgg acggcgtgga ggtgcataat gccaagacaa agccgcggga ggagcagtac | 660 |
| aacagcacgt accgtgtggt cagcgtcctc accgtcctgc accaggactg gctgaatggc | 720 |
| aaggagtaca agtgcaaggt ctccaacaaa gccctcggcg cccccatcga gaaaaccatc | 780 |
| tccaaagcca agggcagccc cgagaaccca ggtgtaca ccctgccccc atcccgggat | 840 |
| gagctgacca agaaccaggt cagcctgacc tgcctggtca aaggcttcta tcccagcgac | 900 |
| atcgccgtgg agtgggagag caatgggcag ccggagaaca actacaagac cacgcctccc | 960 |
| gtgctggact ccgacggctc cttcttcctc tacagcaagc tcaccgtgga caagagcagg | 1020 |
| tggcagcagg ggaacgtctt ctcatgctcc gtgatgcatg aggctctgca caaccactac | 1080 |
| acgcagaaaa gcctctccct gtctccgggt aaa | 1113 |

<210> SEQ ID NO 54
<211> LENGTH: 194
<212> TYPE: PRT
<213> ORGANISM: Homo sapiens

<400> SEQUENCE: 54

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu

```
              100                 105                 110
Glu Asn Asn Tyr Thr Ala Phe Gln Asn Ala Arg His Glu Gly Trp Phe
            115                 120                 125

Met Ala Phe Thr Arg Gln Gly Arg Pro Arg Gln Ala Ser Arg Ser Arg
    130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
                165                 170                 175

Gly Ser Ala Pro Thr Arg Arg Thr Lys Arg Thr Arg Arg Pro Gln Pro
            180                 185                 190

Leu Thr

<210> SEQ ID NO 55
<211> LENGTH: 181
<212> TYPE: PRT
<213> ORGANISM: Artificial Sequence
<220> FEATURE:
<223> OTHER INFORMATION: FGF17 deletion mutant

<400> SEQUENCE: 55

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
        115                 120                 125

Met Ala Phe Thr Arg Gln Gly Arg Pro Arg Gln Ala Ser Arg Ser Arg
    130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
                165                 170                 175

Gly Ser Ala Pro Thr
            180

<210> SEQ ID NO 56
<211> LENGTH: 158
<212> TYPE: PRT
<213> ORGANISM: Artificial Sequence
<220> FEATURE:
<223> OTHER INFORMATION: FGF17 deletion mutant

<400> SEQUENCE: 56

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
```

```
            20                  25                  30
Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
            85                  90                  95

Lys Pro Ser Gly Lys Ser Lys Asp Cys Val Phe Thr Glu Ile Val Leu
        100                 105                 110

Glu Asn Asn Tyr Thr Ala Phe Gln Asn Ala Arg His Glu Gly Trp Phe
    115                 120                 125

Met Ala Phe Thr Arg Gln Gly Arg Pro Arg Gln Ala Ser Arg Ser Arg
        130                 135                 140

Gln Asn Gln Arg Glu Ala His Phe Ile Lys Arg Leu Tyr Gln
145                 150                 155

<210> SEQ ID NO 57
<211> LENGTH: 194
<212> TYPE: PRT
<213> ORGANISM: Artificial Sequence
<220> FEATURE:
<223> OTHER INFORMATION: FGF17 mutant

<400> SEQUENCE: 57

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
            85                  90                  95

Lys Pro Ser Gly Lys Ser Lys Asp Cys Val Phe Thr Glu Ile Val Leu
        100                 105                 110

Glu Asn Asn Tyr Thr Ala Phe Gln Asn Ala Arg His Glu Gly Trp Phe
    115                 120                 125

Met Ala Phe Thr Arg Gln Gly Arg Pro Arg Gln Ala Ser Arg Ser Arg
        130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
            165                 170                 175

Gly Ser Ala Pro Thr Gln Arg Thr Gln Arg Thr Arg Arg Pro Gln Pro
        180                 185                 190

Leu Thr

<210> SEQ ID NO 58
<211> LENGTH: 174
<212> TYPE: PRT
<213> ORGANISM: Artificial Sequence
```

```
<220> FEATURE:
<223> OTHER INFORMATION: FGF17 deletion mutant

<400> SEQUENCE: 58

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
        115                 120                 125

Met Ala Phe Thr Arg Gln Gly Arg Pro Arg Gln Ala Ser Arg Ser Arg
    130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu
                165                 170

<210> SEQ ID NO 59
<211> LENGTH: 194
<212> TYPE: PRT
<213> ORGANISM: Artificial Sequence
<220> FEATURE:
<223> OTHER INFORMATION: FGF17 mutant

<400> SEQUENCE: 59

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
        115                 120                 125

Met Ala Phe Thr Arg Gln Gly Arg Pro Arg Gln Ala Ser Arg Ser Arg
    130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Ala Gln Ala Gln Phe Glu Phe Val
```

```
                165                 170                 175
Gly Ala Ala Pro Thr Arg Arg Thr Lys Arg Thr Arg Arg Pro Gln Pro
            180                 185                 190
Leu Thr

<210> SEQ ID NO 60
<211> LENGTH: 425
<212> TYPE: PRT
<213> ORGANISM: Artificial Sequence
<220> FEATURE:
<223> OTHER INFORMATION: FGF17 fusion

<400> SEQUENCE: 60

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
        115                 120                 125

Met Ala Phe Thr Arg Gln Gly Arg Pro Arg Gln Ala Ser Arg Ser Arg
    130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
                165                 170                 175

Gly Ser Ala Pro Thr Arg Arg Thr Lys Arg Thr Arg Arg Pro Gln Pro
            180                 185                 190

Leu Thr Gly Ser Gly Ser Asp Lys Thr His Thr Cys Pro Pro Cys Pro
        195                 200                 205

Ala Pro Glu Ala Ala Gly Gly Pro Ser Val Phe Leu Phe Pro Pro Lys
    210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
                245                 250                 255

Val Asp Gly Val Glu Val His Asn Ala Lys Thr Lys Pro Arg Glu Glu
            260                 265                 270

Gln Tyr Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
    290                 295                 300

Ala Leu Gly Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Asp Glu Leu
                325                 330                 335
```

-continued

```
Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
            355                 360                 365

Tyr Lys Thr Thr Pro Pro Val Leu Asp Ser Asp Gly Ser Phe Phe Leu
    370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Pro Gly Lys
            420                 425

<210> SEQ ID NO 61
<211> LENGTH: 412
<212> TYPE: PRT
<213> ORGANISM: Artificial Sequence
<220> FEATURE:
<223> OTHER INFORMATION: FGF17 deletion mutant

<400> SEQUENCE: 61

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
        115                 120                 125

Met Ala Phe Thr Arg Gln Gly Arg Pro Arg Gln Ala Ser Arg Ser Arg
    130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
                165                 170                 175

Gly Ser Ala Pro Thr Gly Ser Gly Ser Asp Lys Thr His Thr Cys Pro
            180                 185                 190

Pro Cys Pro Ala Pro Glu Ala Ala Gly Gly Pro Ser Val Phe Leu Phe
        195                 200                 205

Pro Pro Lys Pro Lys Asp Thr Leu Met Ile Ser Arg Thr Pro Glu Val
    210                 215                 220

Thr Cys Val Val Val Asp Val Ser His Glu Asp Pro Glu Val Lys Phe
225                 230                 235                 240

Asn Trp Tyr Val Asp Gly Val Glu Val His Asn Ala Lys Thr Lys Pro
                245                 250                 255

Arg Glu Glu Gln Tyr Asn Ser Thr Tyr Arg Val Val Ser Val Leu Thr
            260                 265                 270
```

```
Val Leu His Gln Asp Trp Leu Asn Gly Lys Glu Tyr Lys Cys Lys Val
            275                 280                 285

Ser Asn Lys Ala Leu Gly Ala Pro Ile Glu Lys Thr Ile Ser Lys Ala
        290                 295                 300

Lys Gly Gln Pro Arg Glu Pro Gln Val Tyr Thr Leu Pro Pro Ser Arg
305                 310                 315                 320

Asp Glu Leu Thr Lys Asn Gln Val Ser Leu Thr Cys Leu Val Lys Gly
            325                 330                 335

Phe Tyr Pro Ser Asp Ile Ala Val Glu Trp Glu Ser Asn Gly Gln Pro
        340                 345                 350

Glu Asn Asn Tyr Lys Thr Thr Pro Pro Val Leu Asp Ser Asp Gly Ser
            355                 360                 365

Phe Phe Leu Tyr Ser Lys Leu Thr Val Asp Lys Ser Arg Trp Gln Gln
        370                 375                 380

Gly Asn Val Phe Ser Cys Ser Val Met His Glu Ala Leu His Asn His
385                 390                 395                 400

Tyr Thr Gln Lys Ser Leu Ser Leu Ser Pro Gly Lys
            405                 410

<210> SEQ ID NO 62
<211> LENGTH: 389
<212> TYPE: PRT
<213> ORGANISM: Artificial Sequence
<220> FEATURE:
<223> OTHER INFORMATION: FGF17 deletion mutant

<400> SEQUENCE: 62

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
            85                  90                  95

Lys Pro Ser Gly Lys Ser Lys Asp Cys Val Phe Thr Glu Ile Val Leu
        100                 105                 110

Glu Asn Asn Tyr Thr Ala Phe Gln Asn Ala Arg His Glu Gly Trp Phe
    115                 120                 125

Met Ala Phe Thr Arg Gln Gly Arg Pro Arg Gln Ala Ser Arg Ser Arg
130                 135                 140

Gln Asn Gln Arg Glu Ala His Phe Ile Lys Arg Leu Tyr Gln Gly Ser
145                 150                 155                 160

Gly Ser Asp Lys Thr His Thr Cys Pro Pro Cys Pro Ala Pro Glu Ala
            165                 170                 175

Ala Gly Gly Pro Ser Val Phe Leu Phe Pro Pro Lys Pro Lys Asp Thr
        180                 185                 190

Leu Met Ile Ser Arg Thr Pro Glu Val Thr Cys Val Val Val Asp Val
            195                 200                 205

Ser His Glu Asp Pro Glu Val Lys Phe Asn Trp Tyr Val Asp Gly Val
    210                 215                 220
```

```
Glu Val His Asn Ala Lys Thr Lys Pro Arg Glu Glu Gln Tyr Asn Ser
225                 230                 235                 240

Thr Tyr Arg Val Val Ser Val Leu Thr Val Leu His Gln Asp Trp Leu
                245                 250                 255

Asn Gly Lys Glu Tyr Lys Cys Lys Val Ser Asn Lys Ala Leu Gly Ala
            260                 265                 270

Pro Ile Glu Lys Thr Ile Ser Lys Ala Lys Gly Gln Pro Arg Glu Pro
            275                 280                 285

Gln Val Tyr Thr Leu Pro Pro Ser Arg Asp Glu Leu Thr Lys Asn Gln
            290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Thr Thr
                325                 330                 335

Pro Pro Val Leu Asp Ser Asp Gly Ser Phe Phe Leu Tyr Ser Lys Leu
            340                 345                 350

Thr Val Asp Lys Ser Arg Trp Gln Gln Gly Asn Val Phe Ser Cys Ser
            355                 360                 365

Val Met His Glu Ala Leu His Asn His Tyr Thr Gln Lys Ser Leu Ser
370                 375                 380

Leu Ser Pro Gly Lys
385

<210> SEQ ID NO 63
<211> LENGTH: 425
<212> TYPE: PRT
<213> ORGANISM: Artificial Sequence
<220> FEATURE:
<223> OTHER INFORMATION: FGF17 mutant

<400> SEQUENCE: 63

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
                20                  25                  30

Tyr Gln Leu Tyr Ser Arg Thr Ser Gly Lys His Val Gln Val Thr Gly
            35                  40                  45

Arg Arg Ile Ser Ala Thr Ala Glu Asp Gly Asn Lys Phe Ala Lys Leu
50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
            115                 120                 125

Met Ala Phe Thr Arg Gln Gly Arg Pro Arg Gln Ala Ser Arg Ser Arg
130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
                165                 170                 175

Gly Ser Ala Pro Thr Gln Arg Thr Gln Arg Thr Arg Arg Pro Gln Pro
            180                 185                 190
```

```
Leu Thr Gly Ser Gly Ser Asp Lys Thr His Thr Cys Pro Cys Pro
            195                 200                 205

Ala Pro Glu Ala Ala Gly Gly Pro Ser Val Phe Leu Phe Pro Lys
        210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
                245                 250                 255

Val Asp Gly Val Glu Val His Asn Ala Lys Thr Lys Pro Arg Glu Glu
            260                 265                 270

Gln Tyr Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
    290                 295                 300

Ala Leu Gly Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Asp Glu Leu
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
    370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Pro Gly Lys
            420                 425

<210> SEQ ID NO 64
<211> LENGTH: 405
<212> TYPE: PRT
<213> ORGANISM: Artificial Sequence
<220> FEATURE:
<223> OTHER INFORMATION: FGF17 deletion mutant

<400> SEQUENCE: 64

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
        115                 120                 125
```

```
Met Ala Phe Thr Arg Gln Gly Arg Pro Arg Gln Ala Ser Arg Ser Arg
            130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Gly Ser
                165                 170                 175

Gly Ser Asp Lys Thr His Thr Cys Pro Pro Cys Pro Ala Pro Glu Ala
            180                 185                 190

Ala Gly Gly Pro Ser Val Phe Leu Phe Pro Pro Lys Pro Lys Asp Thr
        195                 200                 205

Leu Met Ile Ser Arg Thr Pro Glu Val Thr Cys Val Val Val Asp Val
210                 215                 220

Ser His Glu Asp Pro Glu Val Lys Phe Asn Trp Tyr Val Asp Gly Val
225                 230                 235                 240

Glu Val His Asn Ala Lys Thr Lys Pro Arg Glu Gln Tyr Asn Ser
                245                 250                 255

Thr Tyr Arg Val Val Ser Val Leu Thr Val Leu His Gln Asp Trp Leu
            260                 265                 270

Asn Gly Lys Glu Tyr Lys Cys Lys Val Ser Asn Lys Ala Leu Gly Ala
        275                 280                 285

Pro Ile Glu Lys Thr Ile Ser Lys Ala Lys Gly Gln Pro Arg Glu Pro
290                 295                 300

Gln Val Tyr Thr Leu Pro Pro Ser Arg Asp Glu Leu Thr Lys Asn Gln
305                 310                 315                 320

Val Ser Leu Thr Cys Leu Val Lys Gly Phe Tyr Pro Ser Asp Ile Ala
            325                 330                 335

Val Glu Trp Glu Ser Asn Gly Gln Pro Glu Asn Asn Tyr Lys Thr Thr
        340                 345                 350

Pro Pro Val Leu Asp Ser Asp Gly Ser Phe Phe Leu Tyr Ser Lys Leu
            355                 360                 365

Thr Val Asp Lys Ser Arg Trp Gln Gln Gly Asn Val Phe Ser Cys Ser
370                 375                 380

Val Met His Glu Ala Leu His Asn His Tyr Thr Gln Lys Ser Leu Ser
385                 390                 395                 400

Leu Ser Pro Gly Lys
            405

<210> SEQ ID NO 65
<211> LENGTH: 425
<212> TYPE: PRT
<213> ORGANISM: Artificial Sequence
<220> FEATURE:
<223> OTHER INFORMATION: FGF17 mutant

<400> SEQUENCE: 65

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Arg Val Arg Ile Lys Gly Ala
65                  70                  75                  80
```

```
Glu Ser Glu Lys Tyr Ile Cys Met Asn Lys Arg Gly Lys Leu Ile Gly
                 85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
        115                 120                 125

Met Ala Phe Thr Arg Gln Gly Arg Pro Arg Gln Ala Ser Arg Ser Arg
130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Ala Gln Ala Gln Phe Glu Phe Val
                165                 170                 175

Gly Ala Ala Pro Thr Arg Arg Thr Lys Arg Thr Arg Arg Pro Gln Pro
            180                 185                 190

Leu Thr Gly Ser Gly Ser Asp Lys Thr His Thr Cys Pro Pro Cys Pro
        195                 200                 205

Ala Pro Glu Ala Ala Gly Gly Pro Ser Val Phe Leu Phe Pro Pro Lys
    210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
                245                 250                 255

Val Asp Gly Val Glu Val His Asn Ala Lys Thr Lys Pro Arg Glu Glu
            260                 265                 270

Gln Tyr Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
290                 295                 300

Ala Leu Gly Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Asp Glu Leu
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Pro Gly Lys
            420                 425

<210> SEQ ID NO 66
<211> LENGTH: 426
<212> TYPE: PRT
<213> ORGANISM: Artificial Sequence
<220> FEATURE:
<223> OTHER INFORMATION: FGF17 fusion

<400> SEQUENCE: 66

Thr Gln Gly Glu Asn His Pro Ser Pro Asn Phe Asn Gln Tyr Val Arg
1               5                   10                  15
```

```
Asp Gln Gly Ala Met Thr Asp Gln Leu Ser Arg Arg Gln Ile Arg Glu
             20                  25                  30

Tyr Gln Leu Tyr Ser Arg Thr Ser Gly Lys His Val Gln Val Thr Gly
             35                  40                  45

Arg Arg Ile Ser Ala Thr Ala Glu Asp Gly Asn Lys Phe Ala Lys Leu
 50                  55                  60

Ile Val Glu Thr Asp Thr Phe Gly Ser Arg Val Arg Ile Lys Gly Ala
 65                  70                  75                  80

Glu Ser Glu Lys Tyr Ile Cys Met Asn Lys Arg Gly Lys Leu Ile Gly
             85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
            115                 120                 125

Met Ala Phe Thr Arg Gln Gly Arg Pro Arg Gln Ala Ser Arg Ser Arg
130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
            165                 170                 175

Gly Ser Ala Pro Thr Arg Arg Thr Lys Arg Thr Arg Arg Pro Gln Pro
            180                 185                 190

Leu Thr Gly Ser Gly Ser Ala Asp Lys Thr His Thr Cys Pro Pro Cys
            195                 200                 205

Pro Ala Pro Glu Ala Ala Gly Gly Pro Ser Val Phe Leu Phe Pro Pro
            210                 215                 220

Lys Pro Lys Asp Thr Leu Met Ile Ser Arg Thr Pro Glu Val Thr Cys
225                 230                 235                 240

Val Val Val Asp Val Ser His Glu Asp Pro Glu Val Lys Phe Asn Trp
            245                 250                 255

Tyr Val Asp Gly Val Glu Val His Asn Ala Lys Thr Lys Pro Arg Glu
            260                 265                 270

Glu Gln Tyr Asn Ser Thr Tyr Arg Val Val Ser Val Leu Thr Val Leu
            275                 280                 285

His Gln Asp Trp Leu Asn Gly Lys Glu Tyr Lys Cys Lys Val Ser Asn
290                 295                 300

Lys Ala Leu Gly Ala Pro Ile Glu Lys Thr Ile Ser Lys Ala Lys Gly
305                 310                 315                 320

Gln Pro Arg Glu Pro Gln Val Tyr Thr Leu Pro Pro Ser Arg Asp Glu
            325                 330                 335

Leu Thr Lys Asn Gln Val Ser Leu Thr Cys Leu Val Lys Gly Phe Tyr
            340                 345                 350

Pro Ser Asp Ile Ala Val Glu Trp Glu Ser Asn Gly Gln Pro Glu Asn
            355                 360                 365

Asn Tyr Lys Thr Thr Pro Pro Val Leu Asp Ser Asp Gly Ser Phe Phe
            370                 375                 380

Leu Tyr Ser Lys Leu Thr Val Asp Lys Ser Arg Trp Gln Gln Gly Asn
385                 390                 395                 400

Val Phe Ser Cys Ser Val Met His Glu Ala Leu His Asn His Tyr Thr
            405                 410                 415

Gln Lys Ser Leu Ser Leu Ser Pro Gly Lys
            420                 425
```

```
<210> SEQ ID NO 67
<211> LENGTH: 413
<212> TYPE: PRT
<213> ORGANISM: Artificial Sequence
<220> FEATURE:
<223> OTHER INFORMATION: FGF17 deletion mutant

<400> SEQUENCE: 67

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
        115                 120                 125

Met Ala Phe Thr Arg Gln Gly Arg Pro Arg Gln Ala Ser Arg Ser Arg
    130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
                165                 170                 175

Gly Ser Ala Pro Thr Gly Ser Gly Ser Ala Asp Lys Thr His Thr Cys
            180                 185                 190

Pro Pro Cys Pro Ala Pro Glu Ala Ala Gly Gly Pro Ser Val Phe Leu
        195                 200                 205

Phe Pro Pro Lys Pro Lys Asp Thr Leu Met Ile Ser Arg Thr Pro Glu
    210                 215                 220

Val Thr Cys Val Val Val Asp Val Ser His Glu Asp Pro Glu Val Lys
225                 230                 235                 240

Phe Asn Trp Tyr Val Asp Gly Val Glu Val His Asn Ala Lys Thr Lys
                245                 250                 255

Pro Arg Glu Glu Gln Tyr Asn Ser Thr Tyr Arg Val Val Ser Val Leu
            260                 265                 270

Thr Val Leu His Gln Asp Trp Leu Asn Gly Lys Glu Tyr Lys Cys Lys
        275                 280                 285

Val Ser Asn Lys Ala Leu Gly Ala Pro Ile Glu Lys Thr Ile Ser Lys
    290                 295                 300

Ala Lys Gly Gln Pro Arg Glu Pro Gln Val Tyr Thr Leu Pro Pro Ser
305                 310                 315                 320

Arg Asp Glu Leu Thr Lys Asn Gln Val Ser Leu Thr Cys Leu Val Lys
                325                 330                 335

Gly Phe Tyr Pro Ser Asp Ile Ala Val Glu Trp Glu Ser Asn Gly Gln
            340                 345                 350

Pro Glu Asn Asn Tyr Lys Thr Thr Pro Pro Val Leu Asp Ser Asp Gly
        355                 360                 365
```

Ser Phe Phe Leu Tyr Ser Lys Leu Thr Val Asp Lys Ser Arg Trp Gln
370                 375                 380

Gln Gly Asn Val Phe Ser Cys Ser Val Met His Glu Ala Leu His Asn
385                 390                 395                 400

His Tyr Thr Gln Lys Ser Leu Ser Leu Ser Pro Gly Lys
                405                 410

<210> SEQ ID NO 68
<211> LENGTH: 390
<212> TYPE: PRT
<213> ORGANISM: Artificial Sequence
<220> FEATURE:
<223> OTHER INFORMATION: FGF17 mutant

<400> SEQUENCE: 68

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
                20                  25                  30

Tyr Gln Leu Tyr Ser Arg Thr Ser Gly Lys His Val Gln Val Thr Gly
            35                  40                  45

Arg Arg Ile Ser Ala Thr Ala Glu Asp Gly Asn Lys Phe Ala Lys Leu
50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
        115                 120                 125

Met Ala Phe Thr Arg Gln Gly Arg Pro Arg Gln Ala Ser Arg Ser Arg
130                 135                 140

Gln Asn Gln Arg Glu Ala His Phe Ile Lys Arg Leu Tyr Gln Gly Ser
145                 150                 155                 160

Gly Ser Ala Asp Lys Thr His Thr Cys Pro Pro Cys Pro Ala Pro Glu
                165                 170                 175

Ala Ala Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Gly
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Asp Glu Leu Thr Lys Asn
290                 295                 300

Gln Val Ser Leu Thr Cys Leu Val Lys Gly Phe Tyr Pro Ser Asp Ile
305                 310                 315                 320

```
Ala Val Glu Trp Glu Ser Asn Gly Gln Pro Glu Asn Asn Tyr Lys Thr
            325                 330                 335

Thr Pro Pro Val Leu Asp Ser Asp Gly Ser Phe Phe Leu Tyr Ser Lys
        340                 345                 350

Leu Thr Val Asp Lys Ser Arg Trp Gln Gln Gly Asn Val Phe Ser Cys
        355                 360                 365

Ser Val Met His Glu Ala Leu His Asn His Tyr Thr Gln Lys Ser Leu
        370                 375                 380

Ser Leu Ser Pro Gly Lys
385             390

<210> SEQ ID NO 69
<211> LENGTH: 426
<212> TYPE: PRT
<213> ORGANISM: Artificial Sequence
<220> FEATURE:
<223> OTHER INFORMATION: FGF17 mutant

<400> SEQUENCE: 69

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
        115                 120                 125

Met Ala Phe Thr Arg Gln Gly Arg Pro Arg Gln Ala Ser Arg Ser Arg
    130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
                165                 170                 175

Gly Ser Ala Pro Thr Gln Arg Thr Gln Arg Thr Arg Arg Pro Gln Pro
            180                 185                 190

Leu Thr Gly Ser Gly Ser Ala Asp Lys Thr His Thr Cys Pro Pro Cys
        195                 200                 205

Pro Ala Pro Glu Ala Ala Gly Gly Pro Ser Val Phe Leu Phe Pro Pro
    210                 215                 220

Lys Pro Lys Asp Thr Leu Met Ile Ser Arg Thr Pro Glu Val Thr Cys
225                 230                 235                 240

Val Val Val Asp Val Ser His Glu Asp Pro Glu Val Lys Phe Asn Trp
                245                 250                 255

Tyr Val Asp Gly Val Glu Val His Asn Ala Lys Thr Lys Pro Arg Glu
            260                 265                 270

Glu Gln Tyr Asn Ser Thr Tyr Arg Val Val Ser Val Leu Thr Val Leu
        275                 280                 285
```

```
His Gln Asp Trp Leu Asn Gly Lys Glu Tyr Lys Cys Lys Val Ser Asn
    290                 295                 300
Lys Ala Leu Gly Ala Pro Ile Glu Lys Thr Ile Ser Lys Ala Lys Gly
305                 310                 315                 320
Gln Pro Arg Glu Pro Gln Val Tyr Thr Leu Pro Pro Ser Arg Asp Glu
                325                 330                 335
Leu Thr Lys Asn Gln Val Ser Leu Thr Cys Leu Val Lys Gly Phe Tyr
                340                 345                 350
Pro Ser Asp Ile Ala Val Glu Trp Glu Ser Asn Gly Gln Pro Glu Asn
                355                 360                 365
Asn Tyr Lys Thr Thr Pro Pro Val Leu Asp Ser Asp Gly Ser Phe Phe
    370                 375                 380
Leu Tyr Ser Lys Leu Thr Val Asp Lys Ser Arg Trp Gln Gln Gly Asn
385                 390                 395                 400
Val Phe Ser Cys Ser Val Met His Glu Ala Leu His Asn His Tyr Thr
                405                 410                 415
Gln Lys Ser Leu Ser Leu Ser Pro Gly Lys
                420                 425

<210> SEQ ID NO 70
<211> LENGTH: 406
<212> TYPE: PRT
<213> ORGANISM: Artificial Sequence
<220> FEATURE:
<223> OTHER INFORMATION: FGF17 deletion mutant

<400> SEQUENCE: 70

Thr Gln Gly Glu Asn His Pro Ser Pro Asn Phe Asn Gln Tyr Val Arg
1               5                   10                  15
Asp Gln Gly Ala Met Thr Asp Gln Leu Ser Arg Arg Gln Ile Arg Glu
                20                  25                  30
Tyr Gln Leu Tyr Ser Arg Thr Ser Gly Lys His Val Gln Val Thr Gly
            35                  40                  45
Arg Arg Ile Ser Ala Thr Ala Glu Asp Gly Asn Lys Phe Ala Lys Leu
50                  55                  60
Ile Val Glu Thr Asp Thr Phe Gly Ser Arg Val Arg Ile Lys Gly Ala
65                  70                  75                  80
Glu Ser Glu Lys Tyr Ile Cys Met Asn Lys Arg Gly Lys Leu Ile Gly
                85                  90                  95
Lys Pro Ser Gly Lys Ser Lys Asp Cys Val Phe Thr Glu Ile Val Leu
            100                 105                 110
Glu Asn Asn Tyr Thr Ala Phe Gln Asn Ala Arg His Glu Gly Trp Phe
        115                 120                 125
Met Ala Phe Thr Arg Gln Gly Arg Pro Arg Gln Ala Ser Arg Ser Arg
    130                 135                 140
Gln Asn Gln Arg Glu Ala His Phe Ile Lys Arg Leu Tyr Gln Gly Gln
145                 150                 155                 160
Leu Pro Phe Pro Asn His Ala Glu Lys Gln Lys Gln Phe Glu Gly Ser
                165                 170                 175
Gly Ser Ala Asp Lys Thr His Thr Cys Pro Pro Cys Pro Ala Pro Glu
            180                 185                 190
Ala Ala Gly Gly Pro Ser Val Phe Leu Phe Pro Pro Lys Pro Lys Asp
        195                 200                 205
Thr Leu Met Ile Ser Arg Thr Pro Glu Val Thr Cys Val Val Val Asp
    210                 215                 220
```

```
Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
            245                 250                 255

Ser Thr Tyr Arg Val Val Ser Val Leu Thr Val Leu His Gln Asp Trp
        260                 265                 270

Leu Asn Gly Lys Glu Tyr Lys Cys Lys Val Ser Asn Lys Ala Leu Gly
    275                 280                 285

Ala Pro Ile Glu Lys Thr Ile Ser Lys Ala Lys Gly Gln Pro Arg Glu
290                 295                 300

Pro Gln Val Tyr Thr Leu Pro Pro Ser Arg Asp Glu Leu Thr Lys Asn
305                 310                 315                 320

Gln Val Ser Leu Thr Cys Leu Val Lys Gly Phe Tyr Pro Ser Asp Ile
            325                 330                 335

Ala Val Glu Trp Glu Ser Asn Gly Gln Pro Glu Asn Asn Tyr Lys Thr
        340                 345                 350

Thr Pro Pro Val Leu Asp Ser Asp Gly Ser Phe Phe Leu Tyr Ser Lys
    355                 360                 365

Leu Thr Val Asp Lys Ser Arg Trp Gln Gln Gly Asn Val Phe Ser Cys
370                 375                 380

Ser Val Met His Glu Ala Leu His Asn His Tyr Thr Gln Lys Ser Leu
385                 390                 395                 400

Ser Leu Ser Pro Gly Lys
            405

<210> SEQ ID NO 71
<211> LENGTH: 426
<212> TYPE: PRT
<213> ORGANISM: Artificial Sequence
<220> FEATURE:
<223> OTHER INFORMATION: FGF17 mutant

<400> SEQUENCE: 71

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
            85                  90                  95

Lys Pro Ser Gly Lys Ser Lys Asp Cys Val Phe Thr Glu Ile Val Leu
        100                 105                 110

Glu Asn Asn Tyr Thr Ala Phe Gln Asn Ala Arg His Glu Gly Trp Phe
    115                 120                 125

Met Ala Phe Thr Arg Gln Gly Arg Pro Arg Gln Ala Ser Arg Ser Arg
130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Ala Gln Ala Gln Phe Glu Phe Val
            165                 170                 175
```

```
Gly Ala Ala Pro Thr Arg Arg Thr Lys Arg Thr Arg Pro Gln Pro
            180                 185                 190

Leu Thr Gly Ser Gly Ser Ala Asp Lys Thr His Thr Cys Pro Pro Cys
        195                 200                 205

Pro Ala Pro Glu Ala Ala Gly Gly Pro Ser Val Phe Leu Phe Pro Pro
        210                 215                 220

Lys Pro Lys Asp Thr Leu Met Ile Ser Arg Thr Pro Glu Val Thr Cys
225                 230                 235                 240

Val Val Val Asp Val Ser His Glu Asp Pro Glu Val Lys Phe Asn Trp
                245                 250                 255

Tyr Val Asp Gly Val Glu Val His Asn Ala Lys Thr Lys Pro Arg Glu
            260                 265                 270

Glu Gln Tyr Asn Ser Thr Tyr Arg Val Val Ser Val Leu Thr Val Leu
        275                 280                 285

His Gln Asp Trp Leu Asn Gly Lys Glu Tyr Lys Cys Lys Val Ser Asn
    290                 295                 300

Lys Ala Leu Gly Ala Pro Ile Glu Lys Thr Ile Ser Lys Ala Lys Gly
305                 310                 315                 320

Gln Pro Arg Glu Pro Gln Val Tyr Thr Leu Pro Pro Ser Arg Asp Glu
                325                 330                 335

Leu Thr Lys Asn Gln Val Ser Leu Thr Cys Leu Val Lys Gly Phe Tyr
            340                 345                 350

Pro Ser Asp Ile Ala Val Glu Trp Glu Ser Asn Gly Gln Pro Glu Asn
        355                 360                 365

Asn Tyr Lys Thr Thr Pro Pro Val Leu Asp Ser Asp Gly Ser Phe Phe
370                 375                 380

Leu Tyr Ser Lys Leu Thr Val Asp Lys Ser Arg Trp Gln Gln Gly Asn
385                 390                 395                 400

Val Phe Ser Cys Ser Val Met His Glu Ala Leu His Asn His Tyr Thr
                405                 410                 415

Gln Lys Ser Leu Ser Leu Ser Pro Gly Lys
            420                 425

<210> SEQ ID NO 72
<211> LENGTH: 802
<212> TYPE: PRT
<213> ORGANISM: Artificial Sequence
<220> FEATURE:
<223> OTHER INFORMATION: FGF17 fusion

<400> SEQUENCE: 72

His His His His His Ser Gly Asp Ala His Lys Ser Glu Val Ala
1               5                   10                  15

His Arg Phe Lys Asp Leu Gly Glu Glu Asn Phe Lys Ala Leu Val Leu
            20                  25                  30

Ile Ala Phe Ala Gln Tyr Leu Gln Gln Cys Pro Phe Glu Asp His Val
        35                  40                  45

Lys Leu Val Asn Glu Val Thr Glu Phe Ala Lys Thr Cys Val Ala Asp
    50                  55                  60

Glu Ser Ala Glu Asn Cys Asp Lys Ser Leu His Thr Leu Phe Gly Asp
65                  70                  75                  80

Lys Leu Cys Thr Val Ala Thr Leu Arg Glu Thr Tyr Gly Glu Met Ala
                85                  90                  95

Asp Cys Cys Ala Lys Gln Glu Pro Glu Arg Asn Glu Cys Phe Leu Gln
            100                 105                 110
```

-continued

His Lys Asp Asp Asn Pro Asn Leu Pro Arg Leu Val Arg Pro Glu Val
            115                 120                 125

Asp Val Met Cys Thr Ala Phe His Asp Asn Glu Glu Thr Phe Leu Lys
        130                 135                 140

Lys Tyr Leu Tyr Glu Ile Ala Arg Arg His Pro Tyr Phe Tyr Ala Pro
145                 150                 155                 160

Glu Leu Leu Phe Phe Ala Lys Arg Tyr Lys Ala Ala Phe Thr Glu Cys
                165                 170                 175

Cys Gln Ala Ala Asp Lys Ala Ala Cys Leu Leu Pro Lys Leu Asp Glu
            180                 185                 190

Leu Arg Asp Glu Gly Lys Ala Ser Ser Ala Lys Gln Arg Leu Lys Cys
            195                 200                 205

Ala Ser Leu Gln Lys Phe Gly Glu Arg Ala Phe Lys Ala Trp Ala Val
            210                 215                 220

Ala Arg Leu Ser Gln Arg Phe Pro Lys Ala Glu Phe Ala Glu Val Ser
225                 230                 235                 240

Lys Leu Val Thr Asp Leu Thr Lys Val His Thr Glu Cys Cys His Gly
                245                 250                 255

Asp Leu Leu Glu Cys Ala Asp Asp Arg Ala Asp Leu Ala Lys Tyr Ile
                260                 265                 270

Cys Glu Asn Gln Asp Ser Ile Ser Ser Lys Leu Lys Glu Cys Cys Glu
            275                 280                 285

Lys Pro Leu Leu Glu Lys Ser His Cys Ile Ala Glu Val Glu Asn Asp
            290                 295                 300

Glu Met Pro Ala Asp Leu Pro Ser Leu Ala Ala Asp Phe Val Glu Ser
305                 310                 315                 320

Lys Asp Val Cys Lys Asn Tyr Ala Glu Ala Lys Asp Val Phe Leu Gly
                325                 330                 335

Met Phe Leu Tyr Glu Tyr Ala Arg Arg His Pro Asp Tyr Ser Val Val
                340                 345                 350

Leu Leu Leu Arg Leu Ala Lys Thr Tyr Glu Thr Thr Leu Glu Lys Cys
            355                 360                 365

Cys Ala Ala Ala Asp Pro His Glu Cys Tyr Ala Lys Val Phe Asp Glu
            370                 375                 380

Phe Lys Pro Leu Val Glu Glu Pro Gln Asn Leu Ile Lys Gln Asn Cys
385                 390                 395                 400

Glu Leu Phe Glu Gln Leu Gly Glu Tyr Lys Phe Gln Asn Ala Leu Leu
                405                 410                 415

Val Arg Tyr Thr Lys Lys Val Pro Gln Val Ser Thr Pro Thr Leu Val
                420                 425                 430

Glu Val Ser Arg Asn Leu Gly Lys Val Gly Ser Lys Cys Cys Lys His
            435                 440                 445

Pro Glu Ala Lys Arg Met Pro Cys Ala Glu Asp Tyr Leu Ser Val Val
            450                 455                 460

Leu Asn Gln Leu Cys Val Leu His Glu Lys Thr Pro Val Ser Asp Arg
465                 470                 475                 480

Val Thr Lys Cys Cys Thr Glu Ser Leu Val Asn Arg Arg Pro Cys Phe
                485                 490                 495

Ser Ala Leu Glu Val Asp Glu Thr Tyr Val Pro Lys Glu Phe Asn Ala
            500                 505                 510

Glu Thr Phe Thr Phe His Ala Asp Ile Cys Thr Leu Ser Glu Lys Glu
            515                 520                 525

Arg Gln Ile Lys Lys Gln Thr Ala Leu Val Glu Leu Val Lys His Lys

```
                530             535             540
Pro Lys Ala Thr Lys Glu Gln Leu Lys Ala Val Met Asp Asp Phe Ala
545                 550             555                 560

Ala Phe Val Glu Lys Cys Cys Lys Ala Asp Asp Lys Glu Thr Cys Phe
                565             570             575

Ala Glu Glu Gly Lys Lys Leu Val Ala Ala Ser Gln Ala Ala Leu Gly
                580             585             590

Leu Gly Gly Gly Ser Gly Gly Gly Ser Gly Gly Gly Ser
            595             600             605

Thr Gln Gly Glu Asn His Pro Ser Pro Asn Phe Asn Gln Tyr Val Arg
                610             615             620

Asp Gln Gly Ala Met Thr Asp Gln Leu Ser Arg Arg Gln Ile Arg Glu
625                 630             635                 640

Tyr Gln Leu Tyr Ser Arg Thr Ser Gly Lys His Val Gln Val Thr Gly
                645             650             655

Arg Arg Ile Ser Ala Thr Ala Glu Asp Gly Asn Lys Phe Ala Lys Leu
                660             665             670

Ile Val Glu Thr Asp Thr Phe Gly Ser Arg Val Arg Ile Lys Gly Ala
                675             680             685

Glu Ser Glu Lys Tyr Ile Cys Met Asn Lys Arg Gly Lys Leu Ile Gly
                690             695             700

Lys Pro Ser Gly Lys Ser Lys Asp Cys Val Phe Thr Glu Ile Val Leu
705                 710             715                 720

Glu Asn Asn Tyr Thr Ala Phe Gln Asn Ala Arg His Glu Gly Trp Phe
                725             730             735

Met Ala Phe Thr Arg Gln Gly Arg Pro Arg Gln Ala Ser Arg Ser Arg
                740             745             750

Gln Asn Gln Arg Glu Ala His Phe Ile Lys Arg Leu Tyr Gln Gly Gln
                755             760             765

Leu Pro Phe Pro Asn His Ala Glu Lys Gln Lys Gln Phe Glu Phe Val
                770             775             780

Gly Ser Ala Pro Thr Arg Arg Thr Lys Arg Thr Arg Arg Pro Gln Pro
785                 790             795                 800

Leu Thr

<210> SEQ ID NO 73
<211> LENGTH: 438
<212> TYPE: PRT
<213> ORGANISM: Artificial Sequence
<220> FEATURE:
<223> OTHER INFORMATION: FGF17 fusion

<400> SEQUENCE: 73

Thr Gln Gly Glu Asn His Pro Ser Pro Asn Phe Asn Gln Tyr Val Arg
1               5               10              15

Asp Gln Gly Ala Met Thr Asp Gln Leu Ser Arg Arg Gln Ile Arg Glu
                20              25              30

Tyr Gln Leu Tyr Ser Arg Thr Ser Gly Lys His Val Gln Val Thr Gly
            35              40              45

Arg Arg Ile Ser Ala Thr Ala Glu Asp Gly Asn Lys Phe Ala Lys Leu
        50              55              60

Ile Val Glu Thr Asp Thr Phe Gly Ser Arg Val Arg Ile Lys Gly Ala
65              70              75              80

Glu Ser Glu Lys Tyr Ile Cys Met Asn Lys Arg Gly Lys Leu Ile Gly
                85              90              95
```

```
Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
            115                 120                 125

Met Ala Phe Thr Arg Gln Gly Arg Pro Arg Gln Ala Ser Arg Ser Arg
130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
                165                 170                 175

Gly Ser Ala Pro Thr Arg Arg Thr Lys Arg Thr Arg Arg Pro Gln Pro
                180                 185                 190

Leu Thr Gly Gly Gly Gly Ser Gly Gly Gly Gly Ser Gly Gly Gly Gly
            195                 200                 205

Ser Glu Ser Lys Tyr Gly Pro Pro Cys Pro Pro Cys Pro Ala Pro Glu
            210                 215                 220

Phe Leu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser Gln Glu Asp Pro Glu Val Gln Phe Asn Trp Tyr Val Asp Gly
            260                 265                 270

Val Glu Val His Asn Ala Lys Thr Lys Pro Arg Glu Glu Gln Phe Asn
            275                 280                 285

Ser Thr Tyr Arg Val Val Ser Val Leu Thr Val Leu His Gln Asp Trp
            290                 295                 300

Leu Asn Gly Lys Glu Tyr Lys Cys Lys Val Ser Asn Lys Gly Leu Pro
305                 310                 315                 320

Ser Ser Ile Glu Lys Thr Ile Ser Lys Ala Lys Gly Gln Pro Arg Glu
                325                 330                 335

Pro Gln Val Tyr Thr Leu Pro Pro Ser Gln Glu Glu Met Thr Lys Asn
            340                 345                 350

Gln Val Ser Leu Thr Cys Leu Val Lys Gly Phe Tyr Pro Ser Asp Ile
            355                 360                 365

Ala Val Glu Trp Glu Ser Asn Gly Gln Pro Glu Asn Asn Tyr Lys Thr
370                 375                 380

Thr Pro Pro Val Leu Asp Ser Asp Gly Ser Phe Phe Leu Tyr Ser Arg
385                 390                 395                 400

Leu Thr Val Asp Lys Ser Arg Trp Gln Glu Gly Asn Val Phe Ser Cys
                405                 410                 415

Ser Val Met His Glu Ala Leu His Asn His Tyr Thr Gln Lys Ser Leu
                420                 425                 430

Ser Leu Ser Leu Gly Lys
            435

<210> SEQ ID NO 74
<211> LENGTH: 423
<212> TYPE: PRT
<213> ORGANISM: Artificial Sequence
<220> FEATURE:
<223> OTHER INFORMATION: FGF17 fusion

<400> SEQUENCE: 74

Thr Gln Gly Glu Asn His Pro Ser Pro Asn Phe Asn Gln Tyr Val Arg
1               5                   10                  15
```

```
Asp Gln Gly Ala Met Thr Asp Gln Leu Ser Arg Arg Gln Ile Arg Glu
             20                  25                  30

Tyr Gln Leu Tyr Ser Arg Thr Ser Gly Lys His Val Gln Val Thr Gly
             35                  40                  45

Arg Arg Ile Ser Ala Thr Ala Glu Asp Gly Asn Lys Phe Ala Lys Leu
 50                  55                  60

Ile Val Glu Thr Asp Thr Phe Gly Ser Arg Val Arg Ile Lys Gly Ala
 65                  70                  75                  80

Glu Ser Glu Lys Tyr Ile Cys Met Asn Lys Arg Gly Lys Leu Ile Gly
                 85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
            115                 120                 125

Met Ala Phe Thr Arg Gln Gly Arg Pro Arg Gln Ala Ser Arg Ser Arg
130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
                165                 170                 175

Gly Ser Ala Pro Thr Arg Arg Thr Lys Arg Thr Arg Arg Pro Gln Pro
            180                 185                 190

Leu Thr Glu Ser Lys Tyr Gly Pro Pro Cys Pro Pro Cys Pro Ala Pro
            195                 200                 205

Glu Phe Leu Gly Gly Pro Ser Val Phe Leu Phe Pro Pro Lys Pro Lys
            210                 215                 220

Asp Thr Leu Met Ile Ser Arg Thr Pro Glu Val Thr Cys Val Val Val
225                 230                 235                 240

Asp Val Ser Gln Glu Asp Pro Glu Val Gln Phe Asn Trp Tyr Val Asp
                245                 250                 255

Gly Val Glu Val His Asn Ala Lys Thr Lys Pro Arg Glu Glu Gln Phe
            260                 265                 270

Asn Ser Thr Tyr Arg Val Val Ser Val Leu Thr Val Leu His Gln Asp
            275                 280                 285

Trp Leu Asn Gly Lys Glu Tyr Lys Cys Lys Val Ser Asn Lys Gly Leu
290                 295                 300

Pro Ser Ser Ile Glu Lys Thr Ile Ser Lys Ala Lys Gly Gln Pro Arg
305                 310                 315                 320

Glu Pro Gln Val Tyr Thr Leu Pro Pro Ser Gln Glu Glu Met Thr Lys
                325                 330                 335

Asn Gln Val Ser Leu Thr Cys Leu Val Lys Gly Phe Tyr Pro Ser Asp
            340                 345                 350

Ile Ala Val Glu Trp Glu Ser Asn Gly Gln Pro Glu Asn Asn Tyr Lys
            355                 360                 365

Thr Thr Pro Pro Val Leu Asp Ser Asp Gly Ser Phe Phe Leu Tyr Ser
            370                 375                 380

Arg Leu Thr Val Asp Lys Ser Arg Trp Gln Glu Gly Asn Val Phe Ser
385                 390                 395                 400

Cys Ser Val Met His Glu Ala Leu His Asn His Tyr Thr Gln Lys Ser
                405                 410                 415

Leu Ser Leu Ser Leu Gly Lys
            420
```

<210> SEQ ID NO 75
<211> LENGTH: 438
<212> TYPE: PRT
<213> ORGANISM: Artificial Sequence
<220> FEATURE:
<223> OTHER INFORMATION: FGF17 fusion

<400> SEQUENCE: 75

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Gly Gly Gly Ser Gly Gly Gly Ser Gly
225                 230                 235                 240

Gly Gly Ser Thr Gln Gly Glu Asn His Pro Ser Pro Asn Phe Asn
                245                 250                 255

Gln Tyr Val Arg Asp Gln Gly Ala Met Thr Asp Gln Leu Ser Arg Arg
            260                 265                 270

Gln Ile Arg Glu Tyr Gln Leu Tyr Ser Arg Thr Ser Gly Lys His Val
        275                 280                 285

Gln Val Thr Gly Arg Arg Ile Ser Ala Thr Ala Glu Asp Gly Asn Lys
    290                 295                 300

Phe Ala Lys Leu Ile Val Glu Thr Asp Thr Phe Gly Ser Arg Val Arg
305                 310                 315                 320

Ile Lys Gly Ala Glu Ser Glu Lys Tyr Ile Cys Met Asn Lys Arg Gly
                325                 330                 335

Lys Leu Ile Gly Lys Pro Ser Gly Lys Ser Lys Asp Cys Val Phe Thr
            340                 345                 350

Glu Ile Val Leu Glu Asn Asn Tyr Thr Ala Phe Gln Asn Ala Arg His
        355                 360                 365
```

Glu Gly Trp Phe Met Ala Phe Thr Arg Gln Gly Arg Pro Arg Gln Ala
    370                 375                 380

Ser Arg Ser Arg Gln Asn Gln Arg Glu Ala His Phe Ile Lys Arg Leu
385                 390                 395                 400

Tyr Gln Gly Gln Leu Pro Phe Pro Asn His Ala Glu Lys Gln Lys Gln
                405                 410                 415

Phe Glu Phe Val Gly Ser Ala Pro Thr Arg Arg Thr Lys Arg Thr Arg
                420                 425                 430

Arg Pro Gln Pro Leu Thr
            435

<210> SEQ ID NO 76
<211> LENGTH: 67
<212> TYPE: PRT
<213> ORGANISM: Homo sapiens

<400> SEQUENCE: 76

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
                20                  25                  30

Ser Arg Val Ser Arg Arg Ser Arg Gly Ile Val Glu Glu Cys Cys Phe
            35                  40                  45

Arg Ser Cys Asp Leu Ala Leu Leu Glu Thr Tyr Cys Ala Thr Pro Ala
50                  55                  60

Lys Ser Glu
65

<210> SEQ ID NO 77
<211> LENGTH: 298
<212> TYPE: PRT
<213> ORGANISM: Artificial Sequence
<220> FEATURE:
<223> OTHER INFORMATION: IGF2 fusion

<400> SEQUENCE: 77

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
                20                  25                  30

Ser Arg Val Ser Arg Arg Ser Arg Gly Ile Val Glu Glu Cys Cys Phe
            35                  40                  45

Arg Ser Cys Asp Leu Ala Leu Leu Glu Thr Tyr Cys Ala Thr Pro Ala
50                  55                  60

Lys Ser Glu Gly Ser Gly Ser Asp Lys Thr His Thr Cys Pro Pro Cys
65                  70                  75                  80

Pro Ala Pro Glu Ala Ala Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn

```
                165                 170                 175
Lys Ala Leu Gly Ala Pro Ile Glu Lys Thr Ile Ser Lys Ala Lys Gly
            180                 185                 190

Gln Pro Arg Glu Pro Gln Val Tyr Thr Leu Pro Pro Ser Arg Asp Glu
            195                 200                 205

Leu Thr Lys Asn Gln Val Ser Leu Thr Cys Leu Val Lys Gly Phe Tyr
            210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
            245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
            275                 280                 285

Gln Lys Ser Leu Ser Leu Ser Pro Gly Lys
            290                 295

<210> SEQ ID NO 78
<211> LENGTH: 299
<212> TYPE: PRT
<213> ORGANISM: Artificial Sequence
<220> FEATURE:
<223> OTHER INFORMATION: IGF2 fusion

<400> SEQUENCE: 78

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
            35                  40                  45

Arg Ser Cys Asp Leu Ala Leu Leu Glu Thr Tyr Cys Ala Thr Pro Ala
    50                  55                  60

Lys Ser Glu Gly Ser Gly Ser Ala Asp Lys Thr His Thr Cys Pro Pro
65                  70                  75                  80

Cys Pro Ala Pro Glu Ala Ala Gly Gly Pro Ser Val Phe Leu Phe Pro
            85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Lys Phe Asn
            115                 120                 125

Trp Tyr Val Asp Gly Val Glu Val His Asn Ala Lys Thr Lys Pro Arg
            130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
            165                 170                 175

Asn Lys Ala Leu Gly Ala Pro Ile Glu Lys Thr Ile Ser Lys Ala Lys
            180                 185                 190

Gly Gln Pro Arg Glu Pro Gln Val Tyr Thr Leu Pro Pro Ser Arg Asp
            195                 200                 205

Glu Leu Thr Lys Asn Gln Val Ser Leu Thr Cys Leu Val Lys Gly Phe
            210                 215                 220

Tyr Pro Ser Asp Ile Ala Val Glu Trp Glu Ser Asn Gly Gln Pro Glu
```

```
                225                 230                 235                 240
Asn Asn Tyr Lys Thr Thr Pro Pro Val Leu Asp Ser Asp Gly Ser Phe
            245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
            275                 280                 285

Thr Gln Lys Ser Leu Ser Leu Ser Pro Gly Lys
            290                 295

<210> SEQ ID NO 79
<211> LENGTH: 180
<212> TYPE: PRT
<213> ORGANISM: Homo sapiens

<400> SEQUENCE: 79

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125

Gly Leu Pro Ala Leu Leu Arg Ala Arg Arg Gly His Val Leu Ala Lys
    130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                165                 170                 175

Ser Asn Arg Lys
            180

<210> SEQ ID NO 80
<211> LENGTH: 675
<212> TYPE: PRT
<213> ORGANISM: Artificial Sequence
<220> FEATURE:
<223> OTHER INFORMATION: IGF2 fusion

<400> SEQUENCE: 80

His His His His His His Ser Gly Asp Ala His Lys Ser Glu Val Ala
1               5                   10                  15

His Arg Phe Lys Asp Leu Gly Glu Glu Asn Phe Lys Ala Leu Val Leu
            20                  25                  30

Ile Ala Phe Ala Gln Tyr Leu Gln Gln Cys Pro Phe Glu Asp His Val
        35                  40                  45

Lys Leu Val Asn Glu Val Thr Glu Phe Ala Lys Thr Cys Val Ala Asp
    50                  55                  60
```

```
Glu Ser Ala Glu Asn Cys Asp Lys Ser Leu His Thr Leu Phe Gly Asp
 65                  70                  75                  80

Lys Leu Cys Thr Val Ala Thr Leu Arg Glu Thr Tyr Gly Glu Met Ala
                 85                  90                  95

Asp Cys Cys Ala Lys Gln Glu Pro Glu Arg Asn Glu Cys Phe Leu Gln
                100                 105                 110

His Lys Asp Asp Asn Pro Asn Leu Pro Arg Leu Val Arg Pro Glu Val
                115                 120                 125

Asp Val Met Cys Thr Ala Phe His Asp Asn Glu Glu Thr Phe Leu Lys
130                 135                 140

Lys Tyr Leu Tyr Glu Ile Ala Arg Arg His Pro Tyr Phe Tyr Ala Pro
145                 150                 155                 160

Glu Leu Leu Phe Phe Ala Lys Arg Tyr Lys Ala Ala Phe Thr Glu Cys
                165                 170                 175

Cys Gln Ala Ala Asp Lys Ala Ala Cys Leu Leu Pro Lys Leu Asp Glu
                180                 185                 190

Leu Arg Asp Glu Gly Lys Ala Ser Ser Ala Lys Gln Arg Leu Lys Cys
        195                 200                 205

Ala Ser Leu Gln Lys Phe Gly Glu Arg Ala Phe Lys Ala Trp Ala Val
210                 215                 220

Ala Arg Leu Ser Gln Arg Phe Pro Lys Ala Glu Phe Ala Glu Val Ser
225                 230                 235                 240

Lys Leu Val Thr Asp Leu Thr Lys Val His Thr Glu Cys Cys His Gly
                245                 250                 255

Asp Leu Leu Glu Cys Ala Asp Asp Arg Ala Asp Leu Ala Lys Tyr Ile
                260                 265                 270

Cys Glu Asn Gln Asp Ser Ile Ser Ser Lys Leu Lys Glu Cys Cys Glu
                275                 280                 285

Lys Pro Leu Leu Glu Lys Ser His Cys Ile Ala Glu Val Glu Asn Asp
        290                 295                 300

Glu Met Pro Ala Asp Leu Pro Ser Leu Ala Ala Asp Phe Val Glu Ser
305                 310                 315                 320

Lys Asp Val Cys Lys Asn Tyr Ala Glu Ala Lys Asp Val Phe Leu Gly
                325                 330                 335

Met Phe Leu Tyr Glu Tyr Ala Arg Arg His Pro Asp Tyr Ser Val Val
                340                 345                 350

Leu Leu Leu Arg Leu Ala Lys Thr Tyr Glu Thr Thr Leu Glu Lys Cys
                355                 360                 365

Cys Ala Ala Ala Asp Pro His Glu Cys Tyr Ala Lys Val Phe Asp Glu
        370                 375                 380

Phe Lys Pro Leu Val Glu Glu Pro Gln Asn Leu Ile Lys Gln Asn Cys
385                 390                 395                 400

Glu Leu Phe Glu Gln Leu Gly Glu Tyr Lys Phe Gln Asn Ala Leu Leu
                405                 410                 415

Val Arg Tyr Thr Lys Lys Val Pro Gln Val Ser Thr Pro Thr Leu Val
                420                 425                 430

Glu Val Ser Arg Asn Leu Gly Lys Val Gly Ser Lys Cys Cys Lys His
                435                 440                 445

Pro Glu Ala Lys Arg Met Pro Cys Ala Glu Asp Tyr Leu Ser Val Val
        450                 455                 460

Leu Asn Gln Leu Cys Val Leu His Glu Lys Thr Pro Val Ser Asp Arg
465                 470                 475                 480
```

Val Thr Lys Cys Cys Thr Glu Ser Leu Val Asn Arg Arg Pro Cys Phe
            485                 490                 495

Ser Ala Leu Glu Val Asp Glu Thr Tyr Val Pro Lys Glu Phe Asn Ala
            500                 505                 510

Glu Thr Phe Thr Phe His Ala Asp Ile Cys Thr Leu Ser Glu Lys Glu
            515                 520                 525

Arg Gln Ile Lys Lys Gln Thr Ala Leu Val Glu Leu Val Lys His Lys
            530                 535                 540

Pro Lys Ala Thr Lys Glu Gln Leu Lys Ala Val Met Asp Asp Phe Ala
545                 550                 555                 560

Ala Phe Val Glu Lys Cys Cys Lys Ala Asp Asp Lys Glu Thr Cys Phe
            565                 570                 575

Ala Glu Glu Gly Lys Lys Leu Val Ala Ala Ser Gln Ala Ala Leu Gly
            580                 585                 590

Leu Gly Gly Gly Gly Ser Gly Gly Gly Ser Gly Gly Gly Gly Ser
            595                 600                 605

Ala Tyr Arg Pro Ser Glu Thr Leu Cys Gly Gly Glu Leu Val Asp Thr
            610                 615                 620

Leu Gln Phe Val Cys Gly Asp Arg Gly Phe Tyr Phe Ser Arg Pro Ala
625                 630                 635                 640

Ser Arg Val Ser Arg Arg Ser Arg Gly Ile Val Glu Glu Cys Cys Phe
            645                 650                 655

Arg Ser Cys Asp Leu Ala Leu Leu Glu Thr Tyr Cys Ala Thr Pro Ala
            660                 665                 670

Lys Ser Glu
        675

<210> SEQ ID NO 81
<211> LENGTH: 675
<212> TYPE: PRT
<213> ORGANISM: Artificial Sequence
<220> FEATURE:
<223> OTHER INFORMATION: IGF2 mutant

<400> SEQUENCE: 81

His His His His His His Ser Gly Asp Ala His Lys Ser Glu Val Ala
1               5                   10                  15

His Arg Phe Lys Asp Leu Gly Glu Glu Asn Phe Lys Ala Leu Val Leu
            20                  25                  30

Ile Ala Phe Ala Gln Tyr Leu Gln Gln Cys Pro Phe Glu Asp His Val
            35                  40                  45

Lys Leu Val Asn Glu Val Thr Glu Phe Ala Lys Thr Cys Val Ala Asp
            50                  55                  60

Glu Ser Ala Glu Asn Cys Asp Lys Ser Leu His Thr Leu Phe Gly Asp
65                  70                  75                  80

Lys Leu Cys Thr Val Ala Thr Leu Arg Glu Thr Tyr Gly Glu Met Ala
            85                  90                  95

Asp Cys Cys Ala Lys Gln Glu Pro Glu Arg Asn Glu Cys Phe Leu Gln
            100                 105                 110

His Lys Asp Asp Asn Pro Asn Leu Pro Arg Leu Val Arg Pro Glu Val
            115                 120                 125

Asp Val Met Cys Thr Ala Phe His Asp Asn Glu Glu Thr Phe Leu Lys
            130                 135                 140

Lys Tyr Leu Tyr Glu Ile Ala Arg Arg His Pro Tyr Phe Tyr Ala Pro
145                 150                 155                 160

```
Glu Leu Leu Phe Phe Ala Lys Arg Tyr Lys Ala Ala Phe Thr Glu Cys
                165                 170                 175

Cys Gln Ala Ala Asp Lys Ala Ala Cys Leu Leu Pro Lys Leu Asp Glu
            180                 185                 190

Leu Arg Asp Glu Gly Lys Ala Ser Ser Ala Lys Gln Arg Leu Lys Cys
        195                 200                 205

Ala Ser Leu Gln Lys Phe Gly Glu Arg Ala Phe Lys Ala Trp Ala Val
    210                 215                 220

Ala Arg Leu Ser Gln Arg Phe Pro Lys Ala Glu Phe Ala Glu Val Ser
225                 230                 235                 240

Lys Leu Val Thr Asp Leu Thr Lys Val His Thr Glu Cys Cys His Gly
                245                 250                 255

Asp Leu Leu Glu Cys Ala Asp Asp Arg Ala Asp Leu Ala Lys Tyr Ile
            260                 265                 270

Cys Glu Asn Gln Asp Ser Ile Ser Ser Lys Leu Lys Glu Cys Cys Glu
        275                 280                 285

Lys Pro Leu Leu Glu Lys Ser His Cys Ile Ala Glu Val Glu Asn Asp
    290                 295                 300

Glu Met Pro Ala Asp Leu Pro Ser Leu Ala Ala Asp Phe Val Glu Ser
305                 310                 315                 320

Lys Asp Val Cys Lys Asn Tyr Ala Glu Ala Lys Asp Val Phe Leu Gly
                325                 330                 335

Met Phe Leu Tyr Glu Tyr Ala Arg Arg His Pro Asp Tyr Ser Val Val
            340                 345                 350

Leu Leu Leu Arg Leu Ala Lys Thr Tyr Glu Thr Thr Leu Glu Lys Cys
        355                 360                 365

Cys Ala Ala Ala Asp Pro His Glu Cys Tyr Ala Lys Val Phe Asp Glu
    370                 375                 380

Phe Lys Pro Leu Val Glu Glu Pro Gln Asn Leu Ile Lys Gln Asn Cys
385                 390                 395                 400

Glu Leu Phe Glu Gln Leu Gly Glu Tyr Lys Phe Gln Asn Ala Leu Leu
                405                 410                 415

Val Arg Tyr Thr Lys Lys Val Pro Gln Val Ser Thr Pro Thr Leu Val
            420                 425                 430

Glu Val Ser Arg Asn Leu Gly Lys Val Gly Ser Lys Cys Cys Lys His
        435                 440                 445

Pro Glu Ala Lys Arg Met Pro Cys Ala Glu Asp Tyr Leu Ser Val Val
    450                 455                 460

Leu Asn Gln Leu Cys Val Leu His Glu Lys Thr Pro Val Ser Asp Arg
465                 470                 475                 480

Val Thr Lys Cys Cys Thr Glu Ser Leu Val Asn Arg Arg Pro Cys Phe
                485                 490                 495

Ser Ala Leu Glu Val Asp Glu Thr Tyr Val Pro Lys Glu Phe Asn Ala
            500                 505                 510

Glu Thr Phe Thr Phe His Ala Asp Ile Cys Thr Leu Ser Glu Lys Glu
        515                 520                 525

Arg Gln Ile Lys Lys Gln Thr Ala Leu Val Glu Leu Val Lys His Lys
    530                 535                 540

Pro Lys Ala Thr Lys Glu Gln Leu Lys Ala Val Met Asp Asp Phe Ala
545                 550                 555                 560

Ala Phe Val Glu Lys Cys Cys Lys Ala Asp Asp Lys Glu Thr Cys Phe
                565                 570                 575

Ala Glu Glu Gly Lys Lys Leu Val Ala Ala Ser Gln Ala Ala Leu Gly
```

```
                    580                 585                 590
Leu Gly Gly Gly Ser Gly Gly Gly Ser Gly Gly Gly Ser
            595                 600                 605

Ala Tyr Arg Pro Ser Glu Thr Leu Cys Gly Gly Glu Leu Val Asp Thr
            610                 615                 620

Leu Gln Phe Val Cys Gly Asp Arg Gly Phe Tyr Phe Ser Arg Pro Ala
625                 630                 635                 640

Ser Arg Val Ser Ala Arg Ser Arg Gly Ile Val Glu Glu Cys Cys Phe
            645                 650                 655

Arg Ser Cys Asp Leu Ala Leu Leu Glu Thr Tyr Cys Ala Thr Pro Ala
            660                 665                 670

Lys Ser Glu
            675

<210> SEQ ID NO 82
<211> LENGTH: 675
<212> TYPE: PRT
<213> ORGANISM: Artificial Sequence
<220> FEATURE:
<223> OTHER INFORMATION: IGF2 mutant

<400> SEQUENCE: 82

His His His His His His Ser Gly Asp Ala His Lys Ser Glu Val Ala
1               5                   10                  15

His Arg Phe Lys Asp Leu Gly Glu Glu Asn Phe Lys Ala Leu Val Leu
                20                  25                  30

Ile Ala Phe Ala Gln Tyr Leu Gln Gln Cys Pro Phe Glu Asp His Val
            35                  40                  45

Lys Leu Val Asn Glu Val Thr Glu Phe Ala Lys Thr Cys Val Ala Asp
        50                  55                  60

Glu Ser Ala Glu Asn Cys Asp Lys Ser Leu His Thr Leu Phe Gly Asp
65                  70                  75                  80

Lys Leu Cys Thr Val Ala Thr Leu Arg Glu Thr Tyr Gly Glu Met Ala
                85                  90                  95

Asp Cys Cys Ala Lys Gln Glu Pro Glu Arg Asn Glu Cys Phe Leu Gln
            100                 105                 110

His Lys Asp Asp Asn Pro Asn Leu Pro Arg Leu Val Arg Pro Glu Val
        115                 120                 125

Asp Val Met Cys Thr Ala Phe His Asp Asn Glu Glu Thr Phe Leu Lys
130                 135                 140

Lys Tyr Leu Tyr Glu Ile Ala Arg Arg His Pro Tyr Phe Tyr Ala Pro
145                 150                 155                 160

Glu Leu Leu Phe Phe Ala Lys Arg Tyr Lys Ala Ala Phe Thr Glu Cys
                165                 170                 175

Cys Gln Ala Ala Asp Lys Ala Ala Cys Leu Leu Pro Lys Leu Asp Glu
            180                 185                 190

Leu Arg Asp Glu Gly Lys Ala Ser Ser Ala Lys Gln Arg Leu Lys Cys
        195                 200                 205

Ala Ser Leu Gln Lys Phe Gly Glu Arg Ala Phe Lys Ala Trp Ala Val
210                 215                 220

Ala Arg Leu Ser Gln Arg Phe Pro Lys Ala Glu Phe Ala Glu Val Ser
225                 230                 235                 240

Lys Leu Val Thr Asp Leu Thr Lys Val His Thr Glu Cys Cys His Gly
                245                 250                 255

Asp Leu Leu Glu Cys Ala Asp Asp Arg Ala Asp Leu Ala Lys Tyr Ile
```

-continued

```
                260                 265                 270
    Cys Glu Asn Gln Asp Ser Ile Ser Ser Lys Leu Lys Glu Cys Cys Glu
                275                 280                 285
    Lys Pro Leu Glu Lys Ser His Cys Ile Ala Glu Val Glu Asn Asp
        290                 295                 300
    Glu Met Pro Ala Asp Leu Pro Ser Leu Ala Ala Asp Phe Val Glu Ser
    305                 310                 315                 320
    Lys Asp Val Cys Lys Asn Tyr Ala Glu Ala Lys Asp Val Phe Leu Gly
                    325                 330                 335
    Met Phe Leu Tyr Glu Tyr Ala Arg Arg His Pro Asp Tyr Ser Val Val
                340                 345                 350
    Leu Leu Leu Arg Leu Ala Lys Thr Tyr Glu Thr Thr Leu Glu Lys Cys
                355                 360                 365
    Cys Ala Ala Ala Asp Pro His Glu Cys Tyr Ala Lys Val Phe Asp Glu
                370                 375                 380
    Phe Lys Pro Leu Val Glu Glu Pro Gln Asn Leu Ile Lys Gln Asn Cys
    385                 390                 395                 400
    Glu Leu Phe Glu Gln Leu Gly Glu Tyr Lys Phe Gln Asn Ala Leu Leu
                    405                 410                 415
    Val Arg Tyr Thr Lys Lys Val Pro Gln Val Ser Thr Pro Thr Leu Val
                420                 425                 430
    Glu Val Ser Arg Asn Leu Gly Lys Val Gly Ser Lys Cys Cys Lys His
                435                 440                 445
    Pro Glu Ala Lys Arg Met Pro Cys Ala Glu Asp Tyr Leu Ser Val Val
            450                 455                 460
    Leu Asn Gln Leu Cys Val Leu His Glu Lys Thr Pro Val Ser Asp Arg
    465                 470                 475                 480
    Val Thr Lys Cys Cys Thr Glu Ser Leu Val Asn Arg Arg Pro Cys Phe
                    485                 490                 495
    Ser Ala Leu Glu Val Asp Glu Thr Tyr Val Pro Lys Glu Phe Asn Ala
                500                 505                 510
    Glu Thr Phe Thr Phe His Ala Asp Ile Cys Thr Leu Ser Glu Lys Glu
                515                 520                 525
    Arg Gln Ile Lys Lys Gln Thr Ala Leu Val Glu Leu Val Lys His Lys
                530                 535                 540
    Pro Lys Ala Thr Lys Glu Gln Leu Lys Ala Val Met Asp Asp Phe Ala
    545                 550                 555                 560
    Ala Phe Val Glu Lys Cys Cys Lys Ala Asp Asp Lys Glu Thr Cys Phe
                    565                 570                 575
    Ala Glu Glu Gly Lys Lys Leu Val Ala Ala Ser Gln Ala Ala Leu Gly
                580                 585                 590
    Leu Gly Gly Gly Gly Ser Gly Gly Gly Gly Ser Gly Gly Gly Gly Ser
                595                 600                 605
    Ala Tyr Arg Pro Ser Glu Thr Leu Cys Gly Gly Glu Leu Val Asp Thr
                610                 615                 620
    Leu Gln Phe Val Cys Gly Asp Arg Gly Phe Tyr Phe Ser Arg Pro Ala
    625                 630                 635                 640
    Ser Arg Val Ser Gln Arg Ser Arg Gly Ile Val Glu Glu Cys Cys Phe
                    645                 650                 655
    Arg Ser Cys Asp Leu Ala Leu Leu Glu Thr Tyr Cys Ala Thr Pro Ala
                660                 665                 670
    Lys Ser Glu
        675
```

<210> SEQ ID NO 83
<211> LENGTH: 675
<212> TYPE: PRT
<213> ORGANISM: Artificial Sequence
<220> FEATURE:
<223> OTHER INFORMATION: IGF2 mutant

<400> SEQUENCE: 83

```
His His His His His His Ser Gly Asp Ala His Lys Ser Glu Val Ala
1               5                   10                  15

His Arg Phe Lys Asp Leu Gly Glu Glu Asn Phe Lys Ala Leu Val Leu
            20                  25                  30

Ile Ala Phe Ala Gln Tyr Leu Gln Gln Cys Pro Phe Glu Asp His Val
        35                  40                  45

Lys Leu Val Asn Glu Val Thr Glu Phe Ala Lys Thr Cys Val Ala Asp
    50                  55                  60

Glu Ser Ala Glu Asn Cys Asp Lys Ser Leu His Thr Leu Phe Gly Asp
65                  70                  75                  80

Lys Leu Cys Thr Val Ala Thr Leu Arg Glu Thr Tyr Gly Glu Met Ala
                85                  90                  95

Asp Cys Cys Ala Lys Gln Glu Pro Glu Arg Asn Glu Cys Phe Leu Gln
            100                 105                 110

His Lys Asp Asp Asn Pro Asn Leu Pro Arg Leu Val Arg Pro Glu Val
        115                 120                 125

Asp Val Met Cys Thr Ala Phe His Asp Asn Glu Glu Thr Phe Leu Lys
    130                 135                 140

Lys Tyr Leu Tyr Glu Ile Ala Arg Arg His Pro Tyr Phe Tyr Ala Pro
145                 150                 155                 160

Glu Leu Leu Phe Phe Ala Lys Arg Tyr Lys Ala Ala Phe Thr Glu Cys
                165                 170                 175

Cys Gln Ala Ala Asp Lys Ala Ala Cys Leu Leu Pro Lys Leu Asp Glu
            180                 185                 190

Leu Arg Asp Glu Gly Lys Ala Ser Ser Ala Lys Gln Arg Leu Lys Cys
        195                 200                 205

Ala Ser Leu Gln Lys Phe Gly Glu Arg Ala Phe Lys Ala Trp Ala Val
    210                 215                 220

Ala Arg Leu Ser Gln Arg Phe Pro Lys Ala Glu Phe Ala Glu Val Ser
225                 230                 235                 240

Lys Leu Val Thr Asp Leu Thr Lys Val His Thr Glu Cys Cys His Gly
                245                 250                 255

Asp Leu Leu Glu Cys Ala Asp Asp Arg Ala Asp Leu Ala Lys Tyr Ile
            260                 265                 270

Cys Glu Asn Gln Asp Ser Ile Ser Ser Lys Leu Lys Glu Cys Cys Glu
        275                 280                 285

Lys Pro Leu Leu Glu Lys Ser His Cys Ile Ala Glu Val Glu Asn Asp
    290                 295                 300

Glu Met Pro Ala Asp Leu Pro Ser Leu Ala Ala Asp Phe Val Glu Ser
305                 310                 315                 320

Lys Asp Val Cys Lys Asn Tyr Ala Glu Ala Lys Asp Val Phe Leu Gly
                325                 330                 335

Met Phe Leu Tyr Glu Tyr Ala Arg Arg His Pro Asp Tyr Ser Val Val
            340                 345                 350

Leu Leu Leu Arg Leu Ala Lys Thr Tyr Glu Thr Thr Leu Glu Lys Cys
        355                 360                 365
```

Cys Ala Ala Asp Pro His Glu Cys Tyr Ala Lys Val Phe Asp Glu
            370                 375                 380

Phe Lys Pro Leu Val Glu Pro Gln Asn Leu Ile Lys Gln Asn Cys
385                 390                 395                 400

Glu Leu Phe Glu Gln Leu Gly Glu Tyr Lys Phe Gln Asn Ala Leu Leu
                405                 410                 415

Val Arg Tyr Thr Lys Lys Val Pro Gln Val Ser Thr Pro Thr Leu Val
            420                 425                 430

Glu Val Ser Arg Asn Leu Gly Lys Val Gly Ser Lys Cys Cys Lys His
            435                 440                 445

Pro Glu Ala Lys Arg Met Pro Cys Ala Glu Asp Tyr Leu Ser Val Val
450                 455                 460

Leu Asn Gln Leu Cys Val Leu His Glu Lys Thr Pro Val Ser Asp Arg
465                 470                 475                 480

Val Thr Lys Cys Cys Thr Glu Ser Leu Val Asn Arg Arg Pro Cys Phe
                485                 490                 495

Ser Ala Leu Glu Val Asp Glu Thr Tyr Val Pro Lys Glu Phe Asn Ala
            500                 505                 510

Glu Thr Phe Thr Phe His Ala Asp Ile Cys Thr Leu Ser Glu Lys Glu
            515                 520                 525

Arg Gln Ile Lys Lys Gln Thr Ala Leu Val Glu Leu Val Lys His Lys
530                 535                 540

Pro Lys Ala Thr Lys Glu Gln Leu Lys Ala Val Met Asp Asp Phe Ala
545                 550                 555                 560

Ala Phe Val Glu Lys Cys Cys Lys Ala Asp Asp Lys Glu Thr Cys Phe
                565                 570                 575

Ala Glu Glu Gly Lys Lys Leu Val Ala Ala Ser Gln Ala Ala Leu Gly
            580                 585                 590

Leu Gly Gly Gly Gly Ser Gly Gly Gly Ser Gly Gly Gly Gly Ser
            595                 600                 605

Ala Tyr Arg Pro Ser Glu Thr Leu Cys Gly Gly Glu Leu Val Asp Thr
610                 615                 620

Leu Gln Phe Val Cys Gly Asp Arg Gly Phe Tyr Phe Ser Arg Pro Ala
625                 630                 635                 640

Ser Arg Val Ser Arg Arg Ser Ala Gly Ile Val Glu Glu Cys Cys Phe
                645                 650                 655

Arg Ser Cys Asp Leu Ala Leu Leu Glu Thr Tyr Cys Ala Thr Pro Ala
            660                 665                 670

Lys Ser Glu
        675

<210> SEQ ID NO 84
<211> LENGTH: 675
<212> TYPE: PRT
<213> ORGANISM: Artificial Sequence
<220> FEATURE:
<223> OTHER INFORMATION: IGF2 mutant

<400> SEQUENCE: 84

His His His His His Ser Gly Asp Ala His Lys Ser Glu Val Ala
1               5                   10                  15

His Arg Phe Lys Asp Leu Gly Glu Glu Asn Phe Lys Ala Leu Val Leu
            20                  25                  30

Ile Ala Phe Ala Gln Tyr Leu Gln Gln Cys Pro Phe Glu Asp His Val
        35                  40                  45

```
Lys Leu Val Asn Glu Val Thr Glu Phe Ala Lys Thr Cys Val Ala Asp
     50                  55                  60

Glu Ser Ala Glu Asn Cys Asp Lys Ser Leu His Thr Leu Phe Gly Asp
 65                  70                  75                  80

Lys Leu Cys Thr Val Ala Thr Leu Arg Glu Thr Tyr Gly Glu Met Ala
                 85                  90                  95

Asp Cys Cys Ala Lys Gln Glu Pro Glu Arg Asn Glu Cys Phe Leu Gln
                100                 105                 110

His Lys Asp Asp Asn Pro Asn Leu Pro Arg Leu Val Arg Pro Glu Val
            115                 120                 125

Asp Val Met Cys Thr Ala Phe His Asp Asn Glu Glu Thr Phe Leu Lys
            130                 135                 140

Lys Tyr Leu Tyr Glu Ile Ala Arg Arg His Pro Tyr Phe Tyr Ala Pro
145                 150                 155                 160

Glu Leu Leu Phe Phe Ala Lys Arg Tyr Lys Ala Ala Phe Thr Glu Cys
                165                 170                 175

Cys Gln Ala Ala Asp Lys Ala Ala Cys Leu Leu Pro Lys Leu Asp Glu
            180                 185                 190

Leu Arg Asp Glu Gly Lys Ala Ser Ser Ala Lys Gln Arg Leu Lys Cys
            195                 200                 205

Ala Ser Leu Gln Lys Phe Gly Glu Arg Ala Phe Lys Ala Trp Ala Val
        210                 215                 220

Ala Arg Leu Ser Gln Arg Phe Pro Lys Ala Glu Phe Ala Glu Val Ser
225                 230                 235                 240

Lys Leu Val Thr Asp Leu Thr Lys Val His Thr Glu Cys Cys His Gly
                245                 250                 255

Asp Leu Leu Glu Cys Ala Asp Asp Arg Ala Asp Leu Ala Lys Tyr Ile
            260                 265                 270

Cys Glu Asn Gln Asp Ser Ile Ser Ser Lys Leu Lys Glu Cys Cys Glu
            275                 280                 285

Lys Pro Leu Leu Glu Lys Ser His Cys Ile Ala Glu Val Glu Asn Asp
290                 295                 300

Glu Met Pro Ala Asp Leu Pro Ser Leu Ala Ala Asp Phe Val Glu Ser
305                 310                 315                 320

Lys Asp Val Cys Lys Asn Tyr Ala Glu Ala Lys Asp Val Phe Leu Gly
                325                 330                 335

Met Phe Leu Tyr Glu Tyr Ala Arg Arg His Pro Asp Tyr Ser Val Val
            340                 345                 350

Leu Leu Leu Arg Leu Ala Lys Thr Tyr Glu Thr Thr Leu Glu Lys Cys
            355                 360                 365

Cys Ala Ala Ala Asp Pro His Glu Cys Tyr Ala Lys Val Phe Asp Glu
        370                 375                 380

Phe Lys Pro Leu Val Glu Glu Pro Gln Asn Leu Ile Lys Gln Asn Cys
385                 390                 395                 400

Glu Leu Phe Glu Gln Leu Gly Glu Tyr Lys Phe Gln Asn Ala Leu Leu
                405                 410                 415

Val Arg Tyr Thr Lys Lys Val Pro Gln Val Ser Thr Pro Thr Leu Val
            420                 425                 430

Glu Val Ser Arg Asn Leu Gly Lys Val Gly Ser Lys Cys Cys Lys His
            435                 440                 445

Pro Glu Ala Lys Arg Met Pro Cys Ala Glu Asp Tyr Leu Ser Val Val
450                 455                 460
```

```
Leu Asn Gln Leu Cys Val Leu His Glu Lys Thr Pro Val Ser Asp Arg
465                 470                 475                 480

Val Thr Lys Cys Cys Thr Glu Ser Leu Val Asn Arg Arg Pro Cys Phe
                485                 490                 495

Ser Ala Leu Glu Val Asp Glu Thr Tyr Val Pro Lys Glu Phe Asn Ala
            500                 505                 510

Glu Thr Phe Thr Phe His Ala Asp Ile Cys Thr Leu Ser Glu Lys Glu
        515                 520                 525

Arg Gln Ile Lys Lys Gln Thr Ala Leu Val Glu Leu Val Lys His Lys
    530                 535                 540

Pro Lys Ala Thr Lys Glu Gln Leu Lys Ala Val Met Asp Asp Phe Ala
545                 550                 555                 560

Ala Phe Val Glu Lys Cys Cys Lys Ala Asp Asp Lys Glu Thr Cys Phe
                565                 570                 575

Ala Glu Glu Gly Lys Lys Leu Val Ala Ala Ser Gln Ala Ala Leu Gly
            580                 585                 590

Leu Gly Gly Gly Ser Gly Gly Gly Ser Gly Gly Gly Ser
        595                 600                 605

Ala Tyr Arg Pro Ser Glu Thr Leu Cys Gly Gly Glu Leu Val Asp Thr
610                 615                 620

Leu Gln Phe Val Cys Gly Asp Arg Gly Phe Tyr Phe Ser Arg Pro Ala
625                 630                 635                 640

Ser Arg Val Ser Arg Arg Ser Gln Gly Ile Val Glu Cys Cys Phe
                645                 650                 655

Arg Ser Cys Asp Leu Ala Leu Leu Glu Thr Tyr Cys Ala Thr Pro Ala
            660                 665                 670

Lys Ser Glu
        675

<210> SEQ ID NO 85
<211> LENGTH: 311
<212> TYPE: PRT
<213> ORGANISM: Artificial Sequence
<220> FEATURE:
<223> OTHER INFORMATION: IGF2 fusion

<400> SEQUENCE: 85

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Cys Cys Phe
            35                  40                  45

Arg Ser Cys Asp Leu Ala Leu Leu Glu Thr Tyr Cys Ala Thr Pro Ala
    50                  55                  60

Lys Ser Glu Gly Gly Gly Ser Gly Gly Gly Ser Gly Gly Gly
65                  70                  75                  80

Gly Ser Glu Ser Lys Tyr Gly Pro Pro Cys Pro Pro Cys Pro Ala Pro
                85                  90                  95

Glu Phe Leu Gly Gly Pro Ser Val Phe Leu Phe Pro Pro Lys Pro Lys
            100                 105                 110

Asp Thr Leu Met Ile Ser Arg Thr Pro Glu Val Thr Cys Val Val Val
        115                 120                 125

Asp Val Ser Gln Glu Asp Pro Glu Val Gln Phe Asn Trp Tyr Val Asp
    130                 135                 140
```

```
Gly Val Glu Val His Asn Ala Lys Thr Lys Pro Arg Glu Glu Gln Phe
145                 150                 155                 160

Asn Ser Thr Tyr Arg Val Val Ser Val Leu Thr Val Leu His Gln Asp
                165                 170                 175

Trp Leu Asn Gly Lys Glu Tyr Lys Cys Lys Val Ser Asn Lys Gly Leu
            180                 185                 190

Pro Ser Ser Ile Glu Lys Thr Ile Ser Lys Ala Lys Gly Gln Pro Arg
        195                 200                 205

Glu Pro Gln Val Tyr Thr Leu Pro Pro Ser Gln Glu Met Thr Lys
    210                 215                 220

Asn Gln Val Ser Leu Thr Cys Leu Val Lys Gly Phe Tyr Pro Ser Asp
225                 230                 235                 240

Ile Ala Val Glu Trp Glu Ser Asn Gly Gln Pro Glu Asn Asn Tyr Lys
                245                 250                 255

Thr Thr Pro Pro Val Leu Asp Ser Asp Gly Ser Phe Phe Leu Tyr Ser
            260                 265                 270

Arg Leu Thr Val Asp Lys Ser Arg Trp Gln Gln Gly Asn Val Phe Ser
        275                 280                 285

Cys Ser Val Met His Glu Ala Leu His Asn His Tyr Thr Gln Lys Ser
290                 295                 300

Leu Ser Leu Ser Leu Gly Lys
305                 310

<210> SEQ ID NO 86
<211> LENGTH: 296
<212> TYPE: PRT
<213> ORGANISM: Artificial Sequence
<220> FEATURE:
<223> OTHER INFORMATION: IGF2 fusion

<400> SEQUENCE: 86

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
                20                  25                  30

Ser Arg Val Ser Arg Arg Ser Arg Gly Ile Val Glu Glu Cys Cys Phe
            35                  40                  45

Arg Ser Cys Asp Leu Ala Leu Leu Glu Thr Tyr Cys Ala Thr Pro Ala
50                  55                  60

Lys Ser Glu Glu Ser Lys Tyr Gly Pro Pro Cys Pro Pro Cys Pro Ala
65                  70                  75                  80

Pro Glu Phe Leu Gly Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Ser Gln Glu Asp Pro Glu Val Gln Phe Asn Trp Tyr Val
        115                 120                 125

Asp Gly Val Glu Val His Asn Ala Lys Thr Lys Pro Arg Glu Glu Gln
    130                 135                 140

Phe Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Gly
                165                 170                 175

Leu Pro Ser Ser Ile Glu Lys Thr Ile Ser Lys Ala Lys Gly Gln Pro
            180                 185                 190
```

```
Arg Glu Pro Gln Val Tyr Thr Leu Pro Pro Ser Gln Glu Glu Met Thr
            195                 200                 205

Lys Asn Gln Val Ser Leu Thr Cys Leu Val Lys Gly Phe Tyr Pro Ser
    210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Arg Leu Thr Val Asp Lys Ser Arg Trp Gln Glu Gly Asn Val Phe
            260                 265                 270

Ser Cys Ser Val Met His Glu Ala Leu His Asn His Tyr Thr Gln Lys
        275                 280                 285

Ser Leu Ser Leu Ser Leu Gly Lys
    290                 295

<210> SEQ ID NO 87
<211> LENGTH: 311
<212> TYPE: PRT
<213> ORGANISM: Artificial Sequence
<220> FEATURE:
<223> OTHER INFORMATION: IGF2 fusion

<400> SEQUENCE: 87

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Gly Gly Gly Gly Ser Gly Gly Gly Ser Gly
225                 230                 235                 240

Gly Gly Gly Ser Ala Tyr Arg Pro Ser Glu Thr Leu Cys Gly Gly Glu
                245                 250                 255
```

```
Leu Val Asp Thr Leu Gln Phe Val Cys Gly Asp Arg Gly Phe Tyr Phe
            260                 265                 270

Ser Arg Pro Ala Ser Arg Val Ser Arg Ser Arg Gly Ile Val Glu
        275                 280                 285

Glu Cys Cys Phe Arg Ser Cys Asp Leu Ala Leu Leu Glu Thr Tyr Cys
        290                 295                 300

Ala Thr Pro Ala Lys Ser Glu
305             310

<210> SEQ ID NO 88
<211> LENGTH: 311
<212> TYPE: PRT
<213> ORGANISM: Artificial Sequence
<220> FEATURE:
<223> OTHER INFORMATION: IGF2 mutant

<400> SEQUENCE: 88

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Ala Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu Gly Gly Gly Gly Ser Gly Gly Gly Gly Ser Gly Gly Gly
65                  70                  75                  80

Gly Ser Glu Ser Lys Tyr Gly Pro Pro Cys Pro Pro Cys Pro Ala Pro
                85                  90                  95

Glu Phe Leu Gly Gly Pro Ser Val Phe Leu Phe Pro Pro Lys Pro Lys
            100                 105                 110

Asp Thr Leu Met Ile Ser Arg Thr Pro Glu Val Thr Cys Val Val Val
            115                 120                 125

Asp Val Ser Gln Glu Asp Pro Glu Val Gln Phe Asn Trp Tyr Val Asp
        130                 135                 140

Gly Val Glu Val His Asn Ala Lys Thr Lys Pro Arg Glu Glu Gln Phe
145                 150                 155                 160

Asn Ser Thr Tyr Arg Val Val Ser Val Leu Thr Val Leu His Gln Asp
                165                 170                 175

Trp Leu Asn Gly Lys Glu Tyr Lys Cys Lys Val Ser Asn Lys Gly Leu
            180                 185                 190

Pro Ser Ser Ile Glu Lys Thr Ile Ser Lys Ala Lys Gly Gln Pro Arg
        195                 200                 205

Glu Pro Gln Val Tyr Thr Leu Pro Pro Ser Gln Glu Glu Met Thr Lys
    210                 215                 220

Asn Gln Val Ser Leu Thr Cys Leu Val Lys Gly Phe Tyr Pro Ser Asp
225                 230                 235                 240

Ile Ala Val Glu Trp Glu Ser Asn Gly Gln Pro Glu Asn Asn Tyr Lys
                245                 250                 255

Thr Thr Pro Pro Val Leu Asp Ser Asp Gly Ser Phe Phe Leu Tyr Ser
            260                 265                 270

Arg Leu Thr Val Asp Lys Ser Arg Trp Gln Glu Gly Asn Val Phe Ser
        275                 280                 285

Cys Ser Val Met His Glu Ala Leu His Asn His Tyr Thr Gln Lys Ser
    290                 295                 300
```

Leu Ser Leu Ser Leu Gly Lys
305                 310

<210> SEQ ID NO 89
<211> LENGTH: 139
<212> TYPE: PRT
<213> ORGANISM: Homo sapiens

<400> SEQUENCE: 89

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 90
<211> LENGTH: 370
<212> TYPE: PRT
<213> ORGANISM: Artificial Sequence
<220> FEATURE:
<223> OTHER INFORMATION: BMP7 fusion

<400> SEQUENCE: 90

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His Gly Ser Gly Ser Asp
    130                 135                 140

Lys Thr His Thr Cys Pro Pro Cys Pro Ala Pro Glu Ala Ala Gly Gly
145                 150                 155                 160

Pro Ser Val Phe Leu Phe Pro Pro Lys Pro Lys Asp Thr Leu Met Ile

```
            165                 170                 175
Ser Arg Thr Pro Glu Val Thr Cys Val Val Asp Val Ser His Glu
            180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Gly Ala Pro Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Asp Glu Leu Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365

Gly Lys
370

<210> SEQ ID NO 91
<211> LENGTH: 371
<212> TYPE: PRT
<213> ORGANISM: Artificial Sequence
<220> FEATURE:
<223> OTHER INFORMATION: BMP7 fusion

<400> SEQUENCE: 91

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His Gly Ser Gly Ser Ala
    130                 135                 140

Asp Lys Thr His Thr Cys Pro Pro Cys Pro Ala Pro Glu Ala Ala Gly
```

```
                145                 150                 155                 160
Gly Pro Ser Val Phe Leu Phe Pro Pro Lys Pro Lys Asp Thr Leu Met
                    165                 170                 175

Ile Ser Arg Thr Pro Glu Val Thr Cys Val Val Asp Val Ser His
                    180                 185                 190

Glu Asp Pro Glu Val Lys Phe Asn Trp Tyr Val Asp Gly Val Glu Val
                    195                 200                 205

His Asn Ala Lys Thr Lys Pro Arg Glu Glu Gln Tyr Asn Ser Thr Tyr
            210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Ala Leu Gly Ala Pro Ile
                    245                 250                 255

Glu Lys Thr Ile Ser Lys Ala Lys Gly Gln Pro Arg Glu Pro Gln Val
                    260                 265                 270

Tyr Thr Leu Pro Pro Ser Arg Asp Glu Leu Thr Lys Asn Gln Val Ser
                    275                 280                 285

Leu Thr Cys Leu Val Lys Gly Phe Tyr Pro Ser Asp Ile Ala Val Glu
                    290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Lys Leu Thr Val
                    325                 330                 335

Asp Lys Ser Arg Trp Gln Gln Gly Asn Val Phe Ser Cys Ser Val Met
                    340                 345                 350

His Glu Ala Leu His Asn His Tyr Thr Gln Lys Ser Leu Ser Leu Ser
            355                 360                 365

Pro Gly Lys
        370

<210> SEQ ID NO 92
<211> LENGTH: 96
<212> TYPE: DNA
<213> ORGANISM: Artificial Sequence
<220> FEATURE:
<223> OTHER INFORMATION: BMP7 knuckle

<400> SEQUENCE: 92
acggtgccca agccctgctg tgcgcccacg cagctcaatg ccatctccgt cctctacttc     60
gatgacagct ccaacgtcat cctgaagaaa tacaga                              96

<210> SEQ ID NO 93
<211> LENGTH: 32
<212> TYPE: PRT
<213> ORGANISM: Artificial Sequence
<220> FEATURE:
<223> OTHER INFORMATION: BMP7 knuckle

<400> SEQUENCE: 93

Thr Val Pro Lys Pro Cys Cys Ala Pro Thr Gln Leu Asn Ala Ile Ser
1               5                   10                  15

Val Leu Tyr Phe Asp Asp Ser Ser Asn Val Ile Leu Lys Lys Tyr Arg
                20                  25                  30

<210> SEQ ID NO 94
<211> LENGTH: 12
<212> TYPE: DNA
<213> ORGANISM: Artificial Sequence
```

<220> FEATURE:
<223> OTHER INFORMATION: linker

<400> SEQUENCE: 94
ggatcgggat cg                                                          12

<210> SEQ ID NO 95
<211> LENGTH: 15
<212> TYPE: DNA
<213> ORGANISM: Artificial Sequence
<220> FEATURE:
<223> OTHER INFORMATION: linker

<400> SEQUENCE: 95
ggatctggga gcgct                                                       15

<210> SEQ ID NO 96
<211> LENGTH: 45
<212> TYPE: DNA
<213> ORGANISM: Artificial Sequence
<220> FEATURE:
<223> OTHER INFORMATION: linker

<400> SEQUENCE: 96
ggcggaggcg gtagcggagg cggtggctcc ggtggcggag ggtct                      45

<210> SEQ ID NO 97
<211> LENGTH: 681
<212> TYPE: DNA
<213> ORGANISM: Artificial Sequence
<220> FEATURE:
<223> OTHER INFORMATION: IgG1 Fc mutant

<400> SEQUENCE: 97
gacaaaactc acacatgccc accgtgccca gcacctgaag ctgccggggg accgtcagtc      60
ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcggggag gagcagtaca acagcacgtac    240 cgtgtggtca gcgtcctcac cgtcctgcac caggactggc tgaatggcaa ggagtacaag    300
tgcaaggtct ccaacaaagc cctcggcgcc cccatcgaga aaaccatctc caaagccaaa    360
gggcagcccc gagaaccaca ggtgtacacc ctgcccccat cccgggatga gctgaccaag    420
aaccaggtca gcctgacctg cctggtcaaa ggcttctatc ccagcgacat cgccgtggag    480
tgggagagca atgggcagcc ggagaacaac tacaagacca cgcctcccgt gctggactcc    540
gacggctcct tcttcctcta cagcaagctc accgtggaca agagcaggtg gcagcagggg    600
aacgtcttct catgctccgt gatgcatgag gctctgcaca accactacac gcagaaaagc    660
ctctccctgt ctccgggtaa a                                              681

<210> SEQ ID NO 98
<211> LENGTH: 687
<212> TYPE: DNA
<213> ORGANISM: Artificial Sequence
<220> FEATURE:
<223> OTHER INFORMATION: IgG4 Fc mutant

<400> SEQUENCE: 98
gagtccaaat atggtccccc atgcccaccc tgcccagcac ctgagttcct ggggggacca     60
tcagtcttcc tgttcccccc aaaacccaag gacactctca tgatctcccg gacccctgag   120

| | |
|---|---|
| gtcacgtgcg tggtggtgga cgtgagccag gaagacccg aggtccagtt caactggtac | 180 |
| gtggatggcg tggaggtgca taatgccaag acaaagccgc gggaggagca gttcaacagc | 240 |
| acgtaccgtg tggtcagcgt cctcaccgtc ctgcaccagg actggctgaa cggcaaggag | 300 |
| tacaagtgca aggtctccaa caaaggcctc ccgtcctcca tcgagaaaac catctccaaa | 360 |
| gccaaagggc agccccgaga gccacaggtg tacaccctgc ccccatccca ggaggagatg | 420 |
| accaagaacc aggtcagcct gacctgcctg gtcaaaggct tctacccag cgacatcgcc | 480 |
| gtggagtggg agagcaatgg gcagccggag aacaactaca agaccacgcc tcccgtgctg | 540 |
| gactccgacg gctccttctt cctctacagc aggctcaccg tggacaagag caggtggcag | 600 |
| gaggggaatg tcttctcatg ctccgtgatg catgaggctc tgcacaacca ctacacacag | 660 |
| aagagcctct ccctgtctct gggtaaa | 687 |

<210> SEQ ID NO 99
<211> LENGTH: 18
<212> TYPE: DNA
<213> ORGANISM: Artificial Sequence
<220> FEATURE:
<223> OTHER INFORMATION: 6X His

<400> SEQUENCE: 99

| | |
|---|---|
| caccatcacc atcaccat | 18 |

<210> SEQ ID NO 100
<211> LENGTH: 24
<212> TYPE: DNA
<213> ORGANISM: Artificial Sequence
<220> FEATURE:
<223> OTHER INFORMATION: Strept-Tactin binding peptide

<400> SEQUENCE: 100

| | |
|---|---|
| tggagccacc cgcagttcga aaaa | 24 |

<210> SEQ ID NO 101
<211> LENGTH: 1755
<212> TYPE: DNA
<213> ORGANISM: Homo sapiens

<400> SEQUENCE: 101

| | |
|---|---|
| gatgcacaca agagtgaggt tgctcatcgg tttaaagatt tgggagaaga aaatttcaaa | 60 |
| gccttggtgt tgattgcctt tgctcagtat cttcagcagt gtccatttga agatcatgta | 120 |
| aaattagtga atgaagtaac tgaatttgca aaaacatgtg ttgctgatga gtcagctgaa | 180 |
| aattgtgaca atcacttca taccctttttt ggagacaaat tatgcacagt tgcaactctt | 240 |
| cgtgaaacct atggtgaaat ggctgactgc tgtgcaaaac aagaacctga gaaaatgaa | 300 |
| tgcttcttgc aacacaaaga tgacaaccca acctccccc gattggtgag accagaggtt | 360 |
| gatgtgatgt gcactgcttt tcatgacaat gaagagacat ttttgaaaaa atacttatat | 420 |
| gaaattgcca aagacatcc ttactttat gccccggaac tccttttctt tgctaaaagg | 480 |
| tataaagctg cttttacaga atgttgccaa gctgctgata agctgcctg cctgttgcca | 540 |
| aagctcgatg aacttcggga tgaagggaag cttcgtctg ccaaacagag actcaagtgt | 600 |
| gccagtctcc aaaaatttgg agaaagagct ttcaaagcat gggcagtagc tcgcctgagc | 660 |
| cagagatttc ccaaagctga gtttgcagaa gttccaagt tagtgacaga tcttaccaaa | 720 |
| gtccacacgg aatgctgcca tggagatctg cttgaatgtg ctgatgacag gcggacctt | 780 |
| gccaagtata tctgtgaaaa tcaagattcg atctccagta aactgaagga atgctgtgaa | 840 |

```
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt   1140
gtggaagagc tcagaatttt aatcaaacaa aattgtgagc tttttgagca gcttggagag   1200
tacaaattcc agaatgcgct attagttcgt tacaccaaga agtaccccca agtgtcaact   1260
ccaactcttg tagaggtctc aagaaaccta ggaaaagtgg gcagcaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg ctttttcagct ctggaagtcg atgaaacata cgttcccaaa   1500
gagtttaatg ctgaaacatt caccttccat gcagatatat gcacactttc tgagaaggag   1560
agacaaatca gaaacaaac tgcacttgtt gagctcgtga acacaagcc caaggcaaca   1620 aaagagcaac tgaaagctgt tatggatgat ttcgcagctt ttgtagagaa gtgctgcaag   1680
gctgacgata aggagacctg cttttgccgag gagggtaaaa aacttgttgc tgcaagtcaa   1740
gctgccttag gctta                                                    1755
```

<210> SEQ ID NO 102
<211> LENGTH: 4
<212> TYPE: PRT
<213> ORGANISM: Artificial Sequence
<220> FEATURE:
<223> OTHER INFORMATION: linker

<400> SEQUENCE: 102

Gly Ser Gly Ser
1

<210> SEQ ID NO 103
<211> LENGTH: 5
<212> TYPE: PRT
<213> ORGANISM: Artificial Sequence
<220> FEATURE:
<223> OTHER INFORMATION: linker

<400> SEQUENCE: 103

Gly Ser Gly Ser Ala
1               5

<210> SEQ ID NO 104
<211> LENGTH: 15
<212> TYPE: PRT
<213> ORGANISM: Artificial Sequence
<220> FEATURE:
<223> OTHER INFORMATION: linker

<400> SEQUENCE: 104

Gly Gly Gly Gly Ser Gly Gly Gly Ser Gly Gly Gly Ser
1               5                   10                  15

<210> SEQ ID NO 105
<211> LENGTH: 227
<212> TYPE: PRT
<213> ORGANISM: Artificial Sequence
<220> FEATURE:
<223> OTHER INFORMATION: IgG1 Fc mutant

<400> SEQUENCE: 105

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 106
<211> LENGTH: 229
<212> TYPE: PRT
<213> ORGANISM: Artificial Sequence
<220> FEATURE:
<223> OTHER INFORMATION: IgG4 Fc mutant

<400> SEQUENCE: 106

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110
```

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 107
<211> LENGTH: 6
<212> TYPE: PRT
<213> ORGANISM: Artificial Sequence
<220> FEATURE:
<223> OTHER INFORMATION: His tag

<400> SEQUENCE: 107

His His His His His His
1               5

<210> SEQ ID NO 108
<211> LENGTH: 8
<212> TYPE: PRT
<213> ORGANISM: Artificial Sequence
<220> FEATURE:
<223> OTHER INFORMATION: Step-Tactin binding peptide

<400> SEQUENCE: 108

Trp Ser His Pro Gln Phe Glu Lys
1               5

<210> SEQ ID NO 109
<211> LENGTH: 585
<212> TYPE: PRT
<213> ORGANISM: Homo sapiens

<400> SEQUENCE: 109

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

```
Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
```

|     |     |     |     |     |     |     |     |     |     |     |     |
| --- | --- | --- | --- | --- | --- | --- | --- | --- | --- | --- | --- |
| 530 | | | | | 535 | | | | | 540 | |
| Lys | Ala | Val | Met | Asp | Asp | Phe | Ala | Ala | Phe | Val | Glu | Lys | Cys | Cys | Lys |
| 545 | | | | | 550 | | | | | 555 | | | | | 560 |
| Ala | Asp | Asp | Lys | Glu | Thr | Cys | Phe | Ala | Glu | Glu | Gly | Lys | Lys | Leu | Val |
| | | | | 565 | | | | | 570 | | | | | 575 | |
| Ala | Ala | Ser | Gln | Ala | Ala | Leu | Gly | Leu | | | | | | | |
| | | | 580 | | | | | 585 | | | | | | | |